(12) United States Patent
Schulze et al.

(10) Patent No.: US 9,555,022 B2
(45) Date of Patent: Jan. 31, 2017

(54) SUBSTITUTED TRIAZOLOPYRIDINES

(75) Inventors: Volker Schulze, OT Bergfelde (DE); Dirk Kosemund, Berlin (DE); Hartmut Schirok, Langenfeld (DE); Benjamin Bader, Berlin (DE); Philip Lienau, Berlin (DE); Antje Margret Wengner, Berlin (DE); Hans Briem, Berlin (DE); Simon Holton, Berlin (DE); Gerhard Siemeister, Berlin (DE); Stefan Prechtl, Berlin (DE); Marcus Koppitz, Berlin (DE); Detlef Stöckigt, Potsdam (DE); Olaf Prien, Berlin (DE)

(73) Assignee: Bayer Intellectual Property GmbH, Monheim (DE)

(*) Notice: Subject to any disclaimer, the term of this patent is extended or adjusted under 35 U.S.C. 154(b) by 237 days.

(21) Appl. No.: 13/704,859

(22) PCT Filed: Jun. 14, 2011

(86) PCT No.: PCT/EP2011/059806
§ 371 (c)(1),
(2), (4) Date: Feb. 25, 2013

(87) PCT Pub. No.: WO2011/157688
PCT Pub. Date: Dec. 22, 2011

(65) Prior Publication Data
US 2013/0156756 A1 Jun. 20, 2013

(30) Foreign Application Priority Data

Jun. 16, 2010 (EP) .................. 10166149
May 23, 2011 (EP) .................. 11167139

(51) Int. Cl.

| | |
|---|---|
| *C07D 513/02* | (2006.01) |
| *C07D 515/02* | (2006.01) |
| *C07D 249/08* | (2006.01) |
| *A61K 31/44* | (2006.01) |
| *A61K 31/437* | (2006.01) |
| *A61K 45/06* | (2006.01) |
| *C07D 471/04* | (2006.01) |
| *C07D 519/00* | (2006.01) |
| *A61K 31/167* | (2006.01) |
| *A61K 31/277* | (2006.01) |
| *A61K 31/282* | (2006.01) |
| *A61K 31/337* | (2006.01) |
| *A61K 31/427* | (2006.01) |
| *A61K 31/428* | (2006.01) |
| *A61K 31/444* | (2006.01) |
| *A61K 31/4545* | (2006.01) |
| *A61K 31/496* | (2006.01) |
| *A61K 31/513* | (2006.01) |
| *A61K 31/5377* | (2006.01) |

(Continued)

(52) U.S. Cl.
CPC .......... *A61K 31/437* (2013.01); *A61K 31/167* (2013.01); *A61K 31/277* (2013.01); *A61K 31/282* (2013.01); *A61K 31/337* (2013.01); *A61K 31/427* (2013.01); *A61K 31/428* (2013.01); *A61K 31/444* (2013.01); *A61K 31/4545* (2013.01); *A61K 31/496* (2013.01); *A61K 31/513* (2013.01); *A61K 31/5377* (2013.01); *A61K 31/541* (2013.01); *A61K 31/565* (2013.01); *A61K 31/675* (2013.01); *A61K 31/69* (2013.01); *A61K 31/704* (2013.01); *A61K 31/7048* (2013.01); *A61K 33/24* (2013.01); *A61K 38/14* (2013.01); *A61K 39/395* (2013.01); *A61K 45/06* (2013.01); *C07D 471/04* (2013.01); *C07D 491/08* (2013.01); *C07D 491/107* (2013.01); *C07D 519/00* (2013.01)

(58) Field of Classification Search
USPC .............. 546/112, 113, 118, 121; 548/262.2, 548/264.4, 264.8; 514/299, 300, 303
See application file for complete search history.

(56) References Cited

FOREIGN PATENT DOCUMENTS

| | | | | |
|---|---|---|---|---|
| GB | WO 2010092041 A1 | * | 8/2010 | .......... C07D 471/04 |
| JP | 2010111624 A | * | 5/2010 | |

(Continued)

OTHER PUBLICATIONS (Cecil's Textbook of Medicine pp. 1060-1074 published 2000).*
Calabresi and Chabner (Goodman & Gilman's The Pharmacological Basis of Therapeutics, 10th ed, 2001).*

(Continued)

*Primary Examiner* — Timothy Thomas
*Assistant Examiner* — George W Kosturko
(74) *Attorney, Agent, or Firm* — Morrison & Foerster LLP

(57) ABSTRACT

The present invention relates to substituted triazolopyridine compounds of general formula (I): in which $R^1$, $R^2$, $R^3$, $R^4$, and $R^5$ are as given in the description and in the claims, to methods of preparing said compounds, to pharmaceutical compositions and combinations comprising said compounds, to the use of said compounds for manufacturing a pharmaceutical composition for the treatment or prophylaxis of a disease of uncontrolled cell growth, proliferation and/or survival as well as to the use of intermediate compounds for the preparation of said compounds.

(I)

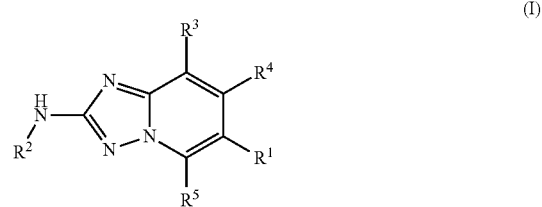

15 Claims, No Drawings

(51) Int. Cl.

| | | |
|---|---|---|
| A61K 31/541 | (2006.01) | |
| A61K 31/565 | (2006.01) | |
| A61K 31/675 | (2006.01) | |
| A61K 31/69 | (2006.01) | |
| A61K 31/704 | (2006.01) | |
| A61K 31/7048 | (2006.01) | |
| A61K 33/24 | (2006.01) | |
| A61K 38/14 | (2006.01) | |
| A61K 39/395 | (2006.01) | |
| C07D 491/08 | (2006.01) | |
| C07D 491/107 | (2006.01) | |

(56) References Cited

FOREIGN PATENT DOCUMENTS

| | | | | |
|---|---|---|---|---|
| WO | 2005030121 A2 | 4/2005 | | |
| WO | 2007065010 A2 | 6/2007 | | |
| WO | 2008025821 A1 | 3/2008 | | |
| WO | WO 2008025821 A1 * | 3/2008 | ........... | C07D 471/04 |
| WO | 2009010530 A1 | 1/2009 | | |
| WO | 2009024824 A1 | 2/2009 | | |
| WO | 2009027283 A1 | 3/2009 | | |
| WO | WO 2009027283 A1 * | 3/2009 | ........... | C07D 471/04 |
| WO | 2009047514 A1 | 4/2009 | | |
| WO | 2009068482 A1 | 6/2009 | | |
| WO | 2010092015 A1 | 8/2010 | | |
| WO | 2010092041 A1 | 8/2010 | | |
| WO | WO 2010092041 A1 * | 8/2010 | ........... | C07D 471/04 |
| WO | 2011026579 A1 | 3/2011 | | |
| WO | 2011063907 A1 | 6/2011 | | |
| WO | 2011063908 A1 | 6/2011 | | |
| WO | 2011064328 A1 | 6/2011 | | |
| WO | 2011086098 A1 | 7/2011 | | |
| WO | 2011086099 A1 | 7/2011 | | |
| WO | 2011092272 A1 | 8/2011 | | |
| WO | 2010124826 A1 | 11/2011 | | |

OTHER PUBLICATIONS

Colombo et al (Cancer Research vol. 70, pp. 10255-10264. Published 2010).*
Cancer Research vol. 70 pp. 10255-10264, published 2010.*
Abrieu, et al., "Mps1 Is a Kinetochore-Associated Kinase Essential for the Vertebrate Mitotic Checkpoint," Cell, Jul. 13, 2001, 106:83-93.
Berge et al., "Pharmaceutical Salts," Journal of Pharmaceutical Sciences, Jan. 1977, 66(1):1-19.
Dorer et al., "A Small-Molecule Inhibitor of Mps1 Blocks the Spindle-Checkpoint Responseto a Lack of Tension on Mitotic Chromosomes," Current Biology, Jun. 7, 2005, 15:1070-1076.
East et al., "DNA gyrase (GyrB)/topoisomerase IV (ParE) inhibitors: Synthesis and antibacterial activity," Bioorganic & Med. Chem. Letters, 2009, 19:894-899.
Fowler et al., "Selective Reduction of Radiotracer Trapping by Deuterium Substitution: Comparison of Carbon-I I-L-Deprenyl and Carbon-11-Deprenyl-D2 for MAO B Mapping," The Journal of Nuclear Medicine, 36(7):1255-1262.
Jelluma et al., "Chromosomal Instability by Inefficient Mps1 Auto-Activation Due to a Weakened Mitotic Checkpoint and Lagging Chromosomes," PloS ONE, Jun. 2008, 3:1-8.
Jones et al., "Chemical Genetics Reveals a Role for Mps1 Kinase in Kinetochore Attachment during Mitosis," Current Biology, Jan. 26, 2005, 15:160-165.
King, R., "When 2+2=5: The origins and fates of aneuploid and tetraploid cells," Biochimica et Biophysica Acta, 2008, 1786:4-14.
Kops et al., "On the Road to Cancer: Aneuploidy and the Mitotic-checkpoint," Nature Reviews/ Cancer, Oct. 2005, 5:773-785.
Musacchio et al., "The spindle-assembly checkpoint in space and time," Nature Reviews/Molecular Cell Biology, May 2007, 8:379-393.
Schmidt, et al., "Mitotic drug targets and the development of novel anti-mitotic anticancer drugs," Drug Resistance Updates, 2007, 10:162-181.
Schmidt et al., "Ablation of the spindle assembly checkpoint by a compound targeting Mps1," EMBO Reports, 2005, 6(9):866-872.
Schmidt et al., "Exploiting the Compromised Spindle Assembly Checkpoint Functionof Tumor Cells," Cell Cycle, Jan. 2006, 5(2):159-163.
Suijkerbuijk et al., "Preventing aneuploidy: The contribution of mitotic checkpoint proteins," Biochimica et Biophysica Acta, 2008, 1786:24-31.
Weaver et al., "Aneuploidy: Instigator and Inhibitor of Tumorigenesis," Cancer Research, 2007, 67(21):10103-10105.
Yuan et al., "Increased Expression of Mitotic Checkpoint Genes in Breast Cancer Cells with Chromosomal Instability," Clinical Cancer Research, Jan. 15, 2006, 12(2):405-410.
Chemical Abstract XP-002574925.
Chemical Abstract XP-002574926.
Chemical Abstract XP-002574927.
Chemical Abstract XP-002574929.
Chemical Abstract XP-002574930.
Chemical Abstract XP-002574931.
Chemical Abstract XP-002574932.
Chemical Abstract XP-002574933.
Chemical Abstract XP-002574934.
Chemical Abstract XP-002574935.
Related copending U.S. Appl. No. 13/512,701, filed Sep. 14, 2012.
Related copending U.S. Appl. No. 13/512,721, filed Aug. 13, 2012.
Related copending U.S. Appl. No. 14/113,017, filed Jan. 6, 2014.
Related copending U.S. Appl. No. 14/362,836, filed Jun. 4, 2014.
SoftFocus Library SFK 39, BioFocus DPI, publicly available Sep 20, 2005.

* cited by examiner

SUBSTITUTED TRIAZOLOPYRIDINES

The present invention relates to substituted triazolopyridine compounds of general formula (I) as described and defined herein, to methods of preparing said compounds, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

BACKGROUND OF THE INVENTION

The present invention relates to chemical compounds that inhibit Mps-1 (Monopolar Spindle 1) kinase (also known as Tyrosine Threonine Kinase, TTK). Mps-1 is a dual specificity Ser/Thr kinase which plays a key role in the activation of the mitotic checkpoint (also known as spindle checkpoint, spindle assembly checkpoint) thereby ensuring proper chromosome segregation during mitosis [Abrieu A et al., Cell, 2001, 106, 83-93]. Every dividing cell has to ensure equal separation of the replicated chromosomes into the two daughter cells. Upon entry into mitosis, chromosomes are attached at their kinetochores to the microtubules of the spindle apparatus. The mitotic checkpoint is a surveillance mechanism that is active as long as unattached kinetochores are present and prevents mitotic cells from entering anaphase and thereby completing cell division with unattached chromosomes [Suijkerbuijk S J and Kops G J, Biochemica et Biophysica Acta, 2008, 1786, 24-31; Musacchio A and Salmon E D, Nat Rev Mol Cell Biol., 2007, 8, 379-93]. Once all kinetochores are attached in a correct amphitelic, i.e. bipolar, fashion with the mitotic spindle, the checkpoint is satisfied and the cell enters anaphase and proceeds through mitosis. The mitotic checkpoint consists of complex network of a number of essential proteins, including members of the MAD (mitotic arrest deficient, MAD 1-3) and Bub (Budding uninhibited by benzimidazole, Bub 1-3) families, the motor protein CENP-E, Mps-1 kinase as well as other components, many of these being over-expressed in proliferating cells (e.g. cancer cells) and tissues [Yuan B et al., Clinical Cancer Research, 2006, 12, 405-10]. The essential role of Mps-1 kinase activity in mitotic checkpoint signalling has been shown by shRNA-silencing, chemical genetics as well as chemical inhibitors of Mps-1 kinase [Jelluma N et al., PLos ONE, 2008, 3, e2415; Jones M H et al., Current Biology, 2005, 15, 160-65; Dorer R K et al., Current Biology, 2005, 15, 1070-76; Schmidt M et al., EMBO Reports, 2005, 6, 866-72].

There is ample evidence linking reduced but incomplete mitotic checkpoint function with aneuploidy and tumorigenesis [Weaver B A and Cleveland D W, Cancer Research, 2007, 67, 10103-5; King R W, Biochimica et Biophysica Acta, 2008, 1786, 4-14]. In contrast, complete inhibition of the mitotic checkpoint has been recognised to result in severe chromosome missegregation and induction of apoptosis in tumour cells [Kops G J et al., Nature Reviews Cancer, 2005, 5, 773-85; Schmidt M and Medema R H, Cell Cycle, 2006, 5, 159-63; Schmidt M and Bastians H, Drug Resistance Updates, 2007, 10, 162-81]. Therefore, mitotic checkpoint abrogation through pharmacological inhibition of Mps-1 kinase or other components of the mitotic checkpoint represents a new approach for the treatment of proliferative disorders including solid tumours such as carcinomas and sarcomas and leukaemias and lymphoid malignancies or other disorders associated with uncontrolled cellular proliferation.

Different compounds have been disclosed in prior art which show an inhibitory effect on Mps-1 kinase:

WO 2009/024824 A1 discloses 2-Anilinopurin-8-ones as inhibitors of Mps-1 for the treatment of proliferate disorders. WO 2010/124826 A1 discloses substituted imidazoquinoxaline compounds as inhibitors of Mps-1 kinase or TTK. WO 2011/026579 A1 discloses substituted aminoquinoxalines as Mps-1 inhibitors.

Substituted triazolopyridine compounds have been disclosed for the treatment or prophylaxis of different diseases:

WO 2008/025821 A1 (Cellzome (UK) Ltd) relates to triazole derivatives as kinase inhibitors, especially inhibitors of ITK or PI3K, for the treatment or prophylaxis of immunological, inflammatory or allergic disorders. Said triazole derivatives are exemplified as possessing an amide, urea or aliphatic amine substituent in position 2.

WO 2009/047514 A1 (Cancer Research Technology Limited) relates to [,2]-triazolo-[1,5-a]-pyridine and [,2]-triazolo-[1,5-c]-pyrimidine compounds which inhibit AXL receptor tyrosine kinase function, and to the treatment of diseases and conditions that are mediated by AXL receptor tyrosine kinase, that are ameliorated by the inhibition of AXL receptor tyrosine kinase function etc., including proliferative conditions such as cancer, etc. Said compounds are exemplified as possessing a substituent in the 5-position of said compounds and a substituent in the 2-position.

WO 2009/010530 A1 discloses bicyclic heteroaryl compounds and their use as phosphatidylinositol (PI) 3-kinase. Among other compounds also substituted triazolopyridines are mentioned.

WO 2009/027283 A1 discloses triazolopyridine compounds and their use as ASK (apoptosis signal-regulating kinase) inhibitors for the treatment of autoimmune diseases and neurodegenerative diseases.

WO 2010/092041 A1 (Fovea Pharmaceuticals SA) relates to [,2]-triazolo-[1,5-a]-pyridines, which are useful as selective kinase inhibitors, to methods for producing such compounds and methods for treating or ameliorating kinase-mediated disorder.

However, the state of the art described above does not describe the substituted triazolopyridine compounds of general formula (I) of the present invention, or a stereoisomer, a tautomer, an N-oxide, a hydrate, a solvate, or a salt thereof, or a mixture of same, as described and defined herein, and as hereinafter referred to as "compounds of the present invention", or their pharmacological activity. It has now been found, and this constitutes the basis of the present invention, that said compounds of the present invention have surprising and advantageous properties.

In particular, said compounds of the present invention have surprisingly been found to effectively inhibit Mps-1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1 kinase, such as, for example, haemotological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

SUMMARY OF THE INVENTION

The present invention covers compounds of general formula (I):

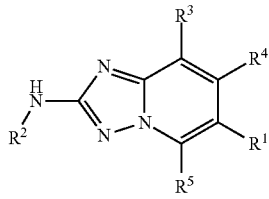

(I)

in which:
R$^1$ represents an aryl or a heteroaryl group
which is substituted, one or more times, identically or differently, with a substituent selected from:
R$^6$—(C$_1$-C$_6$-alkyl)-, R$^6$—(CH$_2$)$_n$(CHOH)(CH$_2$)$_m$—, R$^6$—(C$_1$-C$_6$-alkoxy)-, R$^6$—(CH$_2$)$_n$(CHOH)(CH$_2$)$_p$—O—, R$^6$—(C$_1$-C$_6$-alkoxy-C$_1$-C$_6$-alkyl)-, R$^6$—(C$_1$-C$_6$-alkoxy-C$_1$-C$_6$-alkyl)-O—, R$^6$—O—, —C(=O)R$^6$, —C(=O)O—R$^6$, —OC(=O)—R$^6$, —N(H)C(=O)R$^6$, —N(R$^7$)C(=O)R$^6$, —N(H)C(=O)NR$^6$R$^7$, —N(R$^7$)C(=O)NR$^6$R$^7$, —NR$^6$R$^7$, —C(=O)N(H)R$^6$, —C(=O)NR$^6$R$^7$, R$^6$—S—, R$^6$—S(=O)—, R$^6$—S(=O)$_2$—, —N(H)S(=O)R$^6$, —N(R$^7$)S(=O)R$^6$, —S(=O)N(H)R$^6$, —S(=O)NR$^6$R$^7$, —N(H)S(=O)$_2$R$^6$, —N(R$^7$)S(=O)$_2$R$^6$, —S(=O)$_2$N(H)R$^6$, —S(=O)$_2$ NR$^6$R$^7$, —S(=O)(=NR$^6$)R$^7$, —S(=O)(=NR$^7$)R$^6$, —N=S(=O)(R$^6$)R$^7$;

and which is optionally substituted, one or more times, identically or differently, with a substituent R$^{xy}$ selected from:
halo-, hydroxyl-, cyano-, nitro-, C$_1$-C$_6$-alkyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, R$^8$—(C$_1$-C$_6$-alkyl)-, R$^8$—(CH$_2$)$_n$(CHOH)(CH$_2$)$_m$—, R$^8$—(C$_1$-C$_6$-alkoxy)-, R$^8$—(CH$_2$)$_n$(CHOH)(CH$_2$)$_p$—O—, R$^8$—(C$_1$-C$_6$-alkoxy-C$_1$-C$_6$-alkyl)-, R$^8$—(C$_1$-C$_6$-alkoxy-C$_1$-C$_6$-alkyl)-O—, R$^8$—O—, —C(=O)R$^8$, —C(=O)O—R$^8$, —OC(=O)—R$^8$, —N(H)C(=O)R$^8$, —N(R$^7$)C(=O)R$^8$, —N(H)C(=O)NR$^8$R$^7$, —N(R$^7$)C(=O)NR$^8$R$^7$, —NR$^8$R$^7$, —C(=O)N(H)R$^8$, —C(=O)NR$^8$R$^7$, R$^8$—S—, R$^8$—S(=O)—, R$^8$—S(=O)$_2$—, —N(H)S(=O)R$^8$, —N(R$^7$)S(=O)R$^8$, —S(=O)N(H)R$^8$, —S(=O)NR$^8$R$^7$, —N(H)S(=O)$_2$R$^8$, —N(R$^7$)S(=O)$_2$R$^8$, —S(=O)$_2$N(H)R$^8$, —S(=O)$_2$NR$^8$R$^7$, —S(=O)(=NR$^8$)R$^7$, —S(=O)(=NR$^7$)R$^8$, —N=S(=O)(R$^8$)R$^7$;

R$^2$ represents an aryl group or a heteroaryl group
which is substituted, one or more times, identically or differently, with a substituent selected from:
R$^9$—, R$^9$—(C$_1$-C$_6$-alkyl)-, R$^9$—(CH$_2$)$_n$(CHOH)(CH$_2$)$_m$—, R$^9$—(C$_1$-C$_6$-alkoxy)-, R$^9$—(CH$_2$)$_n$(CHOH)(CH$_2$)$_p$—O—, R$^9$—(C$_1$-C$_6$-alkoxy-C$_1$-C$_6$-alkyl)-, R$^9$—(C$_1$-C$_6$-alkoxy-C$_1$-C$_6$-alkyl)-O—, —O—(CH$_2$)$_n$—C(=O)NR$^9$R$^7$, R$^9$—O—, —C(=O)R$^9$, —C(=O)O—R$^9$, —OC(=O)—R$^9$, —N(H)C(=O)R$^9$, —N(R$^7$)C(=O)R$^9$, —N(H)C(=O)NR$^9$R$^7$, —N(R$^7$)C(=O)NR$^9$R$^7$, —NR$^9$R$^7$, —C(=O)N(H)R$^9$, —C(=O)NR$^9$R$^7$, R$^9$—S—, R$^9$—S(=O)—, R$^9$—S(=O)$_2$—, —N(H)S(=O)R$^9$, —N(R$^7$)S(=O)R$^9$, —S(=O)N(H)R$^9$, —S(=O)NR$^9$R$^7$, —N(H)S(=O)$_2$R$^9$, —N(R$^7$)S(=O)$_2$R$^9$, —S(=O)$_2$N(H)R$^9$, —S(=O)$_2$ NR$^9$R$^7$, —S(=O)(=NR$^9$)R$^7$, —S(=O)(=NR$^7$)R$^9$, —N=S(=O)(R$^9$)R$^7$;

and which is optionally substituted, one or more times, identically or differently, with a substituent selected from:
halo-, hydroxyl-, cyano-, nitro-, C$_1$-C$_6$-alkyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, R$^8$—(C$_1$-C$_6$-alkyl)-, R$^8$—(CH$_2$)$_n$(CHOH)(CH$_2$)$_m$—, R$^8$—(C$_1$-C$_6$-alkoxy)-, R$^8$—(CH$_2$)$_n$(CHOH)(CH$_2$)$_p$—O—, R$^8$—(C$_1$-C$_6$-alkoxy-C$_1$-C$_6$-alkyl)-, R$^8$—(C$_1$-C$_6$-alkoxy-C$_1$-C$_6$-alkyl)-O—, —O—(CH$_2$)$_n$—C(=O)NR$^8$R$^7$, R$^8$—O—, —C(=O)R$^8$, —C(=O)O—R$^8$, —OC(=O)—R$^8$, —N(H)C(=O)R$^8$, —N(R$^7$)C(=O)R$^8$, —N(H)C(=O)NR$^8$R$^7$, —N(R$^7$)C(=O)NR$^8$R$^7$, —NR$^8$R$^7$, —C(=O)N(H)R$^8$, —C(=O)NR$^8$R$^7$, R$^8$—S—, R$^8$—S(=O)—, R$^8$—S(=O)$_2$—, —N(H)S(=O)R$^8$, —N(R$^7$)S(=O)R$^8$, —S(=O)N(H)R$^8$, —S(=O)NR$^8$R$^7$, —N(H)S(=O)$_2$R$^8$, —N(R$^7$)S(=O)$_2$R$^8$, —S(=O)$_2$N(H)R$^8$, —S(=O)$_2$NR$^8$R$^7$, —S(=O)(=NR$^8$)R$^7$, —S(=O)(=NR$^7$)R$^8$, —N=S(=O)(R$^8$)R$^7$;

R$^3$ represents a hydrogen atom, a halogen atom, a hydroxy-, amino-, cyano-, nitro-, C$_1$-C$_4$-alkyl-, halo-C$_1$-C$_4$-alkyl-, C$_1$-C$_4$-alkoxy-, halo-C$_1$-C$_4$-alkoxy-, hydroxy-C$_1$-C$_4$-alkyl-, C$_1$-C$_4$-alkoxy-C$_1$-C$_4$-alkyl-, halo-C$_1$-C$_4$-alkoxy-C$_1$-C$_4$-alkyl-, C$_2$-C$_6$-alkenyl-, C$_2$-C$_6$-alkynyl-, halo-C$_2$-C$_6$-alkenyl-, halo-C$_2$-C$_6$-alkynyl-, C$_3$-C$_6$-cycloalkyl-, or halo-C$_3$-C$_6$-cycloalkyl-group;

R$^4$ represents a hydrogen atom, a halogen atom, a hydroxy-, amino-, cyano-, nitro-, C$_1$-C$_4$-alkyl-, halo-C$_1$-C$_4$-alkyl-, C$_1$-C$_4$-alkoxy-, halo-C$_1$-C$_4$-alkoxy-, hydroxy-C$_1$-C$_4$-alkyl-, C$_1$-C$_4$-alkoxy-C$_1$-C$_4$-alkyl-, halo-C$_1$-C$_4$-alkoxy-C$_1$-C$_4$-alkyl-, C$_2$-C$_6$-alkenyl-, C$_2$-C$_6$-alkynyl-, halo-C$_2$-C$_6$-alkenyl-, halo-C$_2$-C$_6$-alkynyl-, C$_3$-C$_6$-cycloalkyl-, or halo-C$_3$-C$_6$-cycloalkyl-group;

R$^5$ represents a hydrogen atom;

R$^6$ represents a group selected from:
C$_3$-C$_6$-cycloalkyl-, 3- to 10-membered heterocycloalkyl-, aryl-, heteroaryl-, —(CH$_2$)$_q$—(C$_3$-C$_6$-cycloalkyl), —(CH$_2$)$_q$-heteroaryl, —(CH$_2$)$_q$-(3- to 10-membered heterocycloalkyl), —(CH$_2$)$_q$-aryl; said group being optionally substituted, one or more times, identically or differently, with a substituent selected from:
halo-, hydroxyl-, cyano-, nitro-, C$_1$-C$_6$-alkyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, R$^8$—(C$_1$-C$_6$-alkyl)-, R$^8$—(CH$_2$)$_n$(CHOH)(CH$_2$)$_m$—, R$^8$—(C$_1$-C$_6$-alkoxy)-, R$^8$—(CH$_2$)$_n$(CHOH)(CH$_2$)$_p$—O—, R$^8$—(C$_1$-C$_6$-alkoxy-C$_1$-C$_6$-alkyl)-, R$^8$—(C$_1$-C$_6$-alkoxy-C$_1$-C$_6$-alkyl)-O—, aryl-, R$^8$—O—, —C(=O)R$^8$, —C(=O)O—R$^8$, —OC(=O)—R$^8$, —N(H)C(=O)R$^8$, —N(R$^7$)C(=O)R$^8$, —N(H)C(=O)NR$^8$R$^7$, —N(R$^7$)C(=O)NR$^8$R$^7$, —NR$^8$R$^7$, —C(=O)N(H)R$^8$, —C(=O)NR$^8$R$^7$, R$^8$—S—, R$^8$—S(=O)—, R$^8$—S(=O)$_2$—, —N(H)S(=O)R$^8$, —N(R$^7$)S(=O)R$^8$, —S(=O)N(H)R$^8$, —S(=O)NR$^8$R$^7$, —N(H)S(=O)$_2$R$^8$, —N(R$^7$)S $-S(=O)_2R^8$, $-S(=O)_2N(H)R^8$, $-S(=O)_2NR^8R^7$, $-S(=O)(=NR^8)R^7$, $-S(=O)(=NR^7)R^8$, $-N=S(=O)(R^8)R^7$;

R$^7$ represents a hydrogen atom, a $C_1$-$C_6$-alkyl-, or $C_3$-$C_6$-cycloalkyl-group;

or

R$^6$ and R$^7$,
  together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-;

R$^8$ represents a hydrogen atom, a $C_1$-$C_6$-alkyl- or $C_3$-$C_6$-cycloalkyl-group;

R$^9$ represents a group selected from:
  $C_7$-$C_{10}$-cycloalkyl-, 3- to 10-membered heterocycloalkyl-, aryl-, heteroaryl-;
  said group being optionally substituted, one or more times, identically or differently, with a substituent selected from:
    halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $-(CH_2)_q-(C_3$-$C_6$-cycloalkyl), $R^8-(CH_2)_n(CHOH)(CH_2)_m-$, $R^8-(C_1$-$C_6$-alkoxy)-, $R^8-(CH_2)_n(CHOH)(CH_2)_p-O-$, $R^8-(C_1$-$C_6$-alkoxy-$C_1$-$C_6$-alkyl)-, $R^8-(C_1$-$C_6$-alkoxy-$C_1$-$C_6$-alkyl)-O-$, aryl-, $R^8-O-$, $-C(=O)R^8$, $-C(=O)O-R^8$, $-OC(=O)-R^8$, $-N(H)C(=O)R^8$, $-N(R^7)C(=O)R^8$, $-N(H)C(=O)NR^8R^7$, $-N(R^7)C(=O)NR^8R^7$, $-NR^8R^7$, $-C(=O)N(H)R^8$, $-C(=O)NR^8R^7$, $R^8-S-$, $R^8-S(=O)-$, $R^8-S(=O)_2-$, $-N(H)S(=O)R^8$, $-N(R^7)S(=O)R^8$, $-S(=O)N(H)R^8$, $-S(=O)NR^8R^7$, $-N(H)S(=O)_2R^8$, $-N(R^7)S(=O)_2R^8$, $-S(=O)_2N(H)R^8$, $-S(=O)_2NR^8R^7$, $-S(=O)(=NR^8)R^7$, $-S(=O)(=NR^7)R^8$, $-N=S(=O)(R^8)R^7$;

or

R$^9$ and R$^7$,
  together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $-C(=O)O-R^8$ or $C_3$-$C_6$-cycloalkyl-;

n, m, p
  represent, independently from each other, an integer of 0, 1, 2, 3, 4, or 5;
and
q represents an integer of 0, 1, 2 or 3;
or a stereoisomer, a tautomer, an N-oxide, a hydrate, a solvate, or a salt thereof, or a mixture of same.

The present invention further relates to methods of preparing compounds of general formula (I), to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom" or "halo-" is to be understood as meaning a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, $-CF_3$, $-CHF_2$, $-CH_2F$, $-CF_2CF_3$, or $CH_2CF_3$.

The term "$C_1$-$C_6$-alkoxy" is to be understood as preferably meaning a linear or branched, saturated, monovalent, hydrocarbon group of formula $-O-(C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is/are replaced, in identically or differently, by a halogen atom/by halogen atoms. Particularly, said halogen atom is F. Said halo-$C_1$-$C_6$-alkoxy group is, for example, $-OCF_3$, $-OCHF_2$, $-OCH_2F$, $-OCF_2CF_3$, or $-OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is/are replaced, in identically or differently, by a halogen atom/by halogen atoms. Particularly, said halogen atom is F. Said halo-$C_1$-$C_6$-alkoxy-$C_1$-$C_6$-alkyl group is, for example, $-CH_2CH_2OCF_3$, $-CH_2CH_2OCHF_2$, $-CH_2CH_2OCH_2F$, $-CH_2CH_2OCF_2CF_3$, or $-CH_2CH_2OCH_2CF_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl) ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-inyl, hex-3-inyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-inyl, 1,1-dimethylbut-3-ynyl, 1,1-dimethylbut-2-ynyl, or 3,3-dimethyl-but-1-ynyl group. Particularly, said alkynyl group is ethynyl, prop-1-ynyl, or prop-2-inyl.

The term "$C_3$-$C_6$-cycloalkyl" is to be understood as preferably meaning a saturated, monovalent, mono-, or bicyclic hydrocarbon ring which contains 3, 4, 5 or 6 carbon atoms. Said $C_3$-$C_6$-cycloalkyl group is for example, a monocyclic hydrocarbon ring, e.g. a cyclopropyl, cyclobutyl, cyclopentyl, or cyclohexyl or a bicyclic hydrocarbon ring. Said cycloalkyl ring can optionally contain one or more double bonds, e.g. cycloalkenyl, such as a cyclopropenyl, cyclobutenyl, cyclopentenyl or cyclohexenyl group, wherein the bond between said ring with the rest of the molecule may be to any carbon atom of said ring, be it saturated or unsaturated.

The term "heterocyclic ring", as used in the term "4-, 5-, 6-, 7-, 8-, 9- or 10-membered heterocyclic ring", or "4- to 6-membered heterocyclic ring" or "5- to 6-membered heterocyclic ring", for example, as used in the definition of compounds of general formula (I) as defined herein, is to be understood as meaning a saturated or partially unsaturated, mono-, bi- or poly-cyclic nitrogen atom-containing ring, said nitrogen atom being the point of attachment of said heterocyclic ring with the rest of the molecule. Said nitrogen atom-containing ring optionally further contains 1 or 2 heteroatom-containing groups selected from O, C(=O), S, S(=O), S(=O)$_2$, NR', wherein R' is $C_1$-$C_6$-alkyl. Particularly, without being limited thereto, said nitrogen atom-containing ring can be a 4-membered ring, such as an azetidinyl ring, for example, or a 5-membered ring, such as a pyrrolidinyl ring, for example, or a 6-membered ring, such as a piperidinyl, piperazinyl, morpholinyl, or thiomorpholinyl ring, for example, or a 7-membered ring, such as a diazepanyl ring ring, for example, or an 8-, 9-, or 10-membered ring, such as a cycloheptylaminyl, cyclooctylaminyl, or cyclononylaminyl ring, respectively, for example; it being reiterated that any of the above-mentioned nitrogen atom-containing rings can further contain 1 or 2 heteroatom-containing groups selected from O, C(=O), S, S(=O), S(=O)$_2$, NR', wherein R' is $C_1$-$C_6$-alkyl. As mentioned supra, said nitrogen atom-containing ring can be bicyclic, such as, without being limited thereto, a 5,5-membered ring, e.g. a hexahydrocyclopenta[c]pyrrol-2(1H)-yl) ring, or a 5,6-membered bicyclic ring, e.g. a hexahydropyrrolo[1,2-a]pyrazin-2(1H)-yl ring, or for example. As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term "3- to 10-membered heterocycloalkyl" is to be understood as preferably meaning a saturated or partially unsaturated, monovalent, mono- or bicyclic hydrocarbon ring which contains 2, 3, 4, 5, 6, 7, 8, or 9 carbon atoms, and one or more heteroatom-containing groups selected from C(=O), O, S, S(=O), S(=O)$_2$, NH, NR", wherein R" represents a $C_1$-$C_6$-alkyl, $C_3$-$C_6$-cycloalkyl, —C(=O)—($C_1$-$C_6$-alkyl) or —C(=O)—($C_1$-$C_6$-cycloalkyl). Particularly, said ring can contain 2, 3, 4, or 5 carbon atoms, and one or more of the above-mentioned heteroatom-containing groups (a "3- to 6-membered heterocycloalkyl"), more particularly said ring can contain 4 or 5 carbon atoms, and one or more of the above-mentioned heteroatom-containing groups (a "5- to 6-membered heterocycloalkyl"). Said heterocycloalkyl ring is for example, a monocyclic heterocycloalkyl ring such as an oxyranyl, oxetanyl, aziridinyl, azetidinyl, tetrahydrofuranyl, pyrrolidinyl, imidazolidinyl, pyrazolidinyl, pyrrolinyl, tetrahydropyranyl, piperidinyl, morpholinyl, dithianyl, thiomorpholinyl, piperazinyl, trithianyl, or chinuclidinyl group. Optionally, said heterocycloalkyl ring can contain one or more double bonds, e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydro-1,3-oxazolyl, 4,4-dimethyl-4,5-dihydro-1,3-oxazolyl, or 4H-[1,4]thiazinyl group, or, it may be benzo fused.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group, or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group.

The term "heteroaryl" is understood as preferably meaning a monovalent, aromatic, mono- or bicyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and can be monocyclic, bicyclic, or tricyclic, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc. More particularly, heteroaryl is selected from pyridyl, benzofuranyl, benzisoxazolyl, indazolyl, quinazolinyl, thienyl, quinolinyl, benzothienyl, pyrazolyl, or furanyl.

The term "alkylene" is understood as preferably meaning an optionally substituted hydrocarbon chain (or "tether") having 1, 2, 3, 4, 5, or 6 carbon atoms, i.e. an optionally substituted —$CH_2$— ("methylene" or "single membered tether" or, for example —$C(Me)_2$-), —$CH_2$—$CH_2$— ("ethylene", "dimethylene", or "two-membered tether"), —$CH_2$—$CH_2$—$CH_2$— ("propylene", "trimethylene", or "three-membered tether"), —$CH_2$—$CH_2$—$CH_2$—$CH_2$— ("butylene", "tetramethylene", or "four-membered tether"), —$CH_2$—$CH_2$—$CH_2$—$CH_2$—$CH_2$— ("pentylene", "pentamethylene" or "five-membered ether"), or —$CH_2$—$CH_2$—$CH_2$—$CH_2$—$CH_2$—$CH_2$-("hexylene", "hexamethylene", or "six-membered tether") group. Particularly, said alkylene tether has 1, 2, 3, 4, or 5 carbon atoms, more particularly 1 or 2 carbon atoms.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

Further, as used herein, the term "$C_7$-$C_{10}$", as used throughout this text, e.g. in the context of the definition of "$C_7$-$C_{10}$-cycloalkyl", is to be understood as meaning a cycloalkyl group having a finite number of carbon atoms of 7 to 10, i.e. 7, 8, 9, or 10 carbon atoms. It is to be understood further that said term "$C_7$-$C_{10}$" is to be interpreted as any sub-range comprised therein, e.g. $C_7$-$C_{10}$, $C_8$-$C_9$, $C_7$-$C_9$, $C_7$-$C_8$, $C_8$-$C_{10}$, $C_9$-$C_{10}$; particularly $C_7$-$C_{10}$.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

Where the plural form of the word compounds, salts, polymorphs, hydrates, solvates and the like, is used herein, this is taken to mean also a single compound, salt, polymorph, isomer, hydrate, solvate or the like.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, viz.:

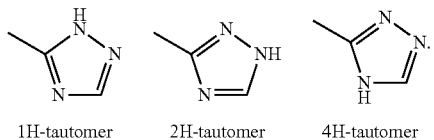

1H-tautomer    2H-tautomer    4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta-etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66: 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers compounds of general formula (I):

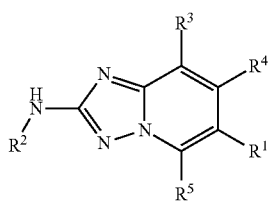

(I)

in which:
$R^1$ represents an aryl or a heteroaryl group
which is substituted, one or more times, identically or differently, with a substituent selected from:
$R^6$—($C_1$-$C_6$-alkyl)-, $R^6$—$(CH_2)_n(CHOH)(CH_2)_m$—, $R^6$—($C_1$-$C_6$-alkoxy)-, $R^6$—$(CH_2)_n(CHOH)(CH_2)_p$—O—, $R^6$—($C_1$-$C_6$-alkoxy-$C_1$-$C_6$-alkyl)-, $R^6$—($C_1$-$C_6$-alkoxy-$C_1$-$C_6$-alkyl)-O—, $R^6$—O—, —C(=O)$R^6$, —C(=O)O—$R^6$, —OC(=O)—$R^6$, —N(H)C(=O)$R^6$, —N($R^7$)C(=O)$R^6$, —N(H)C(=O)N$R^6R^7$, —N($R^7$)C(=O)N$R^6R^7$, —N$R^6R^7$, —C(=O)N(H)$R^6$, —C(=O)N$R^6R^7$, $R^6$—S—, $R^6$—S(=O)—, $R^6$—S(=O)$_2$—, —N(H)S(=O)$R^6$, —N($R^7$)S(=O)$R^6$, —S(=O)N(H)$R^6$, —S(=O)N$R^6R^7$, —N(H)S(=O)$_2R^6$, —N($R^7$)S(=O)$_2R^6$, —S(=O)$_2$N(H)$R^6$, —S(=O)$_2$ N$R^6R^7$, —S(=O)(=N$R^6$)$R^7$, —S(=O)(=N$R^7$)$R^6$, —N=S(=O)($R^6$)$R^7$;
and
which is optionally substituted, one or more times, identically or differently, with a substituent $R^{xy}$ selected from:
halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$;

$R^2$ represents an aryl group or heteroaryl group
which is substituted, one or more times, identically or differently, with a substituent selected from:
$R^9$—, $R^9$—($C_1$-$C_6$-alkyl)-, $R^9$—$(CH_2)_n(CHOH)(CH_2)_m$—, $R^9$—($C_1$-$C_6$-alkoxy)-, $R^9$—$(CH_2)_n(CHOH)(CH_2)_p$—O—, $R^9$—($C_1$-$C_6$-alkoxy-$C_1$-$C_6$-alkyl)-, $R^9$—($C_1$-$C_6$-alkoxy-$C_1$-$C_6$-alkyl)-O—, —O—$(CH_2)_n$—C(=O)N$R^9R^7$, $R^9$—O—, —C(=O)$R^9$, —C(=O)O—$R^9$, —OC(=O)—$R^9$, —N(H)C(=O)$R^9$, —N($R^7$)C(=O)$R^9$, —N(H)C(=O)N$R^9R^7$, —N($R^7$)C(=O)N$R^9R^7$, —N$R^9R^7$, —C(=O)N(H)$R^9$, —C(=O)N$R^9R^7$, $R^9$—S—, $R^9$—S(=O)—, $R^9$—S(=O)$_2$—, —N(H)S(=O)$R^9$, —N($R^7$)S(=O)$R^9$, —S(=O)N(H)$R^9$, —S(=O)N$R^9R^7$, —N(H)S(=O)$_2R^9$, —N($R^7$)S(=O)$_2R^9$, —S(=O)$_2$N(H)$R^9$, —S(=O)$_2$ N$R^9R^7$, —S(=O)(=N$R^9$)$R^7$, —S(=O)(=N$R^7$)$R^9$, —N=S(=O)($R^9$)$R^7$;
and
which is optionally substituted, one or more times, identically or differently, with a substituent selected from:
halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, —O—$(CH_2)_n$—C(=O)N$R^8R^7$, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$;

$R^3$ represents a hydrogen atom, a halogen atom, a hydroxy-, amino-, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl-, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or halo-$C_3$-$C_6$-cycloalkyl-group;

$R^4$ represents a hydrogen atom, a halogen atom, a hydroxy-, amino-, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl-, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or halo-$C_3$-$C_6$-cycloalkyl-group;

$R^5$ represents a hydrogen atom;

$R^6$ represents a group selected from:
  $C_3$-$C_6$-cycloalkyl-, 3- to 10-membered heterocycloalkyl-, aryl-, heteroaryl-, —$(CH_2)_q$—($C_3$-$C_6$-cycloalkyl), —$(CH_2)_q$-(3- to 10-membered heterocycloalkyl), —$(CH_2)_q$-aryl, or —$(CH_2)_q$-heteroaryl;
  said group being optionally substituted, one or more times, identically or differently, with a substituent selected from:
  halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$;

$R^7$ represents a hydrogen atom, a $C_1$-$C_6$-alkyl-, or $C_3$-$C_6$-cycloalkyl-group;
or
$R^6$ and $R^7$,
  together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-;

$R^8$ represents a hydrogen atom, a $C_1$-$C_6$-alkyl- or $C_3$-$C_6$-cycloalkyl-group;

$R^9$ represents a group selected from:
  $C_7$-$C_{10}$-cycloalkyl-, 3- to 10-membered heterocycloalkyl-, aryl-, heteroaryl-;
  said group being optionally substituted, one or more times, identically or differently, with a substituent selected from:
  halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —$(CH_2)_q$—($C_3$-$C_6$-cycloalkyl), $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$;

or
$R^9$ and $R^7$,
  together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, —C(=O)O—$R^8$ or $C_3$-$C_6$-cycloalkyl-;

n, m, p
represent, independently from each other, an integer of 0, 1, 2, 3, 4, or 5;
and
q represents an integer of 0, 1, 2 or 3.

$R^1$ is a substituted aryl or a substituted heteroaryl group. Preferably, $R^1$ is a substituted phenyl or a substituted pyridyl group.

In a preferred embodiment, the invention relates to compounds of formula (I), wherein:
$R^1$ represents an aryl or heteroaryl group
  which is substituted, one or more times, identically or differently, with a substituent selected from:
  $R^6$—$(CH_2)_n(CHOH)(CH_2)_m$—, $R^6$—($C_1$-$C_6$-alkoxy)-, $R^6$—$(CH_2)_n(CHOH)(CH_2)_p$—O—, $R^6$—($C_1$-$C_6$-alkoxy-$C_1$-$C_6$-alkyl)-, $R^6$—($C_1$-$C_6$-alkoxy-$C_1$-$C_6$-alkyl)-O—, $R^6$—O—, —C(=O)$R^6$, —C(=O)O—$R^6$, —OC(=O)—$R^6$, —N(H)C(=O)$R^6$, —N($R^7$)C(=O)$R^6$, —N(H)C(=O)N$R^6R^7$, —N($R^7$)C(=O)N$R^6R^7$, —N$R^6R^7$, —C(=O)N(H)$R^6$, —C(=O)N$R^6R^7$, $R^6$—S—, $R^6$—S(=O)—, $R^6$—S(=O)$_2$—, —N(H)S(=O)$R^6$, —N($R^7$)S(=O)$R^6$, —S(=O)N(H)$R^6$, —S(=O)N$R^6R^7$, —N(H)S(=O)$_2R^6$, —N($R^7$)S(=O)$_2R^6$, —S(=O)$_2$N(H)$R^6$, —S(=O)$_2$N$R^6R^7$, —S(=O)(=N$R^6$)$R^7$, —S(=O)(=N$R^7$)$R^6$, —N=S(=O)($R^6$)$R^7$;
and
which is optionally substituted, one or more times, identically or differently, with a substituent $R^{xy}$ selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —N(H)C(=O)$R^8$, —N($R^7$)C(=O)$R^8$, —C(=O)N(H)$R^8$, —C(=O)N$R^8R^7$.

In another preferred embodiment, the invention relates to compounds of formula (I), wherein:
$R^1$ represents an aryl group
  which is substituted, one or more times, identically or differently, with a substituent selected from:
  $R^6$—$(CH_2)_n(CHOH)(CH_2)_m$—, $R^6$—($C_1$-$C_6$-alkoxy)-, $R^6$—$(CH_2)_n(CHOH)(CH_2)_p$—O—, $R^6$—($C_1$-$C_6$-alkoxy-$C_1$-$C_6$-alkyl)-, $R^6$—($C_1$-$C_6$-alkoxy-$C_1$-$C_6$-alkyl)-O—, $R^6$—O—, —C(=O)$R^6$, —C(=O)O—$R^6$, —OC(=O)—$R^6$, —N(H)C(=O)$R^6$, —N($R^7$)C(=O)$R^6$, —N(H)C(=O)N$R^6R^7$, N($R^7$)C(=O)N$R^6R^7$, —N$R^6R^7$, —C(=O)N(H)$R^6$, —C(=O)N$R^6R^7$, $R^6$—S—, $R^6$—S(=O)—, $R^6$—S(=O)$_2$—, —N(H)S —C(=O)R⁶, —N(R⁷)S(=O)R⁶, —S(=O)N(H)R⁶, —S(=O)NR⁶R⁷, —N(H)S(=O)₂R⁶, —N(R⁷)S(=O)₂R⁶, —S(=O)₂N(H)R⁶, —S(=O)₂NR⁶R⁷, —S(=O)(=NR⁶)R⁷, —S(=O)(=NR⁷)R⁶, —N=S(=O)(R⁶)R⁷;

and which is optionally substituted, one or more times, identically or differently, with a substituent R$^{xy}$ selected from:

halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, R⁸—($C_1$-$C_6$-alkyl)-, R⁸—(CH₂)$_n$(CHOH)(CH₂)$_m$—, R⁸—($C_1$-$C_6$-alkoxy)-, R⁸—(CH₂)$_n$(CHOH)(CH₂)$_p$—O—, R⁸—($C_1$-$C_6$-alkoxy-$C_1$-$C_6$-alkyl)-, R⁸—($C_1$-$C_6$-alkoxy-$C_1$-$C_6$-alkyl)-O—, R⁸—O—, —C(=O)R⁸, —C(=O)O—R⁸, —OC(=O)—R⁸, —N(H)C(=O)R⁸, —N(R⁷)C(=O)R⁸, —N(H)C(=O)NR⁸R⁷, —N(R⁷)C(=O)NR⁸R⁷, —NR⁸R⁷, —C(=O)N(H)R⁸, —C(=O)NR⁸R⁷, R⁸—S—, R⁸—S(=O)—, R⁸—S(=O)₂—, —N(H)S(=O)R⁸, —N(R⁷)S(=O)R⁸, —S(=O)N(H)R⁸, —S(=O)NR⁸R⁷, —N(H)S(=O)₂R⁸, —N(R⁷)S(=O)₂R⁸, —S(=O)₂N(H)R⁸, —S(=O)₂NR⁸R⁷, —S(=O)(=NR⁸)R⁷, —S(=O)(=NR⁷)R⁸, —N=S(=O)(R⁸)R⁷.

In another preferred embodiment, the invention relates to compounds of formula (I), wherein:

R¹ represents an aryl group which is substituted, one or more times, identically or differently, with a substituent selected from:
—C(=O)R⁶, —C(=O)O—R⁶, —OC(=O)—R⁶, —N(H)C(=O)R⁶, —C(=O)N(H)R⁶, —C(=O)NR⁶R⁷, R⁶—S(=O)—, R⁶—S(=O)₂—, —N(H)S(=O)₂R⁶, —S(=O)₂N(H)R⁶, —S(=O)(=NR⁶)R⁷, —S(=O)(=NR⁷)R⁶;

and which is optionally substituted, one or more times, identically or differently, with a substituent R$^{xy}$ selected from:

halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —N(H)C(=O)R⁸, —N(R⁷)C(=O)R⁸, —C(=O)N(H)R⁸, —C(=O)NR⁸R⁷.

Preferably, R¹ represents a substituted phenyl group.

In another preferred embodiment, the invention relates to compounds of formula (I), wherein:

R¹ represents a phenyl group which is substituted, one or more times, identically or differently, with a substituent selected from:
—N(H)C(=O)R⁶, —C(=O)N(H)R⁶;

and which is optionally substituted, one time with a substituent R$^{xy}$ selected from:

halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-.

In another preferred embodiment, the invention relates to compounds of formula (I), wherein:

R¹ represents a phenyl group which is substituted, in para-position to the point of attachment of the phenyl group with the rest of the molecule, with a substituent selected from:
—N(H)C(=O)R⁶, —C(=O)N(H)R⁶;

and which is optionally substituted, one time with a substituent R$^{xy}$ selected from:

halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-.

In another preferred embodiment, the invention relates to compounds of formula (I), wherein:

R¹ represents a phenyl group which is substituted, one or more times, preferably one time, with —N(H)C(=O)R⁶;

and which is optionally substituted, one time with a substituent R$^{xy}$ selected from:

halo-, cyano-, $C_1$-$C_6$-alkyl-, $C_1$-$C_6$-alkoxy-.

In another preferred embodiment, the invention relates to compounds of formula (I), wherein:

R¹ represents a phenyl group which is substituted, one or more times, preferably one time, with —C(=O)N(H)R⁶;

and which is optionally substituted, one time with a substituent R$^{xy}$ selected from:

halo-, cyano-, $C_1$-$C_6$-alkyl-, $C_1$-$C_6$-alkoxy-.

In another preferred embodiment, the invention relates to compounds of formula (I), wherein:

R¹ represents a heteroaryl group which is substituted, one or more times, identically or differently, with a substituent selected from:
R⁶—($C_1$-$C_6$-alkyl)-, R⁶—(CH₂)$_n$(CHOH)(CH₂)$_m$—, R⁶—($C_1$-$C_6$-alkoxy)-, R⁶—(CH₂)$_n$(CHOH)(CH₂)$_p$—O—, R⁶—($C_1$-$C_6$-alkoxy-$C_1$-$C_6$-alkyl)-, R⁶—($C_1$-$C_6$-alkoxy-$C_1$-$C_6$-alkyl)-O—, R⁶—O—, —C(=O)R⁶, —C(=O)O—R⁶, —OC(=O)—R⁶, —N(H)C(=O)R⁶, —N(R⁷)C(=O)R⁶, —N(H)C(=O)NR⁶R⁷, —N(R⁷)C(=O)NR⁶R⁷, —NR⁶R⁷, —C(=O)N(H)R⁶, —C(=O)NR⁶R⁷, R⁶—S—, R⁶—S(=O)—, R⁶—S(=O)₂—, —N(H)S(=O)R⁶, —N(R⁷)S(=O)R⁶, —S(=O)N(H)R⁶, —S(=O)NR⁶R⁷, —N(H)S(=O)₂R⁶, —N(R⁷)S(=O)₂R⁶, —S(=O)₂N(H)R⁶, —S(=O)₂NR⁶R⁷, —S(=O)(=NR⁶)R⁷, —S(=O)(=NR⁷)R⁶, —N=S(=O)(R⁶)R⁷;

and which is optionally substituted, one or more times, identically or differently, with a substituent R$^{xy}$ selected from:

halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, R⁸—($C_1$-$C_6$-alkyl)-, R⁸—(CH₂)$_n$(CHOH)(CH₂)$_m$—, R⁸—($C_1$-$C_6$-alkoxy)-, R⁸—(CH₂)$_n$(CHOH)(CH₂)$_p$—O—, R⁸—($C_1$-$C_6$-alkoxy-$C_1$-$C_6$-alkyl)-, R⁸—($C_1$-$C_6$-alkoxy-$C_1$-$C_6$-alkyl)-O—, R⁸—O—, —C(=O)R⁸, —C(=O)O—R⁸, —OC(=O)—R⁸, —N(H)C(=O)R⁸, —N(R⁷)C(=O)R⁸, —N(H)C(=O)NR⁸R⁷, —N(R⁷)C(=O)NR⁸R⁷, —NR⁸R⁷, —C(=O)N(H)R⁸, —C(=O)NR⁸R⁷, R⁸—S—, R⁸—S(=O)—, R⁸—S(=O)₂—, —N(H)S(=O)R⁸, —N(R⁷)S(=O)R⁸, —S(=O)N(H)R⁸, —S(=O)NR⁸R⁷, —N(H)S(=O)₂R⁸, —N(R⁷)S(=O)₂R⁸, —S(=O)₂N(H)R⁸, —S(=O)₂NR⁸R⁷, —S(=O)(=NR⁸)R⁷, —S(=O)(=NR⁷)R⁸, —N=S(=O)(R⁸)R⁷.

Preferably, R¹ represents a substituted 2-pyridyl, 3-pyridyl or 4-pyridyl group.

In another preferred embodiment, the invention relates to compounds of formula (I), wherein:

R¹ represents a pyridyl group which is substituted, one or more times, identically or differently, with a substituent selected from:
—N(H)C(=O)R⁶, —C(=O)N(H)R⁶;

and
which is optionally substituted, one time with a substituent $R^{xy}$ selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-.

In another preferred embodiment, the invention relates to compounds of formula (I), wherein:
$R^1$ represents a pyridyl group
which is substituted, in para-position to the point of attachment of the phenyl group with the rest of the molecule, with a substituent selected from:
—N(H)C(=O)$R^6$, —C(=O)N(H)$R^6$;
and
which is optionally substituted, one time with a substituent $R^{xy}$ selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-.

In another preferred embodiment, the invention relates to compounds of formula (I), wherein:
$R^1$ represents a pyridyl group
which is substituted, one or more times, preferably one time, with —N(H)C(=O)$R^6$;
and
which is optionally substituted, one time with a substituent $R^{xy}$ selected from:
halo-, cyano-, $C_1$-$C_6$-alkyl-, $C_1$-$C_6$-alkoxy-.

In another preferred embodiment, the invention relates to compounds of formula (I), wherein:
$R^1$ represents a pyridyl group
which is substituted, one or more times, preferably one time, with —C(=O)N(H)$R^6$;
and
which is optionally substituted, one time with a substituent $R^{xy}$ selected from:
halo-, cyano-, $C_1$-$C_6$-alkyl-, $C_1$-$C_6$-alkoxy-.

$R^2$ is a substituted aryl or a substituted heteroaryl group. Preferably, $R^2$ is a substituted phenyl or a substituted pyridyl group.

In a preferred embodiment, the invention relates to compounds of formula (I), wherein:
$R^2$ represents an aryl group or a heteroaryl group
which is substituted, one or more times, identically or differently, with a substituent selected from:
$R^9$—, $R^9$—($C_1$-$C_6$-alkyl)-, $R^9$—($C_1$-$C_6$-alkoxy)-, $R^9$—O—, —C(=O)$R^9$, —N(H)C(=O)$R^9$, —N($R^7$)C(=O)$R^9$, —N(H)C(=O)N$R^9R^7$, —N($R^7$)C(=O)N$R^9R^7$, —N$R^9R^7$, —C(=O)N(H)$R^9$, —C(=O)N$R^9R^7$, $R^9$—S(=O)—, $R^9$—S(=O)$_2$—, —N(H)S(=O)$_2R^9$, —N($R^7$)S(=O)$_2R^9$, —S(=O)$_2$N(H)$R^9$, —S(=O)$_2$N$R^9R^7$, —S(=O)(=N$R^9$)$R^7$, —S(=O)(=N$R^7$)$R^9$;
and
which is optionally substituted, one or more times, identically or differently, with a substituent selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$.

In another preferred embodiment, the invention relates to compounds of formula (I), wherein:
$R^2$ represents an aryl group
which is substituted, one or more times, identically or differently, with a substituent selected from:
$R^9$—, $R^9$—($C_1$-$C_6$-alkyl)-, $R^9$—($C_1$-$C_6$-alkoxy)-, $R^9$—O—, —C(=O)$R^9$, —N(H)C(=O)$R^9$, —N($R^7$)C(=O)$R^9$, —N(H)C(=O)N$R^9R^7$, —N($R^7$)C(=O)N$R^9R^7$, —N$R^9R^7$, —C(=O)N(H)$R^9$, —C(=O)N$R^9R^7$, $R^9$—S(=O)—, $R^9$—S(=O)$_2$—, —N(H)S(=O)$_2R^9$, —N($R^7$)S(=O)$_2R^9$, —S(=O)$_2$N(H)$R^9$, —S(=O)$_2$N$R^9R^7$, —S(=O)(=N$R^9$)$R^7$, —S(=O)(=N$R^7$)$R^9$;
and
which is optionally substituted, one or more times, identically or differently, with a substituent selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$.

Preferably, $R^2$ represents a substituted phenyl group.

In another preferred embodiment, the invention relates to compounds of formula (I), wherein:
$R^2$ represents a phenyl group
which is substituted, one or more times, identically or differently, with a substituent selected from:
$R^9$—, $R^9$—($C_1$-$C_6$-alkyl)-, $R^9$—O—, —C(=O)$R^9$, —N$R^9R^7$, —C(=O)N(H)$R^9$, —C(=O)N$R^9R^7$, —S(=O)$_2$N$R^9R^7$;
and
which is optionally substituted, one or more times, identically or differently, with a substituent selected from:
halo-, $C_1$-$C_6$-alkyl-, halo-$C_1$-$C_6$-alkyl-, $C_1$-$C_6$-alkoxy-, halo-$C_1$-$C_6$-alkoxy-, $R^8$—S—.

In another preferred embodiment, the invention relates to compounds of formula (I), wherein:
$R^2$ represents a phenyl group
which is substituted, one or more times, identically or differently, with a substituent selected from:
$R^9$—, —N$R^9R^7$;
and
which is optionally substituted, one or more times, identically or differently, with a substituent selected from:
$C_1$-$C_6$-alkoxy-, halo-$C_1$-$C_6$-alkoxy-.

In another preferred embodiment, the invention relates to compounds of formula (I), wherein:
$R^2$ represents a phenyl group
which is substituted, one or more times, identically or differently, with a substituent selected from:
—C(=O)$R^9$, —C(=O)N$R^9R^7$;
and
which is optionally substituted, one or more times, identically or differently, with a substituent selected from:
$C_1$-$C_6$-alkoxy-, halo-$C_1$-$C_6$-alkoxy-.

In another preferred embodiment, the invention relates to compounds of formula (I), wherein:
$R^2$ represents a phenyl group
which is substituted, one or more times, preferably one time,
with —C(=O)N(H)$R^9$;

and which is optionally substituted, one or more times, identically or differently, with a substituent selected from: $C_1$-$C_6$-alkoxy-, halo-$C_1$-$C_6$-alkoxy-.

In another preferred embodiment, the invention relates to compounds of formula (I), wherein:

$R^2$ represents a heteroaryl group which is substituted, one or more times, identically or differently, with a substituent selected from:
$R^9$—, $R^9$—($C_1$-$C_6$-alkyl)-, $R^9$—($C_1$-$C_6$-alkoxy)-, $R^9$—O—, —C(=O)$R^9$, —N(H)C(=O)$R^9$, —N($R^7$)C(=O)$R^9$, —N(H)C(=O)N$R^9R^7$, —N($R^7$)C(=O)N$R^9R^7$, —N$R^9R^7$, —C(=O)N(H)$R^9$, —C(=O)N$R^9R^7$, $R^9$—S(=O)—, $R^9$—S(=O)$_2$—, —N(H)S(=O)$_2R^9$, —N($R^7$)S(=O)$_2R^9$, —S(=O)$_2$N(H)$R^9$, —S(=O)$_2$N$R^9R^7$, —S(=O)(=N$R^9$)$R^7$, —S(=O)(=N$R^7$)$R^9$;

and which is optionally substituted, one or more times, identically or differently, with a substituent selected from: halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$.

Preferably, $R^2$ represents a substituted 2-pyridyl, 3-pyridyl or 4-pyridyl group.

In another preferred embodiment, the invention relates to compounds of formula (I), wherein:

$R^2$ represents a phenyl or pyridyl group which is substituted with a substituent selected from:
$R^9$—, $R^9$—($C_1$-$C_6$-alkyl)-, $R^9$—($C_1$-$C_6$-alkoxy)-, $R^9$—O—, —C(=O)$R^9$, —N(H)C(=O)$R^9$, —N($R^7$)C(=O)$R^9$, —N(H)C(=O)N$R^9R^7$, —N($R^7$)C(=O)N$R^9R^7$, —N$R^9R^7$, —C(=O)N(H)$R^9$, —C(=O)N$R^9R^7$, $R^9$—S(=O)—, $R^9$—S(=O)$_2$—, —N(H)S(=O)$_2R^9$, —N($R^7$)S(=O)$_2R^9$, —S(=O)$_2$N(H)$R^9$, —S(=O)$_2$N$R^9R^7$, —S(=O)(=N$R^9$)$R^7$, —S(=O)(=N$R^7$)$R^9$;

and which is substituted with a substituent selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$.

In another preferred embodiment, the invention relates to compounds of formula (I), wherein:

$R^2$ represents a phenyl or pyridyl group which is substituted with a substituent selected from:
$R^9$—, $R^9$—($C_1$-$C_6$-alkyl)-, $R^9$—O—, —C(=O)$R^9$, —N$R^9R^7$, —C(=O)N(H)$R^9$, —C(=O)N$R^9R^7$, —S(=O)$_2$N$R^9R^7$;

and which is substituted with a substituent selected from:
halo-, $C_1$-$C_6$-alkyl-, halo-$C_1$-$C_6$-alkyl-, $C_1$-$C_6$-alkoxy-, halo-$C_1$-$C_6$-alkoxy-, $R^8$—S—.

In another preferred embodiment, the invention relates to compounds of formula (I), wherein:

$R^3$ represents a hydrogen atom, a halogen atom, a hydroxy-, amino, cyano-, $C_1$-$C_4$-alkyl-, hydroxy-$C_1$-$C_4$-alkyl or $C_2$-$C_6$-alkynyl-group.

Preferably, $R^3$ represents a hydrogen atom.

In another preferred embodiment, the invention relates to compounds of formula (I), wherein:

$R^4$ represents a hydrogen atom, a halogen atom, a hydroxy-, amino-, cyano-, $C_1$-$C_4$-alkyl-, hydroxy-$C_1$-$C_4$-alkyl- or $C_2$-$C_6$-alkynyl-group.

Preferably, $R^4$ represents a hydrogen atom.

In another preferred embodiment, the invention relates to compounds of formula (I), wherein:

$R^6$ represents a group selected from:
$C_3$-$C_6$-cycloalkyl-, —(CH$_2$)$_q$—($C_3$-$C_6$-cycloalkyl), —(CH$_2$)$_q$— (3- to 10-membered heterocycloalkyl), —(CH$_2$)$_q$-aryl, or —(CH$_2$)$_q$-heteroaryl;

said group being optionally substituted, one or more times, identically or differently, with a substituent selected from:
halo-, $C_1$-$C_6$-alkyl-, halo-$C_1$-$C_6$-alkyl-, $C_1$-$C_6$-alkoxy-, halo-$C_1$-$C_6$-alkoxy-.

In another preferred embodiment, the invention relates to compounds of formula (I), wherein:

$R^6$ represents —(CH$_2$)$_q$—($C_3$-$C_6$-cycloalkyl);

said group being optionally substituted, one or more times, identically or differently, with a substituent selected from:
halo-, $C_1$-$C_6$-alkyl-, halo-$C_1$-$C_6$-alkyl-, $C_1$-$C_6$-alkoxy-, halo-$C_1$-$C_6$-alkoxy-.

In another preferred embodiment, the invention relates to compounds of formula (I), wherein:

$R^6$ represents —(CH$_2$)$_q$-aryl;

said group being optionally substituted, one or more times, identically or differently, with a substituent selected from:
halo-, $C_1$-$C_6$-alkyl-, halo-$C_1$-$C_6$-alkyl-, $C_1$-$C_6$-alkoxy-, halo-$C_1$-$C_6$-alkoxy-.

In another preferred embodiment, the invention relates to compounds of formula (I), wherein:

$R^6$ represents a group selected from:
—(CH$_2$)$_q$—($C_3$-$C_6$-cycloalkyl), —(CH$_2$)$_q$-aryl;

said group being optionally substituted, one or more times, identically or differently, with a substituent selected from:
halo-, $C_1$-$C_6$-alkyl-.

In another preferred embodiment, the invention relates to compounds of formula (I), wherein:

$R^6$ represents —(CH$_2$)$_q$—($C_3$-$C_6$-cycloalkyl);

said group being optionally substituted, one or more times, identically or differently, with a substituent selected from:
halo-, $C_1$-$C_6$-alkyl-.

In another preferred embodiment, the invention relates to compounds of formula (I), wherein:

$R^6$ represents —(CH$_2$)$_q$-aryl;

said group being optionally substituted, one or more times, identically or differently, with a substituent selected from:
halo-, $C_1$-$C_6$-alkyl-.

In another preferred embodiment, the invention relates to compounds of formula (I), wherein:

$R^7$ represents a hydrogen atom, a $C_1$-$C_6$-alkyl-, or $C_3$-$C_6$-cycloalkyl-group.

Preferably, $R^7$ represents a hydrogen atom or a $C_1$-$C_6$-alkyl-group. More preferably, $R^7$ represents a hydrogen atom.

In another preferred embodiment, the invention relates to compounds of formula (I), wherein:
$R^6$ and $R^7$,
together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-.

In another preferred embodiment, the invention relates to compounds of formula (I), wherein:
$R^6$ and $R^7$,
together with the nitrogen atom to which they are attached, represent a 3- to 10-membered heterocycloalkyl-group, which is optionally substituted, one or more times, identically or differently, with halogen, hydroxy, cyano-, $C_1$-$C_6$-alkyl-, halo-$C_1$-$C_6$-alkyl-, $C_1$-$C_6$-alkoxy-, halo-$C_1$-$C_6$-alkoxy- or $C_3$-$C_6$-cycloalkyl-.

In another preferred embodiment, the invention relates to compounds of formula (I), wherein:
$R^8$ represents a hydrogen atom or a $C_1$-$C_6$-alkyl-group.
Preferably, $R^8$ represents a $C_1$-$C_6$-alkyl-group In another preferred embodiment, the invention relates to compounds of formula (I), wherein:
$R^9$ represents a group selected from:
$C_7$-$C_{10}$-cycloalkyl-, 3- to 10-membered heterocycloalkyl-, aryl-, heteroaryl-;
said group being optionally substituted, one or more times, identically or differently, with a substituent selected from:
halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —$(CH_2)_q$—$(C_3$-$C_6$-cycloalkyl), $R^8$—$(CH_2)_n(CHOH)(CH_2)_m$—, $R^8$—$(C_1$-$C_6$-alkoxy)-, $R^8$—$(CH_2)_n(CHOH)(CH_2)_p$—O—, $R^8$—$(C_1$-$C_6$-alkoxy-$C_1$-$C_6$-alkyl)-, $R^8$—$(C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$.

In another preferred embodiment, the invention relates to compounds of formula (I), wherein:
$R^9$ represents a group selected from:
$C_7$-$C_{10}$-cycloalkyl-, 3- to 10-membered heterocycloalkyl-, heteroaryl-; said group being optionally substituted, one or more times, identically or differently, with a substituent selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —$(CH_2)_q$—$(C_3$-$C_6$-cycloalkyl), —C(=O)$R^8$, —C(=O)O—$R^8$, —N(H)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S(=O)— or $R^8$—S(=O)$_2$—.

In another preferred embodiment, the invention relates to compounds of formula (I), wherein:
$R^9$ represents a group selected from:
$C_7$-$C_{10}$-cycloalkyl-, 3- to 10-membered heterocycloalkyl-;
said group being optionally substituted, one or more times, identically or differently, with a substituent selected from:
halo-, hydroxyl-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —$(CH_2)_q$—$(C_3$-$C_6$-cycloalkyl), —C(=O)$R^8$, —C(=O)O—$R^8$.

In another preferred embodiment, the invention relates to compounds of formula (I), wherein:
$R^9$ represents a 3- to 10-membered heterocycloalkyl-group;
said group being optionally substituted, one or more times, identically or differently, with a substituent selected from:
halo-, hydroxyl-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —$(CH_2)_q$—$(C_3$-$C_6$-cycloalkyl), —C(=O)$R^8$, —C(=O)O—$R^8$.

In another preferred embodiment, the invention relates to compounds of formula (I), wherein:
$R^9$ represents a 3- to 10-membered heterocycloalkyl-group;
said group being optionally substituted, one or more times, identically or differently, with a substituent selected from:
halo-, hydroxyl-, $C_1$-$C_6$-alkyl-, —C(=O)$R^8$, —C(=O)O—$R^8$.

In another preferred embodiment, the invention relates to compounds of formula (I), wherein:
$R^9$ represents a 4- to 7-membered heterocycloalkyl-group;
said group being optionally substituted, one or more times, identically or differently, with a substituent selected from:
halo-, hydroxyl-, $C_1$-$C_6$-alkyl-, —C(=O)$R^8$, —C(=O)O—$R^8$.

In another preferred embodiment, the invention relates to compounds of formula (I), wherein:
$R^9$ is selected from:

wherein * indicates the point of attachment of said group with the rest of the molecule;
said group being optionally substituted, one or more times, identically or differently, with a substituent selected from:
halo-, hydroxyl-, $C_1$-$C_6$-alkyl-, —C(=O)$R^8$, —C(=O)O—$R^8$.

In another preferred embodiment, the invention relates to compounds of formula (I), wherein:
$R^9$ is selected from:

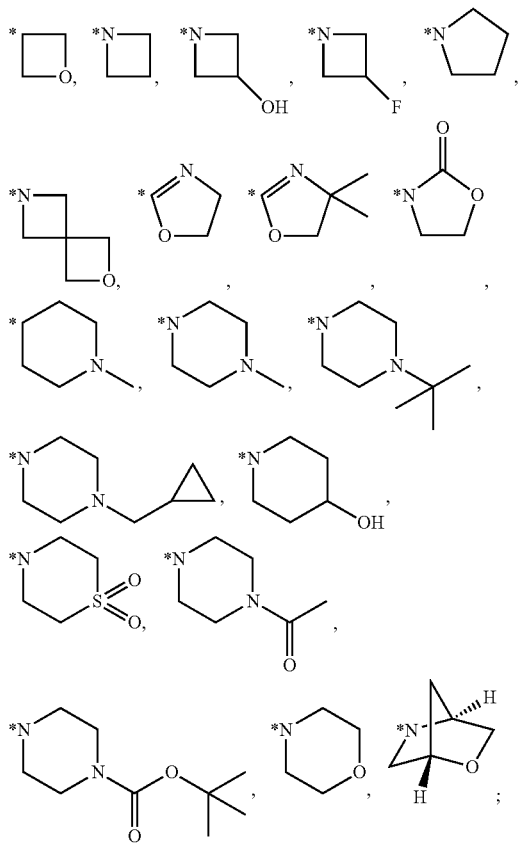

wherein * indicates the point of attachment of said group with the rest of the molecule.

In another preferred embodiment, the invention relates to compounds of formula (I), wherein:
$R^9$ and $R^7$,
together with the nitrogen atom to which they are attached, represent a 3- to 10-membered heterocycloalkyl-group, which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, —C(=O)O—$R^8$ or $C_3$-$C_6$-cycloalkyl-.

In another preferred embodiment, the invention relates to compounds of formula (I), wherein:
$R^9$ and $R^7$,
together with the nitrogen atom to which they are attached, represent a 4- to 7-membered heterocycloalkyl-group, which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, —C(=O)O—$R^8$ or $C_3$-$C_6$-cycloalkyl-.

In another preferred embodiment, the invention relates to compounds of formula (I), wherein:
$R^9$ and $R^7$,
together with the nitrogen atom to which they are attached, represent a group selected from:

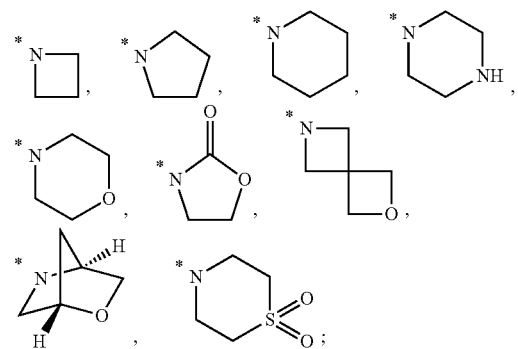

wherein * indicates the point of attachment of said group with the rest of the molecule;
which is optionally substituted, one or more times, identically or differently, with halo-, hydroxy, cyano-, $C_1$-$C_6$-alkyl-, halo-$C_1$-$C_6$-alkyl-, $C_1$-$C_6$-alkoxy-, halo-$C_1$-$C_6$-alkoxy-, —C(=O)O—$R^8$ or $C_3$-$C_6$-cycloalkyl-.

In another preferred embodiment, the invention relates to compounds of formula (I), wherein:
n, m, p
represent, independently from each other, an integer of 0, 1, 2 or 3.

In another preferred embodiment, the invention relates to compounds of formula (I), wherein:
q represents an integer of 1 or 2.
Preferably, q is 1.

It is to be understood that the present invention relates also to any combination of the preferred embodiments described above.

Some examples of combinations are given hereinafter. However, the invention is not limited to these combinations.

In another preferred embodiment, the invention relates to compounds of formula (I), supra, in which:
$R^1$ represents an aryl or heteroaryl group
which is substituted, one or more times, identically or differently, with a substituent selected from:
$R^6$—$(CH_2)_n$(CHOH)$(CH_2)_m$—, $R^6$—($C_1$-$C_6$-alkoxy)-, $R^6$—$(CH_2)_n$(CHOH)$(CH_2)_p$—O—, $R^6$—($C_1$-$C_6$-alkoxy-$C_1$-$C_6$-alkyl)-, $R^6$—($C_1$-$C_6$-alkoxy-$C_1$-$C_6$-alkyl)-O—, $R^6$—O—, —C(=O)$R^6$, —C(=O)O—$R^6$, —OC(=O)—$R^6$, —N(H)C(=O)$R^6$, —N($R^7$)C(=O)$R^6$, —N(H)C(=O)N$R^6R^7$, —N($R^7$)C(=O)N$R^6R^7$, —N$R^6R^7$, —C(=O)N(H)$R^6$, —C(=O)N$R^6R^7$, $R^6$—S—, $R^6$—S(=O)—, $R^6$—S(=O)$_2$—, —N(H)S(=O)$R^6$, —N($R^7$)S(=O)$R^6$, —S(=O)N(H)$R^6$, —S(=O)N$R^6R^7$, —N(H)S(=O)$_2R^6$, —N($R^7$)S(=O)$_2R^6$, —S(=O)$_2$N(H)$R^6$, —S(=O)$_2$N$R^6R^7$, —S(=O)(=N$R^6$)$R^7$, —S(=O)(=N$R^7$)$R^6$, —N=S(=O)($R^6$)$R^7$;
and
which is optionally substituted, one or more times, identically or differently, with a substituent $R^{xy}$ selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —N(H)C(=O)$R^8$, —N($R^7$)C(=O)$R^8$, —C(=O)N(H)$R^8$, —C(=O)N$R^8R^7$;

$R^2$ represents an aryl group or heteroaryl group
which is substituted, one or more times, identically or differently, with a substituent selected from:
$R^9$—, $R^9$—($C_1$-$C_6$-alkyl)-, $R^9$—$(CH_2)_n$(CHOH)$(CH_2)_m$—, $R^9$—($C_1$-$C_6$-alkoxy)-, $R^9$—$(CH_2)_n$(CHOH)$(CH_2)_p$—O—, $R^9$—($C_1$-$C_6$-alkoxy-$C_1$-$C_6$-alkyl)-, $R^9$—($C_1$-$C_6$-alkoxy-$C_1$-$C_6$-alkyl)-O—, —O—$(CH_2)_n$—C(=O)$NR^9R^7$, $R^9$—O—, —C(=O)$R^9$, —C(=O)O—$R^9$, —OC(=O)—$R^9$, —N(H)C(=O)$R^9$, —N($R^7$)C(=O)$R^9$, —N(H)C(=O)$NR^9R^7$, —N($R^7$)C(=O)$NR^9R^7$, —$NR^9R^7$, —C(=O)N(H)$R^9$, —C(=O)$NR^9R^7$, $R^9$—S—, $R^9$—S(=O)—, $R^9$—S(=O)$_2$—, —N(H)S(=O)$R^9$, —N($R^7$)S(=O)$R^9$, —S(=O)N(H)$R^9$, —S(=O)$NR^9R^7$, —N(H)S(=O)$_2R^9$, —N($R^7$)S(=O)$_2R^9$, —S(=O)$_2$N(H)$R^9$, —S(=O)$_2$ $NR^9R^7$, —S(=O)(=$NR^9$)$R^7$, —S(=O)(=$NR^7$)$R^9$, —N=S(=O)($R^9$)$R^7$;
and
which is optionally substituted, one or more times, identically or differently, with a substituent selected from:
halo-, hydroxyl, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n$(CHOH)$(CH_2)_m$—, $R^8$—($C_1$-$C_6$-alkoxy)-, $R^8$—$(CH_2)_n$(CHOH)$(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, —O—$(CH_2)_n$—C(=O)$NR^8R^7$, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)$NR^8R^7$, —N($R^7$)C(=O)$NR^8R^7$, —$NR^8R^7$, —C(=O)N(H)$R^8$, —C(=O)$NR^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)$NR^8R^7$, —N(H)S(=O)$_2R^8$, —N($R^7$)S(=O)$_2R^8$, —S(=O)$_2$N(H)$R^8$, —S(=O)$_2NR^8R^7$, —S(=O)(=$NR^8$)$R^7$, —S(=O)(=$NR^7$)$R^8$, —N=S(=O)($R^8$)$R^7$;

$R^3$ represents a hydrogen atom, a halogen atom, a hydroxy-, amino, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl-, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or halo-$C_3$-$C_6$-cycloalkyl-group;

$R^4$ represents a hydrogen atom, a halogen atom, a hydroxy-, amino, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl-, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or halo-$C_3$-$C_6$-cycloalkyl-group;

$R^5$ represents a hydrogen atom;

$R^6$ represents a group selected from:
$C_3$-$C_6$-cycloalkyl-, 3- to 10-membered heterocycloalkyl-, aryl-, heteroaryl-, —$(CH_2)_q$—($C_3$-$C_6$-cycloalkyl), —$(CH_2)_q$-(3- to 10-membered heterocycloalkyl), —$(CH_2)_q$-aryl, or —$(CH_2)_q$-heteroaryl;
said group being optionally substituted, one or more times, identically or differently, with a substituent selected from:
halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n$(CHOH)$(CH_2)_m$—, $R^8$—($C_1$-$C_6$-alkoxy)-, $R^8$—$(CH_2)_n$(CHOH)$(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)$NR^8R^7$, —N($R^7$)C(=O)$NR^8R^7$, —$NR^8R^7$, —C(=O)N(H)$R^8$, —C(=O)$NR^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)$NR^8R^7$, —N(H)S(=O)$_2R^8$, —N($R^7$)S(=O)$_2R^8$, —S(=O)$_2$N(H)$R^8$, —S(=O)$_2NR^8R^7$, —S(=O)(=$NR^8$)$R^7$, —S(=O)(=$NR^7$)$R^8$, —N=S(=O)($R^8$)$R^7$;

$R^7$ represents a hydrogen atom, a $C_1$-$C_6$-alkyl-, or $C_3$-$C_6$-cycloalkyl-group;
or
$R^6$ and $R^7$,
together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-;

$R^8$ represents a hydrogen atom or a $C_1$-$C_6$-alkyl-group;
$R^9$ represents a group selected from:
$C_7$-$C_{10}$-cycloalkyl-, 3- to 10-membered heterocycloalkyl-, aryl-, heteroaryl-;
said group being optionally substituted, one or more times, identically or differently, with a substituent selected from:
halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —$(CH_2)_q$—($C_3$-$C_6$-cycloalkyl), $R^8$—$(CH_2)_n$(CHOH)$(CH_2)_m$—, $R^8$—($C_1$-$C_6$-alkoxy)-, $R^8$—$(CH_2)_n$(CHOH)$(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)$NR^8R^7$, —N($R^7$)C(=O)$NR^8R^7$, —$NR^8R^7$, —C(=O)N(H)$R^8$, —C(=O)$NR^8R^7$, $R^8$—S—, $R^8$—S(=O)—, $R^8$—S(=O)$_2$—, N(H)S(=O)$R^8$, —N($R^7$)S(=O)$R^8$, —S(=O)N(H)$R^8$, —S(=O)$NR^8R^7$, —N(H)S(=O)$_2R^8$, —N($R^7$)S(=O)$_2R^8$, —S(=O)$_2$N(H)$R^8$, —S(=O)$_2NR^8R^7$, —S(=O)(=$NR^8$)$R^7$, —S(=O)(=$NR^7$)$R^8$, —N=S(=O)($R^8$)$R^7$;
or
$R^9$ and $R^7$,
together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, —C(=O)O—$R^8$ or $C_3$-$C_6$-cycloalkyl-;

n, m, p
represent, independently from each other, an integer of 0, 1, 2, 3, 4, or 5;
and
q represents an integer of 0, 1, 2 or 3.

In another preferred embodiment, the invention relates to compounds of formula (I), supra, in which:

$R^1$ represents an aryl or heteroaryl group which is substituted, one or more times, identically or differently, with a substituent selected from:

$R^6$—$(CH_2)_n(CHOH)(CH_2)_m$—, $R^6$—$(C_1$-$C_6$-alkoxy)-, $R^6$—$(CH_2)_n(CHOH)(CH_2)_p$—O—, $R^6$—$(C_1$-$C_6$-alkoxy-$C_1$-$C_6$-alkyl)-, $R^6$—$(C_1$-$C_6$-alkoxy-$C_1$-$C_6$-alkyl)-O—, $R^6$—O—, —C(=O)$R^6$, —C(=O)O—$R^6$, —OC(=O)—$R^6$, —N(H)C(=O)$R^6$, —N($R^7$)C(=O)$R^6$, —N(H)C(=O)N$R^6R^7$, —N($R^7$)C(=O)N$R^6R^7$, —N$R^6R^7$, —C(=O)N(H)$R^6$, —C(=O)N$R^6R^7$, $R^6$—S—, $R^6$—S(=O)—, $R^6$—S(=O)$_2$—, —N(H)S(=O)$R^6$, —N($R^7$)S(=O)$R^6$, —S(=O)N(H)$R^6$, —S(=O)N$R^6R^7$, —N(H)S(=O)$_2R^6$, —N($R^7$)S(=O)$_2R^6$, —S(=O)$_2$N(H)$R^6$, —S(=O)$_2$N$R^6R^7$, —S(=O)(=N$R^6$)$R^7$, —S(=O)(=N$R^7$)$R^6$, —N=S(=O)($R^6$)$R^7$;

and which is optionally substituted, one or more times, identically or differently, with a substituent $R^{xy}$ selected from: halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —N(H)C(=O)$R^8$, —N($R^7$)C(=O)$R^8$, —C(=O)N(H)$R^8$, —C(=O)N$R^8R^7$;

$R^2$ represents an aryl group or heteroaryl group which is substituted, one or more times, identically or differently, with a substituent selected from:

$R^9$—, $R^9$—($C_1$-$C_6$-alkyl)-, $R^9$—($C_1$-$C_6$-alkoxy)-, $R^9$—O—, —C(=O)$R^9$, —N(H)C(=O)$R^9$, —N($R^7$)C(=O)$R^9$, —N(H)C(=O)N$R^9R^7$, —N($R^7$)C(=O)N$R^9R^7$, —N$R^9R^7$, —C(=O)N(H)$R^9$, —C(=O)N$R^9R^7$, $R^9$—S(=O)—, $R^9$—S(=O)$_2$—, —N(H)S(=O)$_2R^9$, —N($R^7$)S(=O)$_2R^9$, —S(=O)$_2$N(H)$R^9$, —S(=O)$_2$N$R^9R^7$, —S(=O)(=N$R^9$)$R^7$, —S(=O)(=N$R^7$)$R^9$;

and which is optionally substituted, one or more times, identically or differently, with a substituent selected from: halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$;

$R^3$ represents a hydrogen atom, a halogen atom, a hydroxy-, amino, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl-, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or halo-$C_3$-$C_6$-cycloalkyl-group;

$R^4$ represents a hydrogen atom, a halogen atom, a hydroxy-, amino, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl-, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or halo-$C_3$-$C_6$-cycloalkyl-group;

$R^5$ represents a hydrogen atom;

$R^6$ represents a group selected from:
$C_3$-$C_6$-cycloalkyl-, 3- to 10-membered heterocycloalkyl-, aryl-, heteroaryl-, —$(CH_2)_q$—($C_3$-$C_6$-cycloalkyl), —$(CH_2)_q$-(3- to 10-membered heterocycloalkyl), —$(CH_2)_q$-aryl, or —$(CH_2)_q$-heteroaryl;

said group being optionally substituted, one or more times, identically or differently, with a substituent selected from:

halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$;

$R^7$ represents a hydrogen atom, a $C_1$-$C_6$-alkyl-, or $C_3$-$C_6$-cycloalkyl-group;

or $R^6$ and $R^7$, together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-;

$R^8$ represents a hydrogen atom or a $C_1$-$C_6$-alkyl-group;

$R^9$ represents a group selected from:
$C_7$-$C_{10}$-cycloalkyl-, 3- to 10-membered heterocycloalkyl-, aryl-, heteroaryl-;

said group being optionally substituted, one or more times, identically or differently, with a substituent selected from:

halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —$(CH_2)_q$—($C_3$-$C_6$-cycloalkyl), $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$;

or $R^9$ and $R^7$, together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$- alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, —C(=O)O—$R^8$ or $C_3$-$C_6$-cycloalkyl-;

n, m, p
represent, independently from each other, an integer of 0, 1, 2, 3, 4, or 5;
and
q represents an integer of 0, 1, 2 or 3.

In another preferred embodiment, the invention relates to compounds of formula (I), supra, in which:

$R^1$ represents an aryl or heteroaryl group
which is substituted, one or more times, identically or differently, with a substituent selected from:
$R^6$—$(CH_2)_n$(CHOH)$(CH_2)_m$—, $R^6$—$(C_1$-$C_6$-alkoxy)-, $R^6$—$(CH_2)_n$(CHOH)$(CH_2)_p$—O—, $R^6$—$(C_1$-$C_6$-alkoxy-$C_1$-$C_6$-alkyl)-, $R^6$—$(C_1$-$C_6$-alkoxy-$C_1$-$C_6$-alkyl)-O—, $R^6$—O—, —C(=O)$R^6$, —C(=O)O—$R^6$, —OC(=O)—$R^6$, —N(H)C(=O)$R^6$, —N($R^7$)C(=O)$R^6$, —N(H)C(=O)N$R^6R^7$, —N($R^7$)C(=O)N$R^6R^7$, —N$R^6R^7$, —C(=O)N(H)$R^6$, —C(=O)N$R^6R^7$, $R^6$—S—, $R^6$—S(=O)—, $R^6$—S(=O)$_2$—, —N(H)S(=O)$R^6$, —N($R^7$)S(=O)$R^6$, —S(=O)N(H)$R^6$, —S(=O)N$R^6R^7$, —N(H)S(=O)$_2R^6$, —N($R^7$)S(=O)$_2R^6$, —S(=O)$_2$N(H)$R^6$, —S(=O)$_2$N$R^6R^7$, —S(=O)(=N$R^6$)$R^7$, —S(=O)(=N$R^7$)$R^6$, —N=S(=O)($R^6$)$R^7$;
and
which is optionally substituted, one or more times, identically or differently, with a substituent $R^{xy}$ selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —N(H)C(=O)$R^8$, —N($R^7$)C(=O)$R^8$, —C(=O)N(H)$R^8$, —C(=O)N$R^8R^7$;

$R^2$ represents an aryl group or heteroaryl group
which is substituted, one or more times, identically or differently, with a substituent selected from:
$R^9$—, $R^9$—$(C_1$-$C_6$-alkyl)-, $R^9$—$(C_1$-$C_6$-alkoxy)-, $R^9$—O—, —C(=O)$R^9$, —N(H)C(=O)$R^9$, —N($R^7$)C(=O)$R^9$, —N(H)C(=O)N$R^9R^7$, —N($R^7$)C(=O)N$R^9R^7$, —N$R^9R^7$, —C(=O)N(H)$R^9$, —C(=O)N$R^9R^7$, $R^9$—S(=O)—, $R^9$—S(=O)$_2$—, —N(H)S(=O)$_2R^9$, —N($R^7$)S(=O)$_2R^9$, —S(=O)$_2$N(H)$R^9$, —S(=O)$_2$N$R^9R^7$, —S(=O)(=N$R^9$)$R^7$, —S(=O)(=N$R^7$)$R^9$;
and
which is optionally substituted, one or more times, identically or differently, with a substituent selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, —C(=O)$R^8$, —C(=O)O—$R^8$, —OC(=O)—$R^8$, —N(H)C(=O)$R^8$, N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$;

$R^3$ represents a hydrogen atom, a halogen atom, a hydroxy-, amino, cyano-, $C_1$-$C_4$-alkyl-, hydroxy-$C_1$-$C_4$-alkyl or $C_2$-$C_6$-alkynyl-group;

$R^4$ represents a hydrogen atom, a halogen atom, a hydroxy-, amino, cyano-, $C_1$-$C_4$-alkyl-, hydroxy-$C_1$-$C_4$-alkyl or $C_2$-$C_6$-alkynyl-group;

$R^5$ represents a hydrogen atom;

$R^6$ represents a group selected from:
—$(CH_2)_q$—($C_3$-$C_6$-cycloalkyl),
—$(CH_2)_q$-(3- to 10-membered heterocycloalkyl),
—$(CH_2)_q$-aryl, or —$(CH_2)_q$-heteroaryl;
said group being optionally substituted, one or more times, identically or differently, with a substituent selected from:
halo-, $C_1$-$C_6$-alkyl-, halo-$C_1$-$C_6$-alkyl-, $C_1$-$C_6$-alkoxy-, halo-$C_1$-$C_6$-alkoxy-;

$R^7$ represents a hydrogen atom, a $C_1$-$C_6$-alkyl-, or $C_3$-$C_6$-cycloalkyl-group;
or
$R^6$ and $R^7$,
together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-;

$R^8$ represents a hydrogen atom or a $C_1$-$C_6$-alkyl-group;

$R^9$ represents a group selected from:
$C_7$-$C_{10}$-cycloalkyl-, 3- to 10-membered heterocycloalkyl-, aryl-, heteroaryl-;
said group being optionally substituted, one or more times, identically or differently, with a substituent selected from:
halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —$(CH_2)_q$—($C_3$-$C_6$-cycloalkyl), $R^8$—$(CH_2)_n$(CHOH)$(CH_2)_m$—, $R^8$—$(C_1$-$C_6$-alkoxy)-, $R^8$—$(CH_2)_n$(CHOH)$(CH_2)_p$—O—, $R^8$—$(C_1$-$C_6$-alkoxy-$C_1$-$C_6$-alkyl)-, $R^8$—$(C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)N$R^8R^7$, —N(H)S(=O)$_2R^8$, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$, —N=S(=O)($R^8$)$R^7$;
or
$R^9$ and $R^7$,
together with the nitrogen atom to which they are attached, represent a 3- to 10-membered heterocycloalkyl-group, which is optionally substituted, one or more times, identically or differently, with halogen, hydroxy, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, —C(=O)O—$R^8$ or $C_3$-$C_6$-cycloalkyl-;

n, m, p
represent, independently from each other, an integer of 0, 1, 2, 3, 4, or 5;
and
q represents an integer of 0, 1, 2 or 3.

In another preferred embodiment, the invention relates to compounds of formula (I), supra, in which:
$R^1$ represents an aryl group
which is substituted, one or more times, identically or differently, with a substituent selected from:
—C(=O)$R^6$, —C(=O)O—$R^6$, —OC(=O)—$R^6$, —N(H)C(=O)$R^6$, —C(=O)N(H)$R^6$, —C(=O)

NR$^6$R$^7$, R$^6$—S(=O)—, R$^6$—S(=O)$_2$—, —N(H)S(=O)$_2$R$^6$, —S(=O)$_2$N(H)R$^6$, —S(=O)(=NR$^6$)R$^7$, —S(=O)(=NR$^7$)R$^6$;

and which is optionally substituted, one or more times, identically or differently, with a substituent R$^{xy}$ selected from:

halo-, hydroxyl-, cyano-, C$_1$-C$_6$-alkyl-, C$_1$-C$_6$-alkoxy-, hydroxy-C$_1$-C$_6$-alkyl-, —N(H)C(=O)R$^8$, —N(R$^7$)C(=O)R$^8$, —C(=O)N(H)R$^8$, —C(=O)NR$^8$R$^7$;

R$^2$ represents an aryl group or heteroaryl group which is substituted, one or more times, identically or differently, with a substituent selected from:

R$^9$—, R$^9$—(C$_1$-C$_6$-alkyl)-, R$^9$—(C$_1$-C$_6$-alkoxy)-, —C(=O)R$^9$, —N(H)C(=O)R$^9$, —N(R$^7$)C(=O)R$^9$, —N(H)C(=O)NR$^9$R$^7$, —N(R$^7$)C(=O)NR$^9$R$^7$, —NR$^9$R$^7$, —C(=O)N(H)R$^9$, —C(=O)NR$^9$R$^7$, R$^9$—S(=O)—, R$^9$—S(=O)$_2$—, —N(H)S(=O)$_2$R$^9$, —N(R$^7$)S(=O)$_2$R$^9$, —S(=O)$_2$N(H)R$^9$, —S(=O)$_2$NR$^9$R$^7$, —S(=O)(=NR$^9$)R$^7$, —S(=O)(=NR$^7$)R$^9$;

and which is optionally substituted, one or more times, identically or differently, with a substituent selected from:

halo-, hydroxyl-, cyano-, C$_1$-C$_6$-alkyl-, halo-C$_1$-C$_6$-alkyl-, C$_1$-C$_6$-alkoxy-, halo-C$_1$-C$_6$-alkoxy-, —C(=O)R$^8$, —C(=O)O—R$^8$, —OC(=O)—R$^8$, —N(H)C(=O)R$^8$, —N(R$^7$)C(=O)R$^8$, —N(H)C(=O)NR$^8$R$^7$, —N(R$^7$)C(=O)NR$^8$R$^7$, —NR$^8$R$^7$, —C(=O)N(H)R$^8$, —C(=O)NR$^8$R$^7$, R$^8$—S(=O)—, R$^8$—S(=O)$_2$—, —N(R$^7$)S(=O)$_2$R$^8$, —S(=O)$_2$N(H)R$^8$, —S(=O)$_2$NR$^8$R$^7$, —S(=O)(=NR$^8$)R$^7$, —S(=O)(=NR$^7$)R$^8$;

R$^3$ represents a hydrogen atom, a halogen atom, a hydroxy-, amino, cyano-, C$_1$-C$_4$-alkyl-, hydroxy-C$_1$-C$_4$-alkyl or C$_2$-C$_6$-alkynyl-group;

R$^4$ represents a hydrogen atom, a halogen atom, a hydroxy-, amino, cyano-, C$_1$-C$_4$-alkyl-, hydroxy-C$_1$-C$_4$-alkyl or C$_2$-C$_6$-alkynyl-group;

R$^5$ represents a hydrogen atom;

R$^6$ represents a group selected from:

C$_3$-C$_6$-cycloalkyl-, —(CH$_2$)$_q$—(C$_3$-C$_6$-cycloalkyl), —(CH$_2$)$_q$-(3- to 10-membered heterocycloalkyl), —(CH$_2$)$_q$-aryl, or —(CH$_2$)$_q$-heteroaryl;

said group being optionally substituted, one or more times, identically or differently, with a substituent selected from:

halo-, C$_1$-C$_6$-alkyl-, halo-C$_1$-C$_6$-alkyl-, C$_1$-C$_6$-alkoxy-, halo-C$_1$-C$_6$-alkoxy-;

R$^7$ represents a hydrogen atom or a C$_1$-C$_6$-alkyl-group;

or

R$^6$ and R$^7$, together with the nitrogen atom to which they are attached, represent a 3- to 10-membered heterocycloalkyl-group, which is optionally substituted, one or more times, identically or differently, with halogen, hydroxy, cyano-, C$_1$-C$_6$-alkyl-, halo-C$_1$-C$_6$-alkyl-, C$_1$-C$_6$-alkoxy-, halo-C$_1$-C$_6$-alkoxy- or C$_3$-C$_6$-cycloalkyl-;

R$^8$ represents a hydrogen atom or a C$_1$-C$_6$-alkyl-group;

R$^9$ represents a group selected from:

C$_7$-C$_{10}$-cycloalkyl-, 3- to 10-membered heterocycloalkyl-, heteroaryl-; said group being optionally substituted, one or more times, identically or differently, with a substituent selected from:

halo-, hydroxyl-, cyano-, C$_1$-C$_6$-alkyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, —(CH$_2$)$_q$—(C$_3$-C$_6$-cycloalkyl), —C(=O)R$^8$, —C(=O)O—R$^8$, —N(H)C(=O)R$^8$, —N(H)C(=O)NR$^8$R$^7$, —N(R$^7$)C(=O)NR$^8$R$^7$, —NR$^8$R$^7$, —C(=O)N(H)R$^8$, —C(=O)NR$^8$R$^7$, R$^8$—S(=O)— or R$^8$—S(=O)$_2$—;

or

R$^9$ and R$^7$, together with the nitrogen atom to which they are attached, represent a 3- to 10-membered heterocycloalkyl-group, which is optionally substituted, one or more times, identically or differently, with halogen, hydroxy, cyano-, C$_1$-C$_6$-alkyl-, halo-C$_1$-C$_6$-alkyl-, C$_1$-C$_6$-alkoxy-, halo-C$_1$-C$_6$-alkoxy-, —C(=O)O—R$^8$ or C$_3$-C$_6$-cycloalkyl;

q represents an integer of 0, 1, 2 or 3.

In another preferred embodiment, the invention relates to compounds of formula (I), supra, in which:

R$^1$ represents a phenyl group which is substituted, one or more times, identically or differently, with a substituent selected from:

—N(H)C(=O)R$^6$ or —C(=O)N(H)R$^6$;

and which is optionally substituted, one time with a substituent R$^{xy}$ selected from:

halo-, cyano-, C$_1$-C$_6$-alkyl-, C$_1$-C$_6$-alkoxy-;

R$^2$ represents a phenyl or pyridyl group which is substituted, one or more times, identically or differently, with a substituent selected from:

R$^9$—, —C(=O)R$^9$, —N(H)C(=O)R$^9$, —N(R$^7$)C(=O)R$^9$, —N(H)C(=O)NR$^9$R$^7$, —N(R$^7$)C(=O)NR$^9$R$^7$, —NR$^9$R$^7$, —C(=O)N(H)R$^9$ or —C(=O)NR$^9$R$^7$;

and which is optionally substituted, one or more times, identically or differently, with a substituent selected from:

halo-, hydroxyl-, C$_1$-C$_6$-alkyl-, halo-C$_1$-C$_6$-alkyl-, C$_1$-C$_6$-alkoxy-, halo-C$_1$-C$_6$-alkoxy-;

R$^3$ represents a hydrogen atom;

R$^4$ represents a hydrogen atom;

R$^5$ represents a hydrogen atom;

R$^6$ represents a group selected from:

C$_3$-C$_6$-cycloalkyl-, —(CH$_2$)$_q$—(C$_3$-C$_6$-cycloalkyl) or —(CH$_2$)$_q$-aryl;

said group being optionally substituted, one or more times, identically or differently, with a substituent selected from:

halo-;

R$^7$ represents a hydrogen atom;

R$^8$ represents a hydrogen atom or a C$_1$-C$_6$-alkyl-group;

R$^9$ represents a group selected from:

C$_7$-C$_{10}$-cycloalkyl-, 3- to 10-membered heterocycloalkyl-;

said group being optionally substituted, one or more times, identically or differently, with a substituent selected from:

halo-, hydroxyl-, C$_1$-C$_6$-alkyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, —(CH$_2$)$_q$—(C$_3$-C$_6$-cycloalkyl), —C(=O)R$^8$, —C(=O)O—R$^8$;

or

R$^9$ and R$^7$, together with the nitrogen atom to which they are attached, represent a 3- to 10-membered heterocycloalkyl-group, which is optionally substituted, one or more times, identically or differently, with halogen, hydroxy, C$_1$-C$_6$-alkyl-, halo-C$_1$-C$_6$-alkyl-, C$_1$-C$_6$-alkoxy-, halo-C$_1$-C$_6$-alkoxy-, —C(=O)O—R$^8$ or C$_3$-C$_6$-cycloalkyl;

q represents an integer of 1 or 2.

In an embodiment of the above-mentioned embodiments of the above-mentioned aspects, the invention relates to a stereoisomer, a tautomer, an N-oxide, a hydrate, a solvate, or a salt thereof, or a mixture of same, of any of the compounds of formula (I).

It is to be understood that the present invention relates to any sub-combination within any embodiment of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

In a preferred embodiment, the present invention relates to a method of preparing compounds of general formula (I), supra, in which method an intermediate compound of general formula (5):

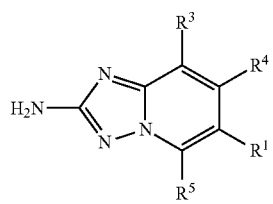

(5)

in which $R^1$, $R^3$, $R^4$, and $R^5$ are as defined for the compounds of general formula (I), supra, is allowed to react with an aryl compound of general formula (5a):

$$R^2—Y \quad (5a)$$

in which $R^2$ is as defined for the compounds of general formula (I), supra, and Y represents a leaving group, such as a halogen atom or a trifluoromethylsulphonyloxy or nonafluorobutylsulphonyloxy group for example, thus providing a compound of general formula (I):

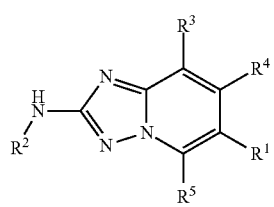

(I)

in which $R^1$, $R^2$, $R^3$, $R^4$, and $R^5$ are as defined for the compounds of general formula (I), supra.

In another embodiment, the present invention relates to a method of preparing compounds of general formula (I), supra, in which method an intermediate compound of general formula (7):

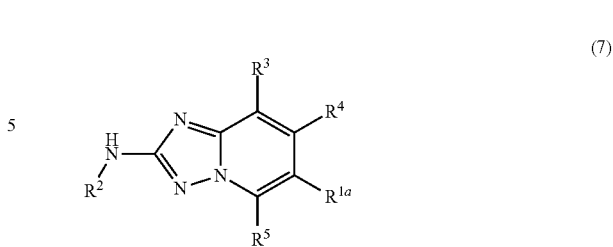

(7)

in which $R^2$, $R^3$, $R^4$, and $R^5$ are as defined for the compounds of general formula (I), supra, and $R^{1a}$ is an aryl or heteroaryl group to which an —$NH_2$ substituent is bound, and to which one or more $R^{xy}$ substituents are optionally bound, is allowed to react with a compound of general formula:

$$R^{1b}—X \quad (7a)$$

in which $R^{1b}$ is —C(=O)$R^6$, —C(=O)NR$^6$R$^7$, —S(=O)$R^6$, or —S(=O)$_2$R$^6$, ($R^6$ and $R^7$ being as defined as for compounds of general formula (I), supra), and X is a suitable functional group (e.g. an —OH, —O—$C_1$-$C_6$-alkyl group, or a halogen atom), via which the $R^{1b}$ of the $R^{1b}$—X compound (7a) can be coupled, via a coupling reaction, such as an amide coupling reaction for example, onto the —$NH_2$ substituent bound to the aryl or heteroaryl group of $R^{1a}$ of compound (7), thereby replacing said X with said $R^{1a}$, thus providing a compound of general formula (I):

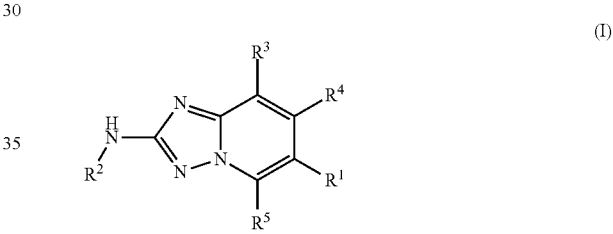

(I)

in which $R^1$, $R^2$, $R^3$, $R^4$, and $R^5$ are as defined for the compounds of general formula (I), supra.

In another embodiment, the present invention relates to a method of preparing compounds of general formula (I), supra, in which method an intermediate compound of general formula (7):

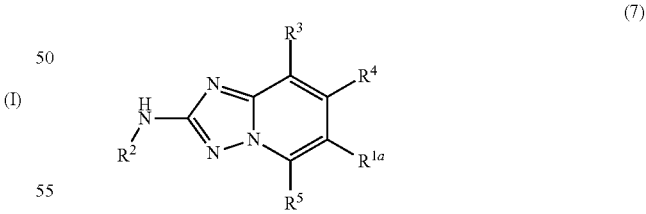

(7)

in which $R^2$, $R^3$, $R^4$, and $R^5$ are as defined for the compounds of general formula (I), supra, and $R^{1a}$ is an aryl or heteroaryl group to which a —COOH substituent is bound, and to which one or more $R^{xy}$ substituents are optionally bound, is allowed to react with a compound of general formula:

$$R^{1b}—X \quad (7a)$$

in which $R^{1b}$ is —NR$^6$R$^7$ ($R^6$ and $R^7$ being as defined as for general formula (I), supra), and X is a suitable functional group (e.g. a hydrogen atom), via which the $R^{1b}$ of the $R^{1b}$—X compound (7a) can be coupled, via a coupling reaction, such as an amide coupling reaction for example, onto the —COOH substituent bound to the aryl or heteroaryl group of $R^{1a}$ of compound (7), thereby replacing said X with said $R^{1a}$, thus providing a compound of general formula (I):

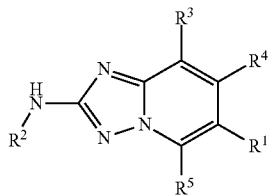

(I)

in which $R^1$, $R^2$, $R^3$, $R^4$, and $R^5$ are as defined for the compounds of general formula (I), supra.

In another embodiment, the present invention relates to a method of preparing compounds of general formula (I), supra, in which method an intermediate compound of general formula (4):

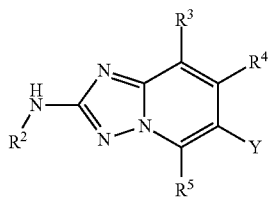

(4)

in which $R^2$, $R^3$, $R^4$, and $R^5$ are as defined for the compounds of general formula (I), supra, and Y represents a leaving group, such as a halogen atom or a trifluoromethylsulphonyloxy or nonafluorobutylsulphonyloxy group for example, is allowed to react with a compound of general formula:

$R^1$—Z in which $R^1$ is as defined for the compounds of general formula (I), supra, and Z represents a suitable functional group like for example a boronic acid or a boronic ester, thus providing a compound of general formula (I):

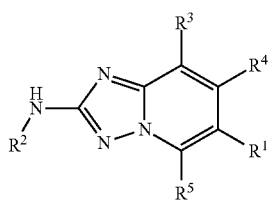

(I)

in which $R^1$, $R^2$, $R^3$, $R^4$, and $R^5$ are as defined for the compounds of general formula (I), supra.

In accordance with a further aspect, the present invention covers intermediate compounds which are useful in the preparation of compounds of the present invention of general formula (I), particularly in the method described herein.

In particular, the present invention covers:
a) compounds of general formula (5):

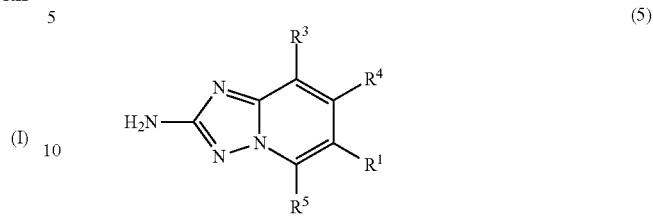

(5)

in which $R^1$, $R^3$, $R^4$, and $R^5$ are as defined for the compounds of general formula (I), supra,
or a stereoisomer, a tautomer, an N-oxide, a hydrate, a solvate, or a salt thereof, or a mixture of same;
and
b) compounds of general formula (7):

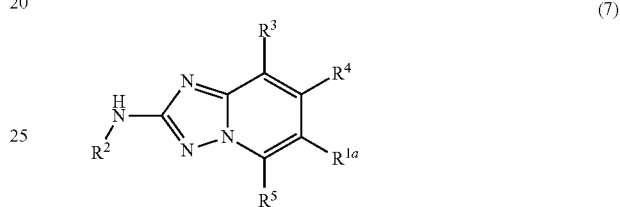

(7)

in which $R^2$, $R^3$, $R^4$, and $R^5$ are as defined for the compounds of general formula (I), supra, and $R^{1a}$ is an aryl or heteroaryl group to which an —NH$_2$ substituent is bound,
or a stereoisomer, a tautomer, an N-oxide, a hydrate, a solvate, or a salt thereof, or a mixture of same;
and
c) compounds of general formula (4):

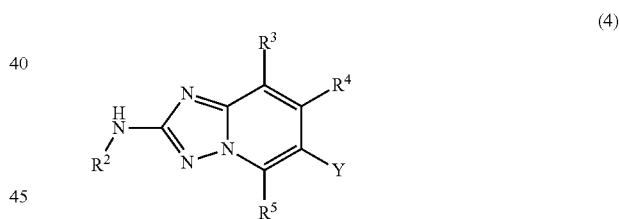

(4)

in which $R^2$, $R^3$, $R^4$, and $R^5$ are as defined for the compounds of general formula (I), supra, and Y represents a leaving group, such as a halogen atom or a trifluoromethylsulphonyloxy or nonafluorobutylsulphonyloxy group for example, or a stereoisomer, a tautomer, an N-oxide, a hydrate, a solvate, or a salt thereof, or a mixture of same.

In accordance with yet another aspect, the present invention covers the use of the intermediate compounds:
a) of general formula (5):

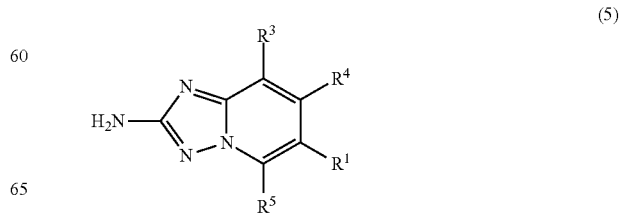

(5)

in which $R^1$, $R^3$, $R^4$, and $R^5$ are as defined for the compounds of general formula (I), supra,
or
b) of general formula (7):

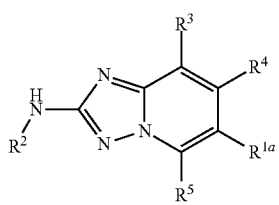

(7)

in which $R^2$, $R^3$, $R^4$, and $R^5$ are as defined for the compounds of general formula (I), supra, and $R^{1a}$ is an aryl or heteroaryl group to which an —$NH_2$ substituent is bound,
or
c) of general formula (4):

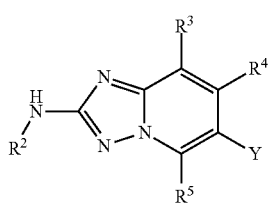

(4)

in which $R^2$, $R^3$, $R^4$, and $R^5$ are as defined for the compounds of general formula (I), supra, and Y represents a leaving group, such as a halogen atom or a trifluoromethylsulphonyloxy or nonafluorobutylsulphonyloxy group for example, for the preparation of compounds of general formula (I) of the present invention as defined in the claims.

EXPERIMENTAL SECTION

The following Table lists the abbreviations used in this paragraph, and in the Examples section. NMR peak forms are stated as they appear in the spectra, possible higher order effects have not been considered.

| Abbreviation | Meaning |
| --- | --- |
| Ac | Acetyl |
| BINAP | 2,2'-bis(diphenylphosphino)-1,1'-binaphthyl |
| Boc | tert-butyloxycarbonyl |
| br | Broad |
| Brett-Phos | 2-(Dicyclohexylphosphino)-3,6-dimethoxy-2'-4'-6'-tri-i-propyl-1,1'-biphenyl |
| c- | Cyclo- |
| d | Doublet |
| dd | doublet of doublets |
| DCM | Dichloromethane |
| DME | 1,2-dimethoxyethane |
| DIPE | Diisopropylether |
| DIPEA | N,N-diisopropylethylamine |
| DMF | N,N-dimethylformamide |
| DMSO | Dimethyl sulfoxide |
| Dppf | 1,1'-bis(di-phenylphosphino)ferrocene |
| Eq | Equivalent |
| ESI | electrospray ionisation |
| HATU | N-[(dimethylamino)(3H-[1,2,3]triazolo[4,5-b]pyridin-3-yloxy)methylene]-N-methylmethanaminium hexafluorophosphate |

-continued

| Abbreviation | Meaning |
| --- | --- |
| Hünig Base | N,N-diisopropylethylamine |
| m | Multiplet |
| m.p. | melting point in ° C. |
| MS | mass spectrometry |
| MW | molecular weight |
| NaOtBu | sodium tert-butoxide; sodium 2-methylpropan-2-olate |
| NMP | N-methylpyrrolidinone |
| NMR | nuclear magnetic resonance spectroscopy: chemical shifts (δ) are given in ppm. |
| $PdCl_2(PPh_3)_2$ | Dichlorobis(triphenylphosphine)palladium(II) |
| $Pd(dba)_2$ | bis-(dibenzylideneacetone)-palladium(0) complex |
| $Pd_2(dba)_3$ | tris-(dibenzylideneacetone)-dipalladium(0)-chloroform complex |
| $Pd(dppf)Cl_2$ | Dichloro[1,1'-bis(diphenylphosphino)ferrocene] palladium(II) |
| $Pd(dppf)Cl_2 \cdot CH_2Cl_2$ | Dichloro[1,1'-bis(diphenylphosphino)ferrocene] palladium(II) dichloromethane adduct |
| Pd-Brett-Phos-pre-cat | Chloro[2-(dicyclohexylphosphino)-3,6-dimethoxy-2'-4'-6'-tri-i-propyl-1,1'-biphenyl][2-(2-aminoethyl)phenyl]palladium(II) |
| Pd—tBu—X-Phos-pre-cat | Chloro(2-di-t-butylphosphino-2',4',6'-tri-i-propyl-1,1'-biphenyl)[2-(2-aminoethyl)phenyl] palladium(II), |
| Pd—X-Phos-pre-cat | Chloro(2-dicyclohexylphosphino-2',4',6'-tri-i-propyl-1,1'-biphenyl)[2-(2-aminoethyl)phenyl] palladium(II) methyl-t-butylether adduct |
| $PPh_3$ | Triphenylphosphine |
| $P(oTol)_3$ | tri-o-tolylphosphine |
| q | Quartet |
| quin | Quintett |
| Rac | Racemic |
| Rt | Room temperature |
| r.t. | Room temperature |
| RT | Retention time in minutes |
| s | Singlet |
| t | Triplet |
| tBu—X-Phos | 2-Di-t-butylphosphino-2',4',6'-tri-i-propyl-1,1'-biphenyl |
| TBTU | N-[(1H-benzotriazol-1-yloxy)(dimethylamino) methylene]-N-methylmethanaminium tetrafluoroborate |
| TEA | Triethylamine |
| TFA | trifluoroacetic acid |
| THF | Tetrahydrofuran |
| Ts | Para toluenesulfonyl; (tosyl) |
| UPLC | ultra performance liquid chromatography |
| X-Phos | 2-Dicyclohexylphosphino-2',4',6'-triisopropylbiphenyl |

The schemes and procedures described below illustrate general synthetic routes to the compounds of general formula (I) of the invention and are not intended to be limiting. It is clear to the person skilled in the art that the order of transformations as exemplified in the Schemes can be modified in various ways. The order of transformations exemplified in the Schemes is therefore not intended to be limiting. In addition, interconversion of any of the substituents, $R^1$, $R^2$, $R^3$, $R^4$, $R^5$, $R^6$, $R^7$, $R^8$ or $R^9$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

A first reaction scheme is outlined infra:

Synthesis of Compounds of General Formula (I) of the Present Invention compound (4), thereby replacing said Y with said $R^1$ moiety. Many aryl halides of the formula $R^2$—Y may be obtained commercially. Reagents of the general structure $R^{1a}$—Z and $R^1$—Z can for example be aryl boronic acids or aryl boronic

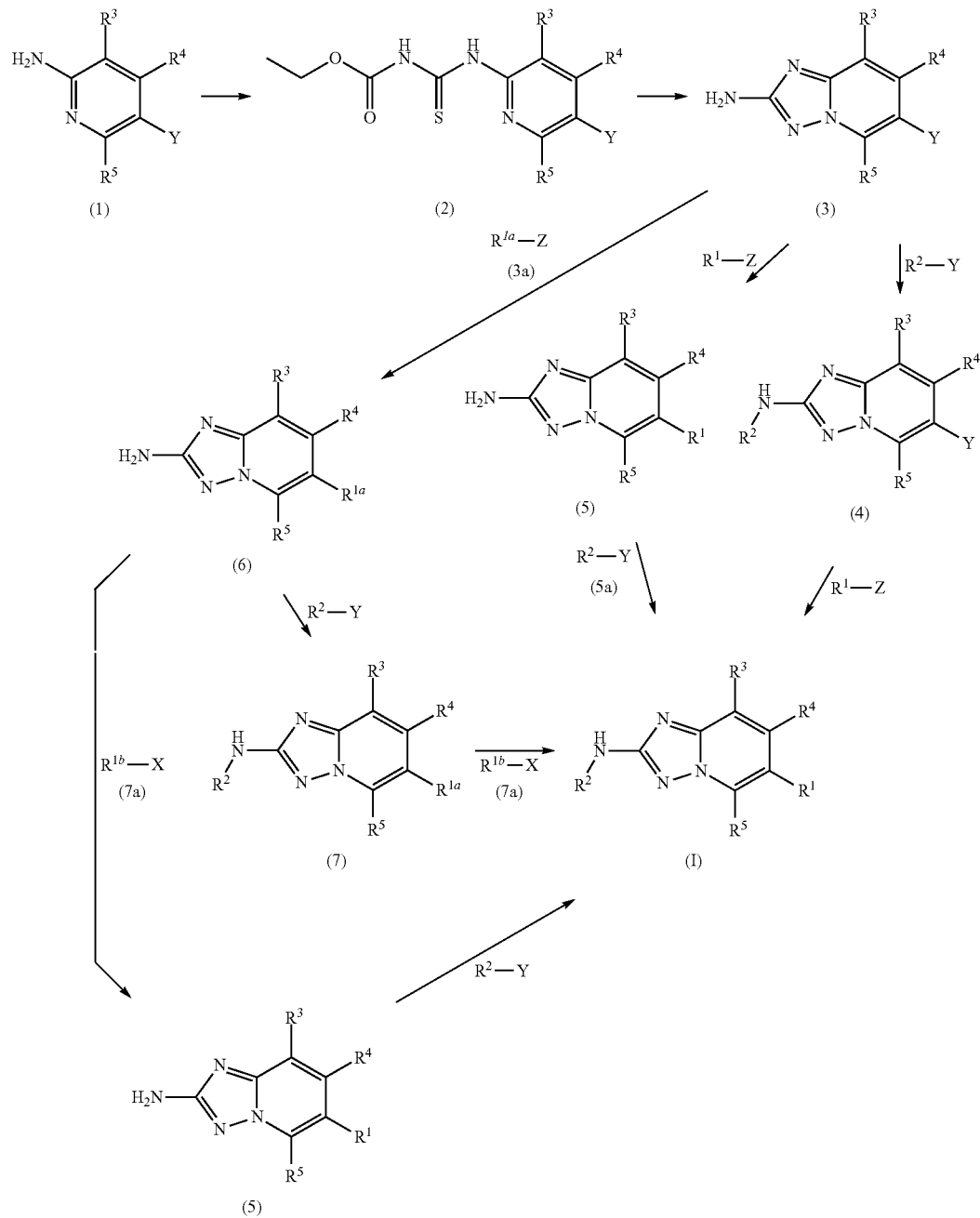

wherein $R^1$, $R^2$, $R^3$, $R^4$ and $R^5$ are as defined for the compounds of general formula (I), supra, and Y represents a leaving group, such as a halogen atom or a trifluoromethylsulphonyloxy or nonafluorobutylsulphonyloxy group for example, and Z represents a suitable functional group via which the $R^1$ of the $R^1$—Z compound can be coupled, by a coupling reaction, onto the Y-bearing carbon atom of a esters. Many such reagents of the general structures $R^{1a}$—Z and $R^1$—Z are also commercially available. Reagents of the general structures $R^{1a}$—Z and $R^1$—Z can be prepared from aryl halides [see for example K. L. Billingslay, T. E. Barde, S. L Buchwald, Angew. Chem. 2007, 119, 5455 or T. Graening, Nachrichten aus der Chemie, January 2009, 57, 34].

R$^{1a}$ can be converted to R$^1$ in one or several steps. Typically, R$^{1a}$ can be a protected aryl-amine, especially -aryl-NH-Boc, or an aryl-carboxylic acid, [-aryl-C(O)OH] or an -aryl-carboxylic acid ester [-aryl-C(O)O-alkyl]. Furthermore, the aryl or heteroaryl group of R$^{1a}$ can optionally be substituted with one or more substituents R$^{xy}$ (R$^{xy}$ being as defined as for compounds of general formula (I) of the present invention as defined supra). For example, when R$^{1a}$ is an aryl group to which one or more substituents R$^{xy}$ are optionally bound, and to which an —NH$_2$ substituent is bound, this —NH$_2$ substituent may be allowed to react with a compound of general formula R$^{1b}$—X (7a), in which R$^{1b}$ is —C(=O)R$^6$, —C(=O)NR$^6$R$^7$, —S(=O)R$^6$, or —S(=O)$_2$R$^6$, (R$^6$ and R$^7$ being as defined as for compounds of general formula (I) of the present invention as defined in the claims), and X is a suitable functional group (e.g. an —OH, —O—C$_1$-C$_6$-alkyl group, or a halogen atom), via which the R$^{1b}$ of the R$^{1b}$—X compound (7a) can be coupled, via a coupling reaction, such as an amide coupling reaction for example, onto the —NH$_2$ substituent bound to the aryl group R$^{1a}$ of compound (7), thereby replacing said X with said R$^{1a}$, thus providing a compound of general formula (I) of the present invention.

Compounds of general formula (I) can be synthesised according to the procedures depicted in Scheme 1.

The person skilled in the art will recognise that there are many precedented methods for synthesising suitable 3,4,6-substituted 5-halo-pyridin-2-ylamines of general formula (I); some 3,4,6-substituted 5-halo-pyridin-2-ylamines may be obtained commercially.

A suitably substituted 5-halo-pyridin-2-ylamine intermediate of general formula (I) is converted to the corresponding intermediate of general formula (2) by reaction with a suitable oxycarbonylisothiocyanat, such as for example ethoxycarbonylisothiocyanat at temperatures ranging from room temperature to the boiling point of the solvent, preferably room temperature [see for example M. Nettekoven, B. Püllnnann, S. Schmitt, Synthesis 2003, 1643-1652].

Intermediates of general formula (2) may be converted to 6-Halo-[1,2,4]triazolo[1,5-a]pyridin-2-ylamine intermediates of general formula (3) by reaction with a suitable reagent, for example hydroxylamine hydrochloride, in presence of a suitable base, such as, for example DIPEA in a suitable solvent system, such as, for example, methanol, ethanol, 1-propanol, 2-propanol or mixtures of these solvents at elevated temperatures, e.g. 60° C. [see for example M. Nettekoven, B. Püllnnann, S. Schmitt, Synthesis 2003, 1643-1652].

Intermediates of general formula (3) can be converted to intermediates of general formula (4) by reaction with suitable aryl compounds R$^2$—Y, preferably aryl bromides, or aryl iodides or for example aryl trifluoromethylsulphonates or aryl nonafluorobutylsulphonates in the presence of a suitable base, such as, for example NaOtBu or caesium carbonate or potassium phosphate, and a suitable catalyst/ligand system, such as for example Pd$_2$(dba)$_3$/rac-BINAP, Pd$_2$ dba$_3$/X-Phos, Pd$_2$ dba$_3$/tBu-X-Phos, Pd$_2$ dba$_3$/Brett-Phos, Pd-X-Phos-pre-cat/X-Phos, Pd-tBu-X-Phos-pre-cat/tBu-X-Phos, Pd-Brett-Phos-pre-cat/Brett-Phos in a suitable solvent such as THF, toluene, xylene, DME, or NMP, or mixtures of these solvents at temperatures ranging from room temperature to the 200° C. The person skilled in the art will recognise that the appropriate choice of reaction conditions, such as temperature, choice of solvent and catalyst system is critical for preferred derivatization at the amino group of intermediates of general formula (3).

Intermediates of general formula (4) can be converted to compounds of general formula (I) by reaction with a suitable reagent, like for example a boronic acid derivative in the presence of a suitable catalyst system, like for example Pd(OAc)$_2$ and P(oTol)$_3$, or PdCl$_2$(PPh$_3$)$_2$ and PPh$_3$ and a suitable base, like for example aqueous potassium carbonate in a suitable solvent, like for example THF, DME, ethanol or 1-propanol or mixtures of these solvents at temperatures ranging from room temperature to 200° C., preferably the boiling point of the used solvent.

In an alternative route for the synthesis of compounds of general formula (I), Intermediates of general formula (3) can be reacted with a suitable reagent, like for example a boronic acid derivative in the presence of a suitable catalyst system, like for example Pd(OAc)$_2$ and P(oTol)$_3$, or PdCl$_2$(PPh$_3$)$_2$ and PPh$_3$ and a suitable base, like for example aqueous potassium carbonate in a suitable solvent, like for example THF, DME, ethanol or 1-propanol or mixtures of these solvents at temperatures ranging from room temperature to 200° C., preferably the boiling point of the used solvent to furnish intermediates of the general formula (5).

Intermediates of general formula (5) can be converted to compounds of general formula (I) by reaction with suitable aryl compounds R$^2$—Y, preferably aryl bromides, or aryl iodides or for example aryl trifluoromethylsulphonates or aryl nonafluorobutylsulphonates in the presence of a suitable base, such as, for example NaOtBu or caesium carbonate or potassium phosphate, and a suitable catalyst/ligand system, such as for example Pd$_2$(dba)$_3$/rac-BINAP, Pd$_2$ dba$_3$/X-Phos, Pd$_2$ dba$_3$/tBu-X-Phos, Pd$_2$ dba$_3$/Brett-Phos, Pd-X-Phos-pre-cat/X-Phos, Pd-tBu-X-Phos-pre-cat/tBu-X-Phos, Pd-Brett-Phos-pre-cat/Brett-Phos in a suitable solvent such as THF, toluene, xylene, DME, or NMP, or mixtures of these solvents at temperatures ranging from room temperature to the 200° C.

Also as depicted in Scheme 1, is a further alternative route for the synthesis of compounds of general formula (I): Intermediates of general formula (3) can be converted to intermediates of general formula (6) by a coupling reaction as described supra for synthesis of intermediate of general formula (5), thereby replacing said Y of intermediates of general formula (3) with said R$^{1a}$ moiety. Intermediates of general formula (6) can then be converted to intermediates of general formula (7) by a coupling reaction as described supra for synthesis of intermediates of general formula (4), thereby forming a bond between NH and said R$^2$ moiety.

Intermediates of general formula (7) can then be converted to compounds of general formula (I) by one or more further transformations. These can be modifications such as cleavage of protecting groups, reduction or oxidation of functional groups, halogenation, metallation, substitution or other reactions known to the person skilled in the art, for example the formation of an amide bond, the formation of a urea, or the formation of a sulfonamide, thereby converting R$^{1a}$ to said R$^1$ moiety.

Also as depicted in Scheme 1, is a further alternative route for the synthesis of compounds of general formula (I): Intermediates of general formula (3) can be converted to intermediates of general formula (6) by a coupling reaction as described supra for synthesis of intermediate of general formula (5), thereby replacing said Y of intermediates of general formula (3) with said R$^{1a}$ moiety. Intermediates of general formula (6) can then be converted to intermediates of general formula (5) by one or more further transformations. These can be modifications such as cleavage of protecting groups, reduction or oxidation of functional groups, halogenation, metallation, substitution or other reactions known to the person skilled in the art, for example the formation of an amide bond, the formation of a urea, or the formation of a sulphonamide, thereby converting $R^{1a}$ to said $R^1$ moiety.

Intermediates of general formula (5) can then be converted to compounds of general formula (I) by a coupling reaction as described supra for synthesis of intermediates of general formula (4), thereby forming a bond between NH and said $R^2$ moiety.

Each of the Schemes 2-8, infra, illustrates specific transformations for the synthesis of some selected compounds according to general formula (I).

Scheme 2: Synthesis of compounds of general formula (11)

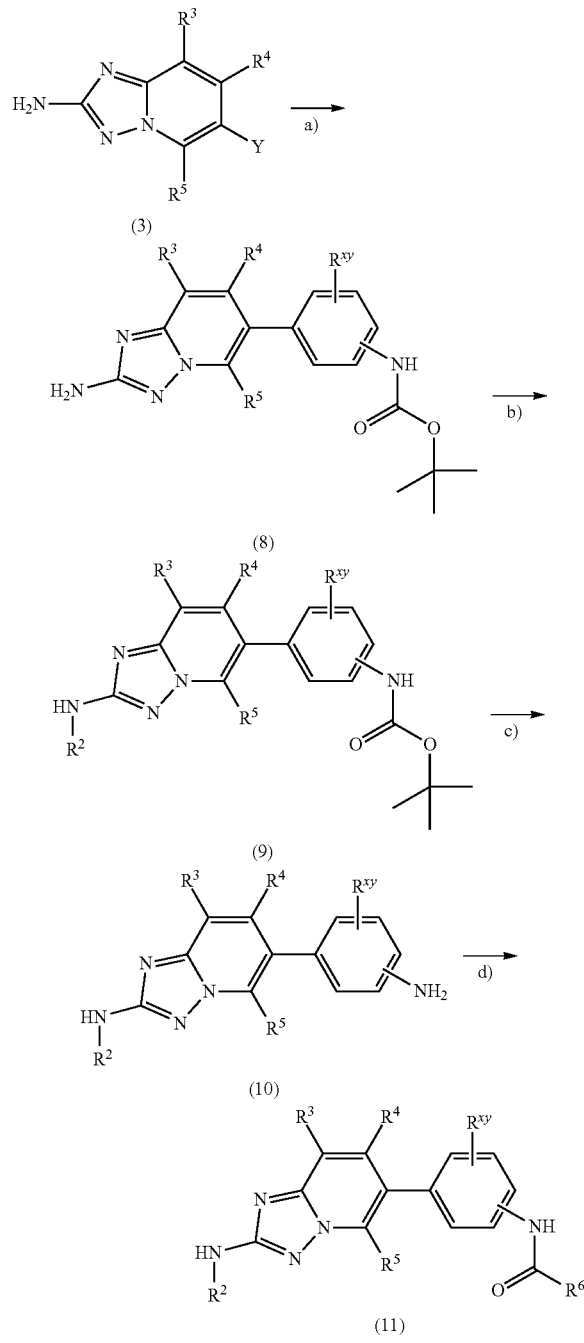

Scheme 2: Synthesis of compounds of general formula (11), wherein $R^2$, $R^3$, $R^4$, $R^5$, $R^6$ and $R^{xy}$ are as defined for the compounds of general formula (I), supra. Y is a leaving group, e.g. a halogen. a) coupling reaction using conditions as described supra for synthesis of intermediates of general formula (5); b) coupling reaction using conditions as described supra for synthesis of intermediates of general formula (4); c) removal of a Boc-protecting group using conditions known to the person skilled in the art (see for example T. W. Greene and P. G. M. Wuts in *Protective Groups in Organic Synthesis*, 3$^{rd}$ edition, Wiley 1999); d) Conditions for the formation of an amide bond, e.g. using coupling reagents like HATU or TBTU and a base like potassium carbonate or DIPEA in an inert solvent like THF, DMF, DCM or NMP.

Scheme 3: Synthesis of compounds of general formula (12)

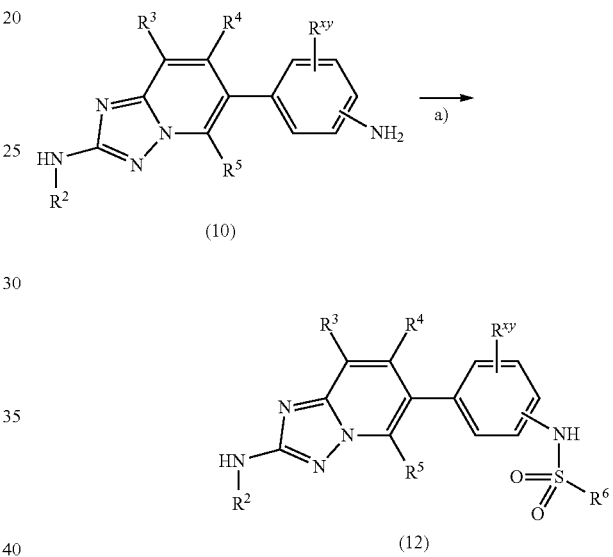

Scheme 3: Synthesis of compounds of general formula (12), wherein $R^2$, $R^3$, $R^4$, $R^5$, $R^6$ and $R^{xy}$ are as defined for the compounds of general formula (I), supra. a) Conditions for the formation of a sulfonamide, e.g. using a sulfonyl chloride and a base like DIPEA in an inert solvent like for example THF, DMF, DCM or NMP at temperatures ranging from room temperature to the 70° C.

Scheme 4: Synthesis of compounds of general formula (13)

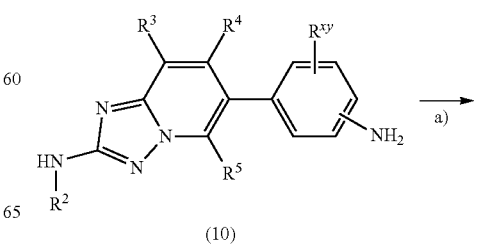

-continued

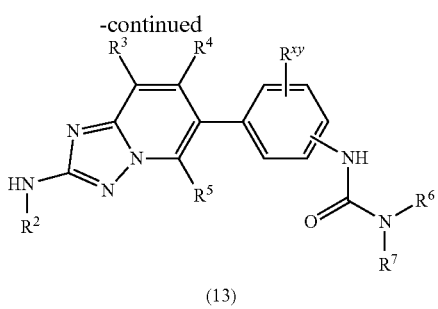

(13)

Scheme 4: Synthesis of compounds of general formula (13), wherein $R^2$, $R^3$, $R^4$, $R^5$, $R^6$, $R^7$ and $R^{xy}$ are as defined for the compounds of general formula (I), supra. a) Conditions for the formation of an urea, e.g. using an isocyanate in an inert solvent like for example THF, DMF, DCM or NMP at temperatures ranging from room temperature to 70° C. Alternatively, a two step procedure which involves reaction of 4-Nitrophenyl chloroformate in an inert solvent like for example THF or DCM and a base like pyridine at temperatures ranging from 0° C. to room temperature, followed by reaction with an amine in an inert solvent like THF or DCM at temperatures ranging from 0° C. to 40° C., can be used.

Scheme 5: Synthesis of compounds of general formula (15)

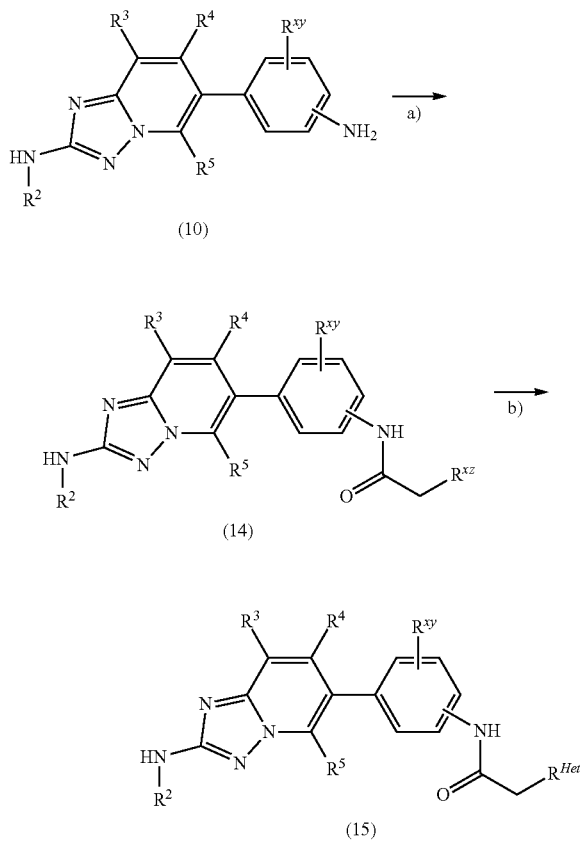

Scheme 5: Synthesis of compounds of general formula (15), wherein $R^2$, $R^3$, $R^4$, $R^5$ and $R^{xy}$ are as defined for the compounds of general formula (I), supra. RXZ is a leaving group, e.g. a halogen. $R^{Het}$ is 3- to 10-membered heterocloalkyl, as defined supra. a) Conditions for the formation of an amide bond, e.g. using coupling reagents like for example HATU or TBTU and a base like for example potassium carbonate or DIPEA in an inert solvent like for example THF, DMF, DCM or NMP. Alternatively, an acid chloride and a base like for example pyridine can be used in an inert solvent like for example THF or DCM. b) Reaction with a heterocyclic amine, like e.g. piperidine in a polar solvent like for example DMF or NMP using a base like for example potassium carbonate and optionally using a catalytic amount of potassium iodide.

Scheme 6: Synthesis of compounds of general formula (11)

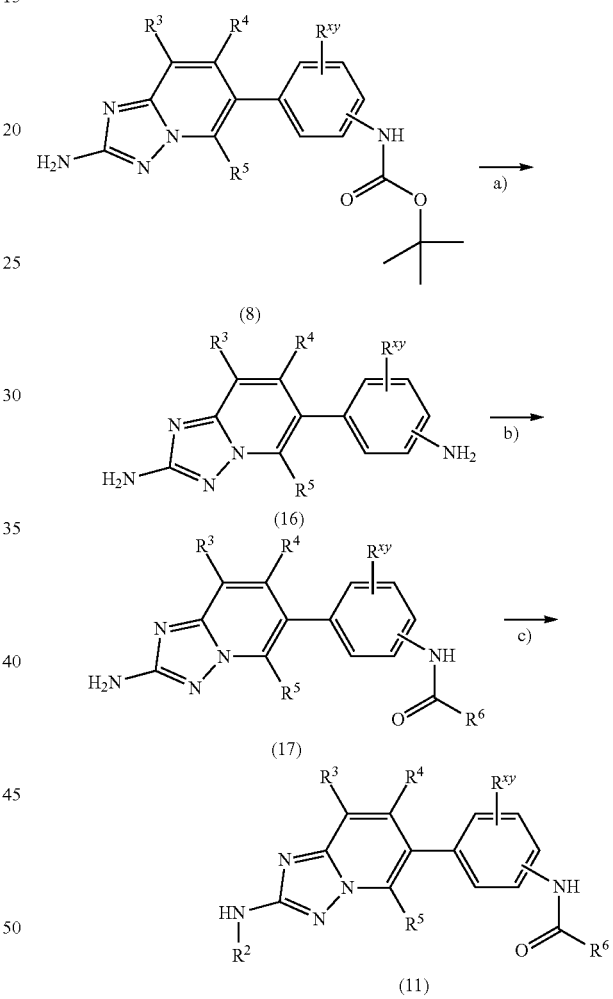

Scheme 6: Synthesis of compounds of general formula (11), wherein $R^2$, $R^3$, $R^4$, $R^5$, $R^6$ and $R^{xy}$ are as defined for the compounds of general formula (I), supra. a) removal of a Boc-protecting group using conditions known to the person skilled in the art (see for example T. W. Greene and P. G. M. Wuts in *Protective Groups in Organic Synthesis*, 3$^{rd}$ edition, Wiley 1999); b) conditions for the formation of an amide bond, e.g. using coupling reagents like for example HATU or TBTU and a base like for example potassium carbonate or DIPEA in an inert solvent like for example THF, DMF, DCM or NMP; c) coupling reaction using conditions as described supra for synthesis of intermediates of general formula (4).

Scheme 7: Synthesis of compounds of general formula (22)

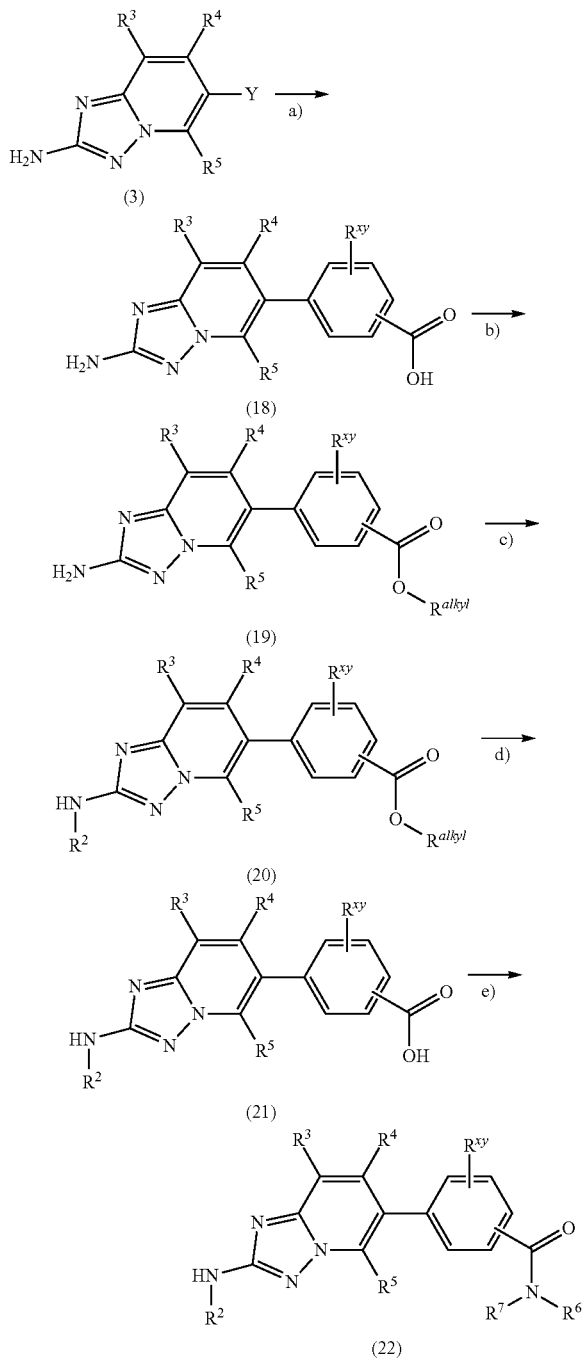

Scheme 8: Synthesis of compounds of general formula (22)

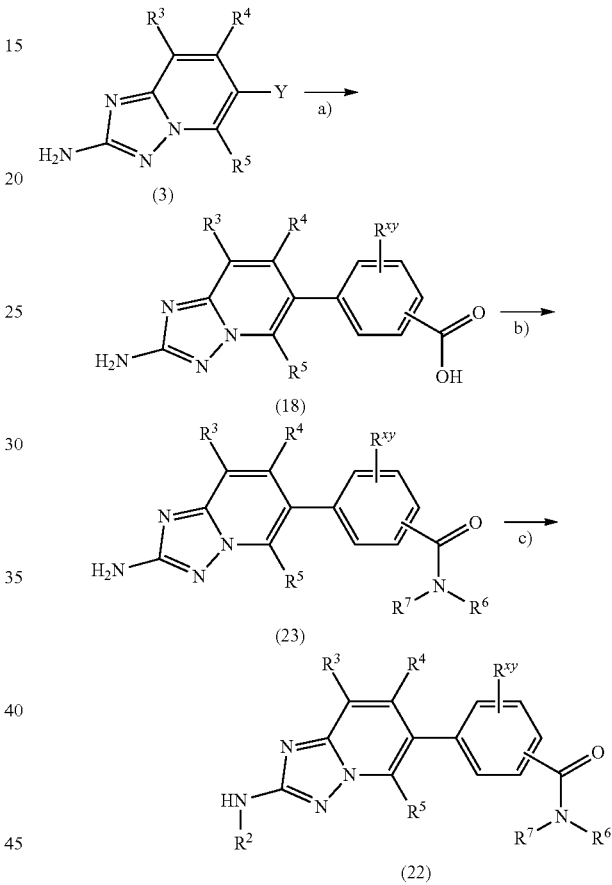

Scheme 7: Synthesis of compounds of general formula (21), wherein $R^2$, $R^3$, $R^4$, $R^5$, $R^6$, $R^7$ and $R^{xy}$ are as defined for the compounds of general formula (I), supra. $R^{alkyl}$ is $C_1$-$C_6$-alkyl. a) coupling reaction using conditions as described supra for synthesis of intermediates of general formula (6); b) formation of an ester using conditions known to the person skilled in the art (see for example T. W. Greene and P. G. M. Wuts in *Protective Groups in Organic Synthesis*, $3^{rd}$ edition, Wiley 1999), e.g. using thionyl chloride in the appropriate alcohol at temperatures ranging from room temperature to 100° C.; c) coupling reaction using conditions as described supra for synthesis of intermediates of general formula (4); d) hydrolysis for an ester using conditions known to the person skilled in the art (see for example T. W. Greene and P. G. M. Wuts in *Protective Groups in Organic Synthesis*, $3^{rd}$ edition, Wiley 1999), e.g. sodium hydroxide in a mixture of THF, methanol an water at r.t.; e) conditions for the formation of an amide bond, e.g. using coupling reagents like for example HATU or TBTU and a base like for example potassium carbonate or DIPEA in an inert solvent like for example THF, DMF, DCM or NMP.

Scheme 8: Synthesis of compounds of general formula (21), wherein $R^2$, $R^3$, $R^4$, $R^5$, $R^6$, $R^7$ and $R^{xy}$ are as defined for the compounds of general formula (I), supra. a) coupling reaction using conditions as described supra for synthesis of intermediates of general formula (6); b) conditions for the formation of an amide bond, e.g. using coupling reagents like for example HATU or TBTU and a base like for example potassium carbonate or DIPEA in an inert solvent like for example THF, DMF, DCM or NMP; c) coupling reaction using conditions as described supra for the synthesis of intermediates of general formula (4).

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be stirred out using a suitable solvent. In some cases, the compounds may be purified by chromatography, particularly flash chromatography, using for example pre-packed silica gel cartridges, e.g. from Separtis such as Isolute® Flash silica gel (silica gel chromatography) or Isolute® Flash NH2 silica gel (aminophase-silica-gel chromatography) in combination with a suitable chromatographic system such as a Flashmaster II (Separtis) or an Isolera system (Biotage) and eluents such as, for example, gradients of hexane/ethyl acetate or DCM/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluents such as, for example, gradients of water and acetonitrile which may contain additives such as trifluoroacetic acid, formic acid or aqueous ammonia.

Analytical UPLC-MS was performed as follows:

Method A: System: UPLC Acquity (Waters) with PDA Detector and Waters ZQ mass spectrometer; Column: Acquity BEH C18 1.7 μm 2.1×50 mm; Temperature: 60° C.; Solvent A: Water+0.1% formic acid; Solvent B: acetonitrile; Gradient: 99% A→1% A (1.6 min)→1% A (0.4 min); Flow: 0.8 mL/min; Injection Volume: 1.0 μl (0.1 mg-1 mg/mL sample concentration); Detection: PDA scan range 210-400 nm—Fixed and ESI (+), scan range 170-800 m/z Names of compounds were generated using ACD/Name Batch ver. 12.00 or ACD/Name Batch ver. 12.01. Names of compounds in table format were generated using ACD/Name Batch ver. 12.00.

Synthesis of Intermediate Compounds

Intermediate Example Int01.01

Ethyl [(5-bromopyridin-2-yl)carbamothioyl]carbamate

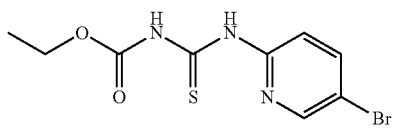 [SMILES: CCOC(=O)NC(=S)Nc1ccc(Br)cn1]

Ethoxycarbonylisothiocyanat (16.7 g) was added to a stirred solution of 2-amino-5-brompyridine (20 g) in dioxane (200 ml). The mixture was stirred for 2 h at room temperature A white solid precipitated. Hexane (20 ml) was added and the white solid was collected by filtration.

Yield: 30.4 g of the title compound.

$^1$H-NMR (300 MHz, DMSO-$d_6$): δ [ppm]=1.22 (t, 3H), 4.19 (q, 2H), 8.08 (dd, 1H), 8.49 (d, 1H), 8.57 (br. d, 1H), 11.37-12.35 (m, 2H).

Intermediate Example Int01.02

6-Bromo[,2]triazolo[1,5-a]pyridin-2-amine

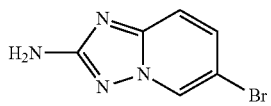

Hydroxylammoniumchlorid (39.8 g) was suspended in methanol (200 ml) and ethanol (190 ml) and Hünig Base (59 ml) was added at room temperature The mixture was heated to 60° C., Int01.01 (30 g) was added portionwise, and the mixture was stirred at 60° C. for 2 h. The solvent was removed in vacuum and water (150 ml) was added. A solid was collected by filtration and was washed with water and dried in vacuum.

Yield: 19.3 g of the title compound.

$^1$H-NMR (300 MHz, DMSO-$d_6$): δ [ppm]=6.10 (s, 2H), 7.28 (dd, 1H), 7.51 (dd, 1H), 8.88 (dd, 1H).

Intermediate Example Int02.01 tert-butyl [4-(2-amino[,2]triazolo[1,5-a]pyridin-6-yl)phenyl]carbamate

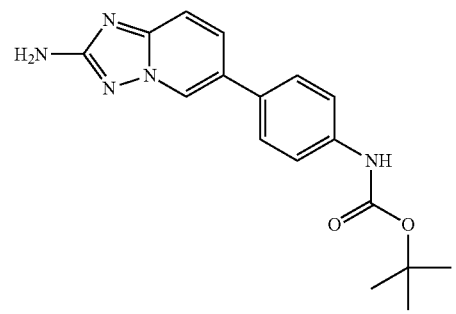 [SMILES: CC(C)(C)OC(=O)Nc1ccc(-c2ccc3nc(N)nn3c2)cc1]

To a stirred solution of Int01.02 (12.0 g) in 1-propanol (350 ml) was added 2M potassium carbonate solution (85 ml), {4-[(tert-butoxycarbonyl)amino]phenyl}boronic acid (14.7 g), triphenylphosphine (739 mg) and PdCl$_2$(PPh$_3$)$_2$ (1.98 g). The mixture was heated to reflux for 1 h, the solvent was removed in vacuum, water (250 mL) was added and the mixture was extracted with ethyl acetate. The organic phase was washed with saturated sodium chloride solution, dried (sodium sulfate), filtered through Celite and the solvent was removed in vacuum. The residue was titurated with DCM to give the title compound as a white solid. Yield: 15.7 g.

$^1$H-NMR (400 MHz, DMSO-$d_6$): δ [ppm]=1.37-1.55 (m, 9H), 5.99 (s, 2H), 7.36 (dd, 1H), 7.48-7.55 (m, 2H), 7.55-7.62 (m, 2H), 7.69 (dd, 1H), 8.78 (dd, 1H), 9.44 (s, 1H).

Intermediate Example Int02.02

6-(4-aminophenyl)[,2]triazolo[1,5-a]pyridin-2-amine

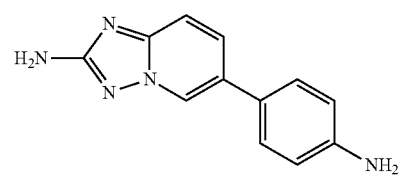 [SMILES: Nc1ccc(-c2ccc3nc(N)nn3c2)cc1]

To a stirred suspension of Int02.01 (7.05 g) in DCM (210 mL) was added TFA (66 mL). The mixture was stirred at room temperature for 1 h. The mixture was concentrated in vacuum. A saturated solution of potassium carbonate was added, until pH 10 was reached and the mixture was extracted for three times with DCM and methanol (10:1). The organic phase was dried (sodium sulfate) and the solvent was removed in vacuum to give 4.6 g of the title compound.

$^1$H-NMR (300 MHz, DMSO-d$_6$): δ [ppm]=5.26 (s, 2H), 5.95 (s, 2H), 6.64 (d, 2H), 7.29-7.45 (m, 3H), 7.64 (dd, 1H), 8.60-8.70 (m, 1H).

Intermediate Example Int02.03

N-[4-(2-amino[,2]triazolo[1,5-a]pyridin-6-yl)phenyl]-2-cyclopropylacetamide

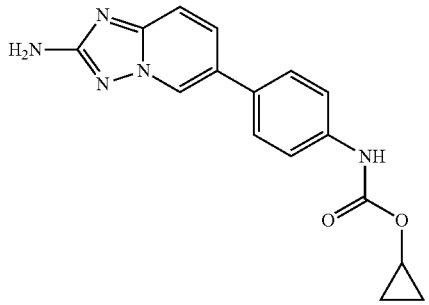 [SMILES: Nc1nc2ccc(-c3ccc(NC(=O)OC4CC4)cc3)cn2n1]

To a stirred solution of Int02.02 (3.0 g) in THF (95 mL) was added Hünig Base (2.75 mL), cyclopropylacetic acid (1.65 g) and HATU (6.1 g). The mixture was stirred at room temperature for 16 h. Water was added and the mixture was stirred at room temperature for 20 minutes. The precipitated solid was collected by filtration, was washed with water and methanol and was dried in vacuum to give 3.08 g of the title compound.

$^1$H-NMR (300 MHz, DMSO-d$_6$): δ [ppm]=0.16 (dd, 2H), 0.39-0.51 (m, 2H), 0.93-1.14 (m, 1H), 2.19 (d, 2H), 5.94-6.05 (m, 2H), 7.37 (d, 1H), 7.57-7.78 (m, 5H), 8.80 (d, 1H), 9.88 (s, 1H).

Intermediate Example Int02.04

N-[4-(2-amino[,2]triazolo[1,5-a]pyridin-6-yl)phenyl]-2-(4-fluorophenyl)acetamide

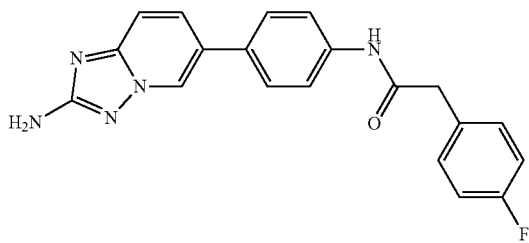 [SMILES: Nc1nc2ccc(-c3ccc(NC(=O)Cc4ccc(F)cc4)cc3)cn2n1]

Starting with Int02.02 (4.0 g) and (4-fluorophenyl)acetic acid (3.15 g), Int02.04 was prepared analogously to the procedure for the preparation of Int2.3. Yield: 5.1 g of the title compound.

$^1$H-NMR (300 MHz, DMSO-d$_6$): δ [ppm]=3.63 (s, 2H), 6.01 (s, 2H), 7.03-7.19 (m, 2H), 7.27-7.41 (m, 3H), 7.58-7.79 (m, 5H), 8.80 (dd, 1H), 10.26 (s, 1H).

Intermediate Example Int02.05

N-[4-(2-amino[,2]triazolo[1,5-a]pyridin-6-yl)phenyl]-2-phenylacetamide

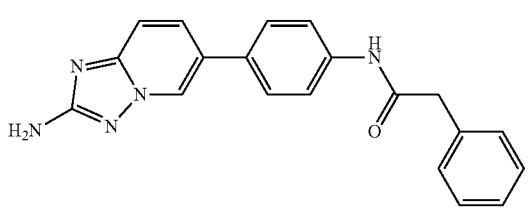 [SMILES: Nc1nc2ccc(-c3ccc(NC(=O)Cc4ccccc4)cc3)cn2n1]

To a stirred suspension of Int02.02 (1.09 g) in DMF (45 mL) was added potassium carbonate (3.3 g), phenylacetic acid (791 mg) and TBTU (3.1 g). The mixture was stirred at room temperature for 24 h. Water was added and the mixture was extracted with ethyl acetate. The organic phase was washed with saturated sodium chloride solution, dried (sodium sulfate) and the solvent was removed in vacuum. Silica gel chromatography gave 870 mg of the title compound.

$^1$H-NMR (400 MHz, DMSO-d$_6$): δ [ppm]=3.67 (s, 2H), 6.04 (s, 2H), 7.22-7.28 (m, 1H), 7.30-7.37 (m, 4H), 7.40 (dd, 1H), 7.63-7.72 (m, 4H), 7.74 (dd, 1H), 8.84 (dd, 1H), 10.31 (s, 1H).

Intermediate Example Int02.06 tert-butyl [4-(2-amino[,2]triazolo[1,5-a]pyridin-6-yl)-2-fluorophenyl]carbamate

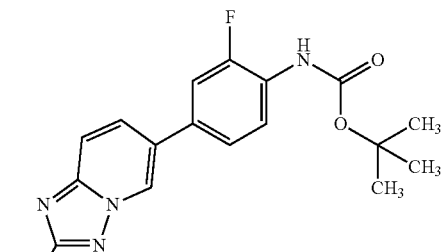

Starting with Int01.02, and {4-[(tert-butoxycarbonyl)amino]-3-fluorophenyl}boronic acid, Int02.06 was prepared analogously to the procedure for the preparation of Int02.01.

$^1$H-NMR (300 MHz, DMSO-d$_6$): δ [ppm]=1.44 (s, 9H), 6.04 (s, 2H), 7.37 (d, 1H), 7.49 (dd, 1H), 7.57-7.70 (m, 2H), 7.75 (dd, 1H), 8.90 (d, 1H), 9.04 (s, 1H).

Intermediate Example Int02.07

6-(4-amino-3-fluorophenyl[,2]triazolo[1,5-a]pyridin-2-amine

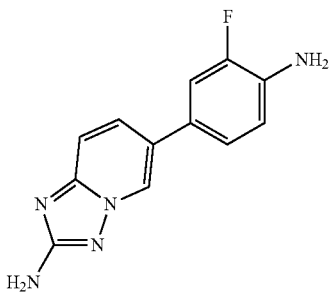 [SMILES: Nc1nc2ccc(-c3ccc(N)c(F)c3)cn2n1]

Starting with Int02.06, Int02.07 was prepared analogously to the procedure for the preparation of Int02.02.
$^1$H-NMR (400 MHz, DMSO-$d_6$): δ [ppm]=5.29 (s, 2H), 5.96 (s, 2H), 6.79 (dd, 1H), 7.24 (dd, 1H), 7.28-7.33 (m, 1H), 7.40 (dd, 1H), 7.65 (dd, 1H), 8.72 (d, 1H).

Intermediate Example Int02.08

N-[4-(2-amino[,2]triazolo[1,5-a]pyridin-6-yl)-2-fluorophenyl]-2-(4-fluorophenyl)acetamide

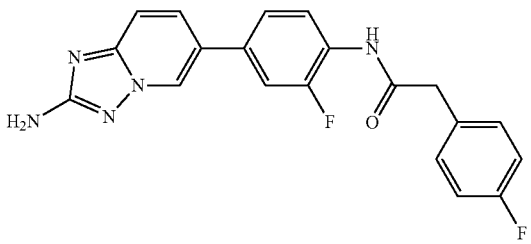 [SMILES: Nc1nc2ccc(-c3ccc(NC(=O)Cc4ccc(F)cc4)c(F)c3)cn2n1]

Starting with Int02.07, and (4-fluorophenyl)acetic acid, Int02.08 was prepared analogously to the procedure for the preparation of Int02.03.
$^1$H-NMR (400 MHz, DMSO-$d_6$): δ [ppm]=3.72 (s, 2H), 6.04 (br. s, 2H), 7.07-7.17 (m, 2H), 7.29-7.41 (m, 3H), 7.52 (dd, 1H), 7.69 (dd, 1H), 7.76 (dd, 1H), 7.90-8.01 (m, 1H), 8.91 (d, 1H), 10.02 (s, 1H).

Intermediate Example Int02.09

(6-{[(4-fluorophenyl)acetyl]amino}pyridin-3-yl)boronic acid

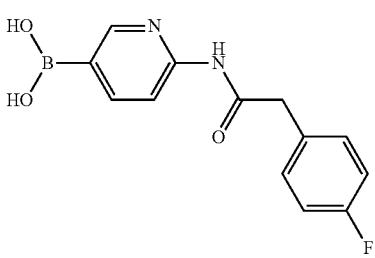 [SMILES: O=C(Cc1ccc(F)cc1)Nc1ccc(B(O)O)cn1]

To a stirred suspension of (4-fluorophenyl)acetic acid (2.0 g) in dichloromethane (25 mL) was added DMF (0.5 mL) and oxalyl chloride (2.25 g). The mixture was stirred at room temperature for 0.5 h. 5-(4,4,5,5-tetramethyl-1,3,2-dioxaborolan-2-yl)pyridin-2-amine (2.60 g) was added and the mixture was stirred at room temperature for 16 h. Hydrochloric acid (1N) was added and the mixture was extracted with a mixture of dichloromethane and methanol (9:1). The organic phase was washed with saturated sodium chloride solution, dried (sodium sulfate) and the solvent was removed in vacuum, to give 3.5 g of the title compound as a crude product, that was used for the next step without purification.

Intermediate Example Int02.10

N-[5-(2-amino[,2]triazolo[1,5-a]pyridin-6-yl)pyridin-2-yl]-2-(4-fluorophenyl)acetamide

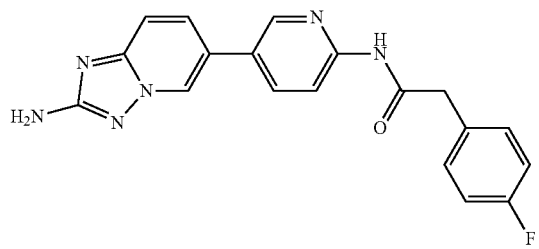 [SMILES: Nc1nc2ccc(-c3ccc(NC(=O)Cc4ccc(F)cc4)nc3)cn2n1]

To a stirred solution of Int01.02 (1.0 g) in 1-propanol (52 ml) was added 2M potassium carbonate solution (7.0 ml), Int02.09 (3.5 g), triphenylphosphine (123 mg) and PdCl$_2$(PPh$_3$)$_2$ (329 g). The mixture was heated to reflux for 2 h, the solvent was removed in vacuum, water (100 mL) was added and the mixture was extracted with ethyl acetate. The organic phase was washed with saturated sodium chloride solution, dried (sodium sulfate), filtered through Celite and the solvent was removed in vacuum. Silica gel chromatography gave a solid that was recrystallized from ethanol. Yield: 430 mg of the title compound.
$^1$H-NMR (300 MHz, DMSO-$d_6$): δ [ppm]=3.71 (s, 2H), 6.05 (s, 2H), 7.05-7.19 (m, 2H), 7.28-7.45 (m, 3H), 7.76 (dd, 1H), 8.03-8.16 (m, 2H), 8.59-8.75 (m, 1H), 8.94 (d, 1H), 10.83 (s, 1H).

Intermediate Example Int03.1

4-(2-amino[,2]triazolo[1,5-a]pyridin-6-yl)benzoic acid

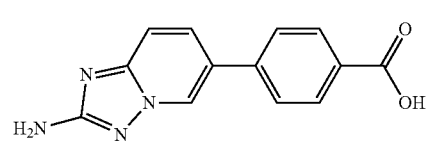

To a stirred solution of Int01.02 (10.0 g) in 1-propanol (470 ml) was added 2M potassium carbonate solution (70 ml), 4-carboxyphenylboronic acid (10.3 g), triphenylphosphine (1.23 g) and PdCl$_2$(PPh$_3$)$_2$ (3.30 g). The mixture was heated to reflux for 1 h. Water (1.0 L) was added and the mixture was extracted with ethyl acetate (2×400 mL). 1 N hydrochloric acid was added to the aqueous phase until pH 5 was reached. The precipitated solid was collected by filtration, was washed with water and ethanol and was dried in vacuum to give 9.55 g of the title compound.

$^1$H-NMR (400 MHz, DMSO-$d_6$): δ [ppm]=6.12 (br. s., 2H), 7.42 (d, 1H), 7.76-7.87 (m, 3H), 7.98 (d, 2H), 8.98 (d, 1H), 12.99 (br. s., 1H).

Intermediate Example Int03.02

4-(2-amino[,2]triazolo[1,5-a]pyridin-6-yl)-N-(cyclopropylmethyl)benzamide

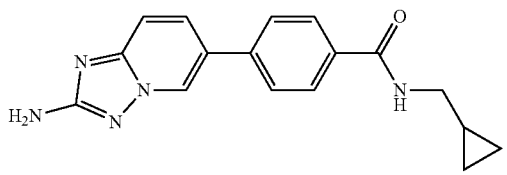 [SMILES: Nc1nc2ccc(-c3ccc(C(=O)NCC4CC4)cc3)cn2n1]

To a stirred suspension of Int03.01 (3.0 g) in THF (80 mL) was added Hünig Base (2.42 mL), 1-cyclopropylmethanamine (1.03 g) and TBTU (4.55 g). The mixture was stirred at room temperature for 72 h. Water was added and the mixture was stirred at room temperature for 20 minutes. The precipitated solid was collected by filtration, was washed with water and methanol and was dried in vacuum to give 1.45 g of the title compound.

$^1$H-NMR (300 MHz, DMSO-$d_6$): δ [ppm]=0.14-0.26 (m, 2H), 0.32-0.47 (m, 2H), 0.91-1.10 (m, 1H), 3.13 (t, 2H), 6.02-6.13 (m, 2H), 7.41 (d, 1H), 7.76-7.85 (m, 3H), 7.87-7.99 (m, 2H), 8.59 (t, 1H), 8.96 (d, 1H).

Intermediate Example Int03.03

4-(2-amino[,2]triazolo[1,5-a]pyridin-6-yl)-N-(4-fluorobenzyl)benzamide

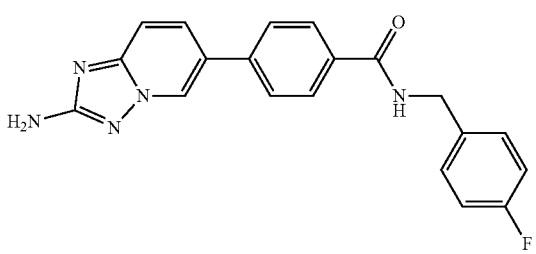 [SMILES: Nc1nc2ccc(-c3ccc(C(=O)NCc4ccc(F)cc4)cc3)cn2n1]

To a stirred suspension of Int03.01 (5.0 g) in THF (160 mL) was added Hünig Base (4.04 mL), 1-(4-fluorophenyl)methanamine (3.77 g) and HATU (8.97 g). The mixture was stirred at room temperature for 24 h. Water and ethyl acetate were added and the mixture was stirred at room temperature for 20 minutes. The precipitated solid was collected by filtration, was washed with water and ethanol and was dried in vacuum to give 1.35 g of the title compound.

$^1$H-NMR (400 MHz, DMSO-$d_6$): δ [ppm]=4.44 (d, 2H), 6.08 (s, 2H), 7.08-7.16 (m, 2H), 7.34 (dd, 2H), 7.41 (dd, 1H), 7.78-7.86 (m, 3H), 7.97 (d, 2H), 8.91-8.99 (m, 1H), 9.16 (t, 1H).

Intermediate Example Int03.04

4-(2-amino[,2]triazolo[1,5-a]pyridin-6-yl)-N-benzylbenzamide

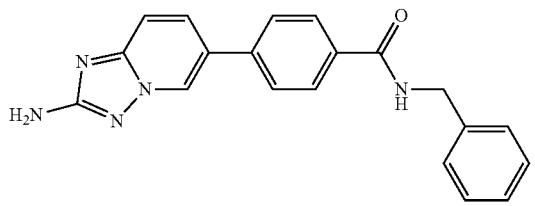 [SMILES: Nc1nc2ccc(-c3ccc(C(=O)NCc4ccccc4)cc3)cn2n1]

To a stirred solution of Int01.02 (4.0 g) in 1-propanol (280 ml) was added 2M potassium carbonate solution (28 ml), [4-(benzylcarbamoyl)phenyl]boronic acid (6.2 g), triphenylphosphine (0.25 g) and PdCl$_2$(PPh$_3$)$_2$ (0.66 g). The mixture was heated to reflux for 1 h. The mixture was concentrated in vacuum, water (100 mL) and ethyl acetate (100 mL) was added and the mixture was stirred at room temperature for 15 minutes. The precipitated solid was collected by filtration, was washed with water and ethanol and was dried in vacuum to give 6.09 g of the title compound.

$^1$H-NMR (300 MHz, DMSO-$d_6$): δ [ppm]=4.47 (d, 2H), 6.08 (s, 2H), 7.16-7.25 (m, 1H), 7.26-7.33 (m, 4H), 7.41 (dd, 1H), 7.75-8.02 (m, 5H), 8.97 (dd, 1H), 9.10 (t, 1H).

Intermediate Example Int03.05

4-(2-amino[,2]triazolo[1,5-a]pyridin-6-yl)-N-(cyclopentylmethyl)benzamide

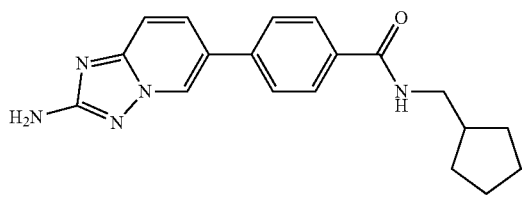 [SMILES: Nc1nc2ccc(-c3ccc(C(=O)NCC4CCCC4)cc3)cn2n1]

To a stirred suspension of Int03.01 (5.0 g) in DMF (100 mL) was added potassium carbonate (13.6 g), 1-cyclopentylmethanamine hydrochloride (5.4 g) and HATU (12.7 g). The mixture was stirred at room temperature for 16 h. The mixture was concentrated in vacuum. Water was added and the reaction mixture was extracted with a mixture of dichloromethane and methanol (10:1). The organic phase was dried (sodium sulfate) and the solvent was removed in vacuum. Silica gel chromatography gave a solid that was recrystallized from ethyl acetate. Yield: 3.9 g of the title compound.

$^1$H-NMR (300 MHz, DMSO-$d_6$): δ [ppm]=1.22 (dd, 2H), 1.36-1.74 (m, 6H), 2.03-2.21 (m, 1H), 3.17 (t, 2H), 6.08 (s, 2H), 7.41 (d, 1H), 7.71-7.96 (m, 5H), 8.51 (t, 1H), 8.96 (s, 1H).

Intermediate Example Int03.06

4-(2-Amino[,2]triazolo[1,5-a]pyridin-6-yl)-N-(4-chlorobenzyl)benzamide

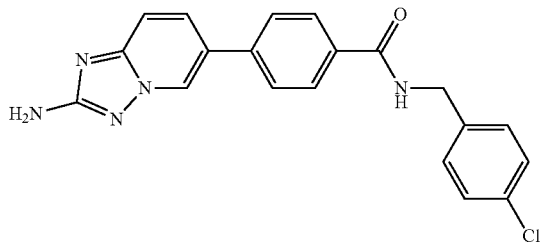 [SMILES: Nc1nc2ccc(-c3ccc(C(=O)NCc4ccc(Cl)cc4)cc3)cn2n1]

Starting with Int03.01 (500 mg) and 4-chlorobenzyamine (402 mg), Int03.06 was prepared analogously to the procedure for the preparation of Int03.03. Yield: 564 mg of the title compound.

$^1$H-NMR (300 MHz, DMSO-$d_6$): δ [ppm]=4.49 (d, 2H), 6.09-6.16 (m, 2H), 7.32-7.43 (m, 4H), 7.45 (d, 1H), 7.82-7.91 (m, 3H), 7.99 (d, 2H), 9.01 (d, 1H), 9.16 (t, 1H).

Intermediate Example Int03.07

4-(2-Amino[,2]triazolo[1,5-a]pyridin-6-yl)-N-(4-methylbenzyl)benzamide

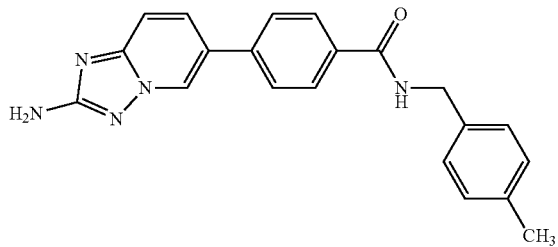 [SMILES: Cc1ccc(CNC(=O)c2ccc(-c3ccc4nc(N)nn4c3)cc2)cc1]

Starting with Int03.01 (500 mg) and 4-methylbenzyamine (344 mg), Int03.07 was prepared analogously to the procedure for the preparation of Int03.03. Yield: 610 mg of the title compound.

$^1$H-NMR (400 MHz, DMSO-$d_6$): δ [ppm]=2.28 (s, 3H), 4.46 (d, 2H), 6.09 (s, 2H), 7.10-7.17 (m, 2H), 7.19-7.25 (m, 2H), 7.45 (d, 1H), 7.82-7.89 (m, 3H), 7.99 (d, 2H), 8.99 (d, 1H), 9.05 (t, 1H).

Intermediate Example Int04.01

4-(2-amino[,2]triazolo[1,5-a]pyridin-6-yl)-2-fluorobenzoic acid

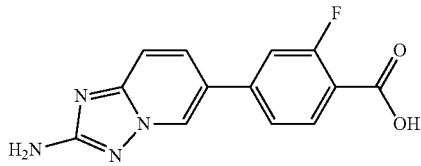

To a stirred solution of Int01.02 (4.45 g) in 1-propanol (150 ml) was added 2M potassium carbonate solution (31 ml), 4-carboxy-3-fluorophenylboronic acid (3.92 g), triphenylphosphine (0.55 g) and PdCl$_2$(PPh$_3$)$_2$ (1.50 g). The mixture was heated to reflux for 2 h. Water (800 mL) was added and the mixture was extracted with ethyl acetate (2×500 mL). 1 N hydrochloric acid was added to the aqueous phase until pH 3 was reached. The precipitated solid was collected by filtration, was washed with water, ethanol and ether and was dried in vacuum to give 3.10 g of the title compound.

$^1$H-NMR (300 MHz, DMSO-$d_6$): δ [ppm]=6.13 (s, 2H), 7.41 (d, 1H), 7.59-7.96 (m, 4H), 9.06 (s, 1H), 13.24 (br. s., 1H).

Intermediate Example Int04.02

4-(2-amino[,2]triazolo[1,5-a]pyridin-6-yl)-2-fluoro-N-(4-fluorobenzyl)benzamide

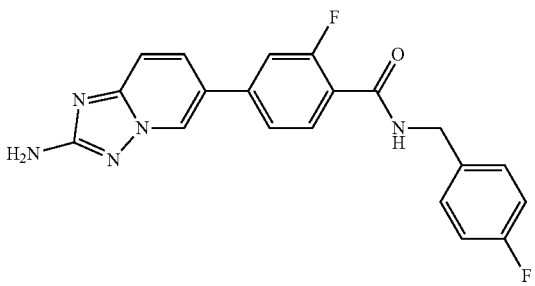 [SMILES: Nc1nc2ccc(-c3ccc(C(=O)NCc4ccc(F)cc4)c(F)c3)cn2n1]

To a stirred suspension of Int04.01 (1.6 g) in DMF (60 mL) was added molecular sives (4A) and the mixture was stirred for 1.5 h. To the stirred mixture was added potassium carbonate (4.1 g), 1-(4-fluorophenyl)methanamine (1.14 g) and HATU (3.35 g). The mixture was stirred at room temperature for 2 h. Solids were removed by filtration. The mixture was concentrated in vacuum. Water was added and the reaction mixture was extracted with a mixture of dichloromethane and methanol (10:1). The organic phase was washed with a saturated solution of sodium bicarbonate, dried (sodium sulfate) and the solvent was removed in vacuum. Trituration of the residue with warm ethanol gave 0.55 g of the title compound.

$^1$H-NMR (400 MHz, DMSO-$d_6$): δ [ppm]=4.43 (d, 2H), 6.11 (s, 2H), 7.10-7.18 (m, 2H), 7.32-7.38 (m, 2H), 7.41 (dd, 1H), 7.64-7.78 (m, 3H), 7.83 (dd, 1H), 8.84-8.91 (m, 1H), 9.03 (d, 1H).

Intermediate Example Int05.01

4-(2-amino[,2]triazolo[1,5-a]pyridin-6-yl)-2-methylbenzoic acid

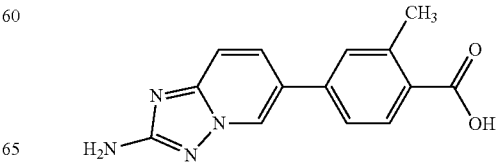

To a stirred solution of Int01.02 (1.45 g) in 1-propanol (65 ml) was added 2M potassium carbonate solution (10 ml), 4-carboxy-3-methylphenylboronic acid (1.22 g), triphenylphosphine (0.17 g) and PdCl$_2$(PPh$_3$)$_2$ (0.35 g). The mixture was heated to reflux for 1 h. Water (200 mL) was added and the mixture was extracted with ethyl acetate (2×100 mL). 1 N hydrochloric acid was added to the aqueous phase until pH 5 was reached. The precipitated solid was collected by filtration, was washed with water, ethanol and ether and was dried in vacuum to give 0.8 g of the title compound.

$^1$H-NMR (400 MHz, DMSO-d$_6$): δ [ppm]=2.57 (s, 3H), 6.37 (br. s., 2H), 7.52 (d, 1H), 7.65 (dd, 1H), 7.70 (s, 1H), 7.89 (d, 1H), 7.95 (dd, 1H), 9.06 (d, 1H), 12.87 (br. s., 1H).

Intermediate Example Int05.2

4-(2-amino[,2]triazolo[1,5-a]pyridin-6-yl)-N-(4-fluorobenzyl)-2-methylbenzamide

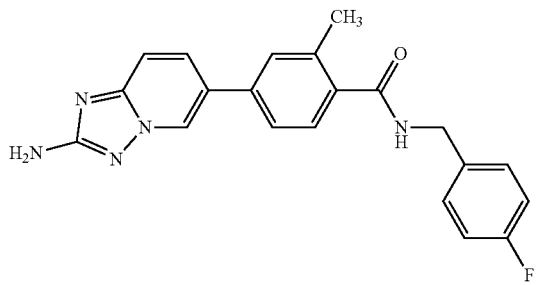 [SMILES: Cc1cc(-c2ccc3nc(N)nn3c2)ccc1C(=O)NCc1ccc(F)cc1]

To a stirred suspension of Int05.01 (0.425 g) in DMF (12 mL) was added potassium carbonate (1.1 g), 1-(4-fluorophenyl)methanamine (0.31 g) and HATU (1.21 g). The mixture was stirred at room temperature for 60 h. A saturated solution of sodium bicarbonate was added, the mixture was stirred at room temperature for 20 minutes and the mixture was extracted with ethyl acetate. The organic phase was dried (sodium sulfate) and the solvent was removed in vacuum. Trituration of the residue with warm ethanol gave 0.58 g of the title compound.

$^1$H-NMR (300 MHz, DMSO-d$_6$): δ [ppm]=2.37 (s, 3H), 4.39 (d, 2H), 6.05 (s, 2H), 7.14 (t, 2H), 7.28-7.46 (m, 4H), 7.50-7.66 (m, 2H), 7.76 (d, 1H), 8.74-8.99 (m, 2H).

Intermediate Example Int05.03

4-(2-amino[,2]triazolo[1,5-a]pyridin-6-yl)-N-(2,4-difluorobenzyl)-2-methylbenzamide

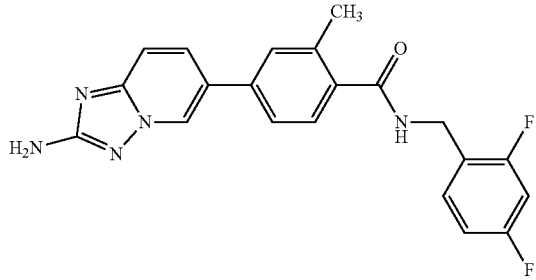 [SMILES: Cc1cc(-c2ccc3nc(N)nn3c2)ccc1C(=O)NCc1ccc(F)cc1F]

To a stirred suspension of Int05.01 (0.75 g) in DMF (22 mL) was added potassium carbonate (1.35 g), 1-(2,4-difluorophenyl)methanamine (0.62 g) and HATU (2.13 g). The mixture was stirred at room temperature for 60 h. Water (10 mL) was added and the mixture was stirred at room temperature for 1 h. Water (200 mL) was added a precipitated solid was isolated by filtration. Trituration of the solid with warm ethanol gave 0.90 g of the title compound.

$^1$H-NMR (400 MHz, DMSO-d$_6$): δ [ppm]=2.39 (s, 3H), 4.45 (d, 2H), 6.06 (s, 2H), 7.09 (td, 1H), 7.23 (td, 1H), 7.40-7.51 (m, 3H), 7.60 (d, 1H), 7.64 (s, 1H), 7.79 (dd, 1H), 8.82 (t, 1H), 8.91 (d, 1H).

Intermediate Example Int06.01

4-(2-amino[,2]triazolo[1,5-a]pyridin-6-yl)-2-chlorobenzoic acid

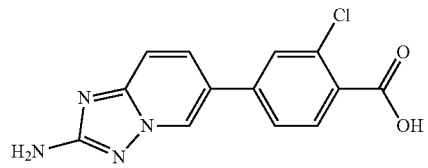

To a stirred solution of Int01.02 (2.0 g) in 1-propanol (100 ml) was added 2M potassium carbonate solution (15 ml), 4-carboxy-3-chlorophenylboronic acid (1.92 g), triphenylphosphine (0.25 g) and PdCl$_2$(PPh$_3$)$_2$ (0.66 g). The mixture was heated to reflux for 1 h. Water (200 mL) was added and the mixture was extracted with ethyl acetate (2×100 mL). 1 N hydrochloric acid was added to the aqueous phase until pH 5 was reached. The precipitated solid was collected by filtration, was washed with water, ethanol and ether and was dried in vacuum to give 1.6 g of the title compound.

$^1$H-NMR (300 MHz, DMSO-d$_6$): δ [ppm]=6.13 (br. s., 2H), 7.41 (d, 1H), 7.73-7.88 (m, 3H), 7.92 (d, 1H), 9.04 (d, 1H), 13.37 (br. s., 1H).

Intermediate Example Int06.02

4-(2-amino[,2]triazolo[1,5-a]pyridin-6-yl)-2-chloro-N-(4-fluorobenzyl)benzamide

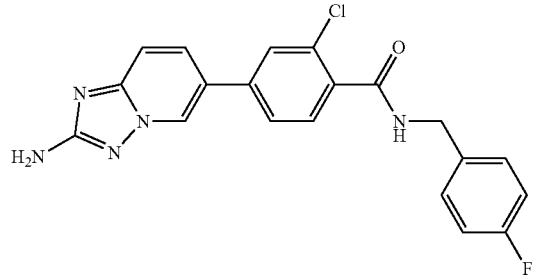 [SMILES: Nc1nc2ccc(-c3ccc(C(=O)NCc4ccc(F)cc4)c(Cl)c3)cn2n1]

To a stirred suspension of Int06.01 (0.425 g) in DMF (12 mL) was added potassium carbonate (1.1 g), 1-(4-fluorophenyl)methanamine (0.38 g) and HATU (1.40 g). The mixture was stirred at room temperature for 24 h. Further 1-(4-fluorophenyl)methanamine (95 mg) and HATU (280 g) was added and the mixture was stirred at room temperature for 16 h. Solids were removed by filtration. A half-saturated solution of sodium bicarbonate was added, the mixture was stirred at room temperature for 20 minutes and the mixture was extracted with a mixture of dichloromethane and methanol (10:1). The organic phase was dried (sodium sulfate) and the solvent was removed in vacuum. Trituration of the residue with warm ethanol gave 0.38 g of the title compound.

$^1$H-NMR (300 MHz, DMSO-$d_6$): δ [ppm]=4.42 (d, 2H), 6.10 (br. s, 2H), 7.09-7.20 (m, 2H), 7.33-7.43 (m, 3H), 7.50 (d, 1H), 7.77 (ddd, 2H), 7.89 (d, 1H), 8.94-9.06 (m, 2H).

Intermediate Example Int07.01

4-(2-amino[,2]triazolo[1,5-a]pyridin-6-yl)-2-methoxybenzoic acid

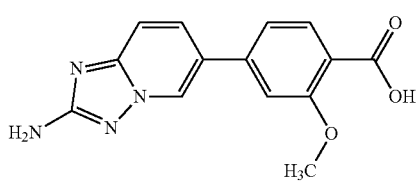 [SMILES: COc1cc(-c2ccc3nc(N)nn3c2)ccc1C(=O)O]

To a stirred solution of Int01.02 (0.52 g) in 1-propanol (24 mL) was added 2M potassium carbonate solution (3.6 mL), 4-carboxy-3-methoxyphenylboronic acid (0.48 g), triphenylphosphine (63 mg) and PdCl$_2$(PPh$_3$)$_2$ (170 mg). The mixture was heated to reflux for 1 h. Water (200 mL) was added and the mixture was extracted with ethyl acetate (2×100 mL). 2 N hydrochloric acid was added to the aqueous phase until pH 4 was reached. The precipitated solid was collected by filtration, was washed with water, ethanol and ether and was dried in vacuum to give 466 mg of the title compound.

$^1$H-NMR (300 MHz, DMSO-$d_6$, detected signals): δ [ppm]=3.98 (s, 3H), 4.46 (d, 2H), 6.08 (s, 2H), 7.07-7.18 (m, 2H), 7.29-7.47 (m, 5H), 7.75-7.88 (m, 2H), 8.72 (t, 1H), 9.03 (dd, 1H).

Intermediate Example Int07.02

4-(2-amino[,2]triazolo[1,5-a]pyridin-6-yl)-N-(4-fluorobenzyl)-2-methoxybenzamide

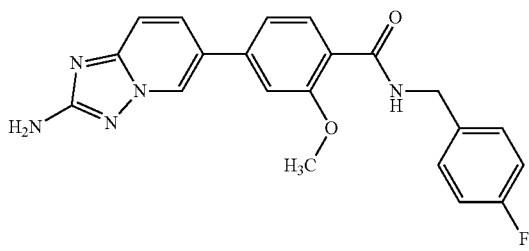 [SMILES: COc1cc(-c2ccc3nc(N)nn3c2)ccc1C(=O)NCc1ccc(F)cc1]

To a stirred suspension of Int07.01 (0.30 g) in DMF (8.5 mL) was added potassium carbonate (0.73 g), 1-(4-fluorophenyl)methanamine (0.20 g) and HATU (0.80 g). The mixture was stirred at room temperature for 16 h. Solids were removed by filtration. The solvent was removed in vacuum. Dichloromethane and methanol (10:1) and a half-saturated solution of sodium bicarbonate was added and the mixture was stirred at room temperature for 20 minutes. The mixture was extracted with a mixture of dichloromethane and methanol (10:1). The organic phase was dried (sodium sulfate) and the solvent was removed in vacuum. Trituration of the residue with warm ethanol gave 0.36 g of the title compound.

$^1$H-NMR (300 MHz, DMSO-$d_6$): δ [ppm]=3.98 (s, 3H), 4.46 (d, 2H), 6.08 (s, 2H), 7.07-7.18 (m, 2H), 7.29-7.47 (m, 5H), 7.75-7.88 (m, 2H), 8.72 (t, 1H), 9.03 (dd, 1H).

Intermediate Example Int08.01

5-(2-amino[,2]triazolo[1,5-a]pyridin-6-yl)pyridine-2-carboxylic acid

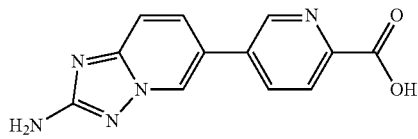 [SMILES: Nc1nc2ccc(-c3ccc(C(=O)O)nc3)cn2n1]

To a stirred solution of Int01.02 (0.60 g) in 1-propanol (28 mL) was added 2M potassium carbonate solution (4.2 mL), 5-(dihydroxyboryl)pyridine-2-carboxylic acid (0.48 g), triphenylphosphine (73 mg) and PdCl$_2$(PPh$_3$)$_2$ (198 mg). The mixture was heated to reflux for 2 h. Further triphenylphosphine (73 mg) and PdCl$_2$(PPh$_3$)$_2$ (198 mg) were added and the mixture was heated to reflux for 2 h. Further triphenylphosphine (73 mg) and PdCl$_2$(PPh$_3$)$_2$ (198 mg) were added and the mixture was heated to reflux for 4 h. Further triphenylphosphine (73 mg) and PdCl$_2$(PPh$_3$)$_2$ (198 mg) were added and the mixture was heated to reflux for 4 h. Water was added and the mixture was extracted with ethyl acetate. 2 N hydrochloric acid was added to the aqueous phase until pH 4 was reached. The precipitated solid was collected by filtration, was washed with water, ethanol and ether and was dried in vacuum to give 230 mg of the title compound.

$^1$H-NMR (300 MHz, DMSO-$d_6$): δ [ppm]=6.14 (br. s., 2H), 7.45 (d, 1H), 7.87 (dd, 1H), 8.06 (d, 1H), 8.30 (dd, 1H), 9.06 (d, 1H), 9.12 (s, 1H), 13.16 (br. s., 1H).

Intermediate Example Int08.02

5-(2-amino[,2]triazolo[1,5-a]pyridin-6-yl)-N-(4-fluorobenzyl)pyridine-2-carboxamide

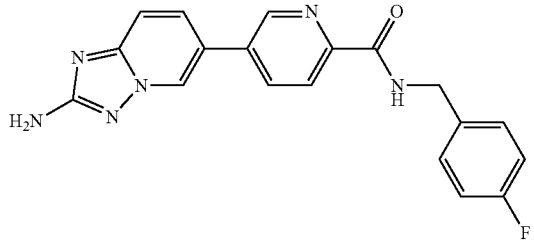 [SMILES: Nc1nc2ccc(-c3ccc(C(=O)NCc4ccc(F)cc4)nc3)cn2n1]

To a stirred solution of Int08.01 (230 mg) in DMF (7 mL) was added potassium carbonate (622 mg), 1-(4-fluorophenyl)methanamine (203 mg) and TBTU (723 mg). The mixture was stirred at r.t. for 16 h. Water was added and the mixture was extracted with ethyl acetate. The organic phase was washed with saturated sodium chloride solution, dried (sodium sulfate) and the solvent was removed in vacuum. Trituration of the residue with dichloromethane followed by aminophase-silica-gel chromatography gave 136 mg of the title compound.

$^1$H-NMR (400 MHz, DMSO-$d_6$): δ [ppm]=4.46 (d, 2H), 6.12 (s, 2H), 7.04-7.16 (m, 2H), 7.30-7.38 (m, 2H), 7.45 (d, 1H), 7.86 (dd, 1H), 8.07 (d, 1H), 8.32 (dd, 1H), 8.94-9.03 (m, 1H), 9.10 (d, 1H), 9.36 (t, 1H).

Intermediate Example Int09.01

(4-bromo-3-methoxyphenyl)(morpholin-4-yl)methanone

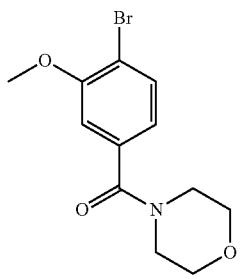 [SMILES: COc1cc(C(=O)N2CCOCC2)ccc1Br]

To a stirred solution of 4-bromo-3-methoxybenzoic acid (3.0 g) in dichloromethane (32 mL) and DMF (1.0 mL) was added oxalyl chloride (1.78 g) at 0° C. The mixture was stirred at room temperature for 1 h. The solvent was removed in vacuum. The residue was dissolved in THF (62 mL) and Hünig Base (6.6 mL) and morpholin (1.66 g) were added. The mixture was stirred at room temperature for 1 h. A half-saturated solution of sodium bicarbonate was added and the mixture was extracted with ethyl acetate. The organic phase was washed with saturated sodium chloride solution, dried (sodium sulfate) and the solvent was removed in vacuum. Silica gel chromatography gave 3.76 g of the title compound.

$^1$H-NMR (400 MHz, CHLOROFORM-d): δ [ppm]=3.74 (br. s., 8H), 3.92 (s, 3H), 6.83 (dd, 1H), 6.98 (d, 1H), 7.56 (d, 1H).

Intermediate Example Int09.02

4-bromo-N-(1-hydroxy-2-methylpropan-2-yl)-3-methoxybenzamide

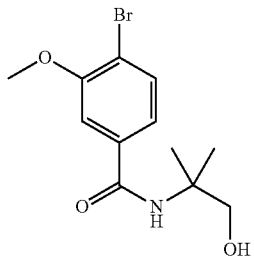 [SMILES: COc1cc(C(=O)NC(C)(C)CO)ccc1Br]

To a stirred solution of 4-bromo-3-methoxybenzoic acid (1.7 g) in dichloromethane (22 mL) and DMF (1.0 mL) was added oxalyl chloride (1.19 g) at 0° C. The mixture was stirred at room temperature for 0.5 h. The solvent was removed in vacuum. The residue was dissolved in dichloromethane (30 mL) and 2-amino-2-methylpropan-1-ol (1.93 g) were added. The mixture was stirred at room temperature for 3 h. A half-saturated solution of sodium bicarbonate was added and the mixture was extracted with ethyl acetate. The organic phase was washed with saturated sodium chloride solution, dried (sodium sulfate) and the solvent was removed in vacuum. Aminophase-silica-gel chromatography gave 1.90 g of the title compound.

$^1$H-NMR (400 MHz, DMSO-$d_6$): δ [ppm]=1.27 (s, 6H), 3.48 (d, 2H), 3.87 (s, 3H), 4.85 (t, 1H), 7.30 (dd, 1H), 7.40 (d, 1H), 7.57-7.62 (m, 2H).

Intermediate Example Int09.03

2-(4-bromo-3-methoxyphenyl)-4,4-dimethyl-4,5-dihydro-1,3-oxazole

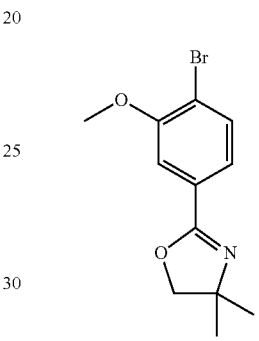

To a stirred solution of Int09.02 (1.0 g) in THF (50 mL) was added Burgess reagent (2.37 g) at 0° C. The mixture was stirred at room temperature for 1 h. Sodium dihydrogen phosphate (1.2 g) and molecular sives (4 Å, 1.0 g) were added. The mixture was stirred at room temperature for 16 h and for 2 h at 40° C. A half-saturated solution of sodium bicarbonate was added and the mixture was extracted with ethyl acetate and methanol (20:1). The organic phase was washed with saturated sodium chloride solution, dried (sodium sulfate) and the solvent was removed in vacuum. Silica gel chromatography gave 0.25 g of the title compound.

$^1$H-NMR (400 MHz, DMSO-$d_6$): δ [ppm]=1.25 (s, 6H), 3.86 (s, 3H), 4.09 (s, 2H), 7.31 (dd, 1H), 7.41 (d, 1H), 7.64 (d, 1H).

Intermediate Example Int09.04

(4-bromo-3-methoxyphenyl)(4-methylpiperazin-1-yl)methanone

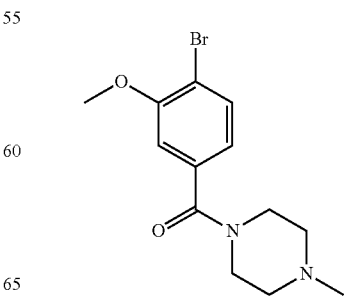

To a stirred solution of 4-bromo-3-methoxybenzoic acid (1.0 g) in THF (50 mL) was added Hünig Base (0.66 g), 1-methylpiperazine (0.51 g) and HATU (1.94 g). The mixture was stirred at r.t. for 16 h. A half-saturated solution of sodium bicarbonate was added and the mixture was extracted with ethyl acetate. The organic phase was washed with aqueous ammonium chloride solution and with saturated sodium chloride solution, dried (sodium sulfate) and the solvent was removed in vacuum. Silica gel chromatography gave 1.00 g of the title compound.

$^1$H-NMR (400 MHz, DMSO-$d_6$): δ [ppm]=2.15 (s, 3H), 2.17-2.38 (m, 4H), 3.21-3.33 (m, 2H), 3.45-3.64 (m, 2H), 3.83 (s, 3H), 6.84 (dd, 1H), 7.04 (d, 1H), 7.59 (d, 1H).

Intermediate Example Int09.05

(4-bromo-3-methoxyphenyl)[(1S,4S)-2-oxa-5-azabicyclo[2.2.1]hept-5-yl]methanone

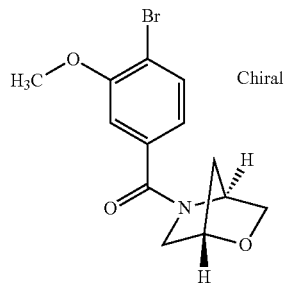 [SMILES: COc1cc(C(=O)N2C[C@@H]3C[C@H]2CO3)ccc1Br]

To a stirred solution of 4-bromo-3-methoxybenzoic acid (1.23 g) in DMF (40 mL) was added potassium carbonate (3.69 g), (1S,4S)-2-oxa-5-azabicyclo[2.2.1]heptane (0.94 g) and TBTU (4.06 g). The mixture was stirred at room temperature for 18 h. Water was added, the mixture was stirred for 15 minutes and the solvent was removed in vacuum. Water was added and the mixture was extracted with ethyl acetate. The organic phase was washed with water, saturated sodium chloride solution, dried (sodium sulfate) and the solvent was removed in vacuum. Silica gel chromatography gave 1.35 g of the title compound.

$^1$H-NMR (400 MHz, DMSO-$d_6$): δ [ppm]=1.63-1.93 (m, 2H), 3.16-3.90 (m, 7H), 4.29-4.83 (m, 2H), 6.92-7.04 (m, 1H), 7.15 (dd, 1H), 7.55-7.65 (m, 1H).

Intermediate Example Int09.06

(4-Bromo-3-methoxyphenyl)(2-oxa-6-azaspiro[3.3]hept-6-yl)methanone

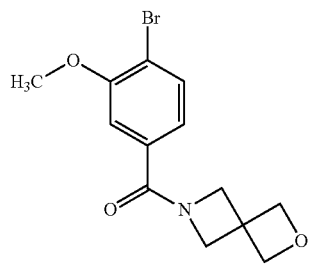 [SMILES: COc1cc(C(=O)N2CC3(COC3)C2)ccc1Br]

Starting with 4-bromo-3-methoxybenzoic acid (1.3 g) and 2-oxa-6-azaspiro[3.3]heptane ethanedioate (2:1) (1.17 g), Int09.06 was prepared analogously to the procedure for the preparation of Int09.05. Yield: 1.23 g of the title compound.

$^1$H-NMR (400 MHz, DMSO-$d_6$): δ [ppm]=3.89 (s, 3H), 4.20 (s, 2H), 4.48 (s, 2H), 4.67 (d, 4H), 7.10 (dd, 1H), 7.24 (d, 1H), 7.65 (d, 1H).

Intermediate Example Int09.07

(4-bromo-3-methoxyphenyl)(1,1-dioxidothiomorpholin-4-yl)methanone

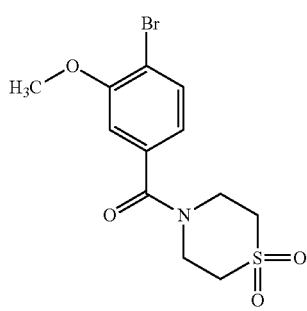 [SMILES: COc1cc(C(=O)N2CCS(=O)(=O)CC2)ccc1Br]

To a stirred suspension of 4-bromo-3-methoxybenzoic acid (1.32 g) in dichloromethane (14 mL) and DMF (0.5 mL) was added oxalyl chloride (0.87 g) at 0° C. The mixture was stirred at room temperature for 1 h. The solvent was removed in vacuum. The residue was dissolved in THF (30 mL) and Hünig Base (3.0 mL) and thiomorpholine 1,1-dioxide (1.2 g) were added. The mixture was stirred at room temperature for 18 h. A half-saturated solution of sodium bicarbonate was added and the mixture was extracted with ethyl acetate and methanol (10:1). The organic phase was washed with saturated sodium chloride solution, dried (sodium sulfate) and the solvent was removed in vacuum. Trituration of the residue with warm ethanol gave 1.8 g of the title compound.

Intermediate Example Int09.08

(4-Bromo-3-methoxyphenyl)(3-hydroxyazetidin-1-yl)methanone

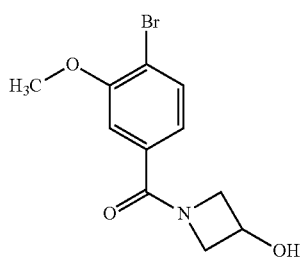 [SMILES: COc1cc(C(=O)N2CC(O)C2)ccc1Br]

Starting with 4-bromo-3-methoxybenzoic acid (1 g) and 3-hydroxyazetidine hydrochloride (649 mg), Int09.08 was prepared analogously to the procedure for the preparation of Int09.05. Yield: 1.14 g of the title compound.

$^1$H-NMR (300 MHz, DMSO-$d_6$): δ [ppm]=3.78 (d, 8H), 3.89 (s, 3H), 4.04 (d, 1H), 4.16-4.34 (m, 1H), 4.37-4.56 (m, 2H), 5.76 (d, 1H), 7.10 (dd, 1H), 7.24 (d, 1H), 7.64 (d, 1H).

Intermediate Example Int09.09

(4-bromo-3-methoxyphenyl)(4-hydroxypiperidin-1-yl)methanone

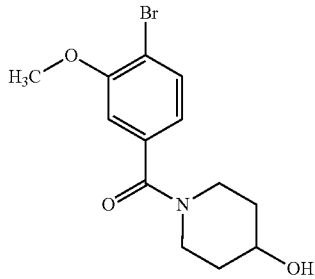 [SMILES: COc1cc(C(=O)N2CCC(O)CC2)ccc1Br]

To a stirred suspension of 4-bromo-3-methoxybenzoic acid (1.82 g) in dichloromethane (60 mL) and DMF (1.0 mL) was added oxalyl chloride (1.69 g) at 0° C. The mixture was stirred at room temperature for 1 h. The solvent was removed in vacuum. The residue was dissolved in THF (60 mL) and Hünig Base (4.1 mL) and 4-hydroxypiperidin (1.22 g) were added. The mixture was stirred at room temperature for 18 h. A half-saturated solution of sodium bicarbonate was added and the mixture was extracted with ethyl acetate and methanol (100:1). The organic phase was washed with saturated ammonium chloride solution, and with saturated sodium chloride solution, dried (sodium sulfate) and the solvent was removed in vacuum. Recrystallization of the residue from ethanol gave 1.3 g of the title compound.

Intermediate Example Int09.10

4-bromo-3-methoxy-N-(oxetan-3-yl)benzamide

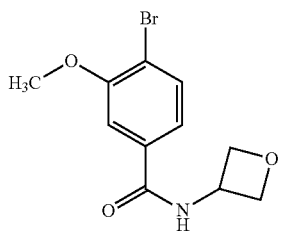 [SMILES: COc1cc(C(=O)NC2COC2)ccc1Br]

To a stirred solution of 4-bromo-3-methoxybenzoic acid (1.5 g) in DMF (180 mL) was added potassium carbonate (4.49 g), oxetan-3-amine hydrochloride (1.1 g) and TBTU (4.94 g). The mixture was stirred at room temperature for 18 h. Further oxetan-3-amine hydrochloride (0.37 g), TBTU (2.47 g) and DMF (80 mL) were added and the mixture was stirred for 1 h. A half-saturated solution of sodium bicarbonate was added and the mixture was extracted with dichloromethane and methanol (100:1). The organic phase was washed with saturated sodium chloride solution, dried (sodium sulfate) and the solvent was removed in vacuum. Silica gel chromatography gave a solid that was recrystallized from ethanol. Yield: 0.58 g of the title compound.

$^1$H-NMR (300 MHz, DMSO-$d_6$): δ [ppm]=3.88 (s, 3H), 4.50-4.61 (m, 2H), 4.75 (t, 2H), 4.88-5.04 (m, 1H), 7.38 (dd, 1H), 7.50 (d, 1H), 7.66 (d, 1H), 9.15 (br. d, 1H).

Intermediate Example Int09.11

Azetidin-1-yl(4-bromo-3-methoxyphenyl)methanone

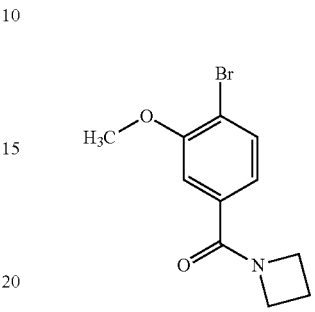

To a stirred solution of 4-bromo-3-methoxybenzoic acid (400 mg) in DMF (4.0 mL) was added potassium carbonate (720 mg), azetidine (148 mg) and TBTU (890 mg). The mixture was stirred at room temperature for 60 h. Water was added, the mixture was stirred for 15 minutes and the solvent was removed in vacuum. Water was added and the mixture was extracted with ethyl acetate. The organic phase was washed with saturated sodium chloride solution, dried (sodium sulfate) and the solvent was removed in vacuum. Silica gel chromatography gave 370 mg of the title compound.

$^1$H-NMR (400 MHz, DMSO-$d_6$): δ [ppm]=2.15-2.27 (m, 2H), 3.85 (s, 3H), 4.00 (t, 2H), 4.26 (t, 2H), 7.07 (dd, 1H), 7.21 (d, 1H), 7.61 (d, 1H).

Intermediate Example Int09.12

(4-Bromo-3-methoxyphenyl)(3-fluoroazetidin-1-yl)methanone

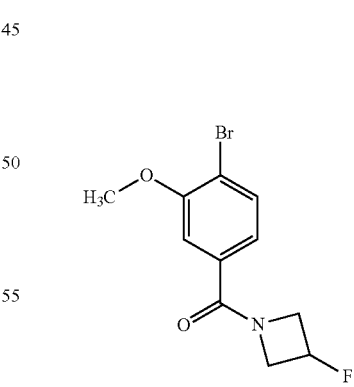

Starting with 4-bromo-3-methoxybenzoic acid (780 mg) and 3-fluoroazetidine hydrochloride (500 mg), Int09.12 was prepared analogously to the procedure for the preparation of Int09.05. Yield: 780 mg of the title compound.

$^1$H-NMR (400 MHz, DMSO-$d_6$): δ [ppm]=3.90 (s, 3H), 3.99-4.16 (m, 1H), 4.31-4.65 (m, 3H), 5.36 (tt, 0.5H), 5.50 (tt, 0.5H), 7.14 (dd, 1H), 7.26 (d, 1H), 7.66 (d, 1H).

Intermediate Example Int09.13

(4-Bromo-3-methoxyphenyl)(3-methoxyazetidin-1-yl)methanone

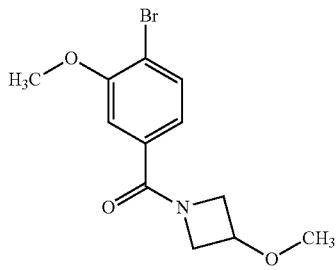

Starting with 4-bromo-3-methoxybenzoic acid (1.1 g) and 3-methoxyazetidine hydrochloride (765 mg), Int09.13 was prepared analogously to the procedure for the preparation of Int09.05. Yield: 980 mg of the title compound.

$^1$H-NMR (400 MHz, DMSO-$d_6$): δ [ppm]=3.22 (s, 3H), 3.78-3.87 (m, 1H), 3.89 (s, 3H), 4.14 (d, 1H), 4.23 (br. s., 2H), 4.43 (br. s., 1H), 7.12 (d, 1H), 7.26 (s, 1H), 7.64 (d, 1H).

Intermediate Example Int10.01 methyl 4-bromo-3-ethoxybenzoate

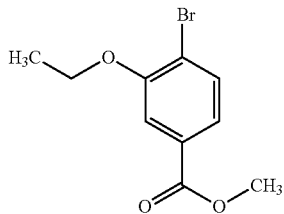

To a stirred solution of methyl 4-bromo-3-hydroxybenzoate (6.4 g) in DMF (35 mL) was added potassium carbonate (11.5 g and iodoethane (6.48 mg). The mixture was stirred at room temperature for 16 h. The solvent was removed in vacuum, ethyl acetate was added and the mixture was washed with water. The organic phase was washed with saturated sodium chloride solution, dried (sodium sulfate) and the solvent was removed in vacuum. Trituration of the residue with warm ethanol gave 5.7 g of the title compound.

$^1$H-NMR (300 MHz, DMSO-$d_6$): δ [ppm]=1.34 (t, 3H), 3.82 (s, 3H), 4.14 (q, 2H), 7.42 (dd, 1H), 7.48 (d, 1H), 7.70 (d, 1H).

Intermediate Example Int10.02

4-bromo-3-ethoxybenzoic acid

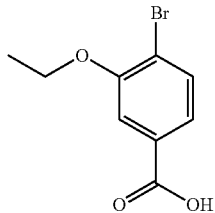

To a stirred solution of methyl 4-bromo-3-ethoxybenzoate (17.3 g) in THF (180 mL), methanol (60 mL) and water (60 mL) was added a 1 M solution of Lithium hydroxide in water (200 mL). The mixture was stirred at room temperature for 1 h. Water was added and 1 N hydrochloric acid was added until pH 4 was reached. The precipitated solid was collected by filtration, was washed with water. The solid was dissolved in dichloromethane and methanol (10:1). The solution was washed with saturated sodium chloride solution, dried (sodium sulfate) and the solvent was removed in vacuum. Trituration of the residue with ether gave 15.4 g of the title compound.

$^1$H-NMR (400 MHz, DMSO-$d_6$): δ [ppm]=1.34 (t, 3H), 4.13 (q, 2H), 7.40 (dd, 1H), 7.48 (d, 1H), 7.67 (d, 1H), 13.17 (br. s., 1H).

Intermediate Example Int10.03

(4-bromo-3-ethoxyphenyl)(morpholin-4-yl)methanone

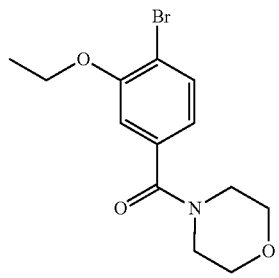 [SMILES: CCOc1cc(C(=O)N2CCOCC2)ccc1Br]

Starting with Int10.02 (6.5 g) and morpholine (4.62 g), Int10.03 was prepared analogously to the procedure for the preparation of Int09.01. Yield: 7.9 g of the title compound.

$^1$H-NMR (300 MHz, CHLOROFORM-d): δ [ppm]=1.47 (t, 3H), 3.25-3.92 (m, 8H), 4.11 (q, 2H), 6.81 (dd, 1H), 6.94 (d, 1H), 7.55 (d, 1H).

Intermediate Example Int10.04 tert-butyl 4-(4-bromo-3-ethoxybenzoyl)piperazine-1-carboxylate

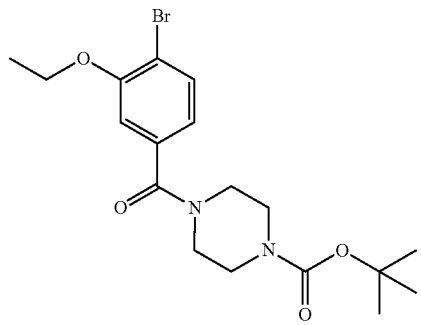 [SMILES: CCOc1cc(C(=O)N2CCN(C(=O)OC(C)(C)C)CC2)ccc1Br]

Starting with Int10.02 (1.0 g) and tert-butyl piperazine-1-carboxylate (760 mg), Int10.04 was prepared analogously to the procedure for the preparation of Int09.01. Yield: 1.31 g of the title compound.

$^1$H-NMR (400 MHz, DMSO-$d_6$): δ [ppm]=1.32 (t, 3H), 1.37 (s, 9H), 3.16-3.62 (m, 8H), 4.10 (q, 2H), 6.86 (dd, 1H), 7.05 (d, 1H), 7.60 (d, 1H).

Intermediate Example Int10.05

4-bromo-3-ethoxy-N-(1-methylpiperidin-4-yl)benzamide

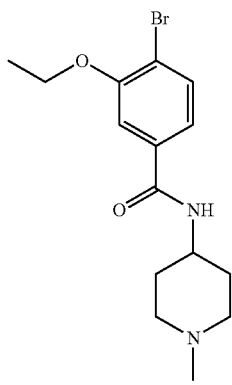 [SMILES: CCOc1cc(C(=O)NC2CCN(C)CC2)ccc1Br]

To a stirred solution of Int10.02 (0.75 g) in THF (40 mL) was added Hünig Base (0.47 g), 1-methylpiperidin-4-amine (0.45 g) and HATU (1.37 g). The mixture was stirred at r.t. for 16 h. A half-saturated solution of sodium bicarbonate was added and the mixture was extracted with ethyl acetate. The organic phase was washed with saturated sodium chloride solution, dried (sodium sulfate) and the solvent was removed in vacuum. Trituration of the residue with dichloromethane gave a solid that was purified by aminophase-silica-gel chromatography. Yield: 565 mg of the title compound.

$^1$H-NMR (300 MHz, DMSO-$d_6$): δ [ppm]=1.34 (t, 3H), 1.44-1.61 (m, 2H), 1.66-1.77 (m, 2H), 1.81-1.95 (m, 2H), 2.12 (s, 3H), 2.73 (br. d, 2H), 3.57-3.79 (m, 1H), 4.13 (q, 2H), 7.33 (dd, 1H), 7.44 (d, 1H), 7.61 (d, 1H), 8.27 (d, 1H).

Intermediate Example Int10.06

(4-bromo-3-ethoxyphenyl)[4-(cyclopropylmethyl)piperazin-1-yl]methanone

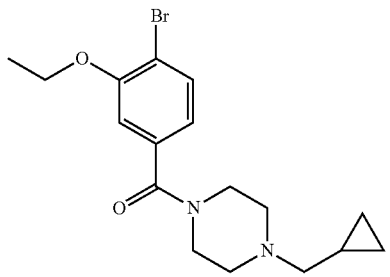 [SMILES: CCOc1cc(C(=O)N2CCN(CC3CC3)CC2)ccc1Br]

Starting with Int10.02 (1.0 g) and 1-(cyclopropylmethyl) piperazine (885 mg), Int10.06 was prepared analogously to the procedure for the preparation of Int09.01. Yield: 1.4 g of the title compound.

$^1$H-NMR (300 MHz, CHLOROFORM-d): δ [ppm]=0.04-0.15 (m, 2H), 0.48-0.59 (m, 2H), 0.77-0.93 (m, 1H), 1.47 (t, 3H), 2.28 (d, 2H), 2.36-2.73 (m, 4H), 3.31-3.93 (m, 4H), 4.11 (q, 2H), 6.82 (dd, 1H), 6.94 (d, 1H), 7.54 (d, 1H).

Intermediate Example Int10.07

(4-Bromo-3-ethoxyphenyl)(2-oxa-6-azaspiro[3.3]hept-6-yl)methanone

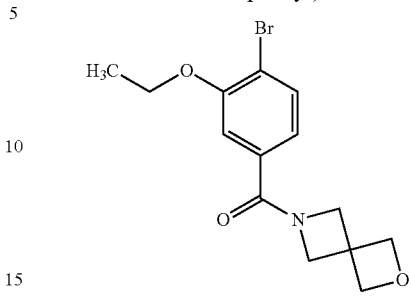

Starting with Int10.02 (1.5 g) and 2-oxa-6-azaspiro[3.3]heptane ethanedioate (2:1) (1.3 g), Int10.07 was prepared analogously to the procedure for the preparation of Int09.05. Yield: 1.47 g of the title compound.

$^1$H-NMR (300 MHz, DMSO-$d_6$): δ [ppm]=1.37 (t, 3H), 4.07-4.24 (m, 4H), 4.47 (s, 2H), 4.67 (s, 4H), 7.09 (dd, 1H), 7.21 (d, 1H), 7.65 (d, 1H).

Intermediate Example Int10.08

(4-bromo-3-ethoxyphenyl)(3-hydroxyazetidin-1-yl)methanone

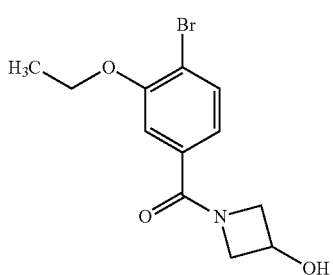 [SMILES: CCOc1cc(C(=O)N2CC(O)C2)ccc1Br]

Starting with Int10.02 (1 g) and 3-hydroxyazetidine hydrochloride (612 mg), Int10.08 was prepared analogously to the procedure for the preparation of Int09.05. Yield: 991 mg of the title compound.

$^1$H-NMR (300 MHz, DMSO-$d_6$): δ [ppm]=1.36 (t, 3H), 3.67-3.86 (m, 1H), 4.03 (d, 1H), 4.09-4.31 (m, 3H), 4.37-4.56 (m, 2H), 5.76 (d, 1H), 7.09 (dd, 1H), 7.22 (d, 1H), 7.64 (d, 1H).

Intermediate Example Int10.09

(4-bromo-3-ethoxyphenyl)(piperazin-1-yl)methanone

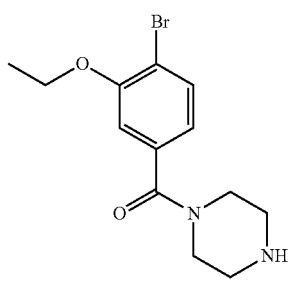 [SMILES: CCOc1cc(C(=O)N2CCNCC2)ccc1Br]

To a stirred suspension of Int10.4 (870 mg) in dichloromethane (10 mL) was added TFA (4.0 mL). The mixture

Intermediate Example Int10.10

1-[4-(4-bromo-3-ethoxybenzoyl)piperazin-1-yl]ethanone

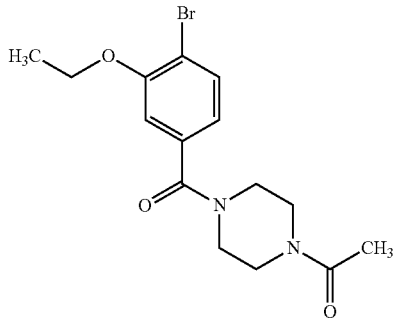 [SMILES: CCOc1cc(C(=O)N2CCN(C(C)=O)CC2)ccc1Br]

To a stirred solution of Int10.09 (585 mg) in dichloromethane (8 mL) was added pyridine (230 μL) and acetyl chloride (160 μL). The mixture was stirred at room temperature for 0.5 h. A saturated solution of ammonium chloride was added and the mixture was extracted with ethyl acetate and methanol. The organic phase was washed with saturated sodium chloride solution, dried (sodium sulfate) and the solvent was removed in vacuum. Silica gel chromatography gave 580 mg of the title compound.

Intermediate Example Int11.01

(3-hydroxy-4-iodophenyl)(morpholin-4-yl)methanone

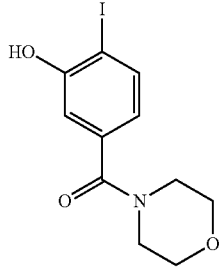 [SMILES: O=C(c1ccc(I)c(O)c1)N1CCOCC1]

3-Hydroxy-4-iodobenzoic acid (WO2006/18325) (15.0 g) was dissolved in a mixture of DCM (131 mL) and DMF (92 mL) and cooled to 0° C. Oxalyl chloride (10.8 g) was added, and the mixture was stirred for 10 min. Subsequently, morpholine (34.6 g) was added, and the mixture was warmed to r.t. The reaction mixture was then diluted with ethyl acetate and water. The aqueous phase was acidified to pH 2 with 4N aqueous hydrochloric acid, and the organic layer was separated. It was washed twice with water (pH 2), aqueous sodium bicarbonate solution (pH 8), brine, and conc. ammonium chloride solution. The organic layer was dried over sodium sulfate, and the solvent was evaporated. The residue was triturated with MTBE and collected by suction filtration to yield 14.8 g (78%) of the title compound.

$^1$H-NMR (400 MHz, DMSO-$d_6$): δ [ppm]=3.57 (br. s., 8H), 6.61 (dd, 1H), 6.86 (d, 1H), 7.73 (d, 1H), 10.61 (br. s, 1H).

was stirred at room temperature for 4 h. A half-saturated solution of sodium bicarbonate was added until pH 9 was reached and the mixture was extracted with ethyl acetate. The organic phase was washed with saturated sodium chloride solution, dried (sodium sulfate) and the solvent was removed in vacuum to give 585 mg of the title compound.

Intermediate Example Int11.02

[4-iodo-3-(2,2,2-trifluoroethoxy)phenyl](morpholin-4-yl)methanone

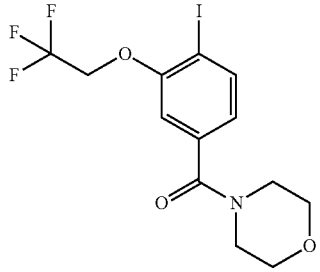 [SMILES: O=C(c1ccc(I)c(OCC(F)(F)F)c1)N1CCOCC1]

(3-Hydroxy-4-iodophenyl)(morpholin-4-yl)methanone, Int11.01, (2.00 g) was dissolved in DMF (12.4 mL) and acetonitrile (0.5 mL), and potassium carbonate (1.66 g) and 2,2,2-trifluoroethyl trifluoromethanesulfonate (1.46 g) were added. The mixture was heated for 30 min in a microwave oven to 150° C. Subsequently, the reaction mixture was diluted with water and three times extracted with ethyl acetate. The combined organic layers were washed three times with aqueous ammonium chloride solution, then with satd. aqueous sodium bicarbonate solution and with brine. It was dried over sodium sulfate, and the solvent was evaporated to yield 2.47 g (99%) of the title compound as an oil.

$^1$H-NMR (400 MHz, DMSO-$d_6$): δ [ppm]=3.47-3.71 (m, 8H), 4.89 (q, 2H), 6.86 (dd, 1H), 7.15 (d, 1H), 7.88 (d, 1H).

Intermediate Example Int11.03 methyl 4-bromo-3-(2,2,2-trifluoroethoxy)benzoate

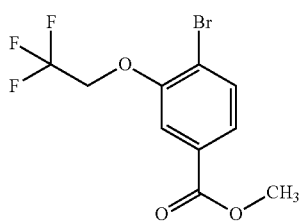 [SMILES: COC(=O)c1ccc(Br)c(OCC(F)(F)F)c1]

To a stirred solution of methyl 4-bromo-3-hydroxybenzoate (2.5 g) in acetonitrile (0.5 mL) and DMF (10 mL) in a microwave tube was added potassium carbonate (2.93 g) and 2,2,2-trifluoroethyl trifluoromethanesulfonate (2.79 g). The mixture was heated to 150° C. in a microwave oven for 30 minutes. The solvent was removed in vacuum, ethyl acetate was added and the mixture was washed with water. The organic phase was washed with saturated sodium chloride solution, dried (sodium sulfate) and the solvent was removed in vacuum. Recrystallization of the residue from ethanol gave 1.2 g of the title compound. The mother liquor was concentrated in vacuum and purified by aminophase-silica-gel chromatography followed by recrystallized from methanol and water to give further 0.64 g of the title compound.

$^1$H-NMR (300 MHz, CHLOROFORM-d): δ [ppm]=3.93 (s, 3H), 4.47 (q, 2H), 7.56 (d, 1H), 7.58-7.70 (m, 2H).

Intermediate Example Int11.04

4-bromo-3-(2,2,2-trifluoroethoxy)benzoic acid

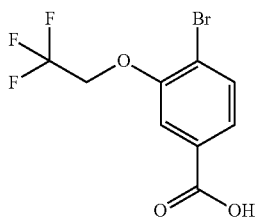 [SMILES: O=C(O)c1ccc(Br)c(OCC(F)(F)F)c1]

To a stirred solution of Int11.03 (1.83 g) in THF (30 mL), methanol (10 mL) and water (10 mL) was added a 1 M solution of lithium hydroxide in water (18 mL). The mixture was stirred at room temperature for 1 h. Water was added and 2 N hydrochloric acid was added until pH 4 was reached. The precipitated solid was collected by filtration, was washed with water. The solid was suspended with toluene and concentrated in vacuum. Trituration of the residue with hexane gave 1.6 g of the title compound.

$^1$H-NMR (300 MHz, DMSO-$d_6$): δ [ppm]=4.95 (q, 2H), 7.51 (dd, 1H), 7.65 (d, 1H), 7.74 (d, 1H), 13.29 (br. s., 1H).

Intermediate Example Int11.05

[4-Bromo-3-(2,2,2-trifluoroethoxy)phenyl](morpholin-4-yl)methanone

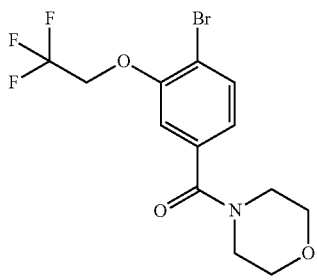 [SMILES: O=C(c1ccc(Br)c(OCC(F)(F)F)c1)N1CCOCC1]

The compound was prepared analogously to Intermediate Example Int11.02 from Intermediate Example Int13.01 and 2,2,2-trifluoroethyl trifluoromethanesulfonate.

$^1$H-NMR (400 MHz, DMSO-$d_6$): δ [ppm]=3.43-3.75 (m, 8H), 4.92 (q, 2H), 7.02 (dd, 1H), 7.27 (d, 1H), 7.70 (d, 1H).

Intermediate Example Int11.06

[4-Bromo-3-(2,2,2-trifluoroethoxy)phenyl](2-oxa-6-azaspiro[3.3]hept-6-yl)methanone

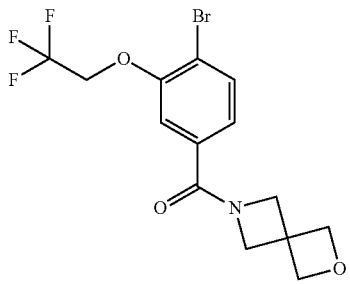 [SMILES: O=C(c1ccc(Br)c(OCC(F)(F)F)c1)N1CC2(COC2)C1]

Starting with Int11.04 (800 mg) and 2-oxa-6-azaspiro[3.3]heptane ethanedioate (2:1) (540 mg), Int11.06 was prepared analogously to the procedure for the preparation of Int09.05. Yield: 626 mg of the title compound.

$^1$H-NMR (400 MHz, DMSO-$d_6$): δ [ppm]=4.21 (s, 2H), 4.48 (s, 2H), 4.60-4.77 (m, 4H), 4.93 (q, 2H), 7.20 (dd, 1H), 7.37 (s, 1H), 7.72 (d, 1H).

Intermediate Example Int11.07

[4-Bromo-3-(2,2,2-trifluoroethoxy)phenyl](3-hydroxyazetidin-1-yl)methanone

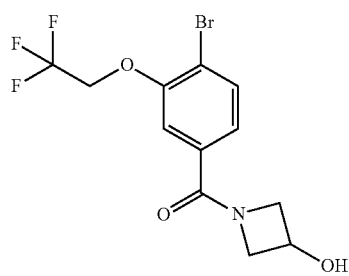 [SMILES: O=C(c1ccc(Br)c(OCC(F)(F)F)c1)N1CC(O)C1]

Starting with Int11.04 (1 g) and 3-hydroxyazetidine hydrochloride (500 mg), Int11.07 was prepared analogously to the procedure for the preparation of Int09.05. Yield: 840 mg of the title compound. $^1$H-NMR (400 MHz, DMSO-$d_6$): δ [ppm]=3.77 (dd, 1H), 4.06 (dd, 1H), 4.17-4.31 (m, 1H), 4.39-4.55 (m, 2H), 14.95 (q, 2H), 5.78 (d, 1H), 7.20 (dd, 1H), 7.38 (d, 1H), 7.70 (d, 1H).

Intermediate Example Int11.08

4-bromo-N-(oxetan-3-yl)-3-(2,2,2-trifluoroethoxy)benzamide

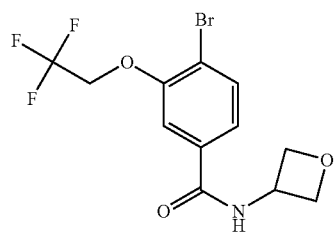 [SMILES: O=C(NC1COC1)c1ccc(Br)c(OCC(F)(F)F)c1]

To a stirred solution of Int11.04 (80 mg) in DMF (2 mL) was added potassium carbonate (111 mg), oxetan-3-amine hydrochloride (35 mg) and TBTU (112 mg). The mixture was stirred at room temperature for 3 h. Further oxetan-3-amine hydrochloride (35 mg), TBTU (112 mg) were added and the mixture was stirred for 4 h. The solvent was removed in vacuum. Water was added and the mixture was extracted with ethyl acetate. The organic phase was washed with saturated sodium chloride solution, dried (sodium sulfate) and the solvent was removed in vacuum. Silica gel chromatography gave 48 mg of the title compound.

Intermediate Example Int12.01

N,N-diethyl-3-hydroxy-4-iodobenzamide

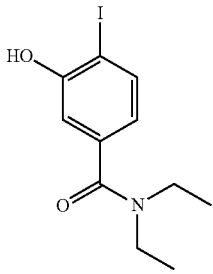

3-Hydroxy-4-iodobenzoic acid (WO2006/18325) (10.0 g) was dissolved in a mixture of DCM (75 mL) and DMF (50 mL) and cooled to 0° C. Oxalyl chloride (7.21 g) was added, and the mixture was stirred for 10 min. Subsequently, diethylamine (6.93 g) was added, and the mixture was warmed to r.t. and stirred for 1.5 h. The reaction mixture was then diluted with water and three times extracted with ethyl acetate. The combined organic layers were washed with aqueous buffer solution (pH 2), satd. sodium bicarbonate solution, and brine, then dried over sodium sulfate, and the solvent was evaporated. The title compound (8.40 g, 66%) was obtained as an oil.

$^1$H-NMR (400 MHz, DMSO-$d_6$): δ [ppm]=1.07 (br. s, 6H), 3.16 (br. s, 2H), 3.39 (br. s, 2H), 6.55 (dd, 1H), 6.80 (d, 1H), 7.71 (d, 1H), 10.56 (br. s, 1H).

Intermediate Example Int12.02

3-(cyclopropylmethoxy)-N,N-diethyl-4-iodobenzamide

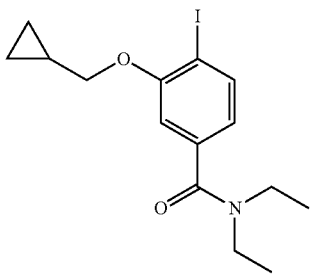 [SMILES: CCN(CC)C(=O)c1ccc(I)c(OCC2CC2)c1]

N,N-Diethyl-3-hydroxy-4-iodobenzamide, Int12.01 (618 mg) was dissolved in DMF (2.7 mL) and acetonitrile (0.1 mL), and potassium carbonate (535 mg) and 1-(bromomethyl)cyclopropane (275 g) were added. The mixture was heated for 30 min in a microwave oven to 150° C. Subsequently, the reaction mixture was diluted with water and extracted three times with ethyl acetate. The combined organic layers were washed three times with aqueous ammonium chloride solution, then with satd. aqueous sodium bicarbonate solution and with brine. It was dried over sodium sulfate, and the solvent was evaporated to yield 498 mg (63%) of the title compound as an oil.

$^1$H-NMR (400 MHz, DMSO-$d_6$): δ [ppm]=0.34-0.40 (m, 2H), 0.54-0.60 (m, 2H), 0.99-1.08 (m, 3H), 1.09-1.16 (m, 3H), 1.17-1.28 (m, 1H), 3.09-3.23 (m, 2H), 3.35-3.45 (m, 2H), 3.94 (d, 2H), 6.68 (dd, 1H), 6.89 (d, 1H), 7.80 (d, 1H).

Intermediate Example Int13.01

(4-Bromo-3-hydroxyphenyl)(morpholin-4-yl)methanone

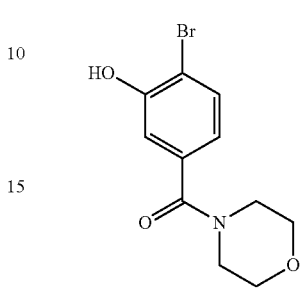

To a stirred solution of 4-bromo-3-hydroxybenzoic acid (3 g) in THF (150 mL) was added Hünig Base (2.1 g), morpholine (1.77 g) and HATU (6.18 g). The mixture was stirred at r.t. for 16 h. Water was added and the organic phase was separated. The organic phase was washed with 2 M HCl, water, and with saturated sodium chloride solution, dried (sodium sulfate) and the solvent was removed in vacuum to yield 3.86 g of the title compound.

$^1$H-NMR (300 MHz, DMSO-$d_6$): δ [ppm]=3.57 (br. s., 8H), 6.76 (dd, 1H), 6.94 (d, 1H), 7.54 (d, 1H), 10.57 (s, 1H).

Intermediate Example Int13.02

[4-Bromo-3-(2,2-difluoroethoxy)phenyl](morpholin-4-yl)methanone

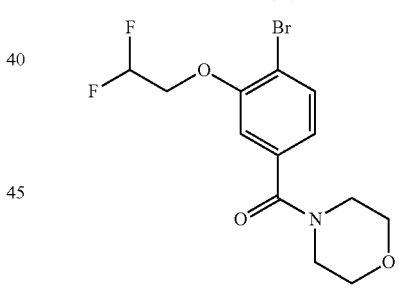

(4-Bromo-3-hydroxyphenyl)(morpholin-4-yl)methanone, Int13.01 (2.8 g) was dissolved in DMF (18 mL) and acetonitrile (0.7 mL), and potassium carbonate (2.41 g) and 2,2-difluoroethyl trifluoromethansulfonate (2.0 g) were added. The mixture was heated for 150 min 150° C. Subsequently, the solvents were removed and the resulting residue was partitioned between water and ethyl acetate. The aqueous layer was extracted three times with ethyl acetate. The combined organic layers were washed three times with aqueous ammonium chloride solution, then with satd. aqueous sodium bicarbonate solution and with brine. It was dried over sodium sulfate, and the solvent was evaporated to yield 2.61 g of the title compound as an oil.

$^1$H-NMR (400 MHz, DMSO-$d_6$): δ [ppm]=3.61 (br. s., 8H), 4.46 (td, 2H), 6.25-6.57 (m, 1H), 6.97 (dd, 1H), 7.22 (d, 1H), 7.68 (d, 1H).

Intermediate Example Int14.01

Methyl 4-bromo-3-(2-fluoroethoxy)benzoate

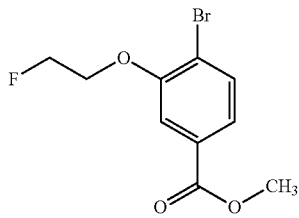

Starting with methyl 4-bromo-3-hydroxybenzoate (5 g) and 1-bromo-2-fluoroethane (3.27 g), Int14.01 was prepared analogously to the procedure for the preparation of Int10.01. Yield: 6 g of the title compound.

$^1$H-NMR (400 MHz, DMSO-d$_6$): δ [ppm]=3.83-3.90 (m, 3H), 4.35-4.42 (m, 1H), 4.43-4.48 (m, 1H), 4.68-4.77 (m, 1H), 4.81-4.89 (m, 1H), 7.50 (dd, 1H), 7.58 (d, 1H), 7.77 (d, 1H).

Intermediate Example Int14.02

4-Bromo-3-(2-fluoroethoxy)benzoic acid

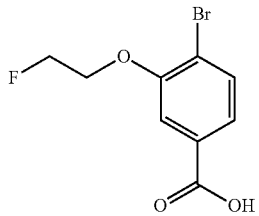 [SMILES: O=C(O)c1ccc(Br)c(OCCF)c1]

Starting with methyl 4-bromo-3-(2-fluoroethoxy)benzoate Int14.01 (2.34 g) Int14.02 was prepared analogously to the procedure for the preparation of Int11.04. Yield: 2.06 g of the title compound.

$^1$H-NMR (400 MHz, DMSO-d$_6$): δ [ppm]=4.33-4.40 (m, 1H), 4.40-4.48 (m, 1H), 4.68-4.76 (m, 1H), 4.80-4.88 (m, 1H), 7.48 (dd, 1H), 7.57 (d, 1H), 7.73 (d, 1H), 13.24 (br. s., 1H).

Intermediate Example Int14.03

[4-Bromo-3-(2-fluoroethoxy)phenyl](2-oxa-6-azaspiro[3.3]hept-6-yl)methanone

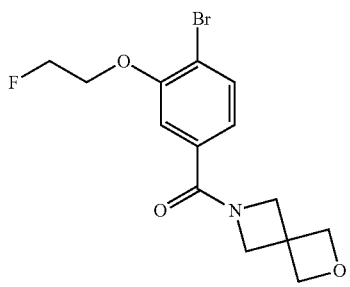 [SMILES: O=C(c1ccc(Br)c(OCCF)c1)N1CC2(COC2)C1]

Starting with Int14.02 (1.0 g) and 2-oxa-6-azaspiro[3.3]heptane ethanedioate (2:1) (767 mg), Int14.03 was prepared analogously to the procedure for the preparation of Int09.05. Yield: 578 mg of the title compound.

$^1$H-NMR (400 MHz, DMSO-d$_6$): δ [ppm]=4.20 (s, 2H), 4.32-4.37 (m, 1H), 4.39-4.44 (m, 1H), 4.48 (s, 2H), 4.67 (d, 4H), 4.71 (dd, 1H), 4.80-4.87 (m, 1H), 7.13 (dd, 1H), 7.27 (d, 1H), 7.67 (d, 1H).

Intermediate Example Int15.01

[4-Bromo-3-(trifluoromethyl)phenyl](morpholin-4-yl)methanone

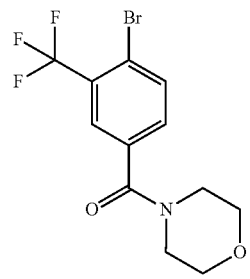 [SMILES: O=C(c1ccc(Br)c(C(F)(F)F)c1)N1CCOCC1]

Starting with 4-bromo-3-(trifluoromethyl)benzoic acid (2.0 g) and morpholine (972 mg), Int15.01 was prepared analogously to the procedure for the preparation of Int09.05. Yield: 2.09 g of the title compound.

$^1$H-NMR (400 MHz, DMSO-d$_6$): δ [ppm]=3.43-3.80 (m, 8H), 7.64 (d, 1H), 7.85 (s, 1H), 7.98 (d, 1H).

Intermediate Example Int16.01

(4-bromo-3-fluorophenyl)(2-oxa-6-azaspiro[3.3]hept-6-yl)methanone

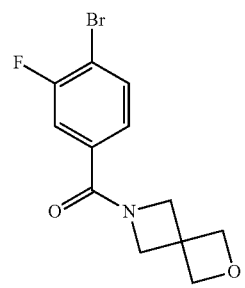 [SMILES: O=C(c1ccc(Br)c(F)c1)N1CC2(COC2)C1]

Starting with 4-bromo-3-fluorobenzoic acid (550 mg) and 2-oxa-6-azaspiro[3.3]heptane ethanedioate (2:1) (700 mg), Int16.01 was prepared analogously to the procedure for the preparation of Int09.05. Yield: 281 mg of the title compound.

$^1$H-NMR (400 MHz, DMSO-d$_6$): δ [ppm]=4.21 (s, 2H), 4.49 (s, 2H), 4.61-4.72 (m, 4H), 7.39 (dd, 1H), 7.56 (dd, 1H), 7.81 (dd, 1H).

Intermediate Example Int16.02

(4-Bromo-3-fluorophenyl)(morpholin-4-yl)methanone

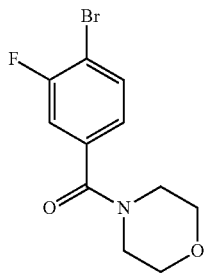

Starting with 4-bromo-3-fluorobenzoic acid (500 mg) and morpholine (292 mg), Int16.02 was prepared analogously to the procedure for the preparation of Int09.05. Yield: 645 mg of the title compound.

$^1$H-NMR (400 MHz, DMSO-d$_6$): δ [ppm]=3.60 (br. s., 8H), 7.21 (dd, 1H), 7.47 (dd, 1H), 7.80 (dd, 1H).

Intermediate Example Int17.01

1-(4-Bromo-3-methoxyphenyl)piperazine

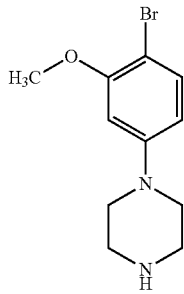

1-(3-Methoxyphenyl)piperazine dihydrochloride (11.97 g) and sodium acetate (4.07 g) were added to a mixture of water (77 ml) and glacial acetic acid (360 ml) at 5° C. Bromine (7.93 g) was added slowly and the mixture was stirred at 0° C. for 1 h. Subsequently, the solvents were removed in vacuo. This residue was dissolved in ethyl acetate and washed with 1N sodium hydroxide solution. The organic layer was dried (sodium sulfate) and the solvent was evaporated. HPLC separation gave 4.39 g of the title compound.

Intermediate Example Int17.02

1-(4-Bromo-3-methoxyphenyl)-4-methylpiperazine

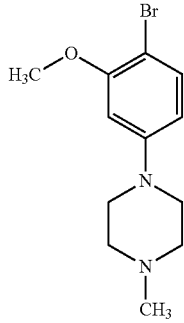 [SMILES: COc1cc(N2CCN(C)CC2)ccc1Br]

To a stirred solution of Int17.01 (1.0 g) in methanol (60 mL) were added acetic acid (0.42 ml) and after 5 min sodium cyanoborohydride (463 mg). After additional 5 min formaldehyde solution (33% in water; 0.59 ml) was added. The reaction mixture was stirred at 60° C. for 16 h. Subsequently, the solvents were removed in vacuo. This residue was dissolved in ethyl acetate and washed with 1N sodium hydroxide solution. The organic layer was dried (sodium sulfate) and the solvent was evaporated. Crystallization from pentanes/methyl tert-butyl ether gave 961 mg of the title compound.

Intermediate Example Int17.03

1-(4-bromo-3-methoxyphenyl)-4-tert-butylpiperazine

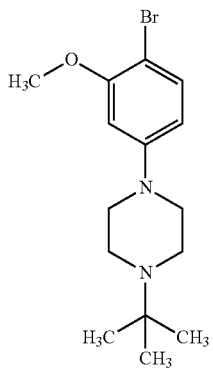 [SMILES: COc1cc(N2CCN(C(C)(C)C)CC2)ccc1Br]

To a stirred solution of 1-tert-butylpiperazine (5.0 g) in THF (25 mL) was added n-butyllithium in hexanes (4.2 mL, c=2.5 M) at −78° C. The solution was stirred for 30 minutes at 0° C. A solution of 1-bromo-4-fluoro-2-methoxybenzene (1.44 g) in THF (2 mL) was added at −78° C. and the reaction mixture was allowed to warm up to 0° C. over 3 h. The mixture was stirred at 0° C. for 2 h. Water was added and the mixture was extracted with ethyl acetate. The organic phase was washed with saturated sodium chloride solution, dried (sodium sulfate) and the solvent was removed in vacuum. Aminophase-silica-gel chromatography gave 490 mg of the title compound.

Intermediate Example Int18.01

2-methoxy-4-(morpholin-4-ylmethyl)phenol

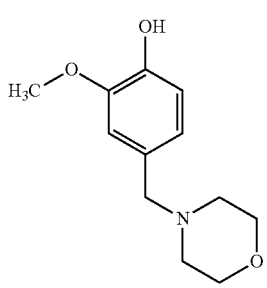 [SMILES: COc1cc(CN2CCOCC2)ccc1O]

To a stirred solution of 4-hydroxy-3-methoxybenzaldehyde (1.0 g) in dichloromethane (20 mL) was added morpholine (0.62 g) and sodium triacetoxyborohydride (2.03 g) and acetic acid (0.37 mL) and the mixture was stirred at room temperature for 16 h. A half-saturated solution of sodium bicarbonate was added and the mixture was extracted with dichloromethane and methanol (100:1). The organic phase was washed with saturated sodium chloride solution, dried (sodium sulfate) and the solvent was removed in vacuum. Aminophase-silica-gel chromatography gave 1.2 g of the title compound.

Intermediate Example Int18.02

2-methoxy-4-(morpholin-4-ylmethyl)phenyl trifluoromethanesulfonate

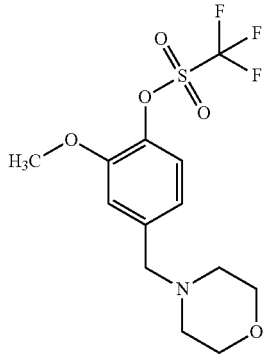 [SMILES: COc1cc(CN2CCOCC2)ccc1OS(=O)(=O)C(F)(F)F]

To a stirred solution of Int18.01 (1.2 g) in dichloromethane (50 mL) was added triethylamine (2.23 mL) the solution was cooled down to −78° C. Trifluoromethanesulfonic anhydride (1.80 g) was added and the solution was stirred at −78° C. for 1 h. The solution was stirred at room temperature for 15 minutes, water was added and the mixture was extracted with dichloromethane. The organic phase was washed with saturated sodium chloride solution, dried (sodium sulfate) and the solvent was removed in vacuum. Aminophase-silica-gel chromatography gave 1.88 g of the title compound.

Intermediate Example Int18.03

2-methoxy-4-[(4-methylpiperazin-1-yl)methyl]phenol

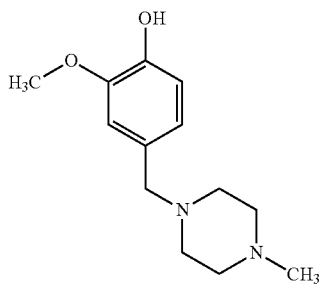

To a stirred solution of 4-hydroxy-3-methoxybenzaldehyde (1.04 g) in dichloromethane (20 mL) was added 1-methylpiperazine (0.81 g) and sodium triacetoxyborohydride (2.11 g) and acetic acid (0.39 mL) and the mixture was stirred at room temperature for 16 h. A half-saturated solution of sodium bicarbonate was added and the mixture was extracted with dichloromethane and methanol (100:1). The organic phase was washed with saturated sodium chloride solution, dried (sodium sulfate) and the solvent was removed in vacuum. Recrystallization of the residue from diisopropyl ether gave 0.9 g of the title compound.

Intermediate Example Int18.04

2-methoxy-4-[(4-methylpiperazin-1-yl)methyl]phenyl trifluoromethanesulfonate

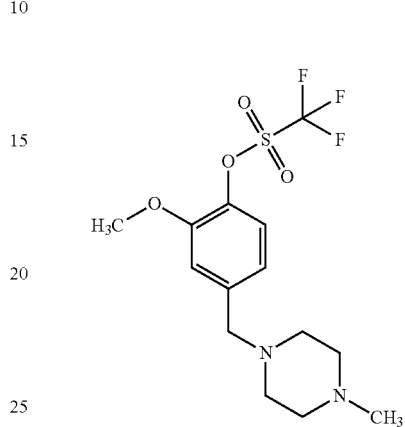

To a stirred solution of Int18.03 (0.86 g) in dichloromethane (35 mL) was added triethylamine (1.5 mL) the solution was cooled down to −78° C. Trifluoromethanesulfonic anhydride (1.22 g) was added and the solution was stirred at −78° C. for 1 h. The solution was stirred at room temperature for 15 minutes, water was added and the mixture was extracted with dichloromethane. The organic phase was washed with saturated sodium chloride solution, dried (sodium sulfate) and the solvent was removed in vacuum. Aminophase-silica-gel chromatography gave 1.2 g of the title compound.

Intermediate Example Int19.01

1-bromo-2-ethoxy-4-fluorobenzene

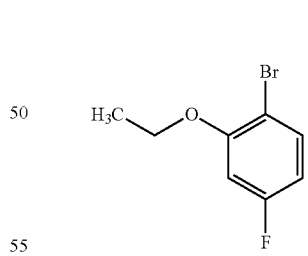

To a stirred solution of 2-bromo-5-fluorophenol (5.0 g) in DMF (30 mL) was added potassium carbonate (10.8 g) and iodoethane (6.12 g). The mixture was stirred at room temperature for 16 h. The solvent was removed in vacuum. Water was added and the mixture was extracted with a mixture of ethyl acetate and hexane (3:1). The organic phase was washed with saturated sodium chloride solution, dried (sodium sulfate) and the solvent was removed in vacuum, to give 5.06 g of the title compound as a crude product, that was used for the next step without purification.

Intermediate Example Int19.02

4-(4-bromo-3-ethoxyphenoxy)-1-methylpiperidine

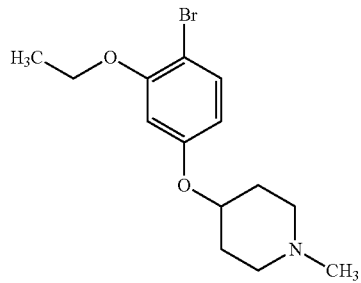 [SMILES: CCOc1cc(OC2CCN(C)CC2)ccc1Br]

To a stirred suspension of sodium hydride (525 mg; 60% w/w sodium hydride in oil) in NMP (15 mL) was added 1-methylpiperidin-4-ol (1.26 g) at 0° C. The mixture was stirred at room temperature for 30 minutes. Int19.01 (1.2 g) was added and the mixture was stirred at 100° C. for 1 h. Water was added and the mixture was extracted with ethyl acetate. Water and hydrochloric acid (4N) were added to the organic phase. The aqueous phase was separated and aqueous sodium hydroxide was added to the aqueous phase until pH 10 was reached. The aqueous phase was extracted with ethyl acetate. The organic phase was dried (sodium sulfate) and the solvent was removed in vacuum to give 930 mg of the title compound, that was used for the next step without purification.

Intermediate Example Int20.01

4-(4-bromo-3-methoxyphenoxy)-1-methylpiperidine

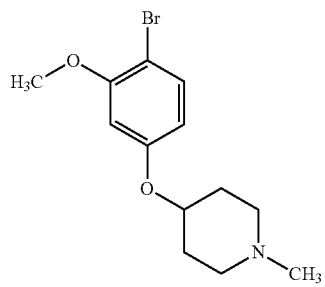

To a stirred suspension of sodium hydride (1.76 g; 60% w/w sodium hydride in oil) in DMF (55 mL) was added 1-methylpiperidin-4-ol (3.37 g) at 0° C. The mixture was stirred at room temperature for 30 minutes. 1-bromo-4-fluoro-2-methoxybenzene (3.0 g) was added and the mixture was stirred at 100° C. for 1 h. Water was added and the mixture was extracted with ethyl acetate. The organic phase was washed with saturated sodium chloride solution, dried (sodium sulfate) and the solvent was removed in vacuum. Aminophase-silica-gel chromatography gave 3.65 g of the title compound.

Intermediate Example Int21.01

4-[4-bromo-3-(methylsulfanyl)phenoxy]-1-methylpiperidine

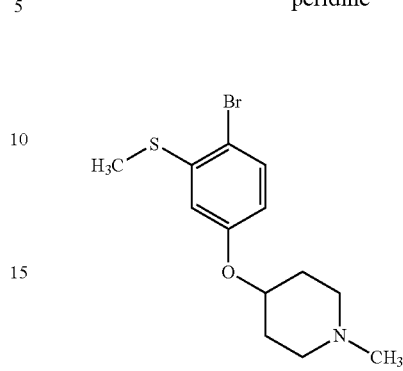

To a stirred suspension of sodium hydride (543 mg; 60% w/w sodium hydride in oil) in DMF (20 mL) was added 1-methylpiperidin-4-ol (782 mg) at 0° C. The mixture was stirred at room temperature for 30 minutes. 1-bromo-4-fluoro-2-(methylsulfanyl)benzene (1.0 g) was added and the mixture was stirred at 100° C. for 1 h. Water was added and the mixture was extracted with ethyl acetate. The organic phase was washed with saturated sodium chloride solution, dried (sodium sulfate) and the solvent was removed in vacuum. Aminophase-silica-gel chromatography gave 1.02 g of the title compound.

Intermediate Example Int22.01

4-[(4-Bromo-3-methoxyphenyl)sulfonyl]morpholine

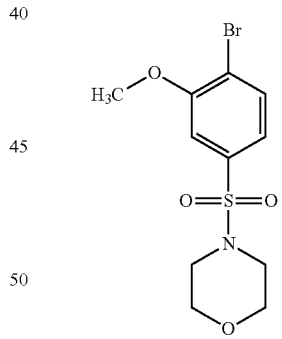

To a stirred solution of 4-bromo-3-methoxybenzenesulfonyl chloride (490 mg) in DMF (6.5 mL) was added morpholine (598 mg) and the mixture was stirred 14 h at r.t. Subsequently, the reaction mixture was evaporated under reduced pressure. The resulting residue was partitioned between water and ethyl acetate. The aqueous layer was extracted three times with ethyl acetate. The combined organic layers were washed with brine, dried over sodium sulfate, and the solvent was evaporated. Silica-gel chromatography gave the title compound (508 mg).

$^1$H-NMR (400 MHz, DMSO-$d_6$): δ [ppm]=2.82-2.92 (m, 4H), 3.57-3.66 (m, 4H), 3.97 (s, 3H), 7.36 (d, 1H), 7.74 (dd, 1H), 7.86 (d, 1H).

Intermediate Example Int23.01

4-bromo-3-methylphenyl)(2-oxa-6-azaspiro[3.3]hept-6-yl)methanone

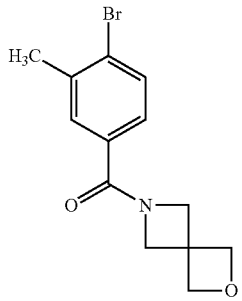

To a stirred solution of 4-bromo-3-methylbenzoic acid (1.5 g) in DMF (55 mL) was added molecular sives (1.9 g) and the mixture was stirred for 1 h. TBTU (4.0 g) was added and the mixture was stirred for 30 minutes. Potassium carbonate (4.8 g) and 2-oxa-6-azaspiro[3.3]heptane ethanedioate (2:1) (1.5 g) were added and the mixture was stirred at r.t. for 16 h. Water was added and the mixture was extracted with ethyl acetate. The organic phase was washed with saturated sodium chloride solution, dried (sodium sulfate) and the solvent was removed in vacuum. Aminophase-silica-gel chromatography gave 1.77 g of the title compound.

Intermediate Example Int23.02

(4-bromo-3-methylphenyl)(morpholin-4-yl)methanone

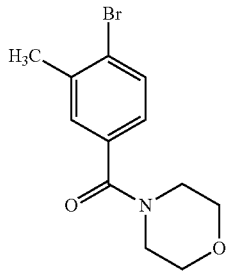 [SMILES: Cc1cc(C(=O)N2CCOCC2)ccc1Br]

To a stirred solution of 4-bromo-3-methylbenzoic acid (2.0 g) in DMF (70 mL) was added potassium carbonate (6.4 g), morpholine (1.46 g) and TBTU (7.47 g). The mixture was stirred at r.t. for 16 h. Water was added and the mixture was extracted with ethyl acetate. The organic phase was washed with saturated sodium chloride solution, dried (sodium sulfate) and the solvent was removed in vacuum. Silica-gel chromatography gave 2.1 g of the title compound.

Intermediate Example Int24.01

Ethyl 4-amino-3-(trifluoromethoxy)benzoate

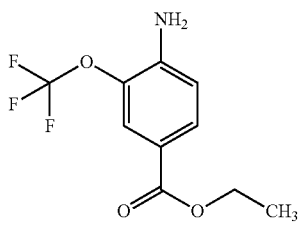 [SMILES: CCOC(=O)c1ccc(N)c(OC(F)(F)F)c1]

To a stirred solution of 4-amino-3-(trifluoromethoxy)benzoic acid (5.0 g) in ethanol (100 mL) was added thionyl chloride (2.47 mL) at 0° C. The mixture was heated to reflux for 3 h. The solvent was removed in vacuum. The residue was dissolved in ethyl acetate and the mixture was washed with a half-saturated solution of sodium bicarbonate and with saturated sodium chloride solution, dried (sodium sulfate) and the solvent was removed in vacuum, to give 4.81 g of the title compound, that was used for the next step without purification.

Intermediate Example Int24.02

Ethyl 4-bromo-3-(trifluoromethoxy)benzoate

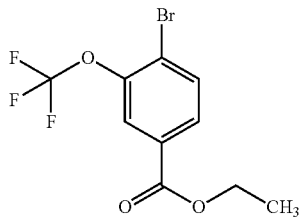 [SMILES: CCOC(=O)c1ccc(Br)c(OC(F)(F)F)c1]

To a stirred solution of Int24.01 (4.8 g) in concentrated aqueous hydrobromic acid (53 mL) was added at 5° C. 9.0 mL of a 3 M solution of sodium nitrite. The mixture was stirred for 10 minutes and copper(1) bromide (2.76 g) was added. The mixture was stirred for 5 minutes and water (125 mL) was added and the mixture was stirred for 1 h. The mixture was extracted with ethyl acetate. The organic phase was washed with saturated sodium chloride solution, dried (sodium sulfate) and the solvent was removed in vacuum. Silica gel chromatography gave 4.1 g of the title compound.

Intermediate Example Int24.03

4-bromo-3-(trifluoromethoxy)benzoic acid

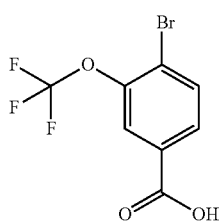

To a stirred solution of Int24.02 (4.1 g) in ethanol (150 mL) was added 9.8 mL of a 2 M solution of sodium hydroxide and the solution was stirred for 2 h at room temperature. An aqueous solution of hydrochloric acid was added until pH 3 was reached. About 100 mL of solvent were removed in vacuum, water was added and the residue was extracted with ethyl acetate. The solution was dried (sodium sulfate) and the solvent was removed in vacuum, to give 3.4 g of the title compound, that was used for the next step without purification.

Intermediate Example Int24.04

[4-bromo-3-(trifluoromethoxy)phenyl](morpholin-4-yl)methanone

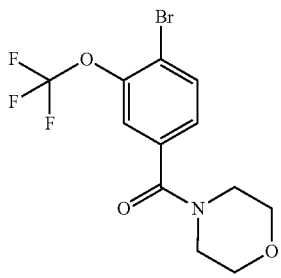 [SMILES: O=C(c1ccc(Br)c(OC(F)(F)F)c1)N1CCOCC1]

To a stirred solution of Int24.03 (1.2 g) in DMF (32 mL) was added potassium carbonate (2.9 g), morpholine (660 mg) and TBTU (3.38 g). The mixture was stirred at r.t. for 16 h. Water was added and the mixture was extracted with ethyl acetate. The organic phase was washed with saturated sodium chloride solution, dried (sodium sulfate) and the solvent was removed in vacuum. Aminophase-silica-gel chromatography followed by silica gel chromatography gave 1.1 g of the title compound.

$^1$H-NMR (400 MHz, DMSO-$d_6$): δ [ppm]=3.43-3.71 (m, 8H), 7.37 (dd, 1H), 7.50-7.59 (m, 1H), 7.88 (d, 1H).

Intermediate Example Int24.05

[4-bromo-3-(trifluoromethoxy)phenyl](2-oxa-6-azaspiro[3.3]hept-6-yl)methanone

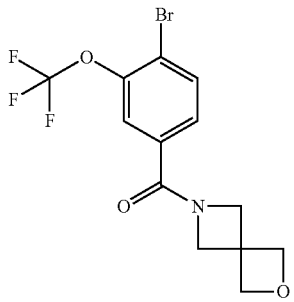 [SMILES: O=C(c1ccc(Br)c(OC(F)(F)F)c1)N1CC2(COC2)C1]

To a stirred solution of Int24.03 (900 mg) in DMF (24 mL) was added molecular sives (1.0 g) and the mixture was stirred for 1 h. TBTU (1.32 g) was added and the mixture was stirred for 30 minutes. Potassium carbonate (2.18 g) and 2-oxa-6-azaspiro[3.3]heptane ethanedioate (2:1) (454 mg) were added and the mixture was stirred at r.t. for 16 h. Further TBTU (500 mg) and 2-oxa-6-azaspiro[3.3]heptane ethanedioate (2:1) (225 mg) were added and the mixture was stirred at r.t. for 1 h. Water was added and the mixture was extracted with ethyl acetate. The organic phase was washed with saturated sodium chloride solution, dried (sodium sulfate) and the solvent was removed in vacuum. Aminophase-silica-gel chromatography gave 386 mg of the title compound.

$^1$H-NMR (400 MHz, DMSO-$d_6$): δ [ppm]=4.18 (s, 2H), 4.46 (s, 2H), 4.63 (s, 4H), 7.53 (dd, 1H), 7.61-7.67 (m, 1H), 7.89 (d, 1H).

Intermediate Example Int25.01

(3-bromo-4-methoxyphenyl)(morpholin-4-yl)methanone

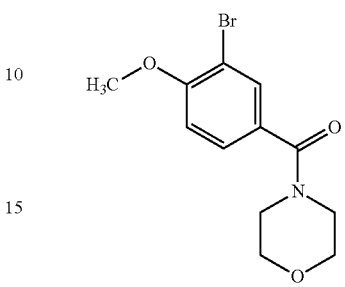

Starting with 3-bromo-4-methoxybenzoic acid (5.0 g) and morpholine (2.82 g), Int25.01 was prepared analogously to the procedure for the preparation of Int09.05. Yield: 6.9 g of the title compound.

$^1$H-NMR (400 MHz, DMSO-$d_6$): δ [ppm]=3.38-3.69 (m, 8H), 3.89 (s, 3H), 7.16 (d, 1H), 7.43 (dd, 1H), 7.62 (d, 1H).

Intermediate Example Int26.01

3-(4-bromo-3-methoxyphenyl)-1,3-oxazolidin-2-one

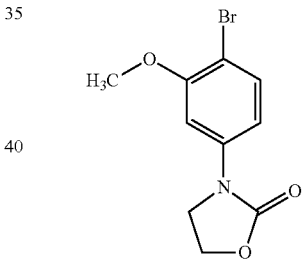

To a stirred solution of 4-Bromo-3-methoxy-aniline (10.0 g) in acetonitrile (176 mL) was added Hünig Base (25 mL) and 2-chloroethyl chloroformate (10.6 g). The mixture was stirred at room temperature for 0.5 h. The solvent was removed in vacuum. The residue was dissolved in tetrahydrofurane (250 mL), and potassium tert.-butoxide (16.2 g) was added. The mixture was stirred at room temperature for 2 h. The solvent was removed in vacuum. The residue was dissolved in ethyl acetate and the mixture was washed with water and with saturated sodium chloride solution, dried (sodium sulfate) and the solvent was removed in vacuum. Silica gel chromatography gave a compound that was crystallized from ethanol. Yield: 7.7 g of the title compound. The mother liquor was concentrated in vacuum and aminophase-silica-gel chromatography gave a solid that was recrystalized from ethanol to give further 2.3 g of the title compound.

$^1$H-NMR (300 MHz, CHLOROFORM-d): δ [ppm]=4.00-4.10 (m, 2H), 4.45-4.55 (m, 2H), 6.66 (dd, 1H), 7.49 (d, 1H), 7.63 (d, 1H).

Intermediate Example Int27.01

4-bromo-3-ethoxyaniline

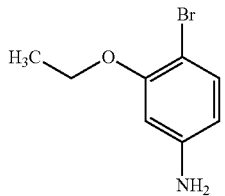

To a stirred solution of 1-bromo-2-ethoxy-4-nitrobenzene (5.0 g) in ethanol (250 mL) was added Raney Nickel (118 mg) and the mixture was stirred and a hydrogen atmosphere for 18 h. The mixture was filtered through celite and the solvent was removed in vacuum to give 4.2 g of the crude product, that was used for the next step without purification.

Intermediate Example Int27.02

2-chloroethyl (4-bromo-3-ethoxyphenyl)carbamate

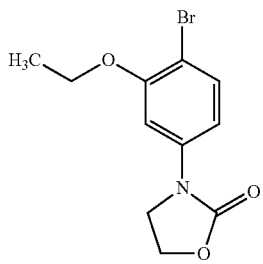 [SMILES: CCOc1cc(N2CCOC2=O)ccc1Br]

To a stirred solution of crude 4-Bromo-3-ethoxyaniline (4.2 g) in acetonitrile (100 mL) was added Hünig Base (9.7 mL) and 2-chloroethyl chloroformate (4.1 g). The mixture was stirred at room temperature for 0.5 h. The solvent was removed in vacuum. The residue was dissolved in ethyl acetate and the mixture was washed with a half-saturated solution of sodium bicarbonate and with saturated sodium chloride solution, dried (sodium sulfate) and the solvent was removed in vacuum. The residue was dissolved in tetrahydrofurane (385 mL), and potassium tert.-butoxide (3.1 g) was added. The mixture was stirred at room temperature for 18 h. The solvent was removed in vacuum. The residue was dissolved in ethyl acetate and the mixture was washed with water and with saturated sodium chloride solution, dried (sodium sulfate) and the solvent was removed in vacuum. Silica gel chromatography gave 1.4 g of the title compound.

$^1$H-NMR (300 MHz, CHLOROFORM-d): δ [ppm]=1.48 (t, 3H), 3.99-4.08 (m, 2H), 4.13 (q, 2H), 4.43-4.54 (m, 2H), 6.66 (dd, 1H), 7.48 (d, 1H), 7.58 (d, 1H).

Intermediate Example Int28.01

3-(5-bromo-4-methylpyridin-2-yl)-1,3-oxazolidin-2-one

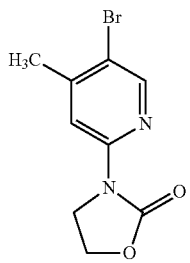

To a solution of 2-amino-5-bromo-4-methylpyridine (10.0 g) in acetonitrile (300 mL) was added 2-chloroethyl chloroformate (11.58 g) and Hünig Base (20.31 g). The mixture was stirred 20 min at ambient temperature. After removal of the solvent the residue was dissolved in THF (700 ml). Potassium tert.-butoxide (17.63 g) was added and the resulting mixture was stirred over night. After removal of the solvent ethyl acetate was added. The solution washed with water and saturated sodium chloride solution, dried (sodium sulfate), and the solvent was removed in vacuum. The resulting material purified by silica gel chromatography to gave 5.79 g of the title compound.

$^1$H-NMR (300 MHz, DMSO-d$_6$): δ [ppm]=2.38 (s, 3H), 4.12 (t, 2H), 4.45 (t, 2H), 8.07 (s, 1H), 8.45 (s, 1H).

Intermediate Example Int29.01

4-bromo-N-(2-fluoroethyl)-3-methoxybenzamide

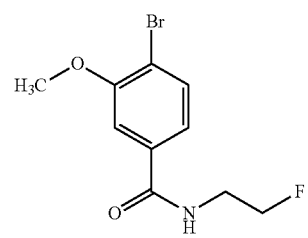

To a stirred solution of 4-bromo-3-methoxybenzoic acid (1.2 g) in THF (60 mL) was added Hünig Base (1.67 g), 2-fluoroethylamine hydrochloride (0.75 g) and HATU (2.37 g). The mixture was stirred at r.t. for 16 h. A half-saturated solution of sodium bicarbonate was added and the mixture was extracted with ethyl acetate. The organic phase was washed with aqueous ammonium chloride solution and with saturated sodium chloride solution, dried (sodium sulfate) and the solvent was removed in vacuum. Silica gel chromatography gave 1.29 g of the title compound.

$^1$H-NMR (400 MHz, DMSO-d$_6$): δ [ppm]=3.54 (d, 1H), 3.60 (d, 1H), 3.91 (s, 3H), 4.48 (t, 1H), 4.60 (t, 1H), 7.40 (dd, 1H), 7.54 (d, 1H), 7.68 (d, 1H), 8.81 (t, 1H).

Intermediate Example Int30.01

4-bromo-N-(2-fluoroethyl)-3-methylbenzamide

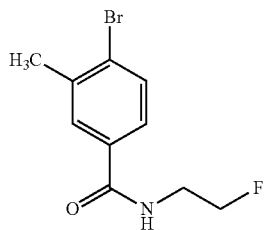

To a stirred solution of 4-bromo-3-methylbenzoic acid (1.25 g) in THF (50 mL) was added Hünig Base (1.82 g), 2-fluoroethylamine hydrochloride (0.93 g) and TBTU (2.35 g). The mixture was stirred at r.t. for 14 h. A half-saturated solution of sodium bicarbonate was added and the mixture was extracted with ethyl acetate. The organic phase was washed with aqueous ammonium chloride solution and with saturated sodium chloride solution, dried (sodium sulfate) and the solvent was removed in vacuum. Silica gel chromatography gave 1.45 g of the title compound.

$^1$H-NMR (400 MHz, DMSO-d$_6$): δ [ppm]=2.39 (s, 26H), 3.52 (q, 1H), 3.58 (q, 1H), 4.47 (t, 1H), 4.59 (t, 1H), 7.56-7.64 (m, 1H), 7.66-7.72 (m, 1H), 7.84 (d, 1H), 8.73 (t, 1H).

Synthesis of Examples

Example 01.01

2-cyclopropyl-N-[4-(2-{[2-methoxy-4-(morpholin-4-ylcarbonyl)phenyl]amino}[,2]-triazolo[1,5-a]pyridin-6-yl)phenyl]acetamide

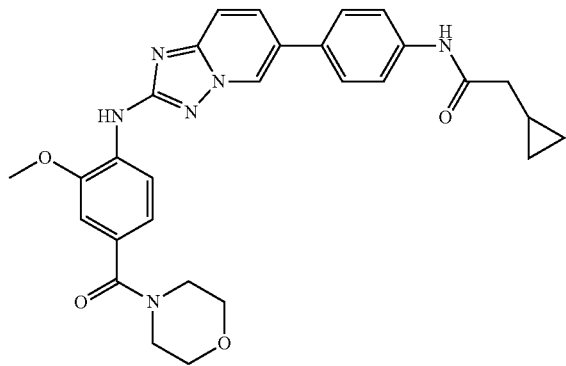 [SMILES: COc1cc(C(=O)N2CCOCC2)ccc1Nc1nc2ccc(-c3ccc(NC(=O)CC4CC4)cc3)cn2n1]

To a stirred suspension of Int2.3 (100 mg) in toluene (3.0 mL) and NMP (0.3 mL) was added Int09.01 (147 mg), chloro(2-dicyclohexylphosphino-2',4',6'-tri-i-propyl-1,1'-biphenyl)[2-(2-aminoethyl)phenyl]palladium(II) methyl-t-butylether adduct (27.1 mg), X-Phos (15.9 mg), and sodium tert-butoxide (157 mg). The flask was twice degassed and backfilled with argon. The mixture was heated to reflux for 1.5 h. Water was added and the reaction mixture was extracted with a mixture of dichloromethane and methanol (100:1). The organic phase was washed with saturated sodium chloride solution, dried (sodium sulfate) and the solvent was removed in vacuum. Silica gel chromatography followed by aminophase-silica-gel chromatography gave a solid that was recrystallized from ethanol. Yield: 130 mg of the title compound.

$^1$H-NMR (400 MHz, DMSO-d$_6$): δ [ppm]=0.13-0.22 (m, 2H), 0.42-0.51 (m, 2H), 0.95-1.10 (m, 1H), 2.20 (d, 2H), 3.41-3.65 (m, 8H), 3.88 (s, 3H), 6.99-7.06 (m, 2H), 7.63 (d, 1H), 7.65-7.75 (m, 4H), 7.91 (dd, 1H), 8.24 (s, 1H), 8.30 (d, 1H), 9.09 (d, 1H), 9.92 (s, 1H).

Example 01.02

2-cyclopropyl-N-[4-(2-{[2-ethoxy-4-(morpholin-4-ylcarbonyl)phenyl]amino}[,2]-triazolo[1,5-a]pyridin-6-yl)phenyl]acetamide

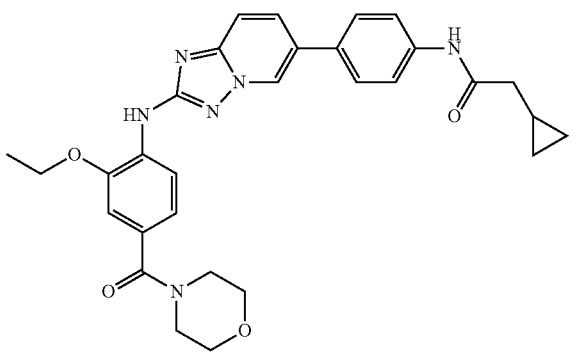 [SMILES: CCOc1cc(C(=O)N2CCOCC2)ccc1Nc1nc2ccc(-c3ccc(NC(=O)CC4CC4)cc3)cn2n1]

To a stirred suspension of Int2.3 (97 mg) in toluene (3.0 mL) and NMP (0.3 mL) was added Int10.03 (150 mg), chloro(2-dicyclohexylphosphino-2',4',6'-tri-i-propyl-1,1'-biphenyl)[2-(2-aminoethyl)phenyl]palladium(II) methyl-t-butylether adduct (26.3 mg), X-Phos (15.5 mg), and sodium tert-butoxide (153 mg). The flask was twice degassed and backfilled with argon. The mixture was heated to reflux for 1.5 h. Water was added and the reaction mixture was extracted with dichloromethane. The organic phase was washed with saturated sodium chloride solution, dried (sodium sulfate) and the solvent was removed in vacuum. Aminophase-silica-gel chromatography gave a solid that was recrystallized from ethanol. Yield: 90 mg of the title compound.

$^1$H-NMR (400 MHz, DMSO-d$_6$): δ [ppm]=0.13-0.21 (m, 2H), 0.39-0.51 (m, 2H), 0.97-1.09 (m, 1H), 1.40 (t, 3H), 2.20 (d, 2H), 3.42-3.64 (m, 8H), 4.14 (q, 2H), 7.00-7.05 (m, 2H), 7.62 (dd, 1H), 7.66-7.74 (m, 4H), 7.91 (dd, 1H), 8.12 (s, 1H), 8.31 (d, 1H), 9.08 (dd, 1H), 9.92 (s, 1H).

Example 01.03

2-cyclopropyl-N-[4-(2-{[2-methoxy-4-(4-methylpiperazin-1-yl)phenyl]amino}[,2]-triazolo[1,5-a]pyridin-6-yl)phenyl]acetamide trifluoroacetate

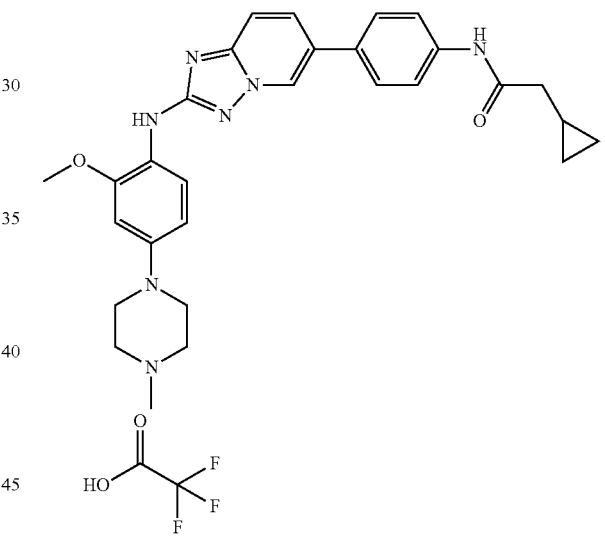

N-[4-(2-Amino[,2]triazolo[1,5-a]pyridin-6-yl)phenyl]-2-cyclopropylacetamide Int2.3 (100 mg), 1-(4-bromo-3-methoxyphenyl)-4-methylpiperazine (US2009/118305) (111 mg), chloro(2-dicyclohexylphosphino-2',4',6'-tri-i-propyl-1,1'-biphenyl)[2-(2-aminoethyl)phenyl]palladium(II) methyl-t-butylether adduct (10.8 mg), X-Phos (6.2 mg), and sodium tert-butoxide (57.1 mg) were pre-mixed, and degassed toluene (2.0 mL) was added. The mixture was heated overnight to 130° C., then diluted with satd. sodium carbonate solution and extracted with ethyl acetate. The organic layer was dried over sodium sulfate, and the solvent was evaporated. The crude product was purified by HPLC to yield 20.6 mg (10%) of the title compound.

$^1$H-NMR (400 MHz, DMSO-d$_6$): δ [ppm]=0.19-0.23 (m, 2H), 0.47-0.52 (m, 2H), 1.02-1.13 (m, 1H), 2.24 (d, 2H), 2.87-2.90 (m, 3H), 2.90-2.97 (m, 2H), 3.13-3.24 (m, 2H), 3.77-3.84 (m, 2H), 3.87 (s, 3H), 6.59 (dd, 1H), 6.73 (d, 1H), 7.58 (d, 1H), 7.72 (s, 4H), 7.84 (s, 1H), 7.89 (dd, 1H), 7.98 (d, 1H), 9.02-9.04 (m, 1H), 9.61 (br. s, 1H), 9.94 (s, 1H).

Example 02.01

2-(4-fluorophenyl)-N-[4-(2-{[2-methoxy-4-(morpholin-4-ylcarbonyl)phenyl]amino}[,2]-triazolo[1,5-a]pyridin-6-yl)phenyl]acetamide

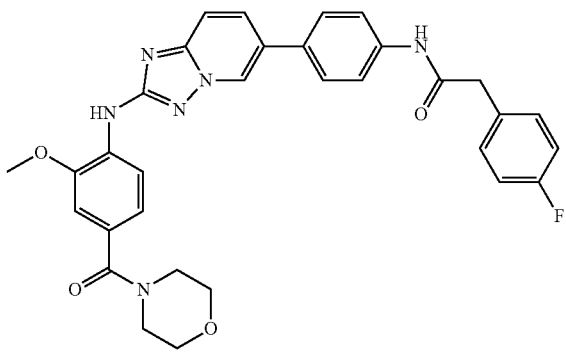 [SMILES: COc1cc(C(=O)N2CCOCC2)ccc1Nc1nc2ccc(-c3ccc(NC(=O)Cc4ccc(F)cc4)cc3)cn2n1]

To a stirred suspension of Int02.04 (300 mg) in toluene (8.0 mL) was added Int09.01 (374 mg), chloro(2-dicyclohexylphosphino-2',4',6'-tri-i-propyl-1,1'-biphenyl)[2-(2-aminoethyl)phenyl]palladium(II) methyl-t-butylether adduct (68.6 mg), X-Phos (40.4 mg), and sodium tert-butoxide (399 mg). The flask was twice degassed and backfilled with argon. The mixture was heated to reflux for 2 h. Water was added and the reaction mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was triturated with DIPE and cyclohexane. Yield: 260 mg of the title compound.

$^1$H-NMR (400 MHz, DMSO-d$_6$): δ [ppm]=3.43-3.61 (m, 8H), 3.64 (s, 2H), 3.88 (s, 3H), 6.99-7.06 (m, 2H), 7.09-7.17 (m, 2H), 7.28-7.38 (m, 2H), 7.63 (d, 1H), 7.65-7.75 (m, 4H), 7.90 (dd, 1H), 8.23 (s, 1H), 8.30 (d, 1H), 9.09 (s, 1H), 10.28 (s, 1H).

Example 02.02

N-[4-(2-{[2-ethoxy-4-(morpholin-4-ylcarbonyl)phenyl]amino}[,2]-triazolo[1,5-a]pyridin-6-yl)phenyl]-2-(4-fluorophenyl)acetamide

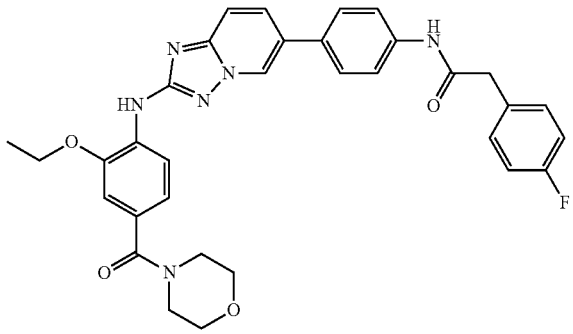 [SMILES: CCOc1cc(C(=O)N2CCOCC2)ccc1Nc1nc2ccc(-c3ccc(NC(=O)Cc4ccc(F)cc4)cc3)cn2n1]

To a stirred suspension of Int02.04 (115 mg) in toluene (3.0 mL) and NMP (0.3 mL) was added Int10.03 (150 mg), chloro(2-dicyclohexylphosphino-2',4',6'-tri-i-propyl-1,1'-biphenyl)[2-(2-aminoethyl)phenyl]palladium(II) methyl-t-butylether adduct (26.3 mg), X-Phos (15.5 mg), and sodium tert-butoxide (153 mg). The flask was twice degassed and backfilled with argon. The mixture was heated to reflux for 1.5 h. Water was added and the reaction mixture was extracted with dichloromethane. The organic phase was washed with saturated sodium chloride solution, dried (sodium sulfate) and the solvent was removed in vacuum. Aminophase-silica-gel chromatography gave a solid that was recrystallized from ethanol. Yield: 120 mg of the title compound.

$^1$H-NMR (300 MHz, DMSO-d$_6$): δ [ppm]=1.40 (t, 3H), 3.57 (br. s., 8H), 3.64 (s, 2H), 4.13 (q, 2H), 6.97-7.06 (m, 2H), 7.07-7.18 (m, 2H), 7.28-7.39 (m, 2H), 7.62 (d, 1H), 7.65-7.76 (m, 4H), 7.90 (dd, 1H), 8.12 (s, 1H), 8.31 (d, 1H), 9.08 (d, 1H), 10.28 (s, 1H).

Example 02.03

N-[4-(2-{[4-(4,4-dimethyl-4,5-dihydro-1,3-oxazol-2-yl)-2-methoxyphenyl]amino}[,2]-triazolo[1,5-a]pyridin-6-yl)phenyl]-2-(4-fluorophenyl)acetamide

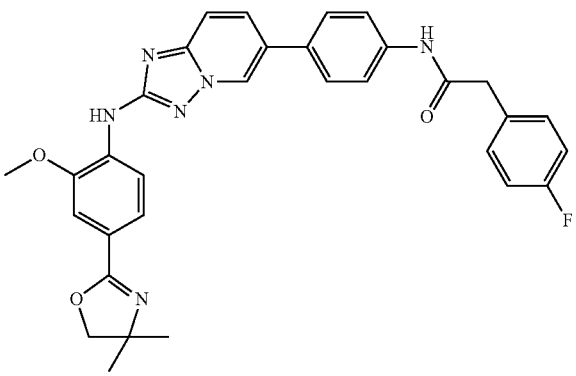 [SMILES: COc1cc(C2=NC(C)(C)CO2)ccc1Nc1nc2ccc(-c3ccc(NC(=O)Cc4ccc(F)cc4)cc3)cn2n1]

To a stirred suspension of Int02.04 (100 mg) in toluene (3.0 mL) and NMP (0.3 mL) was added Int09.03 (118 mg), chloro(2-dicyclohexylphosphino-2',4',6'-tri-i-propyl-1,1'-biphenyl)[2-(2-aminoethyl)phenyl]palladium(II) methyl-t-butylether adduct (22.9 mg), X-Phos (13.5 mg), and sodium tert-butoxide (133 mg). The flask was twice degassed and backfilled with argon. The mixture was heated to reflux for 2 h. Water was added and the reaction mixture was extracted with ethyl acetate. The organic phase was washed with saturated sodium chloride solution, dried (sodium sulfate) and the solvent was removed in vacuum. Water was added and the reaction mixture was extracted with ethyl acetate. The organic phase was washed with saturated sodium chloride solution, dried (sodium sulfate) and the solvent was removed in vacuum. Aminophase-silica-gel chromatography gave 51 mg of the title compound.

$^1$H-NMR (300 MHz, DMSO-d$_6$): δ [ppm]=1.25 (s, 6H), 3.64 (s, 2H), 3.90 (s, 3H), 4.05 (s, 2H), 7.13 (t, 2H), 7.30-7.39 (m, 3H), 7.45 (dd, 1H), 7.58-7.77 (m, 5H), 7.91 (dd, 1H), 8.30-8.38 (m, 2H), 9.10 (d, 1H), 10.28 (s, 1H).

Example 02.04

2-(4-fluorophenyl)-N-{4-[2-({2-methoxy-4-[(4-methylpiperazin-1-yl)carbonyl]phenyl}amino)[,2]triazolo[1,5-a]pyridin-6-yl]phenyl}acetamide

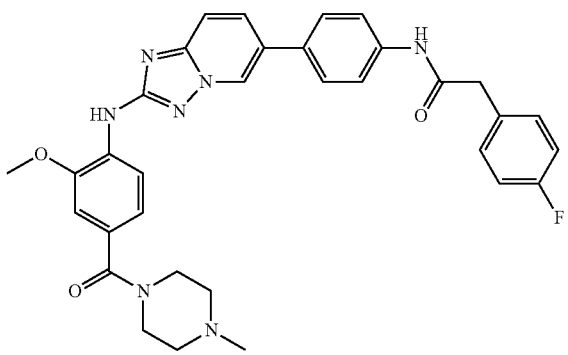 [SMILES: COc1cc(C(=O)N2CCN(C)CC2)ccc1Nc1nc2ccc(-c3ccc(NC(=O)Cc4ccc(F)cc4)cc3)cn2n1]

To a stirred suspension of Int02.04 (100 mg) in toluene (2.0 mL) and NMP (0.2 mL) was added Int09.04 (104 mg), Pd$_2$ dba$_3$ (12.7 mg), rac-BINAP (17.6 mg) and Caesium carbonate (276 mg). The flask was twice degassed and backfilled with argon. The mixture was heated to reflux for 3 h. Ethyl acetate was added and the mixture was filtered through Celite and the solvent was removed in vacuum. Silica gel chromatography gave a solid that was recrystallized from ethanol and ether. Yield: 40 mg of the title compound.

$^1$H-NMR (300 MHz, DMSO-d$_6$): δ [ppm]=2.17 (s, 3H), 2.29 (br. s., 4H), 3.48 (br. s., 4H), 3.64 (s, 2H), 3.87 (s, 3H), 6.96-7.03 (m, 2H), 7.13 (t, 2H), 7.34 (dd, 2H), 7.62 (d, 1H), 7.65-7.75 (m, 4H), 7.90 (dd, 1H), 8.22 (s, 1H), 8.28 (d, 1H), 9.08 (d, 1H), 10.28 (s, 1H).

Example 02.05 tert-butyl 4-(3-ethoxy-4-{[6-(4-{[(4-fluorophenyl)acetyl]amino}phenyl)[,2]triazolo[1,5-a]pyridin-2-yl]amino}benzoyl)piperazine-1-carboxylate

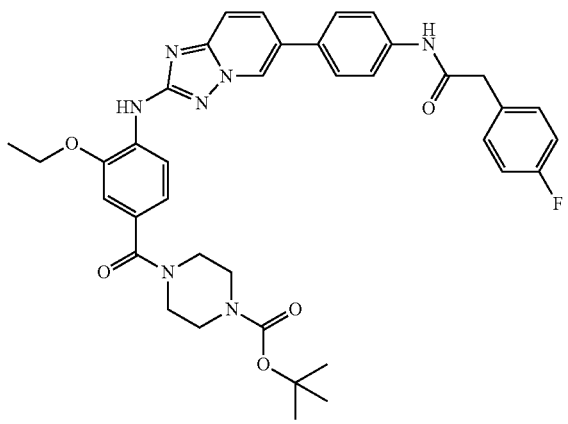 [SMILES: CCOc1cc(C(=O)N2CCN(C(=O)OC(C)(C)C)CC2)ccc1Nc1nc2ccc(-c3ccc(NC(=O)Cc4ccc(F)cc4)cc3)cn2n1]

To a stirred suspension of Int02.04 (120 mg) in toluene (3.1 mL) was added Int10.04 (275 mg), chloro(2-dicyclohexylphosphino-2',4',6'-tri-i-propyl-1,1'-biphenyl)[2-(2-aminoethyl)phenyl]palladium(II) methyl-t-butylether adduct (27.5 mg) and X-Phos (16.2 mg). The flask was twice degassed and backfilled with argon. The mixture was stirred at room temperature for 5 minutes. Sodium tert-butoxide (160 mg) was added, the flask was twice degassed and backfilled with argon, and the mixture was heated to reflux for 3 h. Water was added and the reaction mixture was extracted with ethyl acetate. The organic phase was washed with saturated sodium chloride solution, dried (sodium sulfate) and the solvent was removed in vacuum. Silica gel chromatography gave 145 mg of the title compound.

$^1$H-NMR (600 MHz, DMSO-d$_6$): δ [ppm]=1.41-1.43 (m, 9H), 1.45 (t, 3H), 3.36-3.59 (m, 8H), 3.69 (s, 2H), 4.19 (q, 2H), 7.04-7.10 (m, 2H), 7.17 (t, 2H), 7.39 (dd, 2H), 7.67 (d, 1H), 7.70-7.80 (m, 4H), 7.95 (d, 1H), 8.15 (s, 1H), 8.36 (d, 1H), 9.12 (d, 1H), 10.31 (s, 1H).

Example 02.06

N-[4-(2-{[2-ethoxy-4-(piperazin-1-ylcarbonyl)phenyl]amino}[,2]-triazolo[1,5-a]pyridin-6-yl)phenyl]-2-(4-fluorophenyl)acetamide

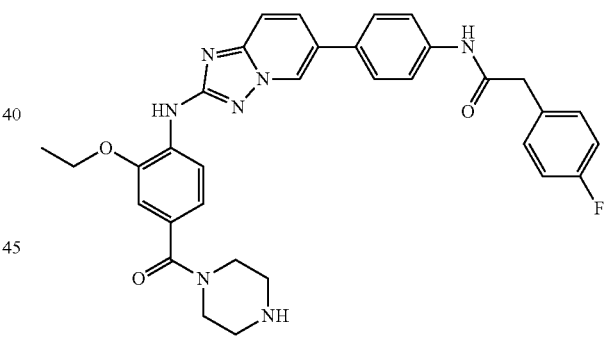

To a stirred suspension of Example 2.5 (130 mg) in DCM (1 mL) was added TFA (0.2 mL). The mixture was stirred at room temperature for 4 h. Ethyl acetate was added and a half-saturated solution of sodium bicarbonate was added until the pH of the solution was basic. The mixture was extracted with ethyl acetate. The organic phase was dried (sodium sulfate) and the solvent was removed in vacuum. Aminophase-silica-gel chromatography gave 73 mg of the title compound.

$^1$H-NMR (300 MHz, DMSO-d$_6$, selected signals): δ [ppm]=1.39 (t, 3H), 2.65 (br. s., 4H), 3.39 (br. s., 4H), 3.64 (s, 2H), 4.13 (d, 2H), 6.93-7.01 (m, 2H), 7.06-7.19 (m, 2H), 7.28-7.40 (m, 2H), 7.62 (d, 1H), 7.65-7.78 (m, 4H), 7.90 (dd, 1H), 8.09 (s, 1H), 8.29 (d, 1H), 9.08 (d, 1H), 10.28 (s, 1H).

Example 02.07

N-(4-{2-[(4-{[4-(cyclopropylmethyl)piperazin-1-yl]carbonyl}-2-ethoxyphenyl)amino][,2]triazolo[1,5-a]pyridin-6-yl}phenyl)-2-(4-fluorophenyl)acetamide

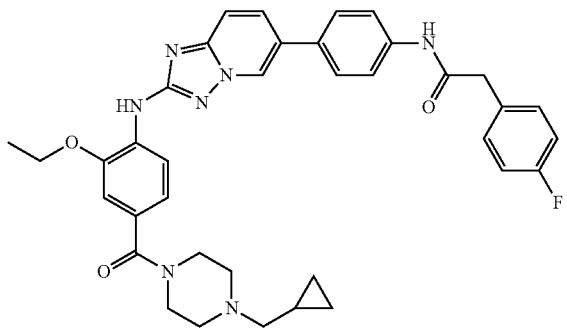 [SMILES: CCOc1cc(C(=O)N2CCN(CC3CC3)CC2)ccc1Nc1nc2ccc(-c3ccc(NC(=O)Cc4ccc(F)cc4)cc3)cn2n1]

To a stirred suspension of Int02.04 (98 mg) in toluene (3.0 mL) and NMP (0.3 mL) was added Int10.06 (150 mg), chloro(2-dicyclohexylphosphino-2',4',6'-tri-i-propyl-1,1'-biphenyl)[2-(2-aminoethyl)phenyl]palladium(II) methyl-t-butylether adduct (22.5 mg), X-Phos (13.2 mg), and sodium tert-butoxide (130 mg). The flask was twice degassed and backfilled with argon. The mixture was heated to reflux for 3 h. Water was added and the reaction mixture was extracted with dichloromethane. The organic phase was washed with saturated sodium chloride solution, dried (sodium sulfate) and the solvent was removed in vacuum. Aminophase-silica-gel chromatography gave a solid that was triturated with DIPE. Yield: 90 mg of the title compound.

$^1$H-NMR (300 MHz, DMSO-d$_6$): δ [ppm]=-0.04-0.09 (m, 2H), 0.34-0.49 (m, 2H), 0.69-0.88 (m, 1H), 1.39 (t, 3H), 2.17 (d, 2H), 2.33-2.44 (m, 4H), 3.49 (br. s., 4H), 3.64 (s, 2H), 4.13 (q, 2H), 6.91-7.02 (m, 2H), 7.13 (d, 2H), 7.25-7.42 (m, 2H), 7.54-7.77 (m, 5H), 7.90 (d, 1H), 8.10 (s, 1H), 8.30 (d, 1H), 9.08 (s, 1H), 10.28 (s, 1H).

Example 02.08

2-(4-fluorophenyl)-N-[4-(2-{[2-methoxy-4-(4-methylpiperazin-1-yl)phenyl]amino}[,2]-triazolo[1,5-a]pyridin-6-yl)phenyl]acetamide trifluoroacetate

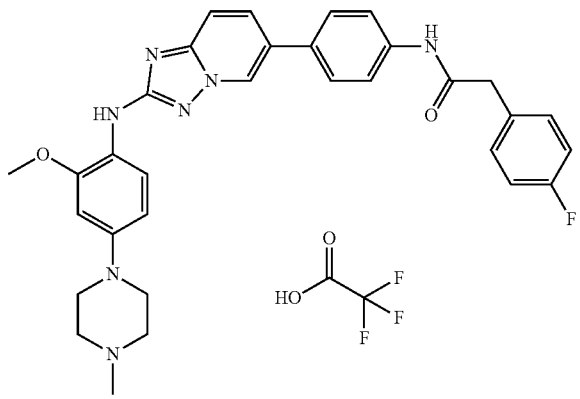 [SMILES: COc1cc(N2CCN(C)CC2)ccc1Nc1nc2ccc(-c3ccc(NC(=O)Cc4ccc(F)cc4)cc3)cn2n1 ; O=C(O)C(F)(F)F]

N-[4-(2-Amino[,2]triazolo[1,5-a]pyridin-6-yl)phenyl]-2-(4-fluorophenyl)acetamide Int02.04 (100 mg), 1-(4-bromo-3-methoxyphenyl)-4-methylpiperazine (US2009/118305) (94.7 mg), chloro(2-dicyclohexylphosphino-2',4',6'-tri-i-propyl-1,1'-biphenyl)[2-(2-aminoethyl)phenyl]palladium(II) methyl-t-butylether adduct (9.2 mg), X-Phos (5.3 mg), and sodium tert-butoxide (48.6 mg) were pre-mixed, and degassed toluene (2.0 mL) was added. The mixture was heated overnight to 130° C., then diluted with satd. sodium carbonate solution and extracted with ethyl acetate. The organic layer was dried over sodium sulfate, and the solvent was evaporated. The crude product was purified by HPLC to yield 28.6 mg (15%) of the title compound.

$^1$H-NMR (400 MHz, DMSO-d$_6$): δ [ppm]=2.86-2.96 (m, 5H), 3.13-3.24 (m, 2H), 3.51-3.57 (m, 2H), 3.67 (s, 2H), 3.77-3.84 (m, 2H), 3.86 (s, 3H), 6.59 (dd, 1H), 6.73 (d, 1H), 7.16 (t, 2H), 7.38 (dd, 2H), 7.57 (d, 1H), 7.68-7.75 (m, 4H), 7.84 (s, 1H), 7.88 (dd, 1H), 7.98 (d, 1H), 9.02 (s, 1H), 9.53 (br. s, 1H), 10.30 (s, 1H).

Example 02.09

2-(4-fluorophenyl)-N-[4-(2-{[4-(morpholin-4-ylcarbonyl)-2-(2,2,2-trifluoroethoxy)phenyl]amino}[,2]-triazolo[1,5-a]pyridin-6-yl)phenyl]acetamide

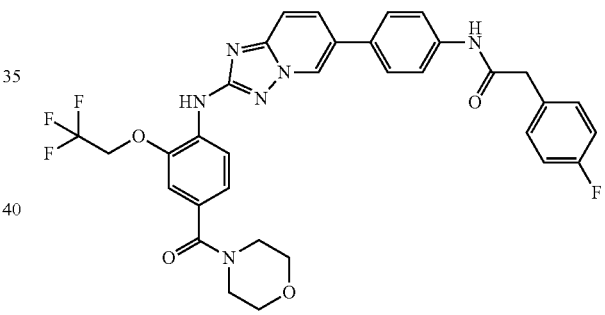

N-[4-(2-Amino[,2]triazolo[1,5-a]pyridin-6-yl)phenyl]-2-(4-fluorophenyl)acetamide Int02.04 (88 mg), [4-iodo-3-(2,2,2-trifluoroethoxy)phenyl](morpholin-4-yl)methanone Int11.02 (121 mg), chloro(2-dicyclohexylphosphino-2',4',6'-tri-i-propyl-1,1'-biphenyl)[2-(2-aminoethyl)phenyl]palladium(II) (18.0 mg), X-Phos (11.6 mg), and sodium tert-butoxide (42.7 mg) were pre-mixed, and degassed toluene (2.7 mL) was added. The mixture was heated for 6 h to 130° C., then diluted with satd. sodium carbonate solution and extracted with DCM. The organic layer was dried over sodium sulfate, and the solvent was evaporated. The crude product was purified by flash chromatography on silica gel (20 g, eluent: ethyl acetate/cyclohexane gradient 2:1 to 8:1). The product was then triturated with n-pentane and collected by suction filtration to yield 61 mg (39%) of the title compound.

$^1$H-NMR (400 MHz, DMSO-d$_6$): δ [ppm]=3.53 (br. s., 4H), 3.62 (br. s., 4H), 3.68 (s, 2H), 4.93 (q, 2H), 7.13-7.20 (m, 3H), 7.26 (d, 1H), 7.35-7.41 (m, 2H), 7.67 (d, 1H), 7.70-7.77 (m, 4H), 7.95 (dd, 1H), 8.20 (s, 1H), 8.36 (d, 1H), 9.13 (br. s, 1H), 10.31 (s, 1H).

Example 02.10

2-(4-fluorophenyl)-N-[4-(2-{[4-(morpholin-4-ylcarbonyl)-2-(trifluoromethoxy)phenyl]amino}[,2]-triazolo[1,5-a]pyridin-6-yl)phenyl]acetamide

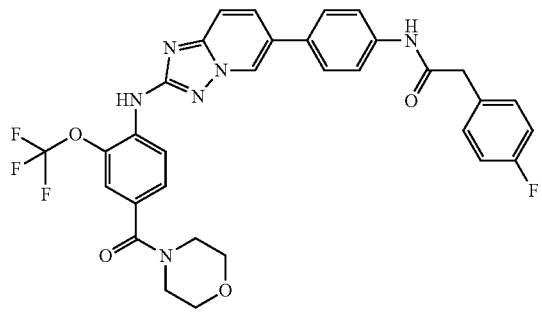 [SMILES: O=C(Cc1ccc(F)cc1)Nc1ccc(-c2ccc3nc(Nc4ccc(C(=O)N5CCOCC5)cc4OC(F)(F)F)nn3c2)cc1]

To a stirred suspension of Int02.04 (100 mg) in toluene (3.0 mL) and NMP (1.0 mL) was added Int24.04 (147 mg), chloro(2-dicyclohexylphosphino-2',4',6'-tri-i-propyl-1,1'-biphenyl)[2-(2-aminoethyl)phenyl]palladium(II) methyl-t-butylether adduct (23 mg) and X-Phos (13 mg) and the flask was twice degassed and backfilled with argon. The mixture was stirred for 5 minutes at room temperature. Powdered potassium phosphate (294 mg) was added and the flask was twice degassed and backfilled with argon. The mixture was heated to reflux for 4 h. The reaction mixture was purified by aminophase-silica-gel chromatography for three times to give 53 mg of the title compound.

$^1$H-NMR (400 MHz, DMSO-$d_6$): δ [ppm]=3.41-3.62 (m, 8H), 3.64 (s, 2H), 7.13 (t, 2H), 7.31-7.40 (m, 3H), 7.43 (dd, 1H), 7.61-7.77 (m, 5H), 7.91 (dd, 1H), 8.46 (d, 1H), 9.07 (d, 1H), 9.59 (s, 1H), 10.27 (s, 1H).

Example 02.11

2-(4-fluorophenyl)-N-[4-(2-{[2-methoxy-4-(2-oxo-1,3-oxazolidin-3-yl)phenyl]amino}[,2]-triazolo[1,5-a]pyridin-6-yl)phenyl]acetamide

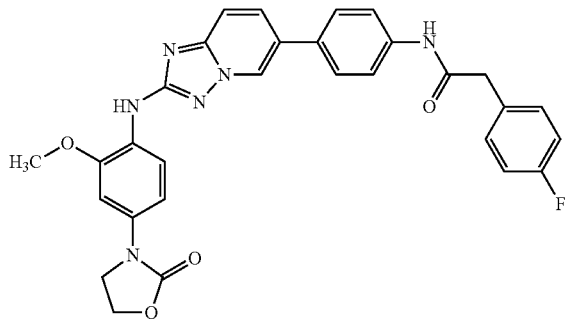 [SMILES: COc1cc(N2CCOC2=O)ccc1Nc1nc2ccc(-c3ccc(NC(=O)Cc4ccc(F)cc4)cc3)cn2n1]

To a stirred suspension of Int02.04 (500 mg) in toluene (12.0 mL) and NMP (3.0 mL) was added Int26.01 (567 mg), chloro(2-dicyclohexylphosphino-2',4',6'-tri-i-propyl-1,1'-biphenyl)[2-(2-aminoethyl)phenyl]palladium(II) methyl-t-butylether adduct (114 mg) and X-Phos (67 mg) and the flask was twice degassed and backfilled with argon. The mixture was stirred for 5 minutes at room temperature. Powdered potassium phosphate (1.47 g) was added and the flask was twice degassed and backfilled with argon. The mixture was heated to reflux for 2 h. The crude mixture was filtered through an aminophase-silica-gel column and the solvent was removed in vacuum. Aminophase-silica-gel chromatography gave a solid that was triturated with dichloromethane to give 480 mg of the title compound.

$^1$H-NMR (400 MHz, DMSO-$d_6$): δ [ppm]=3.64 (s, 2H), 3.84 (s, 3H), 4.01-4.08 (m, 2H), 4.40 (t, 2H), 6.98 (dd, 1H), 7.13 (t, 2H), 7.31-7.40 (m, 3H), 7.57 (d, 1H), 7.63-7.75 (m, 4H), 7.86 (dd, 1H), 7.97 (s, 1H), 8.13 (d, 1H), 9.03 (d, 1H), 10.25 (s, 1H).

Example 02.12

N-[4-(2-{[2-ethoxy-4-(2-oxo-1,3-oxazolidin-3-yl)phenyl]amino}[,2]-triazolo[1,5-a]pyridin-6-yl)phenyl]-2-(4-fluorophenyl)acetamide

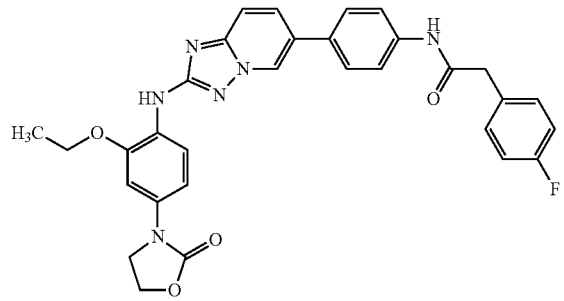 [SMILES: CCOc1cc(N2CCOC2=O)ccc1Nc1nc2ccc(-c3ccc(NC(=O)Cc4ccc(F)cc4)cc3)cn2n1]

To a stirred suspension of Int02.04 (100 mg) in toluene (4.0 mL) and NMP (1 mL) in a sealed tube was added Int27.02 (114 mg), chloro(2-dicyclohexylphosphino-2',4',6'-tri-i-propyl-1,1'-biphenyl)[2-(2-aminoethyl)phenyl]palladium(II) methyl-t-butylether adduct (23 mg), X-Phos (13 mg), and powdered potassium phosphate (294 mg). The flask was twice degassed and backfilled with argon. The mixture was heated to 130° C. with an oil bath for 2 h. Water was added and the reaction mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was triturated with warm ethanol to give 20 mg of the title compound.

$^1$H-NMR (400 MHz, DMSO-$d_6$): δ [ppm]=1.39 (t, 3H), 3.64 (s, 2H), 3.98-4.15 (m, 4H), 4.40 (t, 2H), 6.97 (dd, 1H), 7.13 (t, 2H), 7.29-7.42 (m, 3H), 7.58 (d, 1H), 7.63-7.74 (m, 4H), 7.83-7.95 (m, 2H), 8.16 (d, 1H), 9.04 (s, 1H), 10.28 (s, 1H).

Example 02.13

2-(4-fluorophenyl)-N-[4-(2-{[4-methyl-6-(2-oxo-1,3-oxazolidin-3-yl)pyridin-3-yl]amino}[,2]-triazolo[1,5-a]pyridin-6-yl)phenyl]acetamide

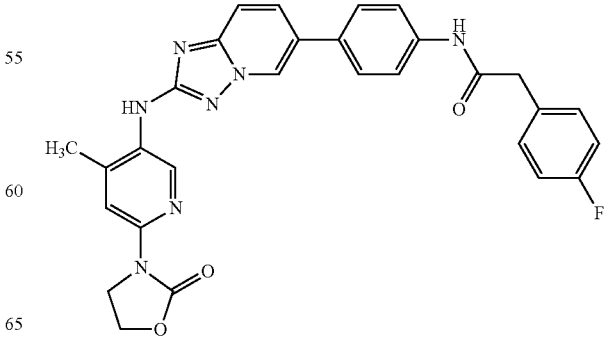

To a suspension of Int02.04 (100 mg) in toluene (3.41 mL) and NMP (0.44 mL) was added Int28.01 (204 mg), Pd-X-Phos-pre-cat (30.7 mg), X-Phos (17.9 mg) and potassium phosphate (282 mg). The tube was twice degassed and backfilled with argon. The mixture was irradiated in the microwave for 3 h at 130° C. Water was added and the mixture was extracted with ethyl acetate. The organic phase was dried (sodium sulfate) and the solvent was removed in vacuum. Silica gel chromatography gave a solid that was triturated in ethanol. Yield: 65.3 mg of the title compound.

$^1$H-NMR (400 MHz, DMSO-d$_6$): δ [ppm]=2.33 (s, 3H), 3.67 (s, 2H), 4.13-4.20 (m, 2H), 4.41-4.49 (m, 2H), 7.12-7.20 (m, 2H), 7.38 (dd, 2H), 7.56 (d, 1H), 7.71 (s, 4H), 7.86 (dd, 1H), 7.93 (s, 1H), 8.69 (s, 1H), 8.73 (s, 1H), 9.01 (d, 1H), 10.28 (s, 1H).

Example 02.14

N-[4-(2-{[4-(4,5-dihydro-1,3-oxazol-2-yl)-2-methoxyphenyl]amino}[,2]-triazolo[1,5-a]pyridin-6-yl)phenyl]-2-(4-fluorophenyl)acetamide

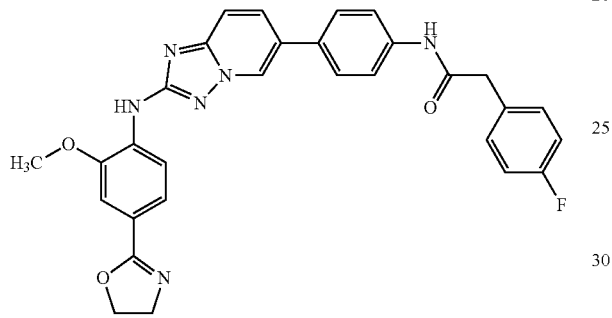

To a suspension of Int02.04 (80 mg) in toluene (2.7 mL) and NMP (0.35 mL) was added Int29.01 (88 mg), chloro(2-dicyclohexylphosphino-2',4',6'-tri-i-propyl-1,1'-biphenyl)[2-(2-aminoethyl)phenyl]palladium(II) methyl-t-butylether adduct (12.3 mg), X-Phos (7.2 mg), and potassium phosphate (225 mg). The tube was twice degassed and backfilled with argon. The mixture was irradiated in the microwave for 3 h at 130° C. Water was added and the mixture was extracted with ethyl acetate. The organic phase was dried (sodium sulfate) and the solvent was removed in vacuum. Silica gel chromatography gave a solid that was triturated with ethanol. Yield: 28.1 mg of the title compound.

$^1$H-NMR (400 MHz, DMSO-d$_6$): δ [ppm]=3.68 (s, 2H), 3.87-4.00 (m, 5H), 4.39 (t, 2H), 7.16 (t, 2H), 7.32-7.42 (m, 2H), 7.46 (s, 1H), 7.51 (d, 1H), 7.64-7.81 (m, 5H), 7.94 (d, 1H), 8.33-8.42 (m, 2H), 9.13 (s, 1H), 10.32 (s, 1H).

Example 02.15

N-[4-(2-{[4-(4,5-dihydro-1,3-oxazol-2-yl)-2-methylphenyl]amino}[,2]triazolo[1,5-a]pyridin-6-yl)phenyl]-2-(4-fluorophenyl)acetamide

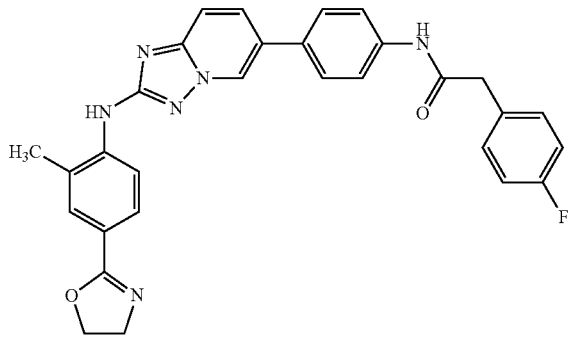 [SMILES: Cc1cc(C2=NCCO2)ccc1Nc1nc2ccc(-c3ccc(NC(=O)Cc4ccc(F)cc4)cc3)cn2n1]

To a suspension of Int02.04 (90 mg) in toluene (3.0 mL) and NMP (0.4 mL) was added Int30.01 (93 mg), chloro(2-dicyclohexylphosphino-2',4',6'-tri-i-propyl-1,1'-biphenyl)[2-(2-aminoethyl)phenyl]palladium(II) methyl-t-butylether adduct (13.8 mg), X-Phos (8.1 mg), and potassium phosphate (254 mg). The tube was twice degassed and backfilled with argon. The mixture was irradiated in the microwave for 3 h at 150° C. Water was added and the mixture was extracted with ethyl acetate. The organic phase was dried (sodium sulfate) and the solvent was removed in vacuum. Silica gel chromatography gave a solid that was triturated with ethyl acetate. Yield: 16 mg of the title compound.

$^1$H-NMR (400 MHz, DMSO-d$_6$): δ [ppm]=2.37 (s, 3H), 3.68 (s, 2H), 3.92 (t, 2H), 4.36 (t, 2H), 7.16 (t, 2H), 7.38 (dd, 2H), 7.64 (d, 1H), 7.66-7.78 (m, 6H), 7.91 (dd, 1H), 8.19 (d, 1H), 8.19 (br. s., 1H), 8.75 (s, 1H), 9.08 (s, 1H), 10.29 (s, 1H).

Example 02.16

2-(4-fluorophenyl)-N-{4-[2-({2-methoxy-4-[(1S,4S)-2-oxa-5-azabicyclo[2.2.1]hept-5-ylcarbonyl]phenyl}amino)[,2]triazolo[1,5-a]pyridin-6-yl]phenyl}acetamide

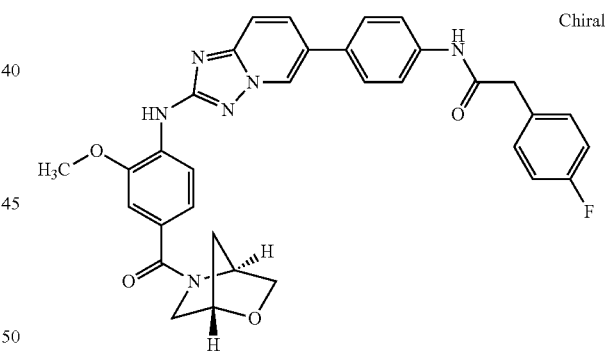

To a stirred suspension of Int02.04 (80 mg) in toluene (2.2 mL) and NMP (1 mL) was added Int09.05 (104 mg), chloro(2-dicyclohexylphosphino-2',4',6'-tri-i-propyl-1,1'-biphenyl)[2-(2-aminoethyl)phenyl]palladium(II) methyl-t-butylether adduct (18 mg), X-Phos (10.8 mg), and powdered potassium phosphate (234 mg). The flask was twice degassed and backfilled with argon. The mixture was heated to reflux for 2 h. The solvent was removed in vacuum. Aminophase-silica-gel chromatography gave 75 mg of the title compound.

$^1$H-NMR (300 MHz, DMSO-d$_6$): δ [ppm]=1.65-1.98 (m, 2H), 3.43-3.98 (m, 9H), 4.42-4.85 (m, 2H), 7.05-7.25 (m, 4H), 7.29-7.41 (m, 2H), 7.58-7.77 (m, 5H), 7.90 (dd, 1H), 8.22-8.38 (m, 2H), 9.09 (s, 1H), 10.28 (s, 1H).

Example 02.17

2-(4-fluorophenyl)-N-[4-(2-{[2-methoxy-4-(2-oxa-6-azaspiro[3.3]hept-6-ylcarbonyl)phenyl]amino}[,2]triazolo[1,5-a]pyridin-6-yl)phenyl]acetamide

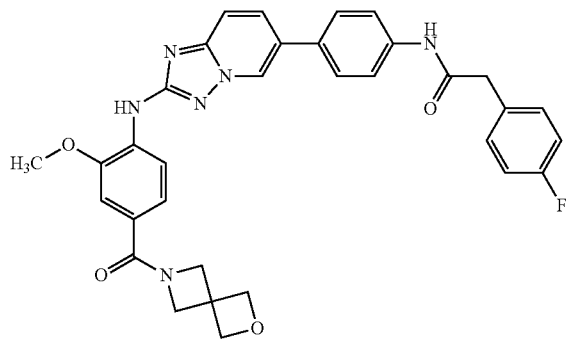 [SMILES: COc1cc(C(=O)N2CC3(COC3)C2)ccc1Nc1nc2ccc(-c3ccc(NC(=O)Cc4ccc(F)cc4)cc3)cn2n1]

Starting with Int02.04 and Int09.06, Example 02.17 was prepared analogously to the procedure for the preparation of Example 02.15.

$^1$H-NMR (400 MHz, DMSO-$d_6$): δ [ppm]=3.68 (s, 2H), 3.93 (s, 3H), 4.20 (br. s., 2H), 4.54 (br. s., 2H), 4.69 (s, 4H), 7.11-7.21 (m, 2H), 7.22-7.32 (m, 2H), 7.34-7.43 (m, 2H), 7.63-7.81 (m, 5H), 7.94 (dd, 1H), 8.30-8.40 (m, 2H), 9.13 (d, 1H), 10.32 (s, 1H).

Example 02.18

N-{4-[2-({4-[(1,1-dioxidothiomorpholin-4-yl)carbonyl]-2-methoxyphenyl}amino)[,2]triazolo[1,5-a]pyridin-6-yl]phenyl}-2-(4-fluorophenyl)acetamide

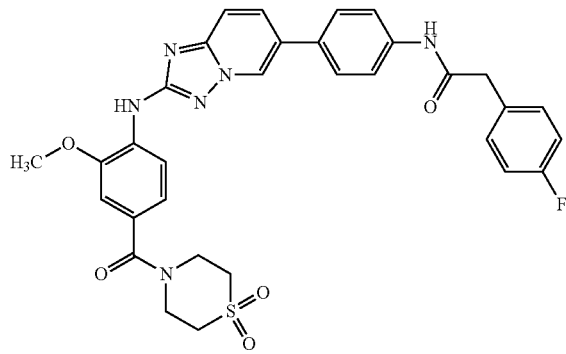 [SMILES: COc1cc(C(=O)N2CCS(=O)(=O)CC2)ccc1Nc1nc2ccc(-c3ccc(NC(=O)Cc4ccc(F)cc4)cc3)cn2n1]

Starting with Int02.04 and Int09.07, Example 02.18 was prepared analogously to the procedure for the preparation of Example 02.12.

$^1$H-NMR (300 MHz, DMSO-$d_6$): δ [ppm]=3.23 (br. s., 4H), 3.64 (s, 2H), 3.76-3.96 (m, 7H), 7.03-7.19 (m, 4H), 7.34 (dd, 2H), 7.59-7.76 (m, 5H), 7.90 (dd, 1H), 8.26 (s, 1H), 8.31 (d, 1H), 9.09 (s, 1H), 10.28 (s, 1H).

Example 02.19

2-(4-fluorophenyl)-N-{4-[2-({4-[(3-hydroxyazetidin-1-yl)carbonyl]-2-methoxyphenyl}amino)[,2]triazolo[1,5-a]pyridin-6-yl]phenyl}acetamide

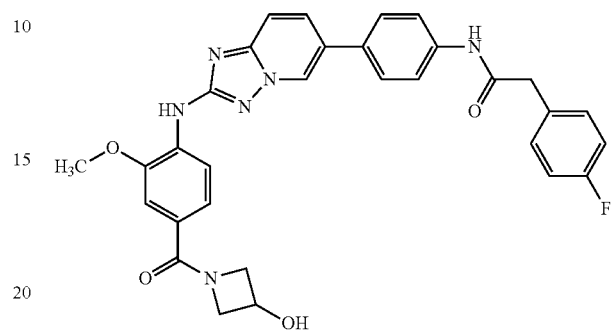

Starting with Int02.04 (100 mg) and Int09.08 (138 mg), Example 02.19 was prepared analogously to the procedure for the preparation of Example 02.15. Yield: 45 mg of the title compound.

$^1$H-NMR (400 MHz, DMSO-$d_6$): δ [ppm]=3.68 (s, 2H), 3.70-3.85 (m, 1H), 3.93 (s, 3H), 4.01-4.16 (m, 1H), 4.17-4.31 (m, 1H), 4.51 (br. s., 2H), 5.74 (d, 1H), 7.12-7.21 (m, 2H), 7.22-7.31 (m, 2H), 7.34-7.43 (m, 2H), 7.63-7.79 (m, 5H), 7.94 (dd, 1H), 8.32-8.39 (m, 2H), 9.13 (d, 1H), 10.32 (s, 1H).

Example 02.20

2-(4-fluorophenyl)-N-{4-[2-({4-[(4-hydroxypiperidin-1-yl)carbonyl]-2-methoxyphenyl}amino)[,2]triazolo[1,5-a]pyridin-6-yl]phenyl}acetamide

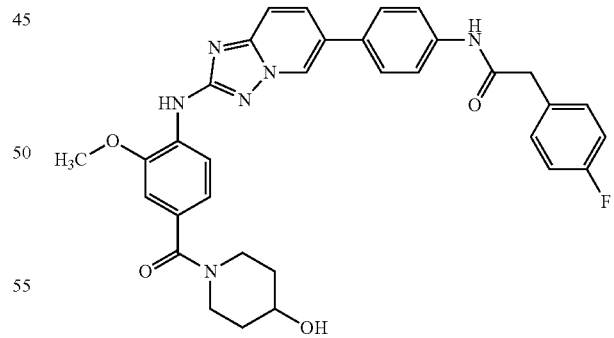

Starting with Int02.04 and Int09.09, Example 02.20 was prepared analogously to the procedure for the preparation of Example 02.12.

$^1$H-NMR (300 MHz, DMSO-$d_6$): δ [ppm]=1.25-1.45 (m, 2H), 1.71 (br. s., 2H), 3.07-3.23 (m, 2H), 3.60-3.94 (m, 8H), 4.75 (d, 1H), 6.95-7.02 (m, 2H), 7.13 (t, 2H), 7.34 (dd, 2H), 7.56-7.76 (m, 5H), 7.89 (dd, 1H), 8.19 (s, 1H), 8.27 (d, 1H), 9.08 (s, 1H), 10.27 (s, 1H).

Example 02.21

4-{[6-(4-{[(4-fluorophenyl)acetyl]amino}phenyl)[,2]triazolo[1,5-a]pyridin-2-yl]amino}-3-methoxy-N-(oxetan-3-yl)benzamide

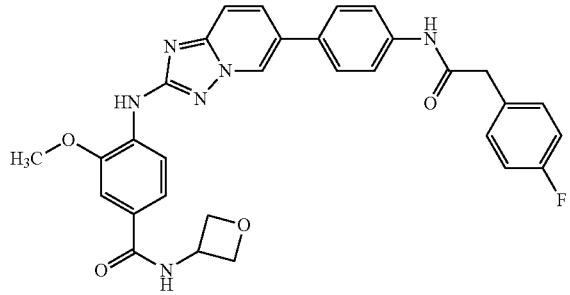 [SMILES: COc1cc(C(=O)NC2COC2)ccc1Nc1nc2ccc(-c3ccc(NC(=O)Cc4ccc(F)cc4)cc3)cn2n1]

Starting with Int02.04 and Int09.10, Example 02.21 was prepared analogously to the procedure for the preparation of Example 02.12.

$^1$H-NMR (400 MHz, DMSO-d$_6$): δ [ppm]=3.64 (s, 2H), 3.92 (s, 3H), 4.58 (t, 2H), 4.76 (t, 2H), 4.92-5.05 (m, 1H), 7.09-7.16 (m, 2H), 7.31-7.38 (m, 2H), 7.51 (d, 1H), 7.54 (dd, 1H), 7.61-7.78 (m, 5H), 7.91 (dd, 1H), 8.28-8.37 (m, 2H), 8.92 (d, 1H), 9.11 (d, 1H), 10.29 (s, 1H).

Example 02.22

N-[4-(2-{[4-(azetidin-1-ylcarbonyl)-2-methoxyphenyl]amino}[,2]-triazolo[1,5-a]pyridin-6-yl)phenyl]-2-(4-fluorophenyl)acetamide

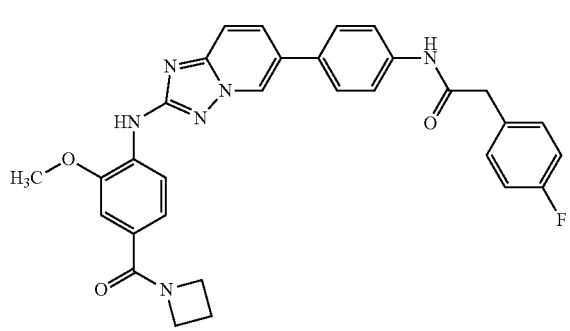 [SMILES: COc1cc(C(=O)N2CCC2)ccc1Nc1nc2ccc(-c3ccc(NC(=O)Cc4ccc(F)cc4)cc3)cn2n1]

Starting with Int02.04 and Int09.11, Example 02.22 was prepared analogously to the procedure for the preparation of Example 02.16.

$^1$H-NMR (300 MHz, DMSO-d$_6$): δ [ppm]=2.23 (quin, 2H), 3.64 (s, 2H), 3.89 (s, 3H), 3.99 (br. s, 2H), 4.32 (br. s, 2H), 7.08-7.17 (m, 2H), 7.20-7.27 (m, 2H), 7.30-7.38 (m, 2H), 7.59-7.76 (m, 5H), 7.90 (dd, 1H), 8.26-8.35 (m, 2H), 9.09 (d, 1H), 10.28 (s, 1H).

Example 02.23

N-[4-(2-{[2-ethoxy-4-(2-oxa-6-azaspiro[3.3]hept-6-ylcarbonyl)phenyl]amino}[,2]triazolo[1,5-a]pyridin-6-yl)phenyl]-2-(4-fluorophenyl)acetamide

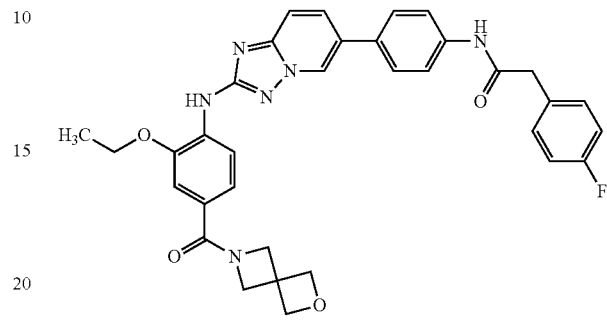

Starting with Int02.04 and Int10.07, Example 02.23 was prepared analogously to the procedure for the preparation of Example 02.15.

$^1$H-NMR (400 MHz, DMSO-d$_6$): δ [ppm]=1.45 (t, 3H), 3.68 (s, 2H), 4.18 (q, 4H), 4.54 (br. s., 2H), 4.69 (s, 4H), 7.10-7.21 (m, 2H), 7.23 (d, 1H), 7.27 (dd, 1H), 7.38 (dd, 2H), 7.67 (d, 1H), 7.70-7.81 (m, 4H), 7.95 (dd, 1H), 8.21 (s, 1H), 8.36 (d, 1H), 9.12 (d, 1H), 10.30 (s, 1H).

Example 02.24

N-{4-[2-({2-ethoxy-4-[(3-hydroxyazetidin-1-yl)carbonyl]phenyl}amino)[,2]triazolo[1,5-a]pyridin-6-yl]phenyl}-2-(4-fluorophenyl)acetamide

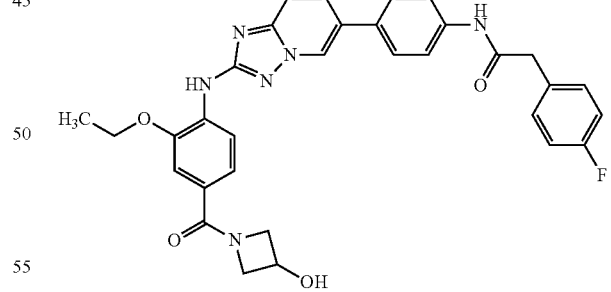

Starting with Int02.04 and Int10.08, Example 02.24 was prepared analogously to the procedure for the preparation of Example 02.15.

$^1$H-NMR (400 MHz, DMSO-d$_6$): δ [ppm]=1.44 (t, 3H), 3.68 (s, 2H), 3.72-3.85 (m, 1H), 4.01-4.14 (m, 1H), 4.18 (q, 3H), 4.44-4.59 (m, 2H), 5.74 (d, 1H), 7.13-7.20 (m, 2H), 7.21-7.30 (m, 2H), 7.34-7.43 (m, 2H), 7.67 (d, 1H), 7.70-7.78 (m, 4H), 7.95 (dd, 1H), 8.22 (s, 1H), 8.36 (d, 1H), 9.13 (d, 1H), 10.32 (s, 1H).

Example 02.25

3-ethoxy-4-{[6-(4-{[(4-fluorophenyl)acetyl]amino}phenyl)[,2]-triazolo[1,5-a]pyridin-2-yl]amino}-N-(1-methylpiperidin-4-yl)benzamide

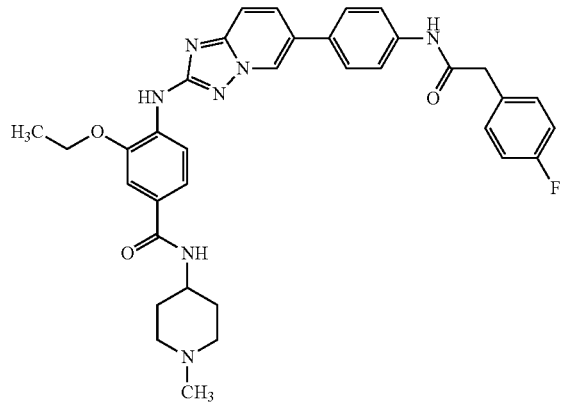 [SMILES: CCOc1cc(C(=O)NC2CCN(C)CC2)ccc1Nc1nc2ccc(-c3ccc(NC(=O)Cc4ccc(F)cc4)cc3)cn2n1]

Starting with Int02.04 and Int10.05, Example 02.25 was prepared analogously to the procedure for the preparation of Example 02.16.

$^1$H-NMR (400 MHz, DMSO-d$_6$): δ [ppm]=1.42 (t, 3H), 1.49-1.62 (m, 2H), 1.68-1.77 (m, 2H), 1.84-1.95 (m, 2H), 2.13 (s, 3H), 2.75 (br. d, 2H), 3.61-3.78 (m, 3H), 4.17 (q, 2H), 7.10-7.17 (m, 2H), 7.32-7.38 (m, 2H), 7.46 (d, 1H), 7.50 (dd, 1H), 7.63 (d, 1H), 7.66-7.75 (m, 4H), 7.91 (dd, 1H), 8.04 (d, 1H), 8.14 (s, 1H), 8.30 (d, 1H), 9.10 (d, 1H), 10.29 (s, 1H).

Example 02.26

2-(4-fluorophenyl)-N-[4-(2-{[4-(2-oxa-6-azaspiro[3.3]hept-6-ylcarbonyl)-2-(2,2,2-trifluoroethoxy)phenyl]amino}[,2]triazolo[1,5-a]pyridin-6-yl)phenyl]acetamide

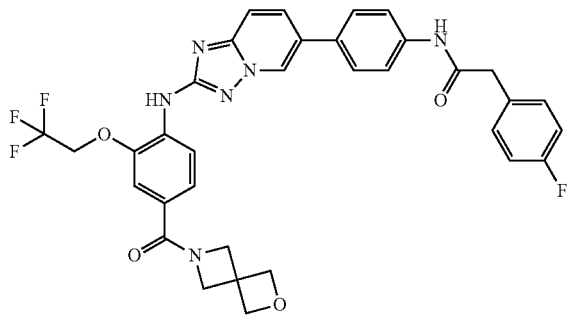 [SMILES: O=C(Cc1ccc(F)cc1)Nc1ccc(-c2ccc3nc(Nc4ccc(C(=O)N5CC6(COC6)C5)cc4OCC(F)(F)F)nn3c2)cc1]

Starting with Int02.04 and Int11.06, Example 02.26 was prepared analogously to the procedure for the preparation of Example 02.15.

$^1$H-NMR (400 MHz, DMSO-d$_6$): δ [ppm]=3.68 (s, 2H), 4.21 (br. s., 2H), 4.54 (br. s., 2H), 4.70 (s, 4H), 4.93 (q, 2H), 7.08-7.22 (m, 2H), 7.32-7.43 (m, 4H), 7.65-7.80 (m, 5H), 7.95 (dd, 1H), 8.26 (s, 1H), 8.39 (d, 1H), 9.13 (d, 1H), 10.30 (s, 1H).

Example 02.27

2-(4-fluorophenyl)-N-{4-[2-({4-[(3-hydroxyazetidin-1-yl)carbonyl]-2-(2,2,2-trifluoroethoxy)phenyl}amino)[,2]triazolo[1,5-a]pyridin-6-yl]phenyl}acetamide

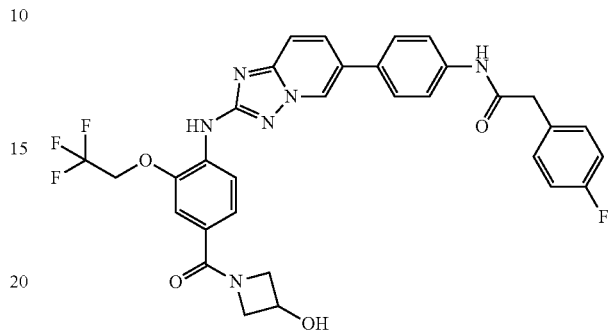

Starting with Int02.04 and Int11.07, Example 02.27 was prepared analogously to the procedure for the preparation of Example 02.15.

$^1$H-NMR (400 MHz, DMSO-d$_6$): δ [ppm]=3.68 (s, 2H), 3.72-3.86 (m, 1H), 4.11 (s, 1H), 4.25 (s, 1H), 4.51 (br. s., 2H), 4.95 (q, 2H), 5.74 (br. s., 1H), 7.16 (t, 2H), 7.34-7.42 (m, 4H), 7.65-7.80 (m, 5H), 7.95 (dd, 1H), 8.25 (s, 1H), 8.38 (d, 1H), 9.13 (s, 1H), 10.30 (s, 1H).

Example 02.28

2-(4-fluorophenyl)-N-[4-(2-{[2-methoxy-4-(4-methylpiperazin-1-yl)phenyl]amino}[,2]-triazolo[1,5-a]pyridin-6-yl)phenyl]acetamide

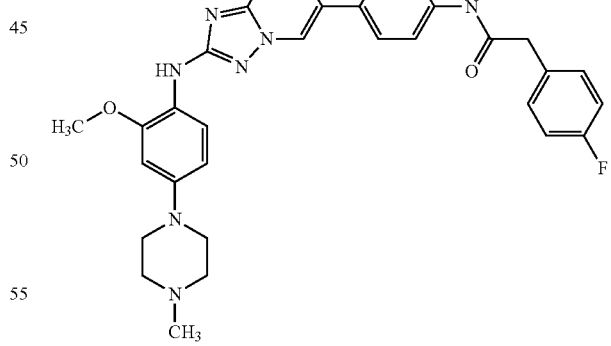

Starting with Int02.04 and Int17.02, Example 02.28 was prepared analogously to the procedure for the preparation of Example 02.16.

$^1$H-NMR (300 MHz, DMSO-d$_6$): δ [ppm]=2.19 (s, 3H), 2.37-2.44 (m, 4H), 2.99-3.13 (m, 4H), 3.63 (s, 2H), 3.80 (s, 3H), 6.47 (dd, 1H), 6.61 (d, 1H), 7.13 (t, 2H), 7.34 (dd, 2H), 7.52 (d, 1H), 7.62-7.74 (m, 5H), 7.78-7.90 (m, 2H), 9.00 (s, 1H), 10.27 (s, 1H).

Example 02.29

2-(4-fluorophenyl)-N-[4-(2-{[4-(morpholin-4-ylcarbonyl)phenyl]amino}[,2]-triazolo[1,5-a]pyridin-6-yl)phenyl]acetamide

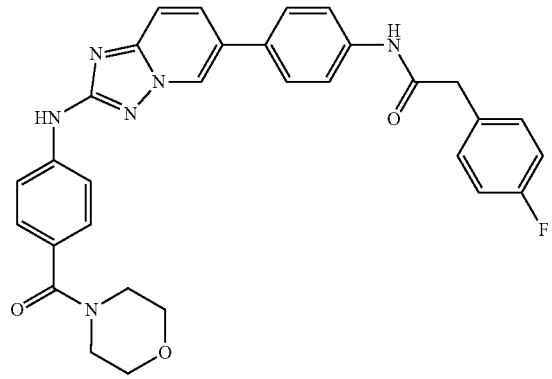 [SMILES: O=C(Cc1ccc(F)cc1)Nc1ccc(-c2ccc3nc(Nc4ccc(C(=O)N5CCOCC5)cc4)nn3c2)cc1]

Starting with Int02.04 and (4-bromophenyl)(morpholin-4-yl)methanone, Example 02.29 was prepared analogously to the procedure for the preparation of Example 02.12.

$^1$H-NMR (300 MHz, DMSO-d$_6$): δ [ppm]=3.48 (br. s., 4H), 3.57 (br. s., 4H), 3.64 (s, 2H), 7.07-7.18 (m, 2H), 7.29-7.39 (m, 4H), 7.62 (d, 1H), 7.65-7.78 (m, 6H), 7.89 (dd, 1H), 9.08 (d, 1H), 9.92 (s, 1H), 10.27 (s, 1H).

Example 02.30

N-[4-(2-{[2-(2-fluoroethoxy)-4-(2-oxa-6-azaspiro[3.3]hept-6-ylcarbonyl)phenyl]amino}[,2]triazolo[1,5-a]pyridin-6-yl)phenyl]-2-(4-fluorophenyl)acetamide

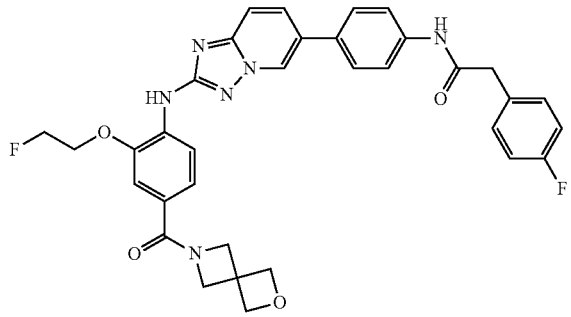 [SMILES: O=C(Cc1ccc(F)cc1)Nc1ccc(-c2ccc3nc(Nc4ccc(C(=O)N5CC6(COC6)C5)cc4OCCF)nn3c2)cc1]

Starting with Int02.04 and Int14.03, Example 02.30 was prepared analogously to the procedure for the preparation of Example 02.15.

$^1$H-NMR (400 MHz, DMSO-d$_6$): δ [ppm]=3.68 (s, 2H), 4.20 (br. s., 2H), 4.34-4.40 (m, 1H), 4.41-4.46 (m, 1H), 4.54 (br. s., 2H), 4.70 (s, 4H), 4.80-4.87 (m, 1H), 4.92-4.99 (m, 1H), 7.16 (t, 2H), 7.28 (d, 1H), 7.31 (dd, 1H), 7.38 (dd, 2H), 7.68 (d, 1H), 7.70-7.79 (m, 4H), 7.95 (dd, 1H), 8.35 (s, 1H), 8.40 (d, 1H), 9.13 (d, 1H), 10.30 (s, 1H).

Example 02.31

N-[4-(2-{[2-(2,2-difluoroethoxy)-4-(morpholin-4-ylcarbonyl)phenyl]amino}[,2]-triazolo[1,5-a]pyridin-6-yl)phenyl]-2-(4-fluorophenyl)acetamide

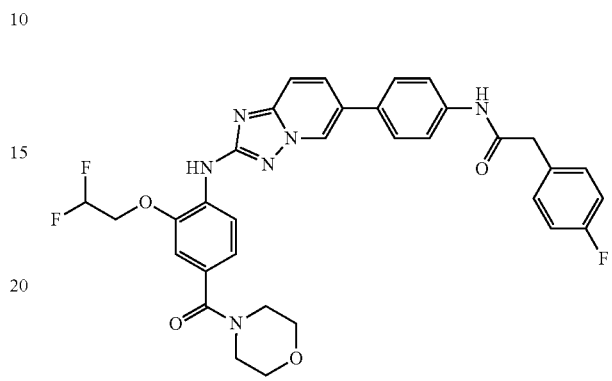

Starting with Int02.04 and Int13.02, Example 02.31 was prepared analogously to the procedure for the preparation of Example 02.15.

$^1$H-NMR (400 MHz, DMSO-d$_6$): δ [ppm]=3.41-3.77 (m, 10H), 4.47 (td, 2H), 6.38-6.73 (m, 1H), 7.08-7.22 (m, 4H), 7.38 (dd, 2H), 7.64-7.82 (m, 5H), 7.94 (dd, 1H), 8.35-8.46 (m, 2H), 9.12 (s, 1H), 10.32 (s, 1H).

Example 02.32

2-(4-fluorophenyl)-N-[4-(2-{[4-(morpholin-4-ylcarbonyl)-2-(trifluoromethyl)phenyl]amino}[,2]-triazolo[1,5-a]pyridin-6-yl)phenyl]acetamide

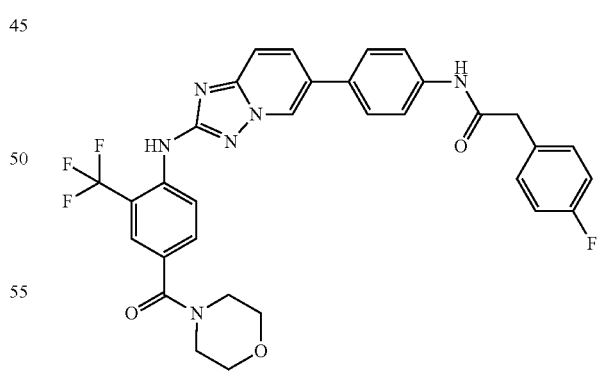

Starting with Int02.04 and Int15.01, Example 02.32 was prepared analogously to the procedure for the preparation of Example 02.15.

$^1$H-NMR (400 MHz, DMSO-d$_6$): δ [ppm]=3.62 (br. s., 8H), 3.67 (s, 2H), 7.12-7.20 (m, 2H), 7.34-7.41 (m, 2H), 7.66 (d, 1H), 7.69-7.78 (m, 6H), 7.94 (dd, 1H), 8.22 (d, 1H), 8.60 (s, 1H), 9.09 (d, 1H), 10.32 (s, 1H).

Example 02.33

2-(4-fluorophenyl)-N-[4-(2-{[2-methoxy-4-(morpholin-4-ylmethyl)phenyl]amino}[,2]-triazolo[1,5-a]pyridin-6-yl)phenyl]acetamide

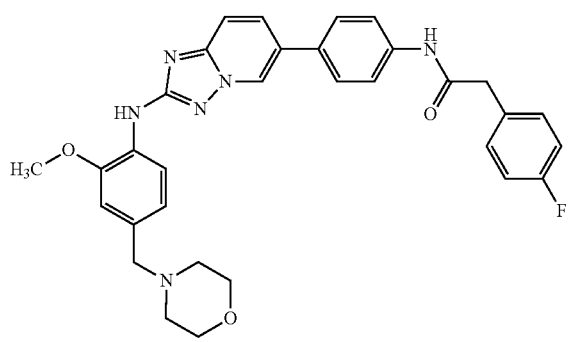 [SMILES: COc1cc(CN2CCOCC2)ccc1Nc1nc2ccc(-c3ccc(NC(=O)Cc4ccc(F)cc4)cc3)cn2n1]

Starting with Int02.04 and Int18.01, Example 02.33 was prepared analogously to the procedure for the preparation of Example 02.12.

¹H-NMR (300 MHz, DMSO-$d_6$): δ [ppm]=2.33 (d, 4H), 3.38 (s, 2H), 3.50-3.58 (m, 4H), 3.64 (s, 2H), 3.84 (s, 3H), 6.86 (dd, 1H), 6.92 (d, 1H), 7.07-7.17 (m, 2H), 7.30-7.39 (m, 2H), 7.54-7.61 (m, 1H), 7.63-7.74 (m, 4H), 7.86 (dd, 1H), 7.91 (s, 1H), 8.11 (d, 1H), 9.04 (d, 1H), 10.26 (s, 1H).

Example 02.34

N-{4-[2-({2-ethoxy-4-[(1-methylpiperidin-4-yl)oxy]phenyl}amino)[,2]triazolo[1,5-a]pyridin-6-yl]phenyl}-2-(4-fluorophenyl)acetamide

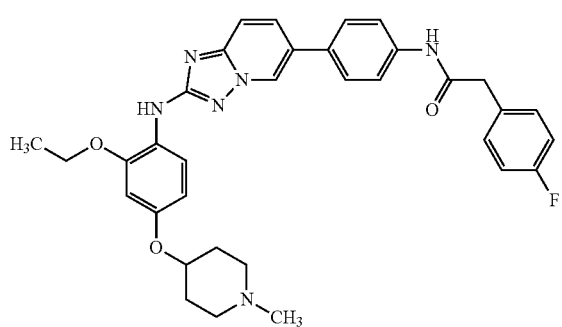 [SMILES: CCOc1cc(OC2CCN(C)CC2)ccc1Nc1nc2ccc(-c3ccc(NC(=O)Cc4ccc(F)cc4)cc3)cn2n1]

Starting with Int02.04 and Int19.02, Example 02.34 was prepared analogously to the procedure for the preparation of Example 02.16.

¹H-NMR (300 MHz, DMSO-$d_6$): δ [ppm]=1.34 (t, 3H), 1.50-1.66 (m, 2H), 1.79-1.96 (m, 2H), 2.05-2.19 (m, 5H), 2.51-2.62 (m, 2H), 3.64 (s, 2H), 4.06 (q, 2H), 4.20-4.34 (m, 1H), 6.52 (d, 1H), 6.59 (d, 1H), 7.08-7.17 (m, 2H), 7.30-7.38 (m, 2H), 7.53 (d, 1H), 7.59-7.73 (m, 5H), 7.84 (dd, 1H), 7.96 (d, 1H), 8.94-9.04 (m, 1H), 10.27 (s, 1H).

Example 02.35

2-(4-fluorophenyl)-N-{4-[2-({2-methoxy-4-[(1-methylpiperidin-4-yl)oxy]phenyl}amino)[,2]triazolo[1,5-a]pyridin-6-yl]phenyl}acetamide

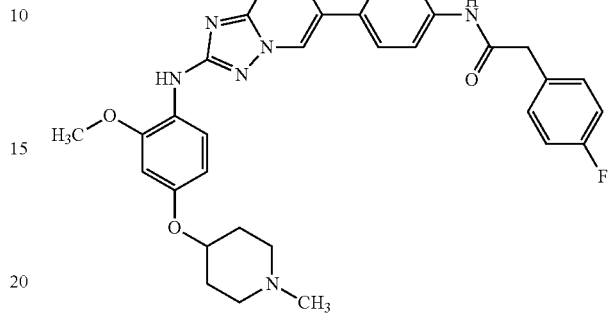

Starting with Int02.04 and Int20.01, Example 02.35 was prepared analogously to the procedure for the preparation of Example 02.16.

¹H-NMR (300 MHz, DMSO-$d_6$): δ [ppm]=1.50-1.67 (m, 2H), 1.82-1.93 (m, 2H), 2.07-2.20 (m, 5H), 2.52-2.64 (m, 2H), 3.64 (s, 2H), 3.79 (s, 3H), 4.21-4.34 (m, 1H), 6.53 (dd, 1H), 6.60 (d, 1H), 7.07-7.18 (m, 2H), 7.34 (dd, 2H), 7.52 (d, 1H), 7.63-7.72 (m, 4H), 7.76 (s, 1H), 7.83 (dd, 1H), 7.91 (d, 1H), 8.99 (d, 1H), 10.26 (s, 1H).

Example 02.36

2-(4-fluorophenyl)-N-{4-[2-({4-[(1-methylpiperidin-4-yl)oxy]-2-(methylsulfanyl)phenyl}amino)[,2]triazolo[1,5-a]pyridin-6-yl]phenyl}acetamide

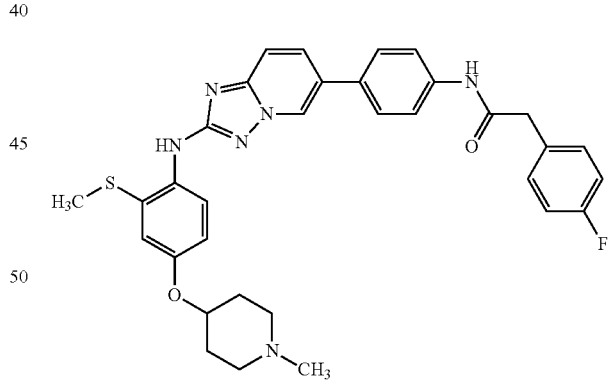

To a stirred suspension of Int02.04 (150 mg) in o-xylene (4.0 mL) and NMP (2.0 mL) was added Int21.01 (197 mg), chloro(2-dicyclohexylphosphino-2',4',6'-tri-i-propyl-1,1'-biphenyl)[2-(2-aminoethyl)phenyl]palladium(II) methyl-t-butylether adduct (34 mg) and X-Phos (20 mg) and the flask was twice degassed and backfilled with argon. The mixture was stirred for 5 minutes at room temperature. Powdered potassium phosphate (440 mg) was added and the flask was twice degassed and backfilled with argon. The mixture was heated to reflux for 3 h. Further chloro(2-dicyclohexylphosphino-2',4',6'-tri-i-propyl-1,1'-biphenyl)[2-(2-aminoethyl)phenyl]palladium(II) methyl-t-butylether adduct (34 mg)

and X-Phos (20 mg) was added, the flask was twice degassed and backfilled with argon and the mixture was heated to reflux for 2 h. Water was added and the mixture was extracted with ethyl acetate. The organic phase was washed with saturated sodium chloride solution, dried (sodium sulfate) and the solvent was removed in vacuum. Aminophase-silica-gel chromatography gave 35 mg of the title compound.

$^1$H-NMR (300 MHz, DMSO-d$_6$): δ [ppm]=1.51-1.68 (m, 2H), 1.83-1.95 (m, 2H), 2.05-2.19 (m, 5H), 2.35 (s, 3H), 2.53-2.64 (m, 2H), 3.63 (s, 2H), 4.27-4.39 (m, 1H), 6.75-6.84 (m, 2H), 7.07-7.18 (m, 2H), 7.29-7.38 (m, 2H), 7.51 (dd, 2H), 7.61-7.70 (m, 4H), 7.80 (dd, 1H), 8.10 (s, 1H), 8.94 (d, 1H), 10.26 (s, 1H).

Example 02.37

2-(4-fluorophenyl)-N-[4-(2-{[2-methoxy-4-(morpholin-4-ylsulfonyl)phenyl]amino}[,2]-triazolo[1,5-a]pyridin-6-yl)phenyl]acetamide

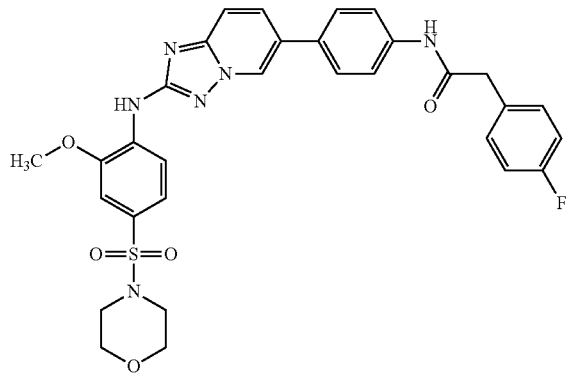 [SMILES: COc1cc(S(=O)(=O)N2CCOCC2)ccc1Nc1nc2ccc(-c3ccc(NC(=O)Cc4ccc(F)cc4)cc3)cn2n1]

Starting with Int02.04 and Int22.01, Example 02.37 was prepared analogously to the procedure for the preparation of Example 02.15.

$^1$H-NMR (400 MHz, DMSO-d$_6$): δ [ppm]=2.87-2.98 (m, 4H), 3.59-3.72 (m, 6H), 3.98 (s, 3H), 7.16 (t, 2H), 7.22-7.29 (m, 1H), 7.30-7.35 (m, 1H), 7.38 (dd, 2H), 7.67 (d, 1H), 7.74 (q, 4H), 7.94 (dd, 1H), 8.55 (s, 1H), 8.68 (d, 1H), 9.06 (s, 1H), 10.32 (s, 1H).

Example 02.38

2-(4-fluorophenyl)-N-[4-(2-{[2-methyl-4-(2-oxa-6-azaspiro[3.3]hept-6-ylcarbonyl)phenyl]amino}[,2]triazolo[1,5-a]pyridin-6-yl)phenyl]acetamide

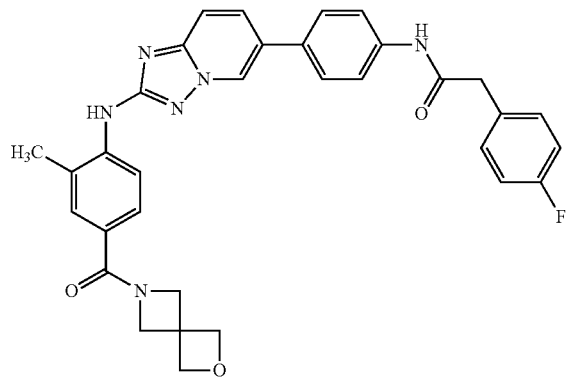 [SMILES: Cc1cc(C(=O)N2CC3(COC3)C2)ccc1Nc1nc2ccc(-c3ccc(NC(=O)Cc4ccc(F)cc4)cc3)cn2n1]

Starting with Int02.04 and Int23.01, Example 02.38 was prepared analogously to the procedure for the preparation of Example 02.16.

$^1$H-NMR (300 MHz, DMSO-d$_6$): δ [ppm]=2.32 (s, 3H), 3.64 (s, 2H), 4.16 (br. s., 2H), 4.47 (br. s., 2H), 4.65 (s, 4H), 7.08-7.17 (m, 2H), 7.31-7.38 (m, 2H), 7.39-7.45 (m, 2H), 7.60 (d, 1H), 7.64-7.76 (m, 4H), 7.88 (dd, 1H), 8.06-8.16 (m, 1H), 8.71 (s, 1H), 9.04 (d, 1H), 10.26 (s, 1H).

Example 02.39

2-(4-fluorophenyl)-N-[4-(2-{[2-methyl-4-(morpholin-4-ylcarbonyl)phenyl]amino}[,2]-triazolo[1,5-a]pyridin-6-yl)phenyl]acetamide

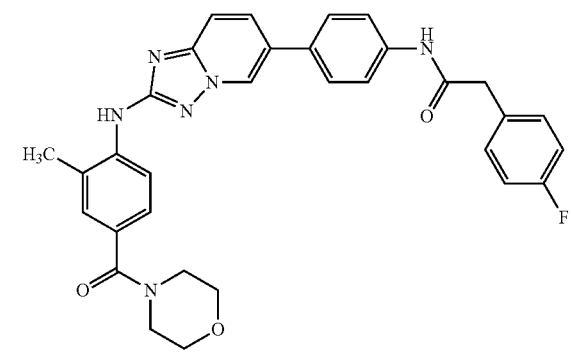 [SMILES: Cc1cc(C(=O)N2CCOCC2)ccc1Nc1nc2ccc(-c3ccc(NC(=O)Cc4ccc(F)cc4)cc3)cn2n1]

Starting with Int02.04 and Int23.02, Example 02.39 was prepared analogously to the procedure for the preparation of Example 02.16.

$^1$H-NMR (300 MHz, DMSO-d$_6$): δ [ppm]=2.31 (s, 3H), 3.48 (br. s., 4H), 3.57 (br. s., 4H), 3.64 (s, 2H), 7.08-7.17 (m, 2H), 7.19-7.25 (m, 2H), 7.34 (dd, 2H), 7.58 (d, 1H), 7.63-7.75 (m, 4H), 7.87 (dd, 1H), 8.01-8.14 (m, 1H), 8.69 (s, 1H), 9.04 (s, 1H), 10.28 (s, 1H).

Example 02.40

2-(4-fluorophenyl)-N-[4-(2-{[4-(2-oxa-6-azaspiro[3.3]hept-6-ylcarbonyl)-2-(trifluoromethoxy)phenyl]amino}[,2]triazolo[1,5-a]pyridin-6-yl)phenyl]acetamide

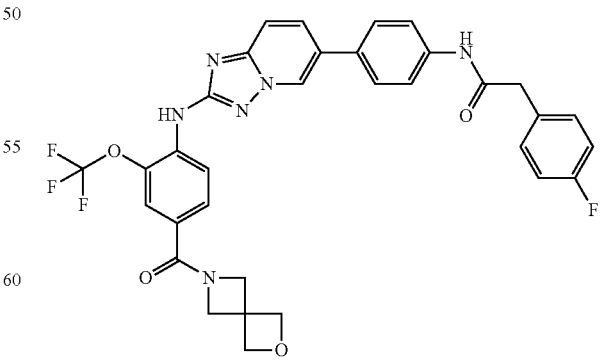

Starting with Int02.04 and Int24.05, Example 02.40 was prepared analogously to the procedure for the preparation of Example 02.16.

¹H-NMR (400 MHz, DMSO-d₆): δ [ppm]=3.65 (s, 2H), 4.18 (br. s., 2H), 4.52 (br. s., 2H), 4.65 (s, 4H), 7.08-7.17 (m, 2H), 7.32-7.38 (m, 2H), 7.53-7.57 (m, 1H), 7.61 (dd, 1H), 7.65-7.76 (m, 5H), 7.93 (dd, 1H), 8.50 (d, 1H), 9.08 (s, 1H), 9.71 (s, 1H), 10.27 (s, 1H).

Example 02.41

2-(4-fluorophenyl)-N-[4-(2-{[2-methoxy-5-(morpholin-4-ylcarbonyl)phenyl]amino}[,2]-triazolo[1,5-a]pyridin-6-yl)phenyl]acetamide

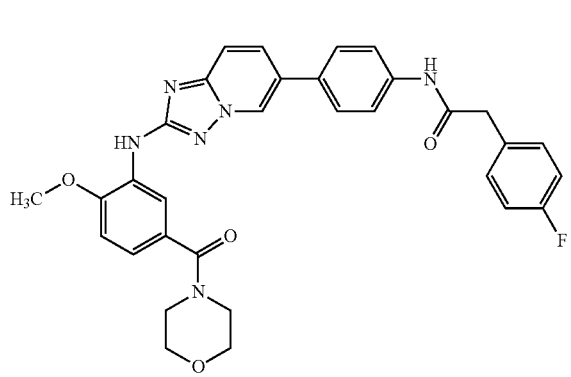 [SMILES: COc1ccc(C(=O)N2CCOCC2)cc1Nc1nc2ccc(-c3ccc(NC(=O)Cc4ccc(F)cc4)cc3)cn2n1]

Starting with Int02.04 and Int25.01, Example 02.41 was prepared analogously to the procedure for the preparation of Example 02.15.

¹H-NMR (400 MHz, DMSO-d₆): δ [ppm]=3.45-3.67 (m, 8H), 3.68 (s, 2H), 3.92 (s, 3H), 6.99-7.05 (m, 1H), 7.06-7.11 (m, 1H), 7.16 (t, 2H), 7.38 (dd, 2H), 7.62-7.68 (m, 1H), 7.68-7.79 (m, 4H), 7.92 (dd, 1H), 8.17 (s, 1H), 8.35 (d, 1H), 9.10 (d, 1H), 10.30 (s, 1H).

Example 02.42

2-(4-fluorophenyl)-N-[4-(2-{[2-methyl-6-(morpholin-4-yl)pyridin-3-yl]amino}[,2]-triazolo[1,5-a]pyridin-6-yl)phenyl]acetamide

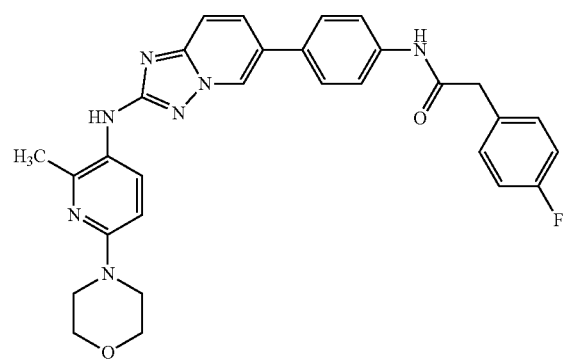 [SMILES: Cc1nc(N2CCOCC2)ccc1Nc1nc2ccc(-c3ccc(NC(=O)Cc4ccc(F)cc4)cc3)cn2n1]

Starting with Int02.04 and 3-bromo-2-methyl-6-morpholinopyridine, Example 02.42 was prepared analogously to the procedure for the preparation of Example 02.15.

¹H-NMR (400 MHz, DMSO-d₆): δ [ppm]=2.33 (s, 3H), 3.35-3.41 (m, 4H), 3.67 (s, 2H), 3.69-3.76 (m, 4H), 6.68 (d, 1H), 7.11-7.23 (m, 2H), 7.37 (dd, 2H), 7.50 (d, 1H), 7.69 (s, 4H), 7.76 (d, 1H), 7.82 (dd, 1H), 8.43 (s, 1H), 8.96 (d, 1H), 10.30 (s, 1H).

Example 02.43

2-(4-fluorophenyl)-N-[4-(2-{[2-methyl-6-(pyrrolidin-1-yl)pyridin-3-yl]amino}[,2]-triazolo[1,5-a]pyridin-6-yl)phenyl]acetamide

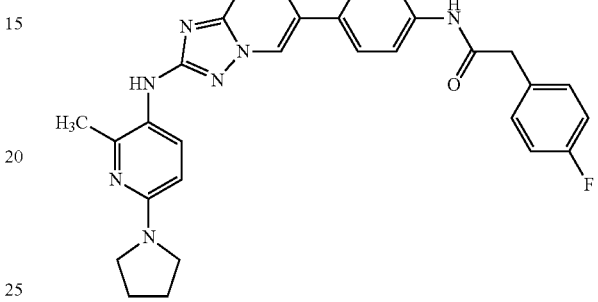

Starting with Int02.04 and 3-bromo-2-methyl-6-(pyrrolidin-1-yl)pyridine, Example 02.43 was prepared analogously to the procedure for the preparation of Example 02.15.

¹H-NMR (400 MHz, DMSO-d₆): δ [ppm]=1.89-1.97 (m, 4H), 2.29 (s, 3H), 3.34-3.39 (m, 4H), 3.66 (s, 2H), 6.28 (d, 1H), 7.16 (t, 2H), 7.37 (dd, 2H), 7.47 (d, 1H), 7.56 (d, 1H), 7.69 (s, 4H), 7.80 (dd, 1H), 8.26 (s, 1H), 8.92 (d, 1H), 10.28 (s, 1H).

Example 02.44

N-{4-[2-({4-[(3-fluoroazetidin-1-yl)carbonyl]-2-methoxyphenyl}amino)[,2]triazolo[1,5-a]pyridin-6-yl]phenyl}-2-(4-fluorophenyl)acetamide

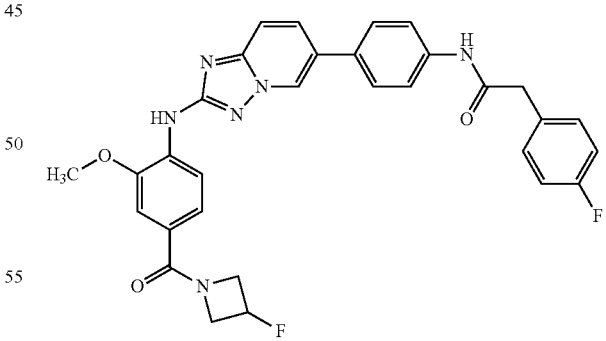

Starting with Int02.04 and Int09.12, Example 02.44 was prepared analogously to the procedure for the preparation of Example 02.15.

¹H-NMR (400 MHz, DMSO-d₆): δ [ppm]=3.68 (s, 2H), 3.94 (s, 3H), 3.99-4.27 (m, 1H), 4.27-4.79 (m, 3H), 5.33-5.56 (m, 1H), 7.13-7.20 (m, 2H), 7.27 (d, 1H), 7.31 (dd, 1H), 7.35-7.41 (m, 2H), 7.67 (d, 1H), 7.70-7.79 (m, 4H), 7.94 (dd, 1H), 8.33-8.40 (m, 2H), 9.12 (d, 1H), 10.30 (s, 1H).

Example 03.01

N-(cyclopropylmethyl)-4-(2-{[2-methoxy-4-(morpholin-4-ylcarbonyl)phenyl]amino}[,2]-triazolo[1,5-a]pyridin-6-yl)benzamide

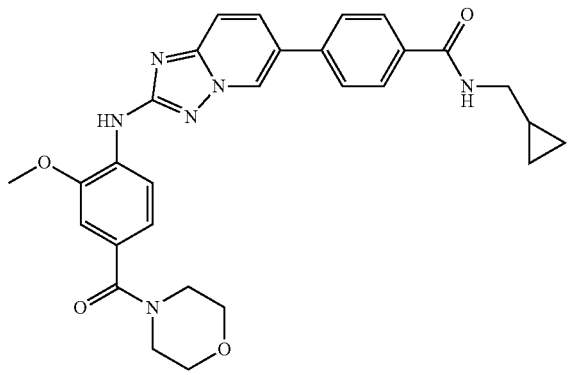 [SMILES: COc1cc(C(=O)N2CCOCC2)ccc1Nc1nc2ccc(-c3ccc(C(=O)NCC4CC4)cc3)cn2n1]

To a stirred suspension of Int03.02 (100 mg) in toluene (3.0 mL) and NMP (0.3 mL) was added Int09.01 (146 mg), chloro(2-dicyclohexylphosphino-2',4',6'-tri-i-propyl-1,1'-biphenyl)[2-(2-aminoethyl)phenyl]palladium(II) methyl-t-butylether adduct (26.9 mg), X-Phos (15.8 mg), and sodium tert-butoxide (156 mg). The flask was twice degassed and backfilled with argon. The mixture was heated to reflux for 1.5 h. Water was added and the reaction mixture was extracted with dichloromethane. The organic phase was washed with saturated sodium chloride solution, dried (sodium sulfate) and the solvent was removed in vacuum. Aminophase-silica-gel chromatography gave a solid that was that was triturated with DIPE. Yield: 90 mg of the title compound.

$^1$H-NMR (400 MHz, DMSO-$d_6$): δ [ppm]=0.17-0.24 (m, 2H), 0.37-0.45 (m, 2H), 1.01-1.07 (m, 1H), 3.14 (t, 2H), 3.41-3.64 (m, 8H), 3.88 (s, 3H), 6.98-7.09 (m, 2H), 7.67 (d, 1H), 7.84-8.04 (m, 5H), 8.25-8.36 (m, 2H), 8.62 (t, 1H), 9.25 (d, 1H).

Example 03.02

N-(cyclopropylmethyl)-4-(2-{[2-ethoxy-4-(morpholin-4-ylcarbonyl)phenyl]amino}[,2]-triazolo[1,5-a]pyridin-6-yl)benzamide

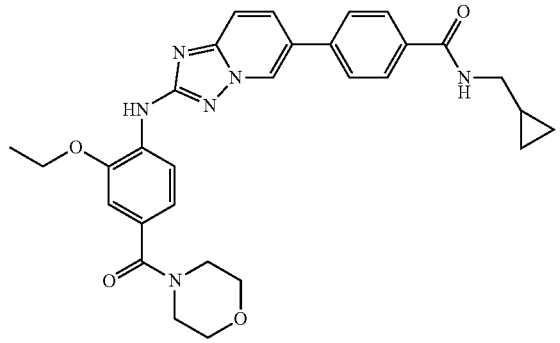 [SMILES: CCOc1cc(C(=O)N2CCOCC2)ccc1Nc1nc2ccc(-c3ccc(C(=O)NCC4CC4)cc3)cn2n1]

To a stirred suspension of Int03.02 (98 mg) in toluene (3.0 mL) and NMP (0.3 mL) was added Int10.03 (150 mg), chloro(2-dicyclohexylphosphino-2',4',6'-tri-i-propyl-1,1'-biphenyl)[2-(2-aminoethyl)phenyl]palladium(II) methyl-t-butylether adduct (26.3 mg), X-Phos (15.5 mg), and sodium tert-butoxide (153 mg). The flask was twice degassed and backfilled with argon. The mixture was heated to reflux for 1.5 h. Water was added and the reaction mixture was extracted with dichloromethane. The organic phase was washed with saturated sodium chloride solution, dried (sodium sulfate) and the solvent was removed in vacuum. Aminophase-silica-gel chromatography gave a solid that was that was triturated with DIPE. Yield: 110 mg of the title compound.

$^1$H-NMR (300 MHz, DMSO-$d_6$): δ [ppm]=0.14-0.27 (m, 2H), 0.33-0.49 (m, 2H), 0.94-1.05 (m, 1H), 1.40 (t, 3H), 3.14 (t, 2H), 3.40-3.66 (m, 8H), 4.14 (q, 2H), 7.03 (dd, 2H), 7.66 (d, 1H), 7.82-8.04 (m, 5H), 8.17 (s, 1H), 8.31 (d, 1H), 8.62 (t, 1H), 9.25 (d, 1H).

Example 03.03

N-(cyclopropylmethyl)-4-(2-{[4-(4,4-dimethyl-4,5-dihydro-1,3-oxazol-2-yl)-2-methoxyphenyl]amino}[,2]-triazolo[1,5-a]pyridin-6-yl)benzamide

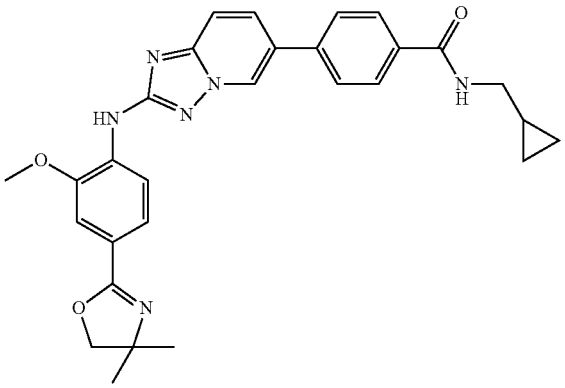 [SMILES: COc1cc(C2=NC(C)(C)CO2)ccc1Nc1nc2ccc(-c3ccc(C(=O)NCC4CC4)cc3)cn2n1]

To a stirred suspension of Int03.02 (85 mg) in toluene (3.0 mL) and NMP (0.3 mL) was added Int09.03 (118 mg), chloro(2-dicyclohexylphosphino-2',4',6'-tri-i-propyl-1,1'-biphenyl)[2-(2-aminoethyl)phenyl]palladium(II) methyl-t-butylether adduct (22.9 mg) and X-Phos (13.5 mg). The flask was twice degassed and backfilled with argon. The mixture was stirred at room temperature for 5 minutes. Sodium tert-butoxide (133 mg) was added, the flask was twice degassed and backfilled with argon, and the mixture was heated to reflux for 3 h. Water was added and the reaction mixture was extracted with ethyl acetate. The organic phase was washed with saturated sodium chloride solution, dried (sodium sulfate) and the solvent was removed in vacuum. Aminophase-silica-gel chromatography gave a solid that was recrystallized from ethanol. Yield: 38 mg of the title compound.

$^1$H-NMR (300 MHz, DMSO-$d_6$): δ [ppm]=0.11-0.26 (m, 2H), 0.34-0.49 (m, 2H), 0.92-1.09 (m, 1H), 1.25 (s, 6H), 3.03-3.18 (m, 2H), 3.90 (s, 3H), 4.05 (s, 2H), 7.39 (d, 1H), 7.45 (dd, 1H), 7.69 (d, 1H), 7.85-7.97 (m, 4H), 8.01 (dd, 1H), 8.35 (d, 1H), 8.38 (s, 1H), 8.62 (t, 1H), 9.27 (d, 1H).

Example 03.04

4-[(6-{4-[(cyclopropylmethyl)carbamoyl]phenyl}[,2]triazolo[1,5-a]pyridin-2-yl)amino]-3-ethoxy-N-(1-methylpiperidin-4-yl)benzamide

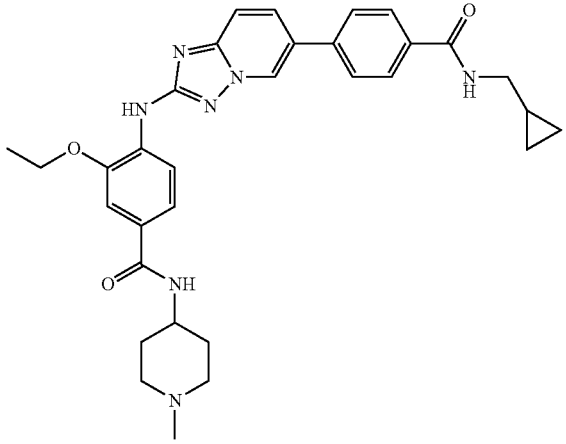 [SMILES: CCOc1cc(C(=O)NC2CCN(C)CC2)ccc1Nc1nc2ccc(-c3ccc(C(=O)NCC4CC4)cc3)cn2n1]

To a stirred suspension of Int03.02 (80 mg) in toluene (2.5 mL) and NMP (0.2 mL) was added Int10.05 (181 mg), Pd$_2$dba$_3$ (23.8 mg) and rac-BINAP (32.4 mg). The flask was twice degassed and backfilled with argon. The mixture was stirred at room temperature for 5 minutes. Caesium carbonate (424 mg) was added, the flask was twice degassed and backfilled with argon and the mixture was heated to reflux for 16 h. Water was added and the reaction mixture was extracted with a mixture of ethyl acetate and methanol (10:1). The organic phase was washed with saturated sodium chloride solution, dried (sodium sulfate) and the solvent was removed in vacuum. Aminophase-silica-gel chromatography gave a solid that was recrystallized from ethanol. Yield: 77 mg of the title compound.

$^1$H-NMR (300 MHz, DMSO-d$_6$): δ [ppm]=0.14-0.28 (m, 2H), 0.34-0.46 (m, 2H), 0.91-1.08 (m, 1H), 1.42 (t, 3H), 1.47-1.65 (m, 2H), 1.67-1.79 (m, 2H), 1.81-1.98 (m, 2H), 2.13 (s, 3H), 2.69-2.83 (m, 2H), 3.14 (d, 2H), 3.60-3.82 (m, 1H), 4.17 (q, 2H), 7.41-7.56 (m, 2H), 7.68 (d, 1H), 7.82-8.10 (m, 6H), 8.19 (s, 1H), 8.30 (d, 1H), 8.62 (t, 1H), 9.26 (d, 1H).

Example 03.05

N-(cyclopropylmethyl)-4-(2-{[2-methoxy-4-(4-methylpiperazin-1-yl)phenyl]amino}[,2]-triazolo[1,5-a]pyridin-6-yl)benzamide trifluoroacetate

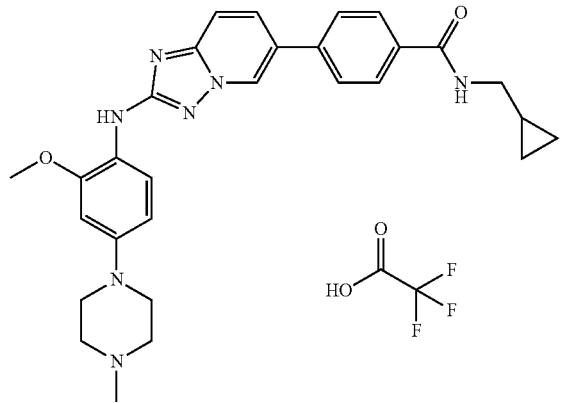 [SMILES: COc1cc(N2CCN(C)CC2)ccc1Nc1nc2ccc(-c3ccc(C(=O)NCC4CC4)cc3)cn2n1 ; O=C(O)C(F)(F)F]

4-(2-Amino[,2]triazolo[1,5-a]pyridin-6-yl)-N-(cyclopropylmethyl)benzamide Int03.02 (100 mg), 1-(4-bromo-3-methoxyphenyl)-4-methylpiperazine (US2009/118305) (112 mg), chloro(2-dicyclohexylphosphino-2',4',6'-tri-i-propyl-1,1'-biphenyl)[2-(2-aminoethyl)phenyl]palladium(II) methyl-t-butylether adduct (10.8 mg), X-Phos (6.2 mg), and sodium tert-butoxide (57.1 mg) were pre-mixed, and degassed toluene (2.0 mL) was added. The mixture was heated overnight to 130° C., then diluted with satd. sodium carbonate solution and extracted with ethyl acetate. The organic layer was dried over sodium sulfate, and the solvent was evaporated. The crude product was purified by HPLC to yield 89 mg (44%) of the title compound.

$^1$H-NMR (400 MHz, DMSO-d$_6$): δ [ppm]=0.22-0.28 (m, 2H), 0.41-0.48 (m, 2H), 1.00-1.11 (m, 1H), 2.87-2.90 (m, 3H), 2.91-2.97 (m, 2H), 3.17 (t, 2H), 3.17-3.24 (m, 2H), 3.54 (d, 2H), 3.81 (d, 2H), 3.87 (s, 3H), 6.59 (dd, 1H), 6.74 (d, 1H), 7.61 (d, 1H), 7.90 (d, 2H), 7.95-8.00 (m, 4H), 8.62 (t, 1H), 9.18 (s, 1H), 9.50 (br. s, 1H).

Example 03.06

N-(cyclopropylmethyl)-4-(2-{[4-(morpholin-4-ylcarbonyl)-2-(2,2,2-trifluoroethoxy)phenyl]amino}[,2]-triazolo[1,5-a]pyridin-6-yl)benzamide

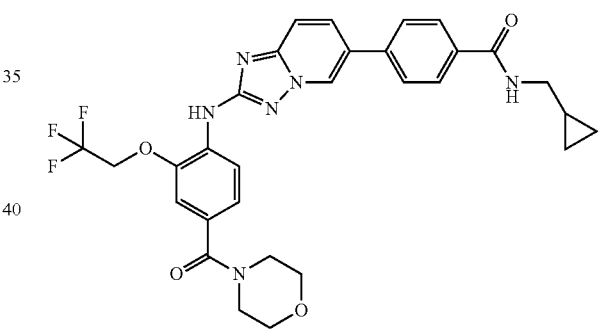

4-(2-Amino[,2]triazolo[1,5-a]pyridin-6-yl)-N-(cyclopropylmethyl)benzamide Int03.02 (100 mg), [4-iodo-3-(2,2,2-trifluoroethoxy)phenyl](morpholin-4-yl)methanone Int11.02 (123 mg), chloro(2-dicyclohexylphosphino-2',4',6'-tri-i-propyl-1,1'-biphenyl)[2-(2-aminoethyl)phenyl]palladium(II) (18.3 mg), X-Phos (11.8 mg), and sodium tert-butoxide (43.4 mg) were pre-mixed, and degassed toluene (1.5 mL) was added. The mixture was heated for 3 h to 130° C., then diluted with satd. sodium carbonate solution and extracted with DCM. The organic layer was dried over sodium sulfate, and the solvent was evaporated. The crude product was purified by flash chromatography on silica gel (20 g, eluent: ethyl acetate/cyclohexane gradient 4:1 to 8:1) to yield 40 mg (27%) of the title compound.

$^1$H-NMR (400 MHz, DMSO-d$_6$): δ [ppm]=0.22-0.27 (m, 2H), 0.42-0.48 (m, 2H), 1.00-1.11 (m, 1H), 3.18 (t, 2H), 3.53 (br. s, 4H), 3.62 (br. s, 4H), 4.93 (q, 2H), 7.19 (dd, 1H), 7.26 (d, 1H), 7.72 (d, 1H), 7.91-7.94 (m, 2H), 7.97-8.01 (m, 2H), 8.05 (dd, 1H), 8.27 (s, 1H), 8.36 (d, 1H), 8.65 (t, 1H), 9.29 (s, 1H).

Example 03.07

N-(cyclopropylmethyl)-4-(2-{[2-methoxy-4-(2-oxa-6-azaspiro[3.3]hept-6-ylcarbonyl)phenyl]amino}[,2]triazolo[1,5-a]pyridin-6-yl)benzamide

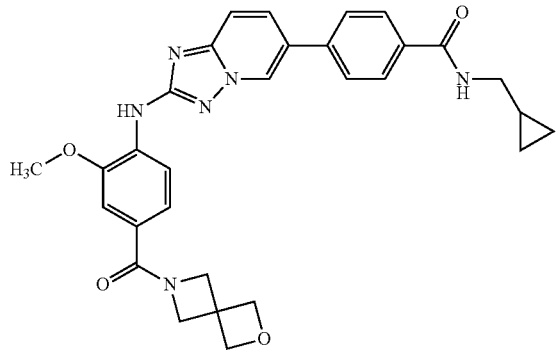 [SMILES: COc1cc(C(=O)N2CC3(COC3)C2)ccc1Nc1nc2ccc(-c3ccc(C(=O)NCC4CC4)cc3)cn2n1]

Starting with Int03.02 and Int09.06, Example 03.07 was prepared analogously to the procedure for the preparation of Example 02.16.

$^1$H-NMR (400 MHz, DMSO-d$_6$): δ [ppm]=0.17-0.24 (m, 2H), 0.38-0.45 (m, 2H), 0.97-1.07 (m, 1H), 3.14 (t, 2H), 3.90 (s, 3H), 4.17 (br. s., 2H), 4.51 (br. s., 2H), 4.66 (s, 4H), 7.21 (d, 1H), 7.25 (dd, 1H), 7.69 (d, 1H), 7.86-7.97 (m, 4H), 8.01 (dd, 1H), 8.30-8.39 (m, 2H), 8.62 (t, 1H), 9.26 (d, 1H).

Example 04.01

N-(4-Fluorbenzyl)-4-(2-{[2-methoxy-4-(morpholin-4-ylcarbonyl)phenyl]amino}[,2]-triazolo[1,5-a]pyridin-6-yl)benzamid

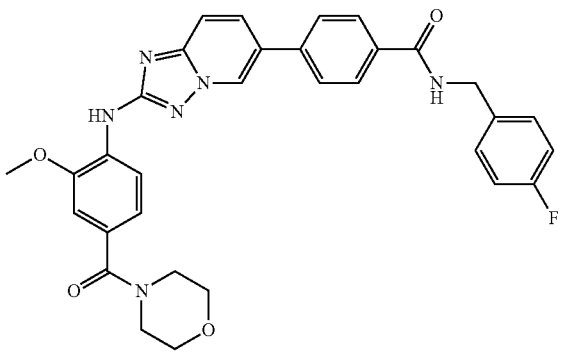 [SMILES: COc1cc(C(=O)N2CCOCC2)ccc1Nc1nc2ccc(-c3ccc(C(=O)NCc4ccc(F)cc4)cc3)cn2n1]

To a stirred suspension of Int03.03 (100 mg) toluene (3.5 mL) and NMP (0.5 mL) was added Int09.01 (131 mg), chloro(2-dicyclohexylphosphino-2',4',6'-tri-i-propyl-1,1'-biphenyl)[2-(2-aminoethyl)phenyl]palladium(II) methyl-t-butylether adduct (16.0 mg) and X-Phos (9.2 mg). The flask was twice degassed and backfilled with argon. The mixture was stirred at room temperature for 5 minutes. Sodium tert-butoxide (133 mg) was added, the flask was twice degassed and backfilled with argon, and the mixture was heated to reflux for 3 h. Water was added and the reaction mixture was extracted with ethyl acetate. The organic phase was washed with saturated sodium chloride solution, dried (sodium sulfate) and the solvent was removed in vacuum. Aminophase-silica-gel chromatography gave a solid that was triturated with ethyl acetate. Yield: 130 mg of the title compound.

$^1$H-NMR (400 MHz, DMSO-d$_6$): δ [ppm]=3.46-3.68 (m, 8H), 3.92 (s, 3H), 4.49 (d, 2H), 7.04-7.10 (m, 2H), 7.12-7.19 (m, 2H), 7.38 (dd, 2H), 7.71 (d, 1H), 7.91-7.96 (m, 2H), 7.98-8.07 (m, 3H), 8.29-8.37 (m, 2H), 9.16 (t, 1H), 9.28 (s, 1H).

Example 04.02

4-(2-{[2-Ethoxy-4-(morpholin-4-ylcarbonyl)phenyl]amino}[,2]-triazolo[1,5-a]pyridin-6-yl)-N-(4-fluorbenzyl)benzamid

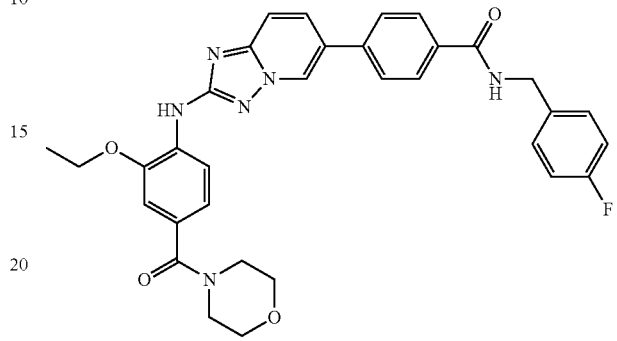

To a stirred suspension of Int03.03 (100 mg) toluene (3.4 mL) and NMP (0.5 mL) was added Int10.03 (131 mg), chloro(2-dicyclohexylphosphino-2',4',6'-tri-i-propyl-1,1'-biphenyl)[2-(2-aminoethyl)phenyl]palladium(II) methyl-t-butylether adduct (15.2 mg) and X-Phos (8.8 mg). The flask was twice degassed and backfilled with argon. The mixture was stirred at room temperature for 5 minutes. Sodium tert-butoxide (126 mg) was added, the flask was twice degassed and backfilled with argon, and the mixture was heated to reflux for 3 h. Water was added and the reaction mixture was extracted with ethyl acetate. The organic phase was washed with saturated sodium chloride solution, dried (sodium sulfate) and the solvent was removed in vacuum. Aminophase-silica-gel chromatography gave 103 mg of the title compound.

$^1$H-NMR (400 MHz, DMSO-d$_6$): δ [ppm]=1.44 (t, 3H), 3.44-3.69 (m, 8H), 4.17 (q, 2H), 4.49 (d, 2H), 7.06 (dd, 2H), 7.17 (t, 2H), 7.38 (dd, 2H), 7.70 (d, 1H), 7.90-7.97 (m, 2H), 7.98-8.07 (m, 3H), 8.22 (s, 1H), 8.32-8.38 (m, 1H), 9.16 (t, 1H), 9.29 (s, 1H).

Example 04.03

N-(4-fluorobenzyl)-4-(2-{[2-methoxy-4-(2-oxo-1,3-oxazolidin-3-yl)phenyl]amino}[,2]-triazolo[1,5-a]pyridin-6-yl)benzamide

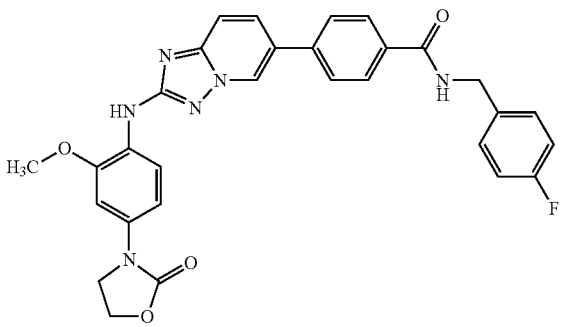 [SMILES: COc1cc(N2CCOC2=O)ccc1Nc1nc2ccc(-c3ccc(C(=O)NCc4ccc(F)cc4)cc3)cn2n1]

To a stirred suspension of Int03.03 (150 mg) in toluene (4.0 mL) and NMP (1 mL) in a sealed tube was added Int26.01 (169 mg), chloro(2-dicyclohexylphosphino-2',4',6'- tri-i-propyl-1,1'-biphenyl)[2-(2-aminoethyl)phenyl]palladium(II) methyl-t-butylether adduct (34 mg), X-Phos (20 mg), and powdered potassium phosphate (441 mg). The flask was twice degassed and backfilled with argon. The mixture was heated to 130° C. with an oil bath for 2 h. Water was added and the reaction mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was triturated with warm ethanol to give 170 mg of the title compound.

$^1$H-NMR (300 MHz, DMSO-$d_6$): δ [ppm]=3.84 (s, 3H), 4.01-4.09 (m, 2H), 4.36-4.49 (m, 4H), 6.98 (dd, 1H), 7.07-7.18 (m, 2H), 7.28-7.42 (m, 3H), 7.56-7.66 (m, 1H), 7.84-8.01 (m, 5H), 8.06 (s, 1H), 8.13 (d, 1H), 9.11 (t, 1H), 9.20 (d, 1H).

Example 04.04

4-(2-{[2-ethoxy-4-(2-oxo-1,3-oxazolidin-3-yl)phenyl]amino}[,2]triazolo[1,5-a]pyridin-6-yl)-N-(4-fluorobenzyl)benzamide

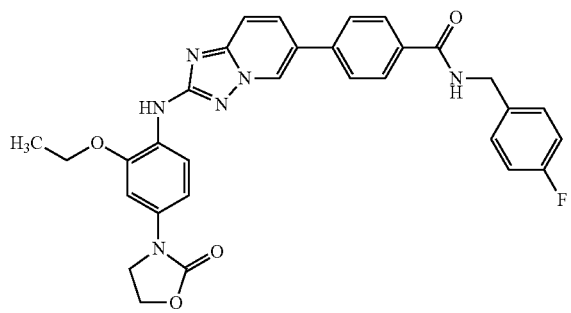 [SMILES: CCOc1cc(N2CCOC2=O)ccc1Nc1nc2ccc(-c3ccc(C(=O)NCc4ccc(F)cc4)cc3)cn2n1]

To a stirred suspension of Int03.03 (100 mg) in toluene (4.0 mL) and NMP (0.5 mL) in a sealed tube was added Int27.02 (118 mg), chloro(2-dicyclohexylphosphino-2',4',6'-tri-i-propyl-1,1'-biphenyl)[2-(2-aminoethyl)phenyl]palladium(II) methyl-t-butylether adduct (23 mg), X-Phos (13 mg), and powdered potassium phosphate (294 mg). The flask was twice degassed and backfilled with argon. The mixture was heated to 130° C. with an oil bath for 2 h. Water was added and the reaction mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was triturated with warm ethanol to give 85 mg of the title compound.

$^1$H-NMR (400 MHz, DMSO-$d_6$): δ [ppm]=1.44 (t, 3H), 4.05-4.11 (m, 2H), 4.15 (q, 2H), 4.42-4.48 (m, 2H), 4.51 (d, 2H), 7.03 (dd, 1H), 7.14-7.21 (m, 2H), 7.36-7.42 (m, 2H), 7.44 (d, 1H), 7.67 (d, 1H), 7.90-8.06 (m, 6H), 8.21 (dd, 1H), 9.14 (t, 1H), 9.23-9.27 (m, 1H).

Example 04.05

4-(2-{[4-(4,5-dihydro-1,3-oxazol-2-yl)-2-methoxyphenyl]amino}[,2]-triazolo[1,5-a]pyridin-6-yl)-N-(4-fluorobenzyl)benzamide

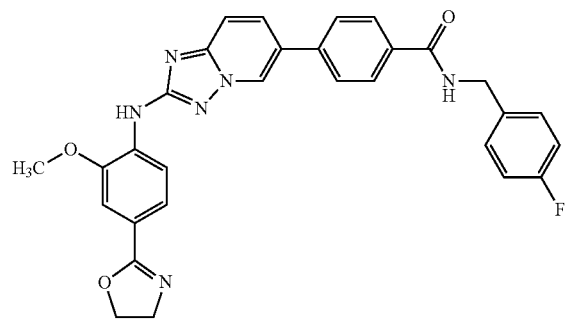 [SMILES: COc1cc(C2=NCCO2)ccc1Nc1nc2ccc(-c3ccc(C(=O)NCc4ccc(F)cc4)cc3)cn2n1]

To a suspension of Int03.03 (80 mg) in toluene (2.75 mL) and NMP (0.35 mL) was added Int29.01 (88 mg), Pd-X-Phos-pre-cat (12.7 mg), X-Phos (7.2 mg) and potassium phosphate (225 mg). The tube was twice degassed and backfilled with argon. The mixture was irradiated in the microwave for 3 h at 130° C. Water was added and the mixture was extracted with ethyl acetate. The organic phase was dried (sodium sulfate) and the solvent was removed in vacuum. Silica gel chromatography gave a solid that was triturated with ethanol. Yield: 24.8 mg of the title compound.

$^1$H-NMR (400 MHz, DMSO-$d_6$): δ [ppm]=3.89-4.01 (m, 5H), 4.39 (t, 2H), 4.49 (d, 2H), 7.16 (t, 2H), 7.32-7.42 (m, 2H), 7.46 (s, 1H), 7.51 (d, 1H), 7.72 (d, 1H), 7.90-7.98 (m, 2H), 7.98-8.09 (m, 3H), 8.35-8.47 (m, 2H), 9.15 (t, 1H), 9.30 (s, 1H).

Example 04.06

N-(4-fluorobenzyl)-4-[2-({2-methoxy-4-[(1S,4S)-2-oxa-5-azabicyclo[2.2.1]hept-5-ylcarbonyl]phenyl}amino)[,2]triazolo[1,5-a]pyridin-6-yl]benzamide

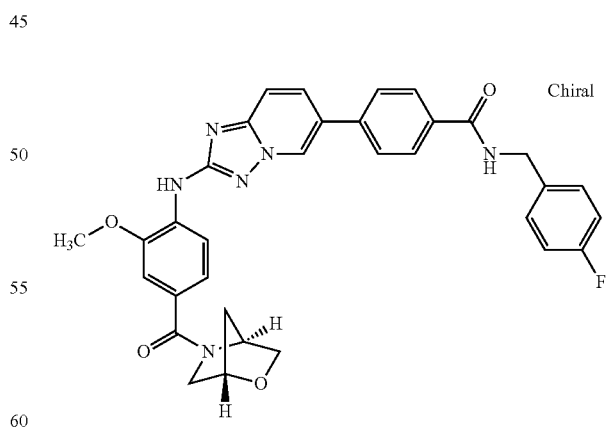

To a stirred suspension of Int03.03 (80 mg) in toluene (4.0 mL) and NMP (0.5 mL) in a sealed tube was added Int09.05 (104 mg), chloro(2-dicyclohexylphosphino-2',4',6'-tri-i-propyl-1,1'-biphenyl)[2-(2-aminoethyl)phenyl]palladium(II) methyl-t-butylether adduct (18 mg), X-Phos (10.8 mg), and powdered potassium phosphate (294 mg). The flask was twice degassed and backfilled with argon. The mixture was heated to 130° C. with an oil bath for 2 h. Water was added and the reaction mixture was extracted with a mixture of dichloromethane and methanol (100:1). The organic phase was washed with saturated sodium chloride solution, dried (sodium sulfate) and the solvent was removed in vacuum. Aminophase-silica-gel chromatography gave a solid that was triturated with warm ethanol to give 85 mg of the title compound.

$^1$H-NMR (300 MHz, DMSO-d$_6$): δ [ppm]=1.66-1.96 (m, 2H), 3.33-3.83 (m, 3H), 3.85-4.00 (m, 4H), 4.39-4.83 (m, 4H), 7.06-7.25 (m, 4H), 7.34 (dd, 2H), 7.67 (d, 1H), 7.84-8.06 (m, 5H), 8.24-8.40 (m, 2H), 9.12 (t, 1H), 9.25 (s, 1H).

Example 04.07

N-(4-fluorobenzyl)-4-(2-{[2-methoxy-4-(2-oxa-6-azaspiro[3.3]hept-6-ylcarbonyl)phenyl]amino}[,2]triazolo[1,5-a]pyridin-6-yl)benzamide

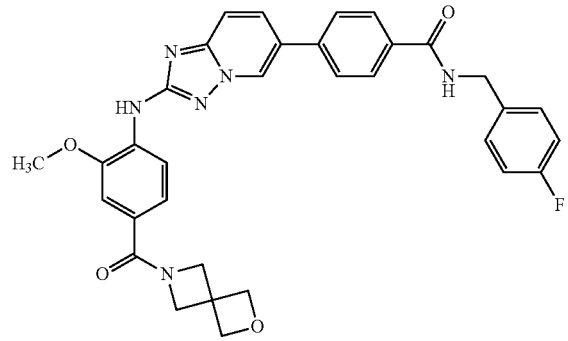 [SMILES: COc1cc(C(=O)N2CC3(COC3)C2)ccc1Nc1nc2ccc(-c3ccc(C(=O)NCc4ccc(F)cc4)cc3)cn2n1]

Starting with Int03.03 and Int09.06, Example 04.07 was prepared analogously to the procedure for the preparation of Example 02.15.

$^1$H-NMR (400 MHz, DMSO-d$_6$): δ [ppm]=3.93 (s, 3H), 4.21 (br. s., 2H), 4.49 (d, 2H), 4.55 (br. s., 2H), 4.70 (s, 4H), 7.12-7.20 (m, 2H), 7.25 (d, 1H), 7.28 (dd, 1H), 7.35-7.41 (m, 2H), 7.72 (dd, 1H), 7.91-7.97 (m, 2H), 7.99-8.08 (m, 3H), 8.37 (d, 1H), 8.41 (s, 1H), 9.15 (t, 1H), 9.30 (d, 1H).

Example 04.08

N-(4-fluorobenzyl)-4-[2-({4-[(3-hydroxyazetidin-1-yl)carbonyl]-2-methoxyphenyl}amino)[,2]-triazolo[1,5-a]pyridin-6-yl]benzamide

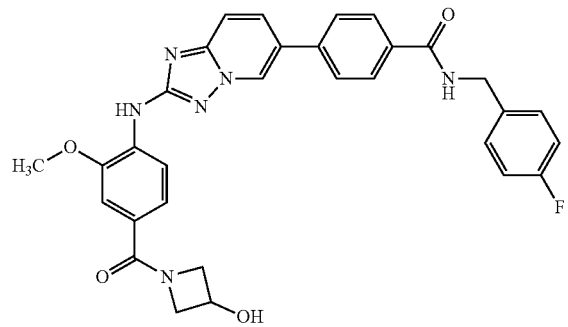 [SMILES: COc1cc(C(=O)N2CC(O)C2)ccc1Nc1nc2ccc(-c3ccc(C(=O)NCc4ccc(F)cc4)cc3)cn2n1]

Starting with Int03.03 and Int09.08, Example 04.08 was prepared analogously to the procedure for the preparation of Example 02.15.

$^1$H-NMR (400 MHz, DMSO-d$_6$): δ [ppm]=3.70-3.84 (m, 1H), 3.93 (s, 3H), 4.04-4.17 (m, 1H), 4.19-4.31 (m, 1H), 4.42-4.59 (m, 4H), 5.76 (br. s., 1H), 7.17 (t, 2H), 7.23-7.32 (m, 2H), 7.38 (dd, 2H), 7.72 (d, 1H), 7.90-7.98 (m, 2H), 7.99-8.07 (m, 3H), 8.36 (d, 1H), 8.41 (s, 1H), 9.16 (t, 1H), 9.30 (d, 1H).

Example 04.09

4-[2-({4-[(1,1-dioxidothiomorpholin-4-yl)carbonyl]-2-methoxyphenyl}amino)[,2]triazolo[1,5-a]pyridin-6-yl]-N-(4-fluorobenzyl)benzamide

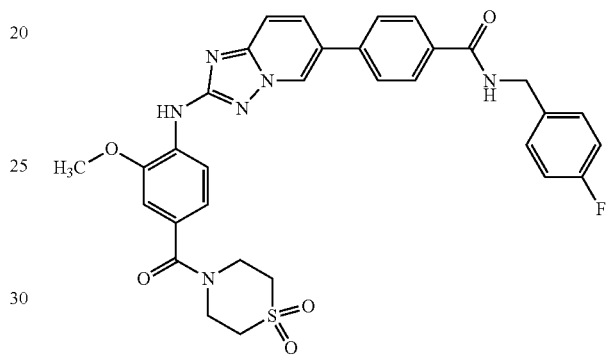

Starting with Int03.03 and Int09.07, Example 04.09 was prepared analogously to the procedure for the preparation of Example 02.12.

$^1$H-NMR (400 MHz, DMSO-d$_6$): δ [ppm]=3.24 (s, 4H), 3.76-3.96 (m, 7H), 4.45 (d, 2H), 7.06-7.18 (m, 4H), 7.34 (dd, 2H), 7.68 (d, 1H), 7.86-8.05 (m, 5H), 8.27-8.37 (m, 2H), 9.12 (t, 1H), 9.26 (d, 1H).

Example 04.10

N-(4-fluorobenzyl)-4-[2-({4-[(4-hydroxypiperidin-1-yl)carbonyl]-2-methoxyphenyl}amino)[,2]triazolo[1,5-a]pyridin-6-yl]benzamide

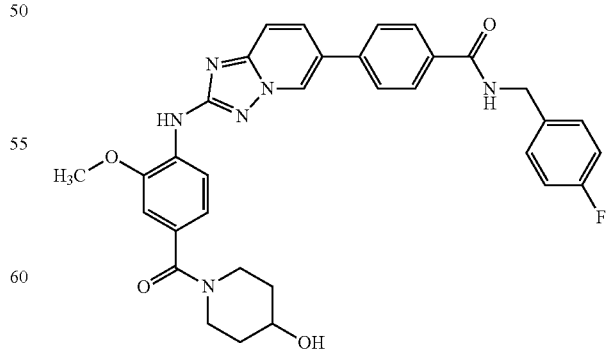

Starting with Int03.03 and Int09.09, Example 04.10 was prepared analogously to the procedure for the preparation of Example 02.12.

¹H-NMR (300 MHz, DMSO-d₆): δ [ppm]=1.23-1.43 (m, 2H), 1.71 (br. s., 2H), 3.07-3.23 (m, 2H), 3.56-3.96 (m, 6H), 4.45 (d, 2H), 4.76 (d, 1H), 6.93-7.03 (m, 2H), 7.08-7.19 (m, 2H), 7.34 (dd, 2H), 7.67 (d, 1H), 7.84-8.04 (m, 5H), 8.22-8.32 (m, 2H), 9.12 (t, 1H), 9.25 (s, 1H).

Example 04.11

4-[(6-{4-[(4-fluorobenzyl)carbamoyl]phenyl}[,2]triazolo[1,5-a]pyridin-2-yl)amino]-3-methoxy-N-(oxetan-3-yl)benzamide

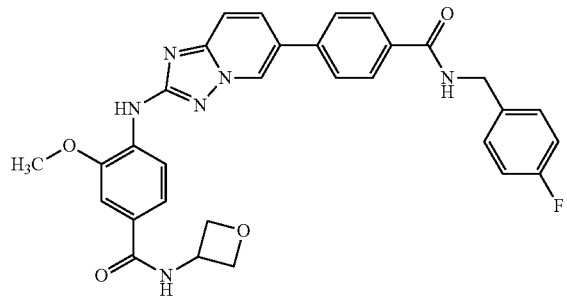 [SMILES: COc1cc(C(=O)NC2COC2)ccc1Nc1nc2ccc(-c3ccc(C(=O)NCc4ccc(F)cc4)cc3)cn2n1]

Starting with Int03.03 and Int09.10, Example 04.11 was prepared analogously to the procedure for the preparation of Example 02.12.

¹H-NMR (300 MHz, DMSO-d₆): δ [ppm]=3.93 (s, 3H), 4.45 (d, 2H), 4.58 (t, 2H), 4.76 (t, 2H), 4.89-5.07 (m, 1H), 7.07-7.20 (m, 2H), 7.34 (dd, 2H), 7.48-7.57 (m, 2H), 7.69 (d, 1H), 7.87-8.06 (m, 5H), 8.29-8.42 (m, 2H), 8.92 (d, 1H), 9.12 (t, 1H), 9.28 (s, 1H).

Example 04.12

4-(2-{[2-ethoxy-4-(2-oxa-6-azaspiro[3.3]hept-6-ylcarbonyl)phenyl]amino}[,2]-triazolo[1,5-a]pyridin-6-yl)-N-(4-fluorobenzyl)benzamide

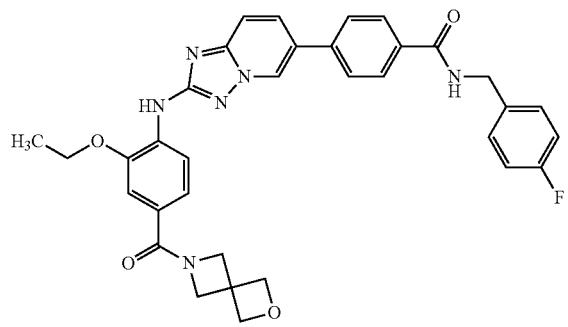 [SMILES: CCOc1cc(C(=O)N2CC3(COC3)C2)ccc1Nc1nc2ccc(-c3ccc(C(=O)NCc4ccc(F)cc4)cc3)cn2n1]

Starting with Int03.03 and Int10.07, Example 04.12 was prepared analogously to the procedure for the preparation of Example 02.15.

¹H-NMR (400 MHz, DMSO-d₆): δ [ppm]=1.45 (t, 3H), 4.19 (q, 4H), 4.49 (d, 2H), 4.54 (br. s., 2H), 4.70 (s, 4H), 7.16 (t, 2H), 7.23 (s, 1H), 7.25-7.31 (m, 1H), 7.38 (dd, 2H), 7.72 (d, 1H), 7.89-7.98 (m, 2H), 7.98-8.09 (m, 3H), 8.27 (s, 1H), 8.37 (d, 1H), 9.13 (t, 1H), 9.29 (s, 1H).

Example 04.13

4-[2-({4-[(4-acetylpiperazin-1-yl)carbonyl]-2-ethoxyphenyl}amino)[,2]triazolo[1,5-a]pyridin-6-yl]-N-(4-fluorobenzyl)benzamide

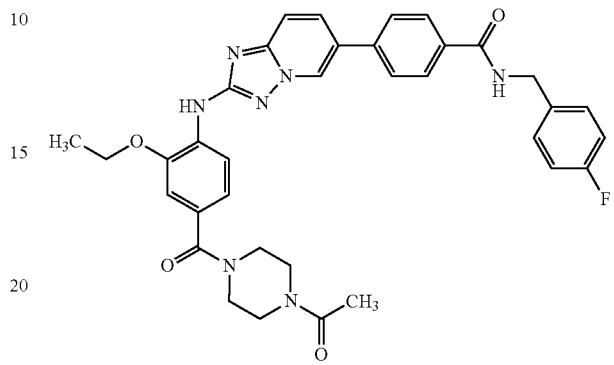

Starting with Int03.03 and Int10.10, Example 04.13 was prepared analogously to the procedure for the preparation of Example 02.16.

¹H-NMR (400 MHz, DMSO-d₆): δ [ppm]=1.41 (t, 3H), 1.99 (s, 3H), 3.46 (br. s., 8H), 4.15 (q, 2H), 4.45 (d, 2H), 7.02-7.06 (m, 2H), 7.09-7.18 (m, 2H), 7.31-7.39 (m, 2H), 7.68 (d, 1H), 7.87-8.04 (m, 5H), 8.20 (s, 1H), 8.32 (d, 1H), 9.12 (t, 1H), 9.26 (d, 1H).

Example 04.14

4-[2-({2-ethoxy-4-[(3-hydroxyazetidin-1-yl)carbonyl]phenyl}amino)[,2]triazolo[1,5-a]pyridin-6-yl]-N-(4-fluorobenzyl)benzamide

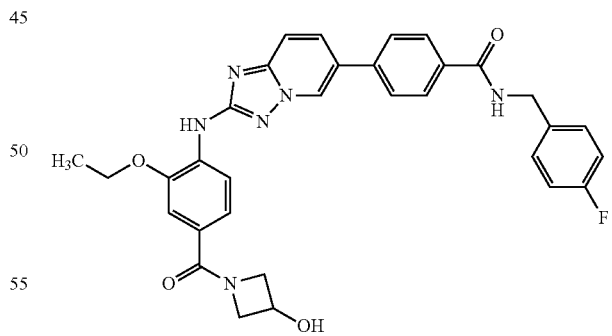

Starting with Int03.03 and Int10.08, Example 04.14 was prepared analogously to the procedure for the preparation of Example 02.15.

¹H-NMR (400 MHz, DMSO-d₆): δ [ppm]=1.45 (t, 3H), 3.79 (br. s., 1H), 4.00-4.14 (m, 1H), 4.19 (q, 3H), 4.49 (d, 4H), 5.75 (br. s., 1H), 7.17 (t, 2H), 7.24 (s, 1H), 7.28 (d, 1H), 7.38 (t, 2H), 7.72 (d, 1H), 7.94 (d, 2H), 7.98-8.10 (m, 3H), 8.28 (s, 1H), 8.37 (d, 1H), 9.16 (t, 1H), 9.30 (s, 1H).

Example 04.15

N-(4-fluorobenzyl)-4-(2-{[4-(2-oxa-6-azaspiro[3.3]hept-6-ylcarbonyl)-2-(2,2,2-trifluoroethoxy)phenyl]amino}[,2]-triazolo[1,5-a]pyridin-6-yl)benzamide

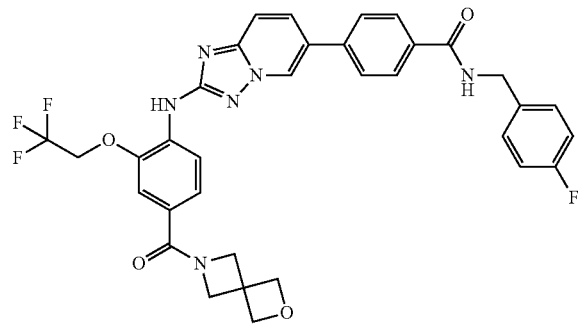 [SMILES: O=C(NCc1ccc(F)cc1)c1ccc(-c2ccc3nc(Nc4ccc(C(=O)N5CC6(COC6)C5)cc4OCC(F)(F)F)nn3c2)cc1]

Starting with Int03.03 and Int11.06, Example 04.15 was prepared analogously to the procedure for the preparation of Example 02.15.

$^1$H-NMR (400 MHz, DMSO-d$_6$): δ [ppm]=4.21 (br. s., 2H), 4.42-4.61 (m, 4H), 4.70 (s, 4H), 4.94 (q, 2H), 7.10-7.21 (m, 2H), 7.33-7.42 (m, 4H), 7.73 (d, 1H), 7.90-7.98 (m, 2H), 7.99-8.08 (m, 3H), 8.33-8.43 (m, 2H), 9.16 (t, 1H), 9.28-9.33 (m, 1H).

Example 04.16

N-(4-fluorobenzyl)-4-[2-({4-[(3-hydroxyazetidin-1-yl)carbonyl]-2-(2,2,2-trifluoroethoxy)phenyl}amino)[,2]triazolo[1,5-a]pyridin-6-yl]benzamide

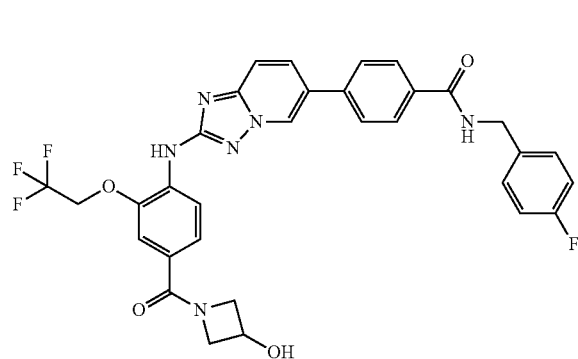 [SMILES: O=C(NCc1ccc(F)cc1)c1ccc(-c2ccc3nc(Nc4ccc(C(=O)N5CC(O)C5)cc4OCC(F)(F)F)nn3c2)cc1]

Starting with Int03.03 and Int11.07, Example 04.16 was prepared analogously to the procedure for the preparation of Example 02.15.

$^1$H-NMR (400 MHz, DMSO-d$_6$): δ [ppm]=3.78 (s, 1H), 4.12 (s, 1H), 4.24 (s, 1H), 4.49 (d, 4H), 4.95 (q, 2H), 5.74 (br. s., 1H), 7.16 (t, 2H), 7.34-7.43 (m, 4H), 7.73 (d, 1H), 7.91-7.95 (m, 2H), 7.98-8.08 (m, 3H), 8.32 (s, 1H), 8.39 (d, 1H), 9.14 (t, 1H), 9.29 (s, 1H).

Example 04.17

N-(4-fluorobenzyl)-4-(2-{[4-(morpholin-4-ylcarbonyl)-2-(2,2,2-trifluoroethoxy)phenyl]amino}[,2]-triazolo[1,5-a]pyridin-6-yl)benzamide

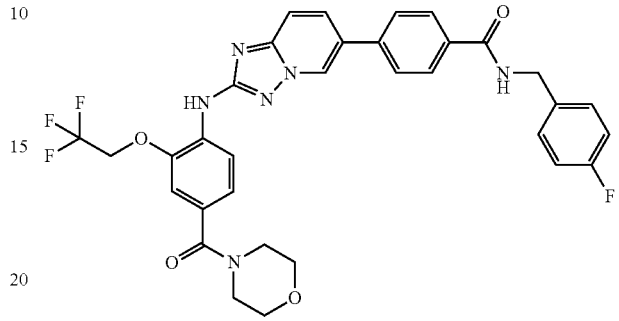

Starting with Int03.03 and Int11.05, Example 04.17 was prepared analogously to the procedure for the preparation of Example 02.15.

$^1$H-NMR (400 MHz, DMSO-d$_6$): δ [ppm]=3.42-3.70 (m, 8H), 4.49 (d, 2H), 4.93 (q, 2H), 7.11-7.22 (m, 3H), 7.26 (s, 1H), 7.34-7.43 (m, 2H), 7.72 (d, 1H), 7.90-7.98 (m, 2H), 7.98-8.09 (m, 3H), 8.28 (s, 1H), 8.35 (d, 1H), 9.15 (t, 1H), 9.29 (s, 1H).

Example 04.18

N-(4-fluorobenzyl)-4-(2-{[2-methoxy-4-(4-methylpiperazin-1-yl)phenyl]amino}[,2]triazolo[1,5-a]pyridin-6-yl)benzamide

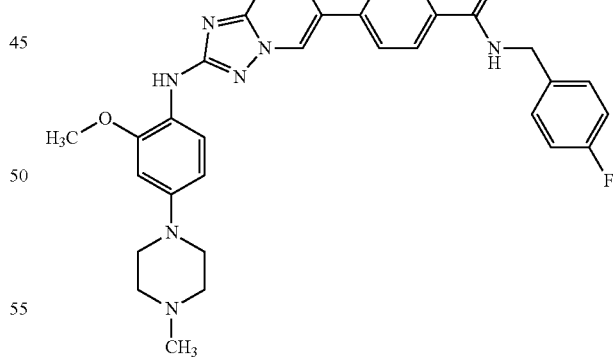

Starting with Int03.03 and Int17.02, Example 04.18 was prepared analogously to the procedure for the preparation of Example 02.16.

$^1$H-NMR (300 MHz, DMSO-d$_6$): δ [ppm]=2.19 (s, 3H), 2.38-2.44 (m, 4H), 3.01-3.11 (m, 4H), 3.81 (s, 3H), 4.45 (d, 2H), 6.48 (dd, 1H), 6.62 (d, 1H), 7.08-7.18 (m, 2H), 7.34 (dd, 2H), 7.56 (d, 1H), 7.76 (s, 1H), 7.82-8.01 (m, 6H), 9.10 (t, 1H), 9.16 (d, 1H).

Example 04.19

4-(2-{[4-(4-tert-butylpiperazin-1-yl)-2-methoxyphenyl]amino}[,2]triazolo[1,5-a]pyridin-6-yl)-N-(4-fluorobenzyl)benzamide

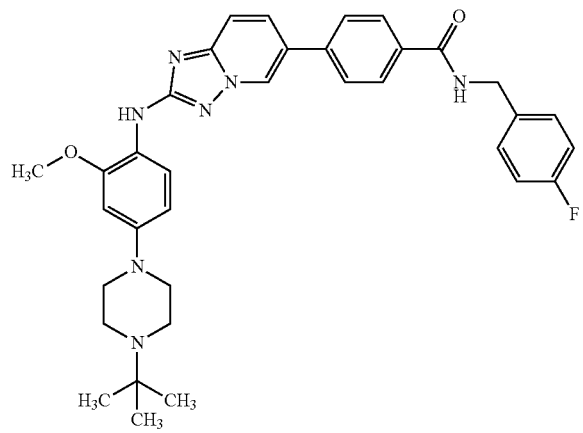 [SMILES: COc1cc(N2CCN(C(C)(C)C)CC2)ccc1Nc1nc2ccc(-c3ccc(C(=O)NCc4ccc(F)cc4)cc3)cn2n1]

Starting with Int03.03 and Int17.03, Example 04.19 was prepared analogously to the procedure for the preparation of Example 02.16.

$^1$H-NMR (300 MHz, DMSO-$d_6$): δ [ppm]=1.03 (br. s., 9H), 2.63 (br. s., 4H), 3.05 (br. s., 4H), 3.81 (s, 3H), 4.45 (d, 2H), 6.48 (d, 1H), 6.61 (d, 1H), 7.08-7.18 (m, 2H), 7.34 (dd, 2H), 7.56 (d, 1H), 7.77 (s, 1H), 7.81-8.02 (m, 6H), 9.10 (t, 1H), 9.15 (d, 1H).

Example 04.20

N-(4-fluorobenzyl)-4-(2-{[2-fluoro-4-(2-oxa-6-azaspiro[3.3]hept-6-ylcarbonyl)phenyl]amino}[,2]triazolo[1,5-a]pyridin-6-yl)benzamide

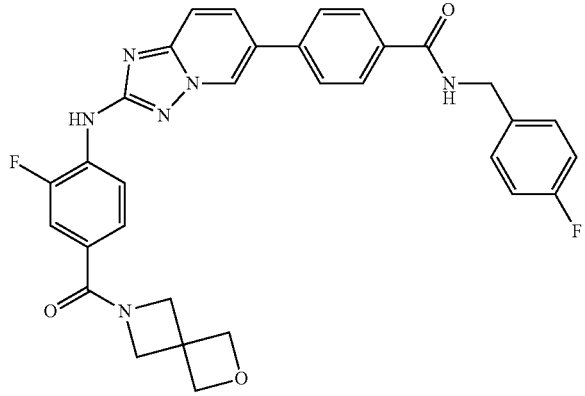 [SMILES: O=C(NCc1ccc(F)cc1)c1ccc(-c2ccc3nc(Nc4ccc(C(=O)N5CC6(COC6)C5)cc4F)nn3c2)cc1]

Starting with Int03.03 and Int16.01, Example 04.20 was prepared analogously to the procedure for the preparation of Example 02.15.

$^1$H-NMR (400 MHz, DMSO-$d_6$): δ [ppm]=4.21 (br. s., 2H), 4.43-4.62 (m, 4H), 4.69 (s, 4H), 7.16 (t, 2H), 7.33-7.43 (m, 2H), 7.43-7.53 (m, 2H), 7.73 (d, 1H), 7.90-7.98 (m, 2H), 7.98-8.09 (m, 3H), 8.41 (t, 1H), 9.14 (t, 1H), 9.28 (s, 1H), 9.67 (s, 1H).

Example 04.21

N-(4-fluorobenzyl)-4-(2-{[2-fluoro-4-(morpholin-4-ylcarbonyl)phenyl]amino}[,2]-triazolo[1,5-a]pyridin-6-yl)benzamide

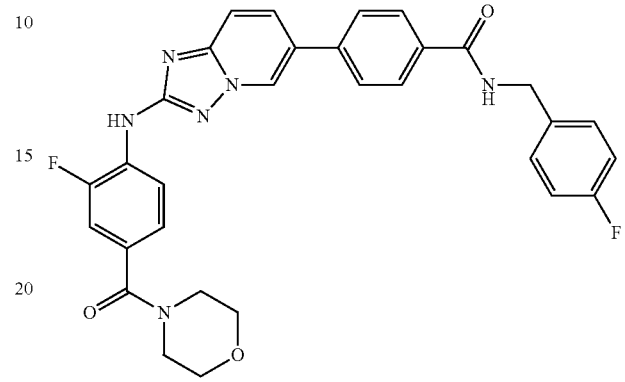

Starting with Int03.03 and Int16.02, Example 04.21 was prepared analogously to the procedure for the preparation of Example 02.15.

$^1$H-NMR (400 MHz, DMSO-$d_6$): δ [ppm]=3.42-3.70 (m, 8H), 4.49 (d, 2H), 7.12-7.22 (m, 2H), 7.25-7.42 (m, 4H), 7.72 (d, 1H), 7.91-7.97 (m, 2H), 7.99-8.08 (m, 3H), 8.37 (t, 1H), 9.15 (t, 1H), 9.28 (s, 1H), 9.59 (s, 1H).

Example 04.22

4-(2-{[2-(2,2-difluoroethoxy)-4-(morpholin-4-ylcarbonyl)phenyl]amino}[,2]triazolo[1,5-a]pyridin-6-yl)-N-(4-fluorobenzyl)benzamide

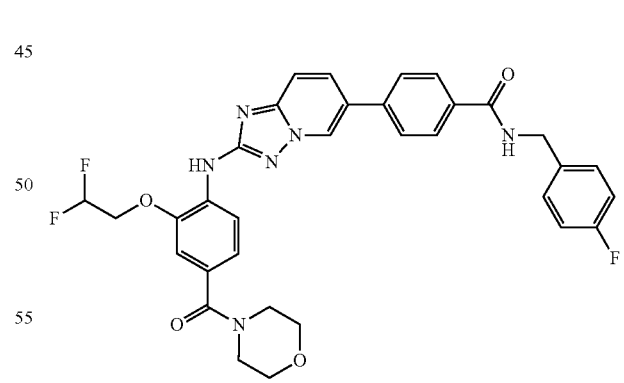

Starting with Int03.03 and Int13.02, Example 04.22 was prepared analogously to the procedure for the preparation of Example 02.15.

$^1$H-NMR (400 MHz, DMSO-$d_6$): δ [ppm]=3.44-3.70 (m, 8H), 4.42-4.55 (m, 4H), 6.39-6.72 (m, 1H), 7.10-7.21 (m, 4H), 7.38 (dd, 2H), 7.72 (d, 1H), 7.90-7.97 (m, 2H), 7.99-8.09 (m, 3H), 8.39 (d, 1H), 8.48 (s, 1H), 9.16 (t, 1H), 9.29 (d, 1H).

Example 04.23

N-(4-fluorobenzyl)-4-(2-{[4-(morpholin-4-ylcarbonyl)-2-(trifluoromethyl)phenyl]amino}[,2]triazolo[1,5-a]pyridin-6-yl)benzamide

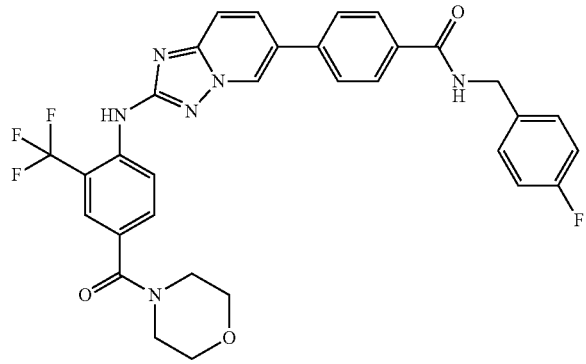 [SMILES: O=C(NCc1ccc(F)cc1)c1ccc(-c2ccc3nc(Nc4ccc(C(=O)N5CCOCC5)cc4C(F)(F)F)nn3c2)cc1]

Starting with Int03.03 and Int15.01, Example 04.23 was prepared analogously to the procedure for the preparation of Example 02.15.

$^1$H-NMR (400 MHz, DMSO-$d_6$): δ [ppm]=3.62 (br. s., 8H), 4.49 (d, 2H), 7.12-7.20 (m, 2H), 7.34-7.41 (m, 2H), 7.70 (d, 1H), 7.72-7.77 (m, 2H), 7.88-7.95 (m, 2H), 7.98-8.06 (m, 3H), 8.21 (d, 1H), 8.67 (s, 1H), 9.15 (t, 1H), 9.25 (d, 1H).

Example 04.24

N-(4-fluorobenzyl)-4-[2-({2-methoxy-4-[(4-methylpiperazin-1-yl)methyl]phenyl}amino)[,2]triazolo[1,5-a]pyridin-6-yl]benzamide

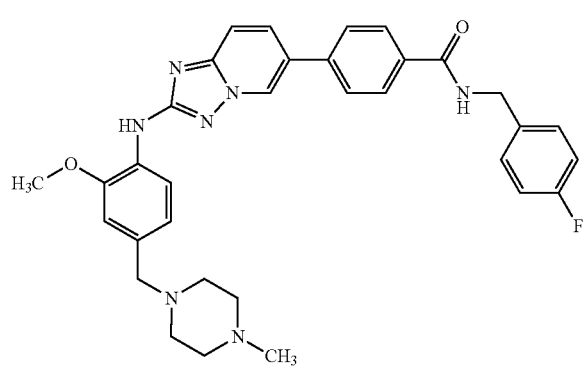 [SMILES: COc1cc(CN2CCN(C)CC2)ccc1Nc1nc2ccc(-c3ccc(C(=O)NCc4ccc(F)cc4)cc3)cn2n1]

Starting with Int03.03 and Int18.04, Example 04.24 was prepared analogously to the procedure for the preparation of Example 02.12.

$^1$H-NMR (300 MHz, DMSO-$d_6$): δ [ppm]=2.11 (s, 3H), 2.31 (br. s., 8H), 3.38 (s, 2H), 3.83 (s, 3H), 4.45 (d, 2H), 6.84 (dd, 1H), 6.91 (d, 1H), 7.07-7.18 (m, 2H), 7.28-7.38 (m, 2H), 7.57-7.66 (m, 1H), 7.85-8.01 (m, 6H), 8.10 (d, 1H), 9.10 (t, 1H), 9.21 (d, 1H).

Example 04.25

N-(4-fluorobenzyl)-4-(2-{[2-methoxy-4-(morpholin-4-ylmethyl)phenyl]amino}[,2]-triazolo[1,5-a]pyridin-6-yl)benzamide

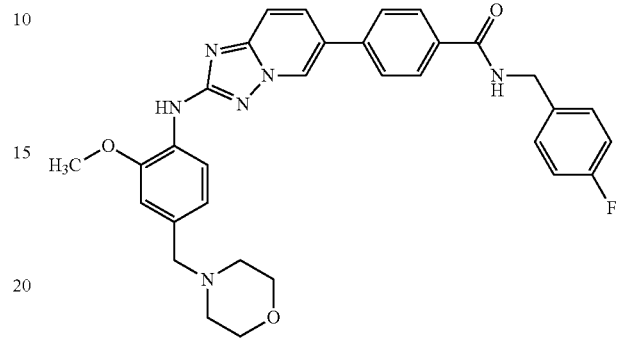

Starting with Int03.03 and Int18.02, Example 04.25 was prepared analogously to the procedure for the preparation of Example 02.12.

$^1$H-NMR (300 MHz, DMSO-$d_6$): δ [ppm]=2.32 (br. s., 4H), 3.39 (s, 2H), 3.50-3.60 (m, 4H), 3.84 (s, 3H), 4.45 (d, 2H), 6.82-6.90 (m, 1H), 6.93 (d, 1H), 7.05-7.19 (m, 2H), 7.28-7.40 (m, 2H), 7.62 (d, 1H), 7.85-8.02 (m, 6H), 8.12 (d, 1H), 9.11 (t, 1H), 9.21 (d, 1H).

Example 04.26

N-(4-fluorobenzyl)-4-[2-({2-methoxy-4-[(1-methylpiperidin-4-yl)oxy]phenyl}amino)[,2]triazolo[1,5-a]pyridin-6-yl]benzamide

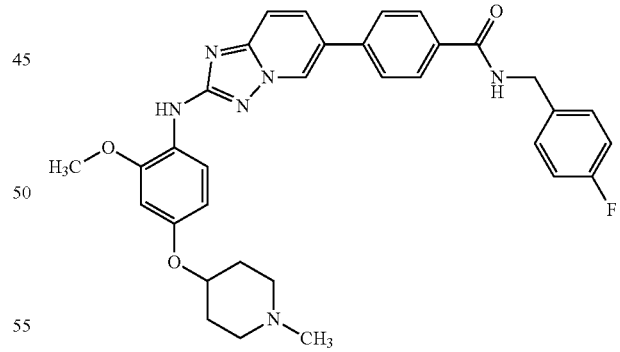

Starting with Int03.03 and Int20.01, Example 04.26 was prepared analogously to the procedure for the preparation of Example 02.12.

$^1$H-NMR (300 MHz, DMSO-$d_6$): δ [ppm]=1.51-1.68 (m, 2H), 1.81-1.95 (m, 2H), 2.03-2.20 (m, 5H), 2.53-2.64 (m, 2H), 3.80 (s, 3H), 4.21-4.36 (m, 1H), 4.45 (d, 2H), 6.53 (dd, 1H), 6.61 (d, 1H), 7.06-7.18 (m, 2H), 7.34 (dd, 2H), 7.57 (d, 1H), 7.80-8.01 (m, 7H), 9.10 (t, 1H), 9.16 (d, 1H).

Example 04.27

N-(4-fluorobenzyl)-4-[2-({4-[(1-methylpiperidin-4-yl)oxy]-2-(methylsulfanyl)phenyl}amino)[,2]triazolo[1,5-a]pyridin-6-yl]benzamide

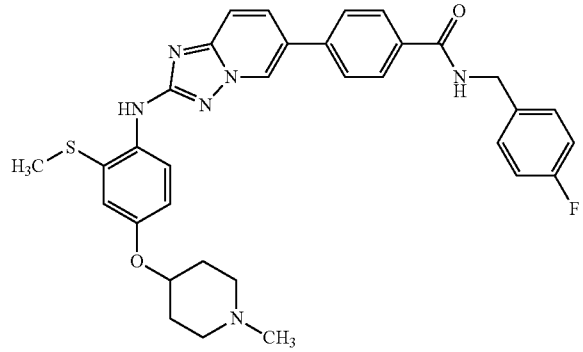

Starting with Int03.03 and Int21.01, Example 04.27 was prepared analogously to the procedure for the preparation of Example 02.36.

¹H-NMR (400 MHz, DMSO-d$_6$, detected signals): δ [ppm]=1.75 (br. s., 2H), 1.98 (br. s., 2H), 2.37 (s, 3H), 2.43 (br. s., 2H), 2.91 (br. s., 2H), 4.41-4.50 (m, 3H), 6.82 (dd, 1H), 6.86 (d, 1H), 7.07-7.17 (m, 2H), 7.30-7.37 (m, 2H), 7.49-7.58 (m, 2H), 7.81-8.00 (m, 5H), 8.20 (s, 1H), 9.07-9.14 (m, 2H).

Example 04.28

N-(4-fluorobenzyl)-4-(2-{[2-methyl-4-(2-oxa-6-azaspiro[3.3]hept-6-ylcarbonyl)phenyl]amino}[,2]triazolo[1,5-a]pyridin-6-yl)benzamide

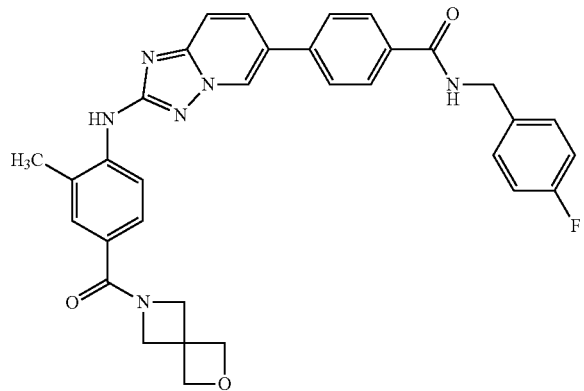 [SMILES: Cc1cc(C(=O)N2CC3(COC3)C2)ccc1Nc1nc2ccc(-c3ccc(C(=O)NCc4ccc(F)cc4)cc3)cn2n1]

Starting with Int03.03 and Int23.01, Example 04.28 was prepared analogously to the procedure for the preparation of Example 02.16.

¹H-NMR (400 MHz, DMSO-d$_6$): δ [ppm]=2.36 (s, 3H), 4.19 (br. s., 2H), 4.43-4.55 (m, 4H), 4.68 (s, 4H), 7.09-7.20 (m, 2H), 7.37 (dd, 2H), 7.42-7.48 (m, 2H), 7.67 (d, 1H), 7.89-8.04 (m, 5H), 8.11-8.17 (m, 1H), 8.79 (s, 1H), 9.12 (t, 1H), 9.24 (d, 1H).

Example 04.29

N-(4-fluorobenzyl)-4-(2-{[2-methyl-4-(morpholin-4-ylcarbonyl)phenyl]amino}[,2]-triazolo[1,5-a]pyridin-6-yl)benzamide

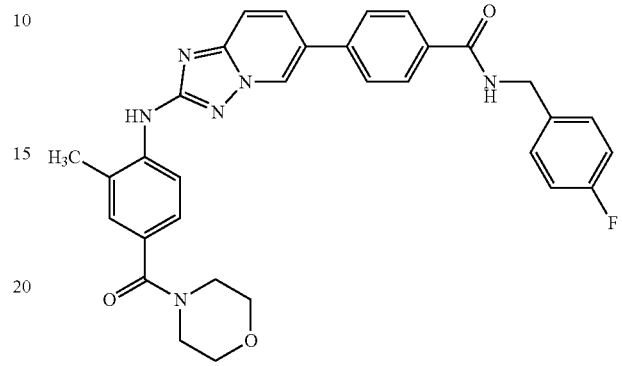

Starting with Int03.03 and Int23.02, Example 04.29 was prepared analogously to the procedure for the preparation of Example 02.16.

¹H-NMR (300 MHz, DMSO-d$_6$): δ [ppm]=2.32 (s, 3H), 3.48 (br. s., 4H), 3.57 (br. s., 4H), 4.45 (d, 2H), 7.07-7.17 (m, 2H), 7.19-7.26 (m, 2H), 7.29-7.40 (m, 2H), 7.63 (d, 1H), 7.84-8.00 (m, 5H), 8.03-8.11 (m, 1H), 8.75 (s, 1H), 9.12 (t, 1H), 9.20 (d, 1H).

Example 04.30

N-(4-fluorobenzyl)-4-(2-{[4-(2-oxa-6-azaspiro[3.3]hept-6-ylcarbonyl)-2-(trifluoromethoxy)phenyl]amino}[,2]-triazolo[1,5-a]pyridin-6-yl)benzamide

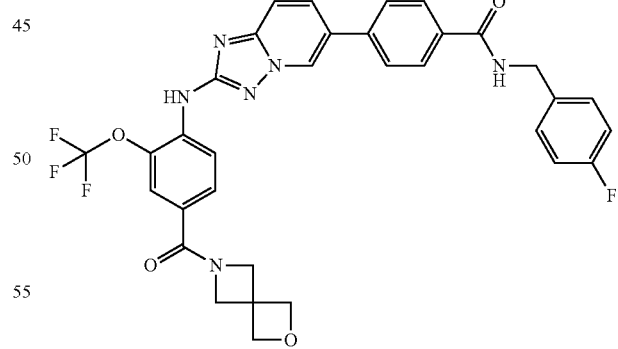

Starting with Int03.03 and Int24.05, Example 04.30 was prepared analogously to the procedure for the preparation of Example 02.16.

¹H-NMR (300 MHz, DMSO-d$_6$): δ [ppm]=4.18 (br. s., 2H), 4.46 (d, 2H), 4.52 (br. s., 2H), 4.65 (s, 4H), 7.08-7.17 (m, 2H), 7.34 (dd, 2H), 7.55 (t, 1H), 7.61 (dd, 1H), 7.71 (d, 1H), 7.86-8.07 (m, 5H), 8.50 (d, 1H), 9.10 (t, 1H), 9.25 (s, 1H), 9.76 (s, 1H).

Example 04.31

N-(4-fluorobenzyl)-4-(2-{[4-(morpholin-4-ylcarbonyl)-2-(trifluoromethoxy)phenyl]amino}[,2]-triazolo[1,5-a]pyridin-6-yl)benzamide

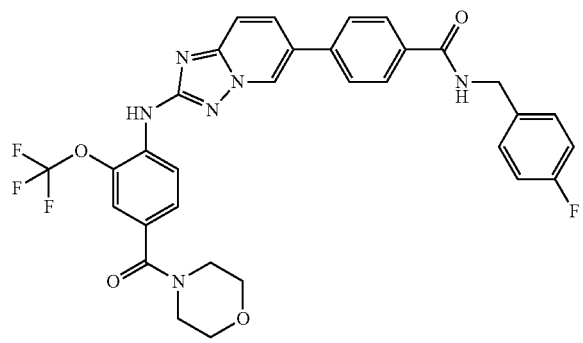 [SMILES: O=C(NCc1ccc(F)cc1)c1ccc(-c2ccc3nc(Nc4ccc(C(=O)N5CCOCC5)cc4OC(F)(F)F)nn3c2)cc1]

Starting with Int03.03 and Int24.04, Example 04.31 was prepared analogously to the procedure for the preparation of Example 02.16.

$^1$H-NMR (300 MHz, DMSO-$d_6$): δ [ppm]=3.36-3.67 (m, 8H), 4.45 (d, 2H), 7.05-7.19 (m, 2H), 7.29-7.48 (m, 4H), 7.70 (d, 1H), 7.85-8.07 (m, 5H), 8.47 (d, 1H), 9.12 (t, 1H), 9.24 (s, 1H), 9.70 (s, 1H).

Example 04.32

N-(4-fluorobenzyl)-4-(2-{[2-methoxy-5-(morpholin-4-ylcarbonyl)phenyl]amino}[,2]-triazolo[1,5-a]pyridin-6-yl)benzamide

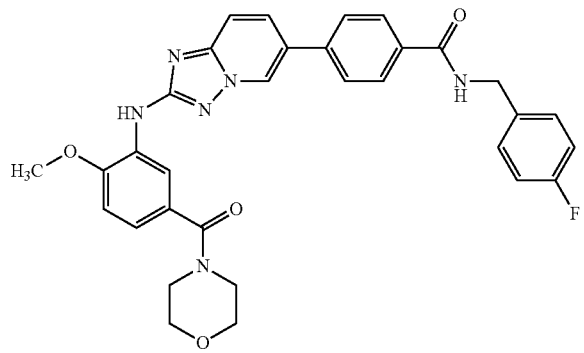 [SMILES: COc1ccc(C(=O)N2CCOCC2)cc1Nc1nc2ccc(-c3ccc(C(=O)NCc4ccc(F)cc4)cc3)cn2n1]

Starting with Int03.03 and Int25.01, Example 04.32 was prepared analogously to the procedure for the preparation of Example 02.15.

$^1$H-NMR (400 MHz, DMSO-$d_6$): δ [ppm]=3.64 (br. s., 8H), 3.93 (s, 3H), 4.49 (d, 2H), 6.99-7.06 (m, 1H), 7.08 (s, 1H), 7.16 (t, 2H), 7.38 (dd, 2H), 7.70 (d, 1H), 7.88-7.98 (m, 2H), 7.97-8.07 (m, 3H), 8.23 (s, 1H), 8.35 (d, 1H), 9.13 (t, 1H), 9.26 (s, 1H).

Example 04.33

N-(4-fluorobenzyl)-4-(2-{[2-methyl-6-(morpholin-4-yl)pyridin-3-yl]amino}[,2]triazolo[1,5-a]pyridin-6-yl)benzamide

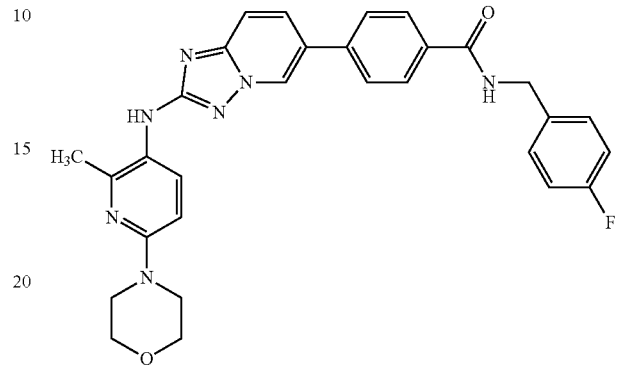

Starting with Int03.03 and 3-bromo-2-methyl-6-morpholinopyridine, Example 04.33 was prepared analogously to the procedure for the preparation of Example 02.15.

$^1$H-NMR (400 MHz, DMSO-$d_6$): δ [ppm]=2.34 (s, 3H), 3.36-3.41 (m, 4H), 3.66-3.75 (m, 4H), 4.48 (d, 2H), 6.68 (d, 1H), 7.16 (t, 2H), 7.37 (dd, 2H), 7.55 (d, 1H), 7.76 (d, 1H), 7.85-7.96 (m, 3H), 7.96-8.03 (m, 2H), 8.49 (s, 1H), 9.09-9.18 (m, 2H).

Example 04.34

N-(4-fluorobenzyl)-4-(2-{[2-methyl-6-(pyrrolidin-1-yl)pyridin-3-yl]amino}[,2]triazolo[1,5-a]pyridin-6-yl)benzamide

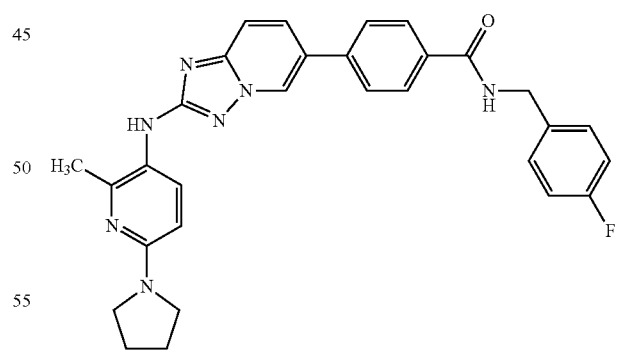

Starting with Int03.03 and 3-bromo-2-methyl-6-(pyrrolidin-1-yl)pyridine, Example 04.34 was prepared analogously to the procedure for the preparation of Example 02.15.

$^1$H-NMR (400 MHz, DMSO-$d_6$): δ [ppm]=1.89-1.99 (m, 4H), 2.29 (s, 3H), 3.29-3.41 (m, 4H), 4.48 (d, 2H), 6.28 (d, 1H), 7.11-7.20 (m, 2H), 7.37 (dd, 2H), 7.51 (d, 1H), 7.56 (d, 1H), 7.84-7.93 (m, 3H), 7.99 (d, 2H), 8.33 (s, 1H), 9.09 (d, 1H), 9.12 (t, 1H).

Example 04.35

4-[2-({4-[(3-fluoroazetidin-1-yl)carbonyl]-2-methoxyphenyl}amino)[,2]triazolo[1,5-a]pyridin-6-yl]-N-(4-fluorobenzyl)benzamide

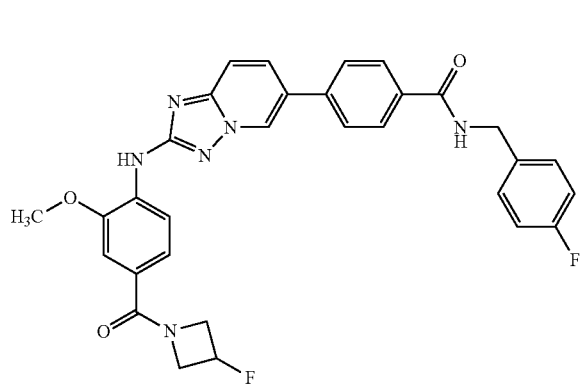 [SMILES: COc1cc(C(=O)N2CC(F)C2)ccc1Nc1nc2ccc(-c3ccc(C(=O)NCc4ccc(F)cc4)cc3)cn2n1]

Starting with Int03.03 and Int09.12, Example 04.35 was prepared analogously to the procedure for the preparation of Example 02.15.

$^1$H-NMR (400 MHz, DMSO-$d_6$): δ [ppm]=3.94 (s, 3H), 3.98-4.26 (m, 1H), 4.49 (d, 5H), 5.34-5.56 (m, 1H), 7.12-7.20 (m, 2H), 7.27 (d, 1H), 7.29-7.34 (m, 1H), 7.38 (dd, 2H), 7.72 (d, 1H), 7.91-7.96 (m, 2H), 8.00-8.07 (m, 3H), 8.38 (d, 1H), 8.41 (s, 1H), 9.14 (t, 1H), 9.29 (d, 1H).

Example 05.01

N-(4-chlorobenzyl)-4-(2-{[2-methoxy-4-(morpholin-4-ylcarbonyl)phenyl]amino}[,2]-triazolo[1,5-a]pyridin-6-yl)benzamide

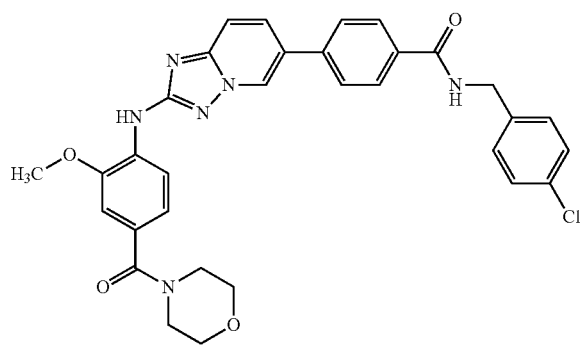 [SMILES: COc1cc(C(=O)N2CCOCC2)ccc1Nc1nc2ccc(-c3ccc(C(=O)NCc4ccc(Cl)cc4)cc3)cn2n1]

Starting with Int03.06 and Int09.01, Example 05.01 was prepared analogously to the procedure for the preparation of Example 02.15.

$^1$H-NMR (400 MHz, DMSO-$d_6$): δ [ppm]=3.47-3.70 (m, 8H), 3.92 (s, 3H), 4.49 (d, 2H), 7.04-7.11 (m, 2H), 7.38 (q, 4H), 7.70 (d, 1H), 7.91-7.97 (m, 2H), 7.99-8.06 (m, 3H), 8.28-8.37 (m, 2H), 9.15 (t, 1H), 9.28 (s, 1H).

Example 05.02

4-(2-{[2-methoxy-4-(morpholin-4-ylcarbonyl)phenyl]amino}[,2]-triazolo[1,5-a]pyridin-6-yl)-N-(4-methylbenzyl)benzamide

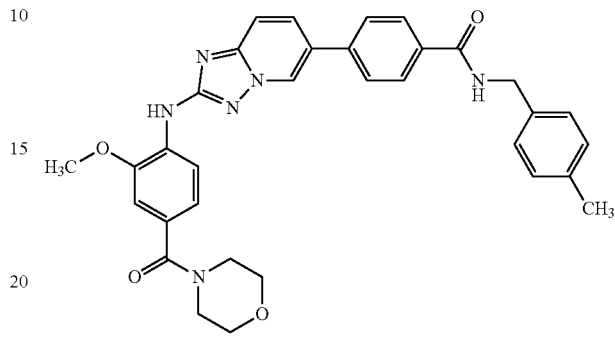

Starting with Int03.07 and Int09.01, Example 05.02 was prepared analogously to the procedure for the preparation of Example 02.15.

$^1$H-NMR (400 MHz, DMSO-$d_6$): δ [ppm]=2.28 (s, 3H), 3.47-3.68 (m, 8H), 3.92 (s, 3H), 4.46 (d, 2H), 7.03-7.11 (m, 2H), 7.12-7.17 (m, 2H), 7.20-7.27 (m, 2H), 7.70 (d, 1H), 7.87-7.96 (m, 2H), 7.99-8.06 (m, 3H), 8.30 (s, 1H), 8.34 (d, 1H), 9.08 (t, 1H), 9.27 (d, 1H).

Example 06.01

2-fluoro-N-(4-fluorobenzyl)-4-(2-{[2-methoxy-4-(morpholin-4-ylcarbonyl)phenyl]amino}[,2]-triazolo[1,5-a]pyridin-6-yl)benzamide

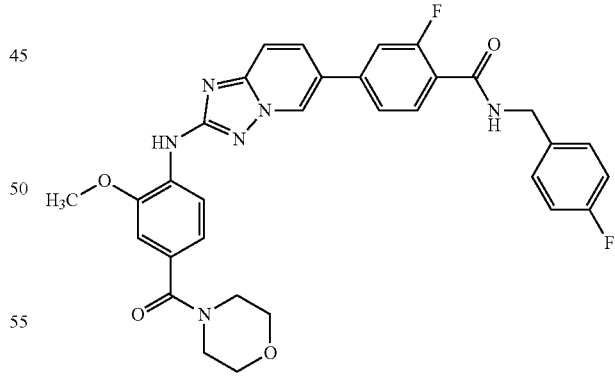

Starting with Int04.02 and Int09.01, Example 06.01 was prepared analogously to the procedure for the preparation of Example 02.16.

$^1$H-NMR (300 MHz, DMSO-$d_6$): δ [ppm]=3.50 (br. s., 4H), 3.58 (br. s., 4H), 3.88 (s, 3H), 4.44 (d, 2H), 6.99-7.06 (m, 2H), 7.14 (t, 2H), 7.36 (dd, 2H), 7.62-7.75 (m, 3H), 7.81 (d, 1H), 8.01 (dd, 1H), 8.23-8.38 (m, 2H), 8.84-8.96 (m, 1H), 9.31 (s, 1H).

Example 06.02

2-fluoro-N-(4-fluorobenzyl)-4-(2-{[2-methoxy-4-(morpholin-4-ylmethyl)phenyl]amino}[,2]-triazolo[1,5-a]pyridin-6-yl)benzamide

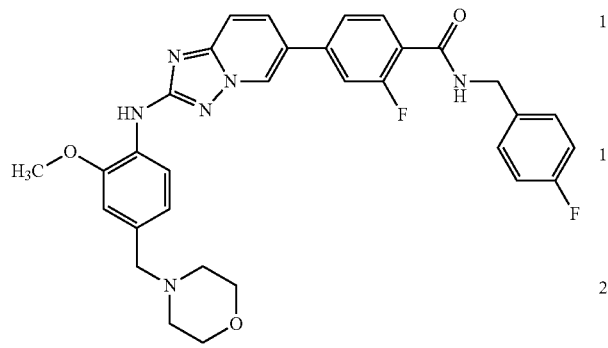

Starting with Int04.02 and Int18.02, Example 06.02 was prepared analogously to the procedure for the preparation of Example 02.12.

$^1$H-NMR (300 MHz, DMSO-$d_6$): δ [ppm]=2.32 (br. s., 4H), 3.39 (s, 2H), 3.50-3.61 (m, 4H), 3.84 (s, 3H), 4.44 (d, 2H), 6.86 (d, 1H), 6.93 (s, 1H), 7.09-7.20 (m, 2H), 7.35 (dd, 2H), 7.62 (d, 1H), 7.68-7.74 (m, 2H), 7.80 (d, 1H), 7.95-8.03 (m, 2H), 8.10 (d, 1H), 8.86-8.98 (m, 1H), 9.27 (s, 1H).

Example 07.01

N-(4-fluorobenzyl)-4-(2-{[2-methoxy-4-(morpholin-4-ylcarbonyl)phenyl]amino}[,2]-triazolo[1,5-a]pyridin-6-yl)-2-methylbenzamide

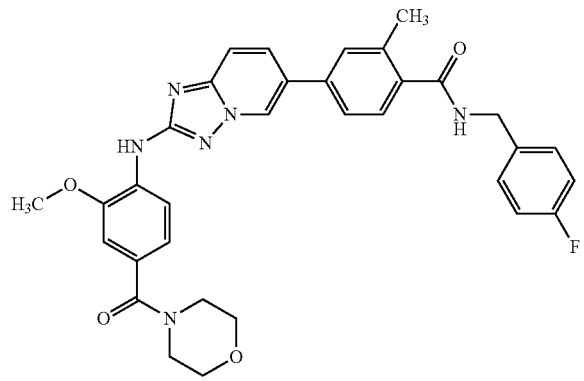 [SMILES: COc1cc(C(=O)N2CCOCC2)ccc1Nc1nc2ccc(-c3ccc(C(=O)NCc4ccc(F)cc4)c(C)c3)cn2n1]

Starting with Int05.02 and Int09.01, Example 07.01 was prepared analogously to the procedure for the preparation of Example 02.16.

$^1$H-NMR (300 MHz, DMSO-$d_6$): δ [ppm]=2.39 (s, 3H), 3.50 (br. s., 4H), 3.58 (br. s., 4H), 3.88 (s, 3H), 4.41 (d, 2H), 7.00-7.07 (m, 2H), 7.10-7.20 (m, 2H), 7.36 (dd, 2H), 7.44 (d, 1H), 7.61-7.74 (m, 3H), 7.95 (dd, 1H), 8.22-8.35 (m, 2H), 8.85 (t, 1H), 9.19 (s, 1H).

Example 07.02

N-(4-fluorobenzyl)-4-(2-{[2-methoxy-4-(2-oxo-1,3-oxazolidin-3-yl)phenyl]amino}[,2]-triazolo[1,5-a]pyridin-6-yl)-2-methylbenzamide

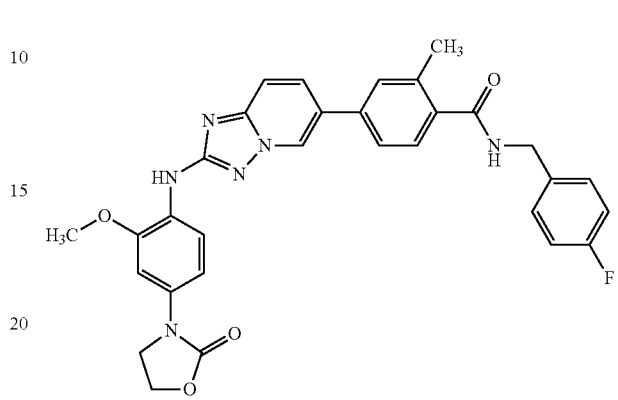

Starting with Int05.02 and Int26.01, Example 07.02 was prepared analogously to the procedure for the preparation of Example 02.16.

$^1$H-NMR (400 MHz, DMSO-$d_6$): δ [ppm]=2.39 (s, 3H), 3.85 (s, 3H), 4.05 (dd, 2H), 4.36-4.45 (m, 4H), 6.99 (dd, 1H), 7.11-7.18 (m, 2H), 7.33-7.40 (m, 3H), 7.44 (d, 1H), 7.58-7.65 (m, 2H), 7.68 (s, 1H), 7.92 (dd, 1H), 8.02 (s, 1H), 8.14 (d, 1H), 8.83 (t, 1H), 9.10-9.16 (m, 1H).

Example 08.01

2-chloro-N-(4-fluorobenzyl)-4-(2-{[2-methoxy-4-(morpholin-4-ylcarbonyl)phenyl]amino}[,2]-triazolo[1,5-a]pyridin-6-yl)benzamide

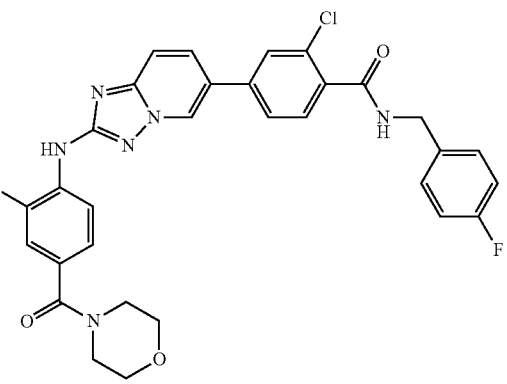

Starting with Int06.02 and Int09.01, Example 08.01 was prepared analogously to the procedure for the preparation of Example 02.16.

$^1$H-NMR (400 MHz, DMSO-$d_6$): δ [ppm]=3.50 (br. s., 4H), 3.56 (br. s, 4H), 3.88 (s, 3H), 4.42 (d, 2H), 6.98-7.08 (m, 2H), 7.16 (t, 2H), 7.38 (dd, 2H), 7.53 (d, 1H), 7.66 (d, 1H), 7.81 (dd, 1H), 7.93-8.03 (m, 2H), 8.24-8.35 (m, 2H), 9.02 (t, 1H), 9.29 (s, 1H).

Example 09.01

N-(4-fluorobenzyl)-2-methoxy-4-(2-{[2-methoxy-4-(morpholin-4-ylcarbonyl)phenyl]amino}[,2]-triazolo[1,5-a]pyridin-6-yl)benzamide

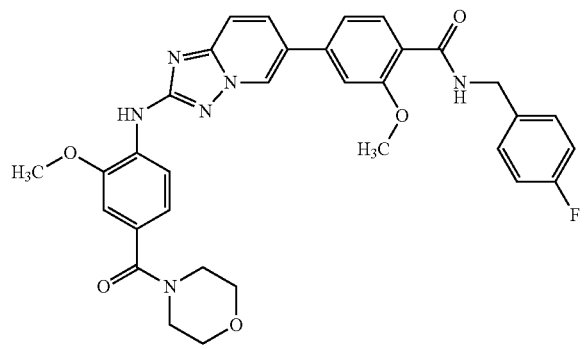 [SMILES: COc1cc(C(=O)N2CCOCC2)ccc1Nc1nc2ccc(-c3ccc(C(=O)NCc4ccc(F)cc4)c(OC)c3)cn2n1]

Starting with Int07.02 and Int09.01, Example 09.01 was prepared analogously to the procedure for the preparation of Example 02.16.

¹H-NMR (300 MHz, DMSO-$d_6$): δ [ppm]=3.50 (br. s., 4H), 3.58 (br. s., 4H), 3.89 (s, 3H), 4.00 (s, 3H), 4.47 (d, 2H), 7.00-7.07 (m, 2H), 7.08-7.19 (m, 2H), 7.35 (dd, 2H), 7.43 (dd, 1H), 7.50 (d, 1H), 7.67 (d, 1H), 7.82 (d, 1H), 8.02 (dd, 1H), 8.20-8.37 (m, 2H), 8.73 (t, 1H), 9.32 (s, 1H).

Example 10.01

N-[2-fluoro-4-(2-{[2-methoxy-4-(morpholin-4-ylcarbonyl)phenyl]amino}[,2]-triazolo[1,5-a]pyridin-6-yl)phenyl]-2-(4-fluorophenyl)acetamide

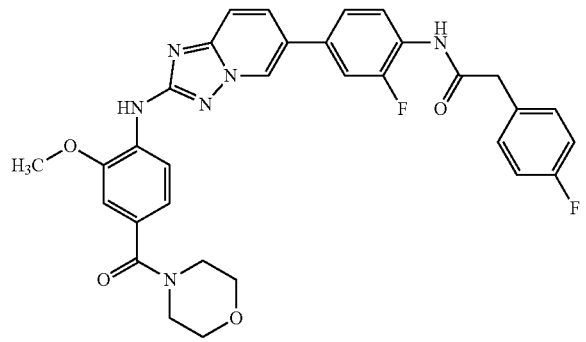 [SMILES: COc1cc(C(=O)N2CCOCC2)ccc1Nc1nc2ccc(-c3ccc(NC(=O)Cc4ccc(F)cc4)c(F)c3)cn2n1]

Starting with Int02.08 and Int09.01, Example 10.01 was prepared analogously to the procedure for the preparation of Example 02.16.

¹H-NMR (400 MHz, DMSO-$d_6$): δ [ppm]=3.50 (br. s., 4H), 3.58 (br. s., 4H), 3.73 (s, 2H), 3.88 (s, 3H), 7.01-7.06 (m, 2H), 7.09-7.17 (m, 2H), 7.35 (dd, 2H), 7.59 (dd, 1H), 7.64 (d, 1H), 7.76 (dd, 1H), 7.91-8.03 (m, 2H), 8.25-8.33 (m, 2H), 9.19 (d, 1H), 10.05 (s, 1H).

Example 11.01

2-(4-fluorophenyl)-N-[5-(2-{[2-methoxy-4-(morpholin-4-ylcarbonyl)phenyl]amino}[,2]triazolo[1,5-a]pyridin-6-yl)pyridin-2-yl]acetamide

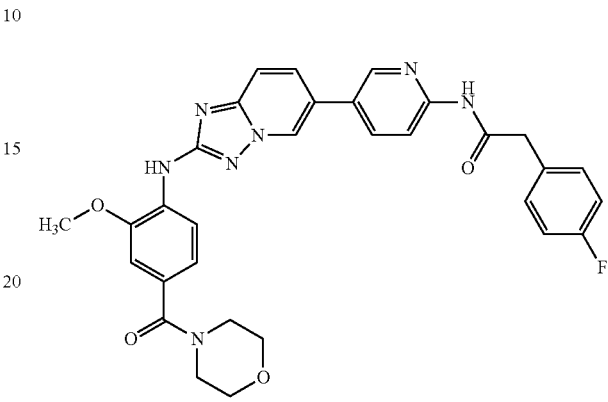

Starting with Int02.10 and Int09.01, Example 11.01 was prepared analogously to the procedure for the preparation of Example 02.16.

¹H-NMR (300 MHz, DMSO-$d_6$): δ [ppm]=3.49 (br. s., 4H), 3.57 (br. s., 4H), 3.71 (s, 2H), 3.88 (s, 3H), 6.98-7.05 (m, 2H), 7.08-7.18 (m, 2H), 7.29-7.42 (m, 2H), 7.66 (d, 1H), 7.90-8.01 (m, 1H), 8.07-8.22 (m, 2H), 8.24-8.34 (m, 2H), 8.75 (d, 1H), 9.22 (d, 1H), 10.86 (s, 1H).

Example 11.02

N-[5-(2-{[2-ethoxy-4-(morpholin-4-ylcarbonyl)phenyl]amino}[,2]triazolo[1,5-a]pyridin-6-yl)pyridin-2-yl]-2-(4-fluorophenyl)acetamide

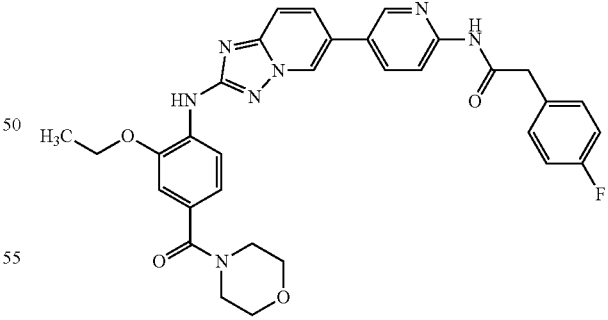

Starting with Int02.10 and Int10.03, Example 11.02 was prepared analogously to the procedure for the preparation of Example 02.16.

¹H-NMR (300 MHz, DMSO-$d_6$): δ [ppm]=1.40 (t, 3H), 3.49 (br. s., 4H), 3.57 (br. s., 4H), 3.72 (s, 2H), 4.14 (q, 2H), 6.99-7.05 (m, 2H), 7.08-7.17 (m, 2H), 7.30-7.40 (m, 2H), 7.66 (d, 1H), 7.97 (dd, 1H), 8.07-8.23 (m, 3H), 8.30 (d, 1H), 8.68-8.81 (m, 1H), 9.23 (s, 1H), 10.86 (s, 1H).

Example 12.01

N-(2,4-difluorobenzyl)-4-(2-{[2-methoxy-4-(2-oxo-1,3-oxazolidin-3-yl)phenyl]amino}[,2]triazolo[1,5-a]pyridin-6-yl)-2-methylbenzamide

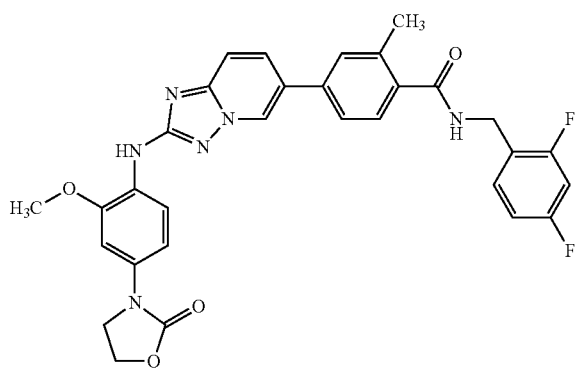 [SMILES: COc1cc(N2CCOC2=O)ccc1Nc1nc2ccc(-c3ccc(C(=O)NCc4ccc(F)cc4F)c(C)c3)cn2n1]

Starting with Int05.03 and Int26.01, Example 12.01 was prepared analogously to the procedure for the preparation of Example 02.16.

$^1$H-NMR (300 MHz, DMSO-d$_6$): δ [ppm]=2.38 (s, 3H), 3.85 (s, 3H), 3.98-4.10 (m, 2H), 4.34-4.49 (m, 4H), 6.98 (dd, 1H), 7.02-7.11 (m, 1H), 7.20 (ddd, 1H), 7.34-7.51 (m, 3H), 7.56-7.74 (m, 3H), 7.91 (dd, 1H), 8.01 (s, 1H), 8.13 (d, 1H), 8.81 (t, 1H), 9.13 (d, 1H).

Example 13.01

N-(4-fluorobenzyl)-5-(2-{[2-methoxy-4-(2-oxa-6-azaspiro[3.3]hept-6-ylcarbonyl)phenyl]amino}[,2]triazolo[1,5-a]pyridin-6-yl)pyridine-2-carboxamide

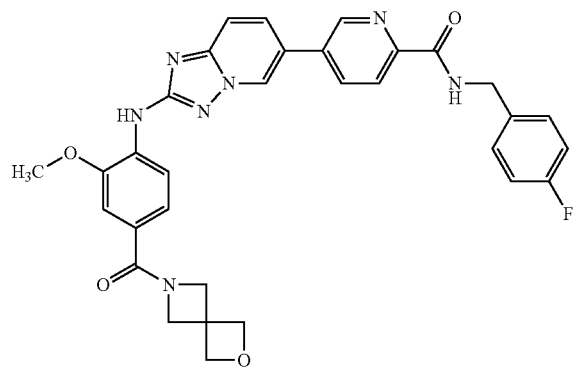 [SMILES: COc1cc(C(=O)N2CC3(COC3)C2)ccc1Nc1nc2ccc(-c3ccc(C(=O)NCc4ccc(F)cc4)nc3)cn2n1]

Starting with Int08.02 and Int09.06, Example 13.01 was prepared analogously to the procedure for the preparation of Example 02.16.

$^1$H-NMR (400 MHz, DMSO-d$_6$): δ [ppm]=3.90 (s, 3H), 4.17 (br. s., 2H), 4.47 (d, 2H), 4.51 (br. s., 2H), 4.66 (s, 4H), 7.08-7.15 (m, 2H), 7.22 (d, 1H), 7.25 (dd, 1H), 7.32-7.40 (m, 2H), 7.73 (d, 1H), 8.05 (dd, 1H), 8.10 (d, 1H), 8.32 (d, 1H), 8.36-8.42 (m, 2H), 9.07 (d, 1H), 9.33-9.45 (m, 2H).

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media.

For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science a Technology 1998, 52(5), 238-311; Strickley, R. G "Parenteral Formulations of Small Molecule Therapeutics Marketed in the United States (1999)—Part-1" PDA Journal of Pharmaceutical Science a Technology 1999, 53(6), 324-349; and Nema, S. et al., "Excipients and Their Use in Injectable Products" PDA Journal of Pharmaceutical Science a Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulfate, letrozole, leucovorin, leuprolide, leuprolide acetate, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, RDEA 119, rebif, rhenium-186 etidronate, rituximab, roferon-A, romurtide, salagen, sandostatin, sargramostim, semustine, sizofuran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib, avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

Optional anti-hyper-proliferative agents which can be added to the composition include but are not limited to compounds listed on the cancer chemotherapy drug regimens in the 11th Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-llinked lintuzumab, EM-1421, HyperAcute vaccine, tucotuzumab celmoleukin, galiximab, HPV-16-E7, Javelin-prostate cancer, Javelin-melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit Mps-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assay: Proliferation Assay

Cultivated tumor cells (MCF7, hormone dependent human mammary carcinoma cells, ATCC HTB22; NCI-H460, human non-small cell lung carcinoma cells, ATCC HTB-177; DU 145, hormone-independent human prostate carcinoma cells, ATCC HTB-81; HeLa-MaTu, human cervical carcinoma cells, EPO-GmbH, Berlin; HeLa-MaTu-ADR, multidrug-resistant human cervical carcinoma cells, EPO-GmbH, Berlin; HeLa human cervical tumor cells, ATCC CCL-2; B16F10 mouse melanoma cells, ATCC CRL-6475) were plated at a density of 5000 cells/well (MCF7, DU145, HeLa-MaTu-ADR), 3000 cells/well (NCI-H460, HeLa-MaTu, HeLa), or 1000 cells/well (B16F10) in a 96-well multititer plate in 200 µl of their respective growth medium supplemented 10% fetal calf serum. After 24 hours, the cells of one plate (zero-point plate) were stained with crystal violet (see below), while the medium of the other plates was replaced by fresh culture medium (200 µl), to which the test substances were added in various concentrations (0 µM, as well as in the range of 0.01-30 µM; the final concentration of the solvent dimethyl sulfoxide was 0.5%). The cells were incubated for 4 days in the presence of test substances. Cell proliferation was determined by staining the cells with crystal violet: the cells were fixed by adding 20 µl/measuring point of an 11% glutaric aldehyde solution for 15 minutes at room temperature. After three washing cycles of the fixed cells with water, the plates were dried at room temperature. The cells were stained by adding 100 µl/measuring point of a 0.1% crystal violet solution (pH 3.0). After three washing cycles of the stained cells with water, the plates were dried at room temperature. The dye was dissolved by adding 100 µl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 µm) cells (=100%). The IC50 values were determined by means of a 4 parameter fit using the company's own software.

Mps-1 Kinase Assay

The human kinase Mps-1 phosphorylates a biotinylated substrate peptide. Detection of the phosphorylated product is achieved by time-resolved fluorescence resonance energy transfer (TR-FRET) from Europium-labelled anti-phospho-Serine/Threonine antibody as donor to streptavidin labelled with cross-linked allophycocyanin (SA-XLent) as acceptor. Compounds are tested for their inhibition of the kinase activity.

N-terminally GST-tagged human full length recombinant Mps-1 kinase (purchased from Invitrogen, Karslruhe, Germany, cat. no PV4071) was used. As substrate for the kinase reaction a biotinylated peptide of the amino-acid sequence PWDPDDADITEILG (C-terminus in amide form, purchased from Biosynthan GmbH, Berlin) was used.

For the assay 50 nl of a 100-fold concentrated solution of the test compound in DMSO was pipetted into a black low volume 384 well microtiter plate (Greiner Bio-One, Frickenhausen, Germany), 2 µl of a solution of Mps-1 in assay buffer [0.1 mM sodium-ortho-vanadate, 10 mM MgCl$_2$, 2 mM DTT, 25 mM Hepes pH 7.7, 0.05% BSA, 0.001% Pluronic F-127] were added and the mixture was incubated for 15 min at 22° C. to allow pre-binding of the test compounds to Mps-1 before the start of the kinase reaction. Then the kinase reaction was started by the addition of 3 µl of a solution of 16.7 adenosine-tri-phosphate (ATP, 16.7 µM=>final conc. in the 5 µl assay volume is 10 µM) and peptide substrate (1.67 µM=>final conc. in the 5 µl assay volume is 1 µM) in assay buffer and the resulting mixture was incubated for a reaction time of 60 min at 22° C. The concentration of Mps-1 in the assay was adjusted to the activity of the enzyme lot and was chosen appropriate to have the assay in the linear range, typical enzyme concentrations were in the range of about 1 nM (final conc. in the 5 µl assay volume). The reaction was stopped by the addition of 3 µl of a solution of HTRF detection reagents (100 mM Hepes pH 7.4, 0.1% BSA, 40 mM EDTA, 140 nM Streptavidin-XLent [#61GSTXLB, Fa. Cis Biointernational, Marcoule, France], 1.5 nM anti-phospho(Ser/Thr)-Europium-antibody [#AD0180, PerkinElmer LAS, Rodgau-Jügesheim, Germany].

The resulting mixture was incubated 1 h at 22° C. to allow the binding of the phosphorylated peptide to the anti-phospho(Ser/Thr)-Europium-antibody. Subsequently the amount of phosphorylated substrate was evaluated by measurement of the resonance energy transfer from the Europium-labelled anti-phospho(Ser/Thr) antibody to the Streptavidin-XLent. Therefore, the fluorescence emissions at 620 nm and 665 nm after excitation at 350 nm was measured in a Viewlux TR-FRET reader (PerkinElmer LAS, Rodgau-Jügesheim, Germany). The "blank-corrected normalized ratio" (a Viewlux specific readout, similar to the traditional ratio of the emissions at 665 nm and at 622 nm, in which blank and Eu-donor crosstalk are subtracted from the 665 nm signal before the ratio is calculated) was taken as the measure for the amount of phosphorylated substrate. The data were normalised (enzyme reaction without inhibitor=0% inhibition, all other assay components but no enzyme=100% inhibition). Test compounds were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and IC$_{50}$ values were calculated by a 4 parameter fit using an inhouse software.

| Example Number | Mps-1 Inhibition, IC$_{50}$ in M |
| --- | --- |
| Example 01.01 | 5.56E−09 |
| Example 01.02 | ≤1.00E−09 |
| Example 01.03 | 6.02E−09 |
| Example 02.01 | ≤1.00E−09 |
| Example 02.02 | ≤1.00E−09 |
| Example 02.03 | 1.04E−09 |
| Example 02.04 | ≤1.00E−09 |
| Example 02.05 | ≤1.00E−09 |
| Example 02.06 | ≤1.00E−09 |
| Example 02.07 | ≤1.00E−09 |
| Example 02.08 | 1.05E−09 |
| Example 02.09 | ≤1.00E−09 |
| Example 02.10 | ≤1.00E−09 |
| Example 02.11 | ≤1.00E−09 |
| Example 02.12 | ≤1.00E−09 |
| Example 02.13 | ≤1.00E−09 |
| Example 02.14 | ≤1.00E−09 |
| Example 02.15 | ≤1.00E−09 |
| Example 02.16 | ≤1.00E−09 |
| Example 02.17 | ≤1.00E−09 |
| Example 02.18 | ≤1.00E−09 |
| Example 02.19 | ≤1.00E−09 |
| Example 02.20 | ≤1.00E−09 |
| Example 02.21 | ≤1.00E−09 |
| Example 02.22 | ≤1.00E−09 |
| Example 02.23 | ≤1.00E−09 |
| Example 02.24 | ≤1.00E−09 |
| Example 02.25 | ≤1.00E−09 |
| Example 02.26 | ≤1.00E−09 |
| Example 02.27 | ≤1.00E−09 |
| Example 02.28 | ≤1.00E−09 |
| Example 02.29 | ≤1.00E−09 |
| Example 02.30 | ≤1.00E−09 |
| Example 02.31 | ≤1.00E−09 |
| Example 02.32 | ≤1.00E−09 |
| Example 02.33 | ≤1.00E−09 |
| Example 02.34 | ≤1.00E−09 |
| Example 02.35 | ≤1.00E−09 |
| Example 02.36 | ≤1.00E−09 |
| Example 02.37 | ≤1.00E−09 |
| Example 02.38 | ≤1.00E−09 |
| Example 02.39 | ≤1.00E−09 |
| Example 02.40 | ≤1.00E−09 |
| Example 02.41 | ≤1.00E−09 |
| Example 02.42 | ≤1.00E−09 |
| Example 02.43 | ≤1.00E−09 |
| Example 02.44 | ≤1.00E−09 |
| Example 02.45 | ≤1.00E−09 |
| Example 02.46 | ≤1.00E−09 |
| Example 03.01 | 2.71E−09 |
| Example 03.02 | ≤1.00E−09 |
| Example 03.03 | 5.51E−09 |
| Example 03.04 | ≤1.00E−09 |
| Example 03.05 | 6.33E−09 |
| Example 03.06 | ≤1.00E−09 |
| Example 03.07 | ≤1.00E−09 |
| Example 04.01 | ≤1.00E−09 |
| Example 04.02 | ≤1.00E−09 |
| Example 04.03 | ≤1.00E−09 |
| Example 04.04 | ≤1.00E−09 |
| Example 04.05 | ≤1.00E−09 |
| Example 04.06 | ≤1.00E−09 |
| Example 04.07 | ≤1.00E−09 |
| Example 04.08 | ≤1.00E−09 |
| Example 04.09 | ≤1.00E−09 |
| Example 04.10 | ≤1.00E−09 |
| Example 04.11 | ≤1.00E−09 |
| Example 04.12 | ≤1.00E−09 |
| Example 04.13 | ≤1.00E−09 |
| Example 04.14 | ≤1.00E−09 |
| Example 04.15 | ≤1.00E−09 |
| Example 04.16 | ≤1.00E−09 |
| Example 04.17 | ≤1.00E−09 |
| Example 04.18 | ≤1.00E−09 |
| Example 04.19 | ≤1.00E−09 |
| Example 04.20 | ≤1.00E−09 |
| Example 04.21 | ≤1.00E−09 |
| Example 04.22 | ≤1.00E−09 |
| Example 04.23 | ≤1.00E−09 |
| Example 04.24 | ≤1.00E−09 |
| Example 04.25 | ≤1.00E−09 |
| Example 04.26 | ≤1.00E−09 |
| Example 04.27 | ≤1.00E−09 |
| Example 04.28 | ≤1.00E−09 |
| Example 04.29 | ≤1.00E−09 |
| Example 04.30 | ≤1.00E−09 |
| Example 04.31 | ≤1.00E−09 |
| Example 04.32 | ≤1.00E−09 |
| Example 04.33 | ≤1.00E−09 |
| Example 04.34 | ≤1.00E−09 |
| Example 04.35 | ≤1.00E−09 |
| Example 04.36 | ≤1.00E−09 |
| Example 05.01 | ≤1.00E−09 |
| Example 05.02 | ≤1.00E−09 |
| Example 06.01 | ≤1.00E−09 |
| Example 06.02 | ≤1.00E−09 |

-continued

| Example Number | Mps-1 Inhibition, IC$_{50}$ in M |
|---|---|
| Example 07.01 | ≤1.00E−09 |
| Example 07.02 | 1.1E−09 |
| Example 08.01 | ≤1.00E−09 |
| Example 09.01 | ≤1.00E−09 |
| Example 10.01 | ≤1.00E−09 |
| Example 11.01 | 1.62E−09 |
| Example 11.02 | ≤1.00E−09 |
| Example 12.01 | ≤1.00E−09 |
| Example 13.01 | ≤1.00E−09 |

Spindle Assembly Checkpoint Assay

The spindle assembly checkpoint assures the proper segregation of chromosomes during mitosis. Upon entry into mitosis, chromosomes begin to condensate which is accompanied by the phosphorylation of histone H3 on serine 10. Dephosphorylation of histone H3 on serine 10 begins in anaphase and ends at early telophase. Accordingly, phosphorylation of histone H3 on serine 10 can be utilized as a marker of cells in mitosis. Nocodazole is a microtubule destabilizing substance. Thus, nocodazole interferes with microtubule dynamics and mobilises the spindle assembly checkpoint. The cells arrest in mitosis at G2/M transition and exhibit phosphorylated histone H3 on serine 10. An inhibition of the spindle assembly checkpoint by Mps-1 inhibitors overrides the mitotic blockage in the presence of nocodazole, and the cells complete mitosis prematurely. This alteration is detected by the decrease of cells with phosphorylation of histone H3 on serine 10. This decline is used as a marker to determine the capability of compounds of the present invention to induce a mitotic breakthrough.

Cultivated cells of the human cervical tumor cell line HeLa (ATCC CCL-2) were plated at a density of 2500 cells/well in a 384-well microtiter plate in 20 μl Dulbeco's Medium (w/o phenol red, w/o sodium pyruvate, w 1000 mg/ml glucose, w pyridoxine) supplemented with 1% (v/v) glutamine, 1% (v/v) penicillin, 1% (v/v) streptomycin and 10% (v/v) fetal calf serum. After incubation overnight at 37° C., 10 μl/well nocodazole at a final concentration of 0.1 μg/ml were added to cells. After 24 h incubation, cells were arrested at G2/M phase of the cell cycle progression. Test compounds solubilised in dimethyl sulfoxide (DMSO) were added at various concentrations (0 μM, as well as in the range of 0.005 μM-10 μM; the final concentration of the solvent DMSO was 0.5% (v/v)). Cells were incubated for 4 h at 37° C. in the presence of test compounds. Thereafter, cells were fixed in 4% (v/v) paraformaldehyde in phosphate buffered saline (PBS) at 4° C. overnight then permeabilised in 0.1% (v/v) Triton X™ 100 in PBS at room temperature for 20 min and blocked in 0.5% (v/v) bovine serum albumin (BSA) in PBS at room temperature for 15 min. After washing with PBS, 20 μl/well antibody solution (anti-phospho-histone H3 clone 3H10, FITC; Upstate, Cat#16-222; 1:200 dilution) was added to cells, which were incubated for 2 h at room temperature. Afterwards, cells were washed with PBS and 20 μl/well HOECHST 33342 dye solution (5 μg/ml) was added to cells and cells were incubated 12 min at room temperature in the dark. Cells were washed twice with PBS then covered with PBS and stored at 4° C. until analysis. Images were acquired with a Perkin Elmer OPERA™ High-Content Analysis reader. Images were analyzed with image analysis software MetaXpress™ from Molecular devices utilizing the Cell Cycle application module. In this assay both labels HOECHST 33342 and phosphorylated Histone H3 on serine 10 were measured. HOECHST 33342 labels DNA and is used to count cell number. The staining of phosphorylated Histone H3 on serine 10 determines the number of mitotic cells. Inhibition of Mps-1 decreases the number of mitotic cells in the presence of nocodazole indicating an inappropriate mitotic progression. The raw assay data were further analysed by four parameter logistic regression analysis to determine the IC$_{50}$ value for each tested compound.

It will be apparent to persons skilled in the art that assays for other Mps kinases may be performed in analogy using the appropriate reagents.

Thus the compounds of the present invention effectively inhibit one or more Mps-1 kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The invention claimed is:
1. A compound of general formula (I):

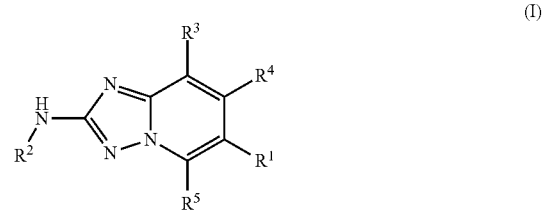

in which:
R$^1$ represents an aryl or heteroaryl group
which is substituted, one or more times, identically or differently, with a substituent selected from:
R$^6$—(C$_1$-C$_6$-alkyl)-,   R$^6$—(CH$_2$)$_n$(CHOH)(CH$_2$)$_m$—, R$^6$—(C$_1$-C$_6$-alkoxy)-,   R$^6$—(CH$_2$)$_n$(CHOH)(CH$_2$)$_p$—O—,   R$^6$—(C$_1$-C$_6$-alkoxy-C$_1$-C$_6$-alkyl)-, R$^6$—(C$_1$-C$_6$-alkoxy-C$_1$-C$_6$-alkyl)-O—,   R$^6$—O—, —C(=O)R$^6$,   —C(=O)O—R$^6$,   —OC(=O)—R$^6$, —N(H)C(=O)R$^6$,   —N(R$^7$)C(=O)R$^6$,   —N(H)C(=O)NR$^6$R$^7$,   —N(R$^7$)C(=O)NR$^6$R$^7$,   —NR$^6$R$^7$, —C(=O)N(H)R$^6$,   —C(=O)NR$^6$R$^7$,   R$^6$—S—, R$^6$—S(=O)—,   R$^6$—S(=O)$_2$—,   —N(H)S(=O)R$^6$, —N(R$^7$)S(=O)R$^6$,   —S(=O)N(H)R$^6$,   —S(=O)NR$^6$R$^7$,   —N(H)S(=O)$_2$R$^6$,   —N(R$^7$)S(=O)$_2$R$^6$, —S(=O)$_2$N(H)R$^6$,   —S(=O)$_2$NR$^6$R$^7$,   —S(=O)(=NR$^6$)R$^7$,   —S(=O)(=NR$^7$)R$^6$,   —N=S(=O)(R$^6$)R$^7$;
and which is optionally substituted, one or more times, identically or differently, with a substituent $R^{xy}$ selected from:

halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)$NR^8R^7$, —N($R^7$)C(=O)$NR^8R^7$, —$NR^8R^7$, —C(=O)N(H)$R^8$, —C(=O)$NR^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)$NR^8R^7$, —N(H)S(=O)$_2R^8$, —N($R^7$)S(=O)$_2R^8$, —S(=O)$_2$N(H)$R^8$, —S(=O)$_2NR^8R^7$, —S(=O)(=$NR^8$)$R^7$, —S(=O)(=$NR^7$)$R^8$, —N=S(=O)($R^8$)$R^7$;

$R^2$ represents an aryl group or heteroaryl group
which is substituted, one or more times, identically or differently, with a substituent selected from:
$R^9$—, $R^9$—($C_1$-$C_6$-alkyl)-, $R^9$—$(CH_2)_n(CHOH)(CH_2)_m$—, $R^9$—($C_1$-$C_6$-alkoxy)-, $R^9$—$(CH_2)_n(CHOH)(CH_2)_p$—O—, $R^9$—($C_1$-$C_6$-alkoxy-$C_1$-$C_6$-alkyl)-, $R^9$—($C_1$-$C_6$-alkoxy-$C_1$-$C_6$-alkyl)-O—, —O—$(CH_2)_n$—C(=O)$NR^9R^7$, $R^9$—O—, —C(=O)$R^9$, —C(=O)O—$R^9$, —OC(=O)—$R^9$, —N(H)C(=O)$R^9$, —N($R^7$)C(=O)$R^9$, —N(H)C(=O)$NR^9R^7$, —N($R^7$)C(=O)$NR^9R^7$, —$NR^9R^7$, —C(=O)N(H)$R^9$, —C(=O)$NR^9R^7$, $R^9$—S—, $R^9$—S(=O)—, $R^9$—S(=O)$_2$—, —N(H)S(=O)$R^9$, —N($R^7$)S(=O)$R^9$, —S(=O)N(H)$R^9$, —S(=O)$NR^9R^7$, —N(H)S(=O)$_2R^9$, —N($R^7$)S(=O)$_2R^9$, —S(=O)$_2$N(H)$R^9$, —S(=O)$_2NR^9R^7$, —S(=O)(=$NR^9$)$R^7$, —S(=O)(=$NR^7$)$R^9$, —N=S(=O)($R^9$)$R^7$;

and which is optionally substituted, one or more times, identically or differently, with a substituent selected from:

halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n(CHOH)(CH_2)^m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, —O—$(CH_2)_n$—C(=O)$NR^8R$, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)$NR^8R^7$, —N($R^7$)C(=O)$NR^8R^7$, —$NR^8R^7$, —C(=O)N(H)$R^8$, —C(=O)$NR^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)$NR^8R^7$, —N(H)S(=O)$_2R^8$, —N($R^7$)S(=O)$_2R^8$, —S(=O)$_2$N(H)$R^8$, —S(=O)$_2NR^8R^7$, —S(=O)(=$NR^8$)$R^7$, —S(=O)(=$NR^7$)$R^8$, —N=S(=O)($R^8$)$R^7$;

$R^3$ represents a hydrogen atom, a halogen atom, a hydroxy-, amino, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or halo-$C_3$-$C_6$-cycloalkyl-group;

$R^4$ represents a hydrogen atom, a halogen atom, a hydroxy-, amino, cyano-, nitro-, $C_1$-$C_4$-alkyl-, halo-$C_1$-$C_4$-alkyl-, $C_1$-$C_4$-alkoxy-, halo-$C_1$-$C_4$-alkoxy-, hydroxy-$C_1$-$C_4$-alkyl, $C_1$-$C_4$-alkoxy-$C_1$-$C_4$-alkyl-, halo-$C_1$-$C_4$-alkoxy-$C_1$-$C_4$-alkyl-, $C_2$-$C_6$-alkenyl-, $C_2$-$C_6$-alkynyl-, halo-$C_2$-$C_6$-alkenyl-, halo-$C_2$-$C_6$-alkynyl-, $C_3$-$C_6$-cycloalkyl-, or halo-$C_3$-$C_6$-cycloalkyl-group;

$R^5$ represents a hydrogen atom;

$R^6$ represents a group selected from:
$C_3$-$C_6$-cycloalkyl-, 3- to 10-membered heterocycloalkyl-, aryl-, heteroaryl-, —$(CH_2)_q$—($C_3$-$C_6$-cycloalkyl), —$(CH_2)_q$-(3- to 10-membered heterocycloalkyl), —$(CH_2)_q$-aryl, or —$(CH_2)_q$-heteroaryl;

said group being optionally substituted, one or more times, identically or differently, with a substituent selected from:

halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^8$—($C_1$-$C_6$-alkyl)-, $R^8$—$(CH_2)_n(CHOH)(CH_2)_m$—, $R^8$—($C_1$-$C_6$-alkoxy)-, $R^8$—$(CH_2)_n(CHOH)(CH_2)_p$—O—, $R^8$—($C_1$-$C_6$-alkoxy-$C_1$-$C_6$-alkyl)-, $R^8$—($C_1$-$C_6$-alkoxy-$C_1$-$C_6$-alkyl)-O—, aryl-, $R^8$—O—, —C(=O)$R^8$, —C(=O)O—$R^8$, —OC(=O)—$R^8$, —N(H)C(=O)$R^8$, —N($R^7$)C(=O)$R^8$, —N(H)C(=O)$NR^8R^7$, —N($R^7$)C(=O)$NR^8R^7$, —$NR^8R^7$, —C(=O)N(H)$R^8$, —C(=O)$NR^8R^7$, $R^8$—S—, $R^8$—S(=O)—, $R^8$—S(=O)$_2$—, —N(H)S(=O)$R^8$, —N($R^7$)S(=O)$R^8$, —S(=O)N(H)$R^8$, —S(=O)NR8R7, —N(H)S(=O)$_2R^8$, —N($R^7$)S(=O)$_2R^8$, —S(=O)$_2$N(H)$R^8$, —S(=O)$_2NR^8R^7$, —S(=O)(=$NR^8$)$R^7$, —S(=O)(=$NR^7$)$R^8$, —N=S(=O)($R^8$)$R^7$;

$R^7$ represents a hydrogen atom, a $C_1$-$C_6$-alkyl-, or $C_3$-$C_6$-cycloalkyl-group;

or $R^6$ and $R^7$,
together with the nitrogen atom to which they are attached,
represent a 3- to 10-membered heterocycloalkyl-group,
which is optionally substituted, one or more times, identically or differently, with halogen, hydroxy, cyano-, nitro-, $C_1$-$C_6$-alkyl-,
halo-$C_1$-$C_6$-alkyl-, $C_1$-$C_6$-alkoxy-, halo-$C_1$-$C_6$-alkoxy-,
hydroxy-$C_1$-$C_6$-alkyl-, $C_1$-$C_6$-alkoxy-$C_1$-$C_6$-alkyl-,
halo-$C_1$-$C_6$-alkoxy-$C_1$-$C_6$-alkyl-, $C_2$-$C_6$-alkenyl-, $C_2$-$C_6$-alkynyl- or $C_3$-$C_6$-cycloalkyl-;

$R^8$ represents a hydrogen atom or a $C_1$-$C_6$-alkyl-group;

$R^9$ represents a group selected from:
$C_7$-$C_{10}$-cycloalkyl-, 3- to 10-membered heterocycloalkyl-, aryl-, heteroaryl-;

said group being optionally substituted, one or more times, identically or differently, with a substituent selected from:

halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, —$(CH_2)_q$—($C_3$-$C_6$-cycloalkyl), $R^8$—$(CH_2)_n(CHOH)(CH_2)_m$—, $R^8$—($C_1$-$C_6$-alkoxy)-, $R^8$—

$(CH_2)_n(CHOH)(CH_2)_p$—O—, $R^8$—$(C_1$-$C_6$-alkoxy-$C_1$-$C_6$-alkyl)-, $R^8$—$(C_1$-$C_6$-alkoxy-$C_1$-$C_6$-alkyl)-O—, aryl-, $R^8$—O—, —$C(=O)R^8$, —$C(=O)O$—$R^8$, —$OC(=O)$—$R^8$, —$N(H)C(=O)R^8$, —$N(R^7)C(=O)R^8$, —$N(H)C(=O)NR^8R^7$, —$N(R^7)C(=O)NR^8R^7$, —$NR^8R^7$, —$C(=O)N(H)R^8$, —$C(=O)NR^8R^7$, $R^8$—S—, $R^8$—$S(=O)$—, $R^8$—$S(=O)_2$—, —$N(H)S(=O)R^8$, —$N(R^7)S(=O)R^8$, —$S(=O)N(H)R^8$, —$S(=O)NR^8R^7$, —$N(H)S(=O)_2R^8$, —$N(R^7)S(=O)_2R^8$, —$S(=O)_2N(H)R^8$, —$S(=O)_2NR^8R^7$, —$S(=O)(=NR^8)R^7$, —$S(=O)(=NR^7)R^8$, —$N=S(=O)(R^8)R^7$;

or $R^9$ and $R^7$,
together with the nitrogen atom to which they are attached,
represent a 3- to 10-memberered heterocycloalkyl-group,
which is optionally substituted, one or more times, identically or differently, with halogen, hydroxy, cyano-, nitro-, $C_1$-$C_6$-alkyl-,
halo-$C_1$-$C_6$-alkyl-, $C_1$-$C_6$-alkoxy-, halo-$C_1$-$C_6$-alkoxy-,
hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-,
—$C(=O)O$—$R^8$ or $C_3$-$C_6$-cycloalkyl-;

n, m, p
represent, independently from each other, an integer of 0, 1, 2, 3, 4, or 5;

q represents an integer of 0, 1, 2 or 3;

or a stereoisomer, a tautomer, an N-oxide, a hydrate, a solvate, or a salt thereof, or a mixture of same.

2. The compound according to claim 1, wherein:
$R^1$ represents an aryl or heteroaryl group
which is substituted, one or more times, identically or differently, with a substituent selected from:
$R^6$—$(CH_2)_n(CHOH)(CH_2)_m$—, $R^6$—$(C_1$-$C_6$-alkoxy)-, $R^6$—$(CH_2)_n(CHOH)(CH_2)_p$—O—, $R^6$—$(C_1$-$C_6$-alkoxy-$C_1$-$C_6$-alkyl)-, $R^6$—$(C_1$-$C_6$-alkoxy-$C_1$-$C_6$-alkyl)-O—, $R^6$—O—, —$C(=O)R^6$, —$C(=O)O$—$R^6$, —$OC(=O)$—$R^6$, —$N(H)C(=O)R^6$, —$N(R^7)C(=O)R^6$, —$N(H)C(=O)NR^6R^7$, —$N(R^7)C(=O)NR^6R^7$, —$NR^6R^7$, —$C(=O)N(H)R^6$, —$C(=O)NR^6R^7$, $R^6$—S—, $R^6$—$S(=O)$—, $R^6$—$S(=O)_2$—, —$N(H)S(=O)R^6$, —$N(R^7)S(=O)R^6$, —$S(=O)N(H)R^6$, —$S(=O)NR^6R^7$, —$N(H)S(=O)_2R^6$, —$N(R^7)S(=O)_2R^6$, —$S(=O)_2N(H)R^6$, —$S(=O)_2NR^6R^7$, —$S(=O)(=NR^6)R^7$, —$S(=O)(=NR^7)R^6$, —$N=S(=O)(R^6)R^7$;

and
which is optionally substituted, one or more times, identically or differently, with a substituent $R^{xy}$ selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —$N(H)C(=O)R^8$, —$N(R^7)C(=O)R^8$, —$C(=O)N(H)R^8$, —$C(=O)NR^8R^7$;

or a stereoisomer, a tautomer, an N-oxide, a hydrate, a solvate, or a salt thereof, or a mixture of same.

3. The compound according to claim 1, wherein:
$R^2$ represents an aryl group or heteroaryl group
which is substituted, one or more times, identically or differently, with a substituent selected from:
$R^9$—, $R^9$—$(C_1$-$C_6$-alkyl)-, $R^9$—$(C_1$-$C_6$-alkoxy)-, $R^9$—O—, —$C(=O)R^9$, —$N(H)C(=O)R^9$, —$N(R^7)C(=O)R^9$, —$N(H)C(=O)NR^9R^7$, —$N(R^7)C(=O)NR^9R^7$, —$NR^9R^7$, —$C(=O)N(H)R^9$, —$C(=O)NR^9R^7$, $R^9$—$S(=O)$—, $R^9$—$S(=O)_2$—, —$N(H)S(=O)_2R^9$, $N(R^7)S(=O)_2R^9$, —$S(=O)_2N(H)R^9$, —$S(=O)_2NR^9R^7$, —$S(=O)(=NR^9)R^7$, —$S(=O)(=NR^7)R^9$;

and
which is optionally substituted, one or more times, identically or differently, with a substituent selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, —$C(=O)R^8$, —$C(=O)O$—$R^8$, —$OC(=O)$—$R^8$, —$N(H)C(=O)R^8$, —$N(R^7)C(=O)R^8$, —$N(H)C(=O)NR^8R^7$, —$N(R^7)C(=O)NR^8R^7$, —$NR^8R^7$, —$C(=O)N(H)R^8$, —$C(=O)NR^8R^7$, $R^8$—S—, $R^8$—$S(=O)$—, $R^8$—$S(=O)_2$—, —$N(R^7)S(=O)_2R^8$, —$S(=O)_2N(H)R^8$, —$S(=O)_2NR^8R^7$, —$S(=O)(=NR^8)R^7$, —$S(=O)(=NR^7)R^8$;

or a stereoisomer, a tautomer, an N-oxide, a hydrate, a solvate, or a salt thereof, or a mixture of same.

4. The compound according to claim 1, wherein:
$R^3$ represents a hydrogen atom, a halogen atom, a hydroxy-, amino, cyano-, $C_1$-$C_4$-alkyl-, hydroxy-$C_1$-$C_4$-alkyl or $C_2$-$C_6$-alkynyl-group;

$R^4$ represents a hydrogen atom, a halogen atom, a hydroxy-, amino, cyano-, $C_1$-$C_4$-alkyl-, hydroxy-$C_1$-$C_4$-alkyl or $C_2$-$C_6$-alkynyl-group;

$R^6$ represents a group selected from:
—$(CH_2)_q$—$(C_3$-$C_6$-cycloalkyl),
—$(CH_2)_q$-(3- to 10-membered heterocycloalkyl),
—$(CH_2)_q$-aryl, or
—$(CH_2)_q$-heteroaryl;
said group being optionally substituted, one or more times, identically or differently, with a substituent selected from:
halo-, $C_1$-$C_6$-alkyl-, halo-$C_1$-$C_6$-alkyl-, $C_1$-$C_6$-alkoxy-, halo-$C_1$-$C_6$-alkoxyor a stereoisomer, a tautomer, an N-oxide, a hydrate, a solvate, or a salt thereof, or a mixture of same.

5. The compound according to claim 1, wherein:
$R^1$ represents an aryl group
which is substituted, one or more times, identically or differently, with a substituent selected from:
—$C(=O)R^6$, —$C(=O)O$—$R^6$, —$OC(=O)$—$R^6$, —$N(H)C(=O)R^6$, —$C(=O)N(H)R^6$, —$C(=O)NR^6R^7$, $R^6$—$S(=O)$—, $R^6$—$S(=O)_2$—, —$N(H)S(=O)_2R^6$, —$S(=O)_2N(H)R^6$, —$S(=O)(=NR^6)R^7$, —$S(=O)(=NR^7)R^6$;

and
which is optionally substituted, one or more times, identically or differently, with a substituent $R^{xy}$ selected from:
halo-, hydroxyl-, cyano-, $C_1$-$C_6$-alkyl-, $C_1$-$C_6$-alkoxy-, hydroxy-$C_1$-$C_6$-alkyl-, —$N(H)C(=O)R^8$, —$N(R^7)C(=O)R^8$, —$C(=O)N(H)R^8$, —$C(=O)NR^8R^7$;

$R^2$ represents an aryl group or heteroaryl group
which is substituted, one or more times, identically or differently, with a substituent selected from:
$R^9$—, $R^9$—$(C_1$-$C_6$-alkyl)-, $R^9$—$(C_1$-$C_6$-alkoxy)-, —$C(=O)R^9$, —$N(H)C(=O)R^9$, —$N(R^7)C(=O)R^9$, —$N(H)C(=O)NR^9R^7$, —$N(R^7)C(=O)NR^9R^7$, —$NR^9R^7$, —$C(=O)N(H)R^9$, —$C(=O)NR^9R^7$, $R^9$—$S(=O)$—, $R^9$—$S(=O)_2$—, —$N(H)S(=O)_2R^9$, —$N(R^7)S(=O)_2R^9$, —$S(=O)_2N(H)R^9$, —$S(=O)_2NR^9R^7$, —$S(=O)(=NR^9)R^7$, —$S(=O)(=NR^7)R^9$;

and
which is optionally substituted, one or more times, identically or differently, with a substituent selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, —C(=O)$R^8$, —C(=O)O—$R^8$, —OC(=O)—$R^8$, —N(H)C(=O)$R^8$, —N($R^7$)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S(=O)—, $R^8$—S(=O)$_2$—, —N($R^7$)S(=O)$_2R^8$, —S(=O)$_2$N(H)$R^8$, —S(=O)$_2$N$R^8R^7$, —S(=O)(=N$R^8$)$R^7$, —S(=O)(=N$R^7$)$R^8$;

$R^3$ represents a hydrogen atom, a halogen atom, a hydroxy-, amino, cyano-, $C_1$-$C_4$-alkyl-, hydroxy-$C_1$-$C_4$-alkyl or $C_2$-$C_6$-alkynyl-group;

$R^4$ represents a hydrogen atom, a halogen atom, a hydroxy-, amino, cyano-, $C_1$-$C_4$-alkyl-, hydroxy-$C_1$-$C_4$-alkyl or $C_2$-$C_6$-alkynyl-group;

$R^5$ represents a hydrogen atom;

$R^6$ represents a group selected from:
$C_3$-$C_6$-cycloalkyl-, —(CH$_2$)$_q$—($C_3$-$C_6$-cycloalkyl), —(CH$_2$)$_q$-(3- to 10-membered heterocycloalkyl), —(CH$_2$)$_q$-aryl, or —(CH$_2$)$_q$-heteroaryl;
said group being optionally substituted, one or more times, identically or differently, with a substituent selected from:
halo-, $C_1$-$C_6$-alkyl-, halo-$C_1$-$C_6$-alkyl-, $C_1$-$C_6$-alkoxy-, halo-$C_1$-$C_6$-alkoxy-;

$R^7$ represents a hydrogen atom or a $C_1$-$C_6$-alkyl-group;
or
$R^6$ and $R^7$,
together with the nitrogen atom to which they are attached,
represent a 3- to 10-membered heterocycloalkyl-group, which is optionally substituted, one or more times, identically or differently, with halogen, hydroxy, cyano-, $C_1$-$C_6$-alkyl-, halo-$C_1$-$C_6$-alkyl-, $C_1$-$C_6$-alkoxy-, halo-$C_1$-$C_6$-alkoxy- or $C_3$-$C_6$-cycloalkyl-;

$R^8$ represents a hydrogen atom or a $C_1$-$C_6$-alkyl-group;

$R^9$ represents a group selected from:
$C_7$-$C_{10}$-cycloalkyl-, 3- to 10-membered heterocycloalkyl-, heteroaryl-;
said group being optionally substituted, one or more times, identically or differently, with a substituent selected from:
halo-, hydroxyl-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —(CH$_2$)$_q$—($C_3$-$C_6$-cycloalkyl), —C(=O)$R^8$, —C(=O)O—$R^8$, —N(H)C(=O)$R^8$, —N(H)C(=O)N$R^8R^7$, —N($R^7$)C(=O)N$R^8R^7$, —N$R^8R^7$, —C(=O)N(H)$R^8$, —C(=O)N$R^8R^7$, $R^8$—S(=O)— or $R^8$—S(=O)$_2$—;
or
$R^9$ and $R^7$,
together with the nitrogen atom to which they are attached,
represent a 3- to 10-membered heterocycloalkyl-group, which is optionally substituted, one or more times, identically or differently, with halogen, hydroxy, cyano-, $C_1$-$C_6$-alkyl-, halo-$C_1$-$C_6$-alkyl-, $C_1$-$C_6$-alkoxy-, halo-$C_1$-$C_6$-alkoxy-, —C(=O)O—$R^8$ or $C_3$-$C_6$-cycloalkyl;

q represents an integer of 0, 1, 2 or 3;

or a stereoisomer, a tautomer, an N-oxide, a hydrate, a solvate, or a salt thereof, or a mixture of same.

6. The compound according to claim 1, wherein:
$R^1$ represents a phenyl group
which is substituted, one or more times, identically or differently, with a substituent selected from:
—N(H)C(=O)$R^6$ or —C(=O)N(H)$R^6$;
and
which is optionally substituted, one time with a substituent $R^{xy}$ selected from:
halo-, cyano-, $C_1$-$C_6$-alkyl-, $C_1$-$C_6$-alkoxy-;

$R^2$ represents a phenyl or pyridyl group
which is substituted, one or more times, identically or differently, with a substituent selected from:
$R^9$—, —C(=O)$R^9$, —N(H)C(=O)$R^9$, —N($R^7$)C(=O)$R^9$, —N(H)C(=O)N$R^9R^7$, —N($R^7$)C(=O)N$R^9R^7$, —N$R^9R^7$, —C(=O)N(H)$R^9$ or —C(=O)N$R^9R^7$; and
which is optionally substituted, one or more times, identically or differently, with a substituent selected from:
halo-, hydroxyl-, $C_1$-$C_6$-alkyl-, halo-$C_1$-$C_6$-alkyl-, $C_1$-$C_6$-alkoxy-, halo-$C_1$-$C_6$-alkoxy-;

$R^3$ represents a hydrogen atom;
$R^4$ represents a hydrogen atom;
$R^5$ represents a hydrogen atom;
$R^6$ represents a group selected from:
$C_3$-$C_6$-cycloalkyl-, —(CH$_2$)$_q$—($C_3$-$C_6$-cycloalkyl) or —(CH$_2$)$_q$-aryl;
said group being optionally substituted, one or more times, identically or differently, with a substituent selected from:
halo-;

$R^7$ represents a hydrogen atom;
$R^8$ represents a hydrogen atom or a $C_1$-$C_6$-alkyl-group;
$R^9$ represents a group selected from:
$C_7$-$C_{10}$-cycloalkyl-, 3- to 10-membered heterocycloalkyl-;
said group being optionally substituted, one or more times, identically or differently, with a substituent selected from:
halo-, hydroxyl-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, —(CH$_2$)$_q$—($C_3$-$C_6$-cycloalkyl), —C(=O)$R^8$, —C(=O)O—$R^8$;
or
$R^9$ and $R^7$,
together with the nitrogen atom to which they are attached,
represent a 3- to 10-membered heterocycloalkyl-group, which is optionally substituted, one or more times, identically or differently, with halogen, hydroxy, $C_1$-$C_6$-alkyl-, halo-$C_1$-$C_6$-alkyl-, $C_1$-$C_6$-alkoxy-, halo-$C_1$-$C_6$-alkoxy-, —C(=O)O—$R^8$ or $C_3$-$C_6$-cycloalkyl-;

q represents an integer of 1 or 2;

or a stereoisomer, a tautomer, an N-oxide, a hydrate, a solvate, or a salt thereof, or a mixture of same.

7. The compound according to claim 1, which is selected from the group consisting of:
2-cyclopropyl-N-[4-(2-{[2-methoxy-4-(morpholin-4-ylcarbonyl)phenyl]amino}[1,2,4]triazolo[1,5-a]pyridin-6-yl)phenyl]acetamide,
2-cyclopropyl-N-[4-(2-{[2-ethoxy-4-(morpholin-4-ylcarbonyl)phenyl]amino}[1,2,4]triazolo[1,5-a]pyridin-6-yl)phenyl]acetamide, 2-cyclopropyl-N-[4-(2-{[2-methoxy-4-(4-methylpiperazin-1-yl)phenyl]amino}[1, 2,4]triazolo[1,5-a] pyridin-6-yl)phenyl]acetamide trifluoroacetate, 2-(4-fluorophenyl)-N-[4-(2-{[2-methoxy-4-(morpholin-4-ylcarbonyl)phenyl]amino}[1,2,4]triazolo[1,5-a]pyridin-6-yl)phenyl]acetamide, N-[4-(2-{[2-ethoxy-4-(morpholin-4-ylcarbonyl)phenyl]amino}[1,2,4]triazolo[1,5-a]pyridin-6-yl)phenyl]-2-(4-fluorophenyl)acetamide, N-[4-(2-{[4-(4,4-dimethyl-4,5-dihydro-1, 3-oxazol-2-yl)-2-methoxyphenyl]amino}[1,2,4]triazolo[1,5-a]pyridin-6-yl)phenyl]-2-(4-fluorophenyl)acetamide, 2-(4-fluorophenyl)-N-{4-[2-({2-methoxy-4-[(4-methylpiperazin-1-yl)carbonyl] phenyl}amino)[1,2,4]triazolo[1,5-a]pyridin-6-yl]phenyl}acetamide, tert-butyl 4-(3-ethoxy-4-{[6-(4-{[(4-fluorophenyl)acetyl]amino}phenyl)[1,2,4]triazolo[1,5-a]pyridin-2-yl]amino}benzoyl)piperazine-1-carboxylate, N-[4-(2-{[2-ethoxy-4-(piperazin-1-ylcarbonyl)phenyl]amino}[1,2,4]triazolo[1,5-a]pyridin-6-yl)phenyl]-2-(4-fluorophenyl)acetamide, N-(4-{2-[(4-{[4-(cyclopropylmethyl)piperazin-1-yl]carbonyl}-2-ethoxyphenyl)amino] [1,2,4]triazolo[1,5-a]pyridin-6-yl}phenyl)-2-(4-fluorophenyl)acetamide, 2-(4-fluorophenyl)-N-[4-(2-{[2-methoxy-4-(4-methylpiperazin-1-yl)phenyl]amino}[1, 2,4]triazolo[1,5-a]pyridin-6-yl)phenyl]acetamide trifluoroacetate, 2-(4-fluorophenyl)-N-[4-(2-{[4-(morpholin-4-ylcarbonyl)-2-(2,2,2-trifluoroethoxy)phenyl]amino}[1,2,4]triazolo[1,5-a]pyridin-6-yl)phenyl]acetamide, N-(cyclopropylmethyl)-4-(2-{[2-methoxy-4-(morpholin-4-ylcarbonyl)phenyl]amino}[1,2,4]triazolo[1, 5-a]pyridin-6-yl)benzamide, N-(cyclopropylmethyl)-4-(2-{[2-ethoxy-4-(morpholin-4-ylcarbonyl)phenyl]amino}[1,2,4]triazolo[1, 5-a]pyridin-6-yl)benzamide, N-(cyclopropylmethyl)-4-(2-{[4-(4,4-dimethyl-4, 5-dihydro-1, 3-oxazol-2-yl)-2-methoxyphenyl]amino}[1, 2,4]triazolo[1, 5-a]pyridin-6-yl)benzamide, 4-[(6-{4-[(cyclopropylmethyl)carbamoyl]phenyl}[1,2,4]triazolo[1,5-a]pyridin-2-yl)amino]-3-ethoxy-N-(1-methylpiperidin-4-yl)benzamide, N-(cyclopropylmethyl)-4-(2-{[2-methoxy-4-(4-methylpiperazin-1-yl)phenyl]amino}[1, 2,4]triazolo[1,5-a]pyridin-6-yl)benzamide trifluoroacetate, N-(cyclopropylmethyl)-4-(2-{[4-(morpholin-4-ylcarbonyl)-2-(2,2,2-trifluoroethoxy)phenyl]amino}[1,2,4]triazolo[1, 5-a]pyridin-6-yl)benzamide, N-(4-Fluorbenzyl)-4-(2-{[2-methoxy-4-(morpholin-4-ylcarbonyl)phenyl]amino}[1,2,4]triazolo[1, 5-a]pyridin-6-yl)benzamid, 4-(2-{[2-Ethoxy-4-(morpholin-4-ylcarbonyl)phenyl}amino[1,2,4]triazolo[1,5-a]pyridin-6-yl)-N-(4-fluorbenzyl)benzamid, 2-(4-fluorophenyl)-N-[4-(2-{[4-(morpholin-4-ylcarbonyl)-2-(trifluoromethoxy)phenyl]amino}[1,2,4]triazolo[1,5-a] pyridin-6-yl)phenyl]acetamide, 2-(4-fluorophenyl)-N-[4-(2-{[2-methoxy-4-(2-oxo-1,3-oxazolidin-3-yl)phenyl]amino}[1, 2,4]triazolo[1,5-a]pyridin-6-yl)phenyl]acetamide, N-[4-(2-{[2-ethoxy-4-(2-oxo-1,3-oxazolidin-3-yl)phenyl]amino}[1,2,4]triazolo[1,5-a]pyridin-6-yl)phenyl]-2-(4-fluorophenyl)acetamide, 2-(4-fluorophenyl)-N-[4-(2-{[4-methyl-6-(2-oxo-1, 3-oxazolidin-3-yl)pyridin-3-yl]amino}[1,2,4]triazolo[1,5-a]pyridin-6-yl)phenyl]acetamide, N-[4-(2-{[4-(4,5-dihydro-1,3-oxazol-2-yl)-2-methoxyphenyl]amino}[1,2,4]triazolo[1,5-a]pyridin-6-yl)phenyl]-2-(4-fluorophenyl)acetamide, N-[4-(2-{[4-(4,5-dihydro-1,3-oxazol-2-yl)-2-methylphenyl]amino}[1,2,4]triazolo[1,5-a]pyridin-6-yl)phenyl]-2-(4-fluorophenyl)acetamide, 2-(4-fluorophenyl)-N-{4-[2-({2-methoxy-4-[(1 S,4S)-2-oxa-5-azabicyclo[2.2.1] hept-5-ylcarbonyl]phenyl}amino)[1,2,4]triazolo[1, 5-a]pyridin-6-yl]phenyl}acetamide, 2-(4-fluorophenyl)-N-[4-(2-{[2-methoxy-4-(2-oxa-6-azaspiro[3.3]hept-6-ylcarbonyl)phenyl]amino}[1,2,4]triazolo[1, 5-a]pyridin-6-yl)phenyl]acetamide, N-{4-[2-({4-[(1,1-dioxidothiomorpholin-4-yl)carbonyl]-2-methoxyphenyl}amino)[1,2,4]triazolo[1, 5-a]pyridin-6-yl]phenyl}-2-(4-fluorophenyl)acetamide, 2-(4-fluorophenyl)-N-{4-[2-({4-[(3-hydroxyazetidin-1-yl)carbonyl]-2-methoxyphenyl}amino)[1,2,4]triazolo[1, 5-a]pyridin-6-yl]phenyl}acetamide, 2-(4-fluorophenyl)-N-{4-[2-({4-[(4-hydroxypiperidin-1-yl)carbonyl]-2-methoxyphenyl}amino)[1, 2,4]triazolo[1, 5-a]pyridin-6-yl]phenyl}acetamide, 4-{[6-(4-{[(4-fluorophenyl)acetyl]amino}phenyl)[1,2,4]triazolo[1,5-a]pyridin-2-yl]amino}-3-methoxy-N-(oxetan-3-yl)benzamide, N-[4-(2-{[4-(azetidin-1-ylcarbonyl)-2-methoxyphenyl]amino}[1,2,4]triazolo[1,5-a]pyridin-6-yl)phenyl]-2-(4-fluorophenyl)acetamide, N-[4-(2-{[2-ethoxy-4-(2-oxa-6-azaspiro[3.3]hept-6-ylcarbonyl)phenyl]amino}[1,2,4]triazolo[1, 5-a]pyridin-6-yl)phenyl]-2-(4-fluorophenyl)acetamide, N-{4-[2-({2-ethoxy-4-[(3-hydroxyazetidin-1-yl)carbonyl] phenyl}amino)[1, 2,4]triazolo[1,5-a]pyridin-6-yl]phenyl}-2-(4-fluorophenyl)acetamide, 3-ethoxy-4-{[6-(4-{[(4-fluorophenyl)acetyl]amino}phenyl)[1,2,4]triazolo[1,5-a] pyridin-2-yl]amino}-N-(1-methylpiperidin-4-yl)benzamide, 2-(4-fluorophenyl)-N-[4-(2-{[4-(2-oxa-6-azaspiro[3.3]hept-6-ylcarbonyl)-2-(2,2,2-trifluoroethoxy)phenyl]amino}[1,2,4]triazolo[1,5-a]pyridin-6-yl)phenyl]acetamide, 2-(4-fluorophenyl)-N-4-[2-({4-[(3-hydroxyazetidin-1-yl)carbonyl]-2-(2,2,2-trifluoroethoxy)phenyl}amino)[1,2,4]triazolo[1,5-a]pyridin-6-yl]phenyl}acetamide, 2-(4-fluorophenyl)-N-[4-(2-{[2-methoxy-4-(4-methylpiperazin-1-yl)phenyl]amino}[1, 2,4]triazolo[1,5-a]pyridin-6-yl)phenyl]acetamide, 2-(4-fluorophenyl)-N-[4-(2-{[4-(morpholin-4-ylcarbonyl)phenyl]amino}[1,2,4]triazolo[1, 5-a]pyridin-6-yl)phenyl]acetamide, N-[4-(2-{[2-(2-fluoroethoxy)-4-(2-oxa-6-azaspiro[3.3]hept-6-ylcarbonyl)phenyl]amino}[1,2,4]triazolo[1,5-a]pyridin-6-yl)phenyl]-2-(4-fluorophenyl)acetamide, N-[4-(2-{[2-(2,2-difluoroethoxy)-4-(morpholin-4-ylcarbonyl)phenyl]amino}[1,2,4]triazolo[1, 5-a]pyridin-6-yl)phenyl]-2-(4-fluorophenyl)acetamide, 2-(4-fluorophenyl)-N-[4-(2-{[4-(morpholin-4-ylcarbonyl)-2-(trifluoromethyl)phenyl]amino}[1,2,4]triazolo[1,5-a]pyridin-6-yl)phenyl]acetamide, 2-(4-fluorophenyl)-N-[4-(2-{[2-methoxy-4-(morpholin-4-ylmethyl)phenyl] amino}[1, 2,4]triazolo[1,5-a] pyridin-6-yl)phenyl]acetamide, N-{4-[2-({2-ethoxy-4-[(1-methylpiperidin-4-yl)oxy]phenyl}amino)[1,2,4]triazolo[1,5-a]pyridin-6-yl] phenyl}-2-(4-fluorophenyl)acetamide, 2-(4-fluorophenyl)-N-{4-[2-({2-methoxy-4-[(1-methyl-piperidin-4-yl)oxy]phenyl}amino)[1,2,4]triazolo[1,5-a]pyridin-6-yl] phenyl}acetamide, 2-(4-fluorophenyl)-N-{4-[2-({4-[(1-methylpiperidin-4-yl)oxy]-2-(methylsulfanyl)phenyl}amino) [1, 2,4] triazolo[1, 5-a] pyridin-6-yl] phenyl}acetamide, 2-(4-fluorophenyl)-N-[4-(2-{[2-methoxy-4-(morpholin-4-ylsulfonyl)phenyl]amino}[1, 2,4]triazolo[1,5-a]pyridin-6-yl)phenyl]acetamide, 2-(4-fluorophenyl)-N-[4-(2-{[2-methyl-4-(2-oxa-6-azaspiro[3.3]hept-6-ylcarbonyl)phenyl]amino}[1,2,4]triazolo[1, 5-a]pyridin-6-yl)phenyl]acetamide, 2-(4-fluorophenyl)-N-[4-(2-{[2-methyl-4-(morpholin-4-ylcarbonyl)phenyl]amino}[1,2,4]triazolo[1, 5-a]pyridin-6-yl)phenyl]acetamide, 2-(4-fluorophenyl)-N-[4-(2-{[4-(2-oxa-6-azaspiro[3.3]hept-6-ylcarbonyl)-2-(trifluoromethoxy)phenyl]amino}[1,2,4]triazolo[1,5-a] pyridin-6-yl)phenyl]acetamide, 2-(4-fluorophenyl)-N-[4-(2-{[2-methoxy-5-(morpholin-4-ylcarbonyl)phenyl]amino}[1,2,4]triazolo[1, 5-a] pyridin-6-yl)phenyl]acetamide, 2-(4-fluorophenyl)-N-[4-(2-{[2-methyl-6-(morpholin-4-yl)pyridin-3-yl]amino}[1, 2,4]triazolo[1, 5-a]pyridin-6-yl)phenyl]acetamide, 2-(4-fluorophenyl)-N-[4-(2-{[2-methyl-6-(pyrrolidin-1-yl)pyridin-3-yl]amino}[1, 2,4]triazolo[1, 5-a]pyridin-6-yl)phenyl]acetamide, N-{4-[2-({4-[(3-fluoroazetidin-1-yl)carbonyl]-2-methoxyphenyl}amino)[1,2,4]triazolo[1, 5-a]pyridin-6-yl]phenyl}-2-(4-fluorophenyl)acetamide, N-(cyclopropylmethyl)-4-(2-{[2-methoxy-4-(2-oxa-6-azaspiro[3.3] hept-6-ylcarbonyl)phenyl]amino}[1,2,4]triazolo[1,5-a]pyridin-6-yl)benzamide, N-(4-fluorobenzyl)-4-(2-{[2-methoxy-4-(2-oxo-1,3-oxazolidin-3-yl)phenyl]amino}[1, 2,4]triazolo[1,5-a]pyridin-6-yl)benzamide, 4-(2-{[2-ethoxy-4-(2-oxo-1,3-oxazolidin-3-yl)phenyl]amino}[1,2,4]triazolo[1,5-a]pyridin-6-yl)-N-(4-fluorobenzyl)benzamide, 4-(2-{[4-(4,5-dihydro-1,3-oxazol-2-yl)-2-methoxyphenyl]amino}[1,2,4]triazolo[1,5-a]pyridin-6-yl)-N-(4-fluorobenzyl)benzamide, N-(4-fluorobenzyl)-4-(2-({2-methoxy-4-[(1 S,4S)-2-oxa-5-azabicyclo[2.2.1]hept-5-ylcarbonyl] phenyl}amino) [1,2,4]triazolo[1, 5-a]pyridin-6-yl]benzamide, N-(4-fluorobenzyl)-4-(2-{[2-methoxy-4-(2-oxa-6-azaspiro[3.3]hept-6-ylcarbonyl)phenyl]amino}[1,2,4]triazolo[1,5-a]pyridin-6-yl)benzamide, N-(4-fluorobenzyl)-4-(2-({4-[(3-hydroxyazetidin-1-yl)carbonyl]-2-methoxyphenyl}amino)[1,2,4]triazolo[1, 5-a]pyridin-6-yl)benzamide, 4-[2-({4-[(1,1-dioxidothiomorpholin-4-yl)carbonyl]-2-methoxyphenyl}amino)[1,2,4]triazolo[1,5-a]pyridin-6-yl]-N-(4-fluorobenzyl)benzamide, N-(4-fluorobenzyl)-4-[2-({4-[(4-hydroxypiperidin-1-yl)carbonyl]-2-methoxyphenyl}amino)[1,2,4]triazolo[1, 5-a]pyridin-6-yl]benzamide, 4-[(6-{4-[(4-fluorobenzyl)carbamoyl]phenyl}[1,2,4]triazolo[1,5-a]pyridin-2-yl)amino]-3-methoxy-N-(oxetan-3-yl)benzamide, 4-(2-{[2-ethoxy-4-(2-oxa-6-azaspiro[3.3]hept-6-ylcarbonyl)phenyl]amino}[1,2,4]triazolo[1,5-a]pyridin-6-yl)-N-(4-fluorobenzyl)benzamide, 4-[2-({4-[(4-acetylpiperazin-1-yl)carbonyl]-2-ethoxyphenyl}amino)[1,2,4]triazolo[1,5-a] pyridin-6-yl]-N-(4-fluorobenzyl)benzamide, 4-[2-({2-ethoxy-4-[(3-hydroxyazetidin-1-yl)carbonyl]phenyl}amino)[1,2,4]triazolo[1, 5-a] pyridin-6-yl]-N-(4-fluorobenzyl)benzamide, N-(4-fluorobenzyl)-4-(2-{[4-(2-oxa-6-azaspiro[3.3]hept-6-ylcarbonyl)-2-(2,2,2-trifluoroethoxy)phenyl]amino}[1,2,4]triazolo[1,5-a]pyridin-6-yl)benzamide, N-(4-fluorobenzyl)-4-[2-({4-[(3-hydroxyazetidin-1-yl)carbonyl]-2-(2,2,2-trifluoroethoxy)phenyl}amino)[1,2,4]triazolo[1,5-a]pyridin-6-yl]benzamide, N-(4-fluorobenzyl)-4-(2-{[4-(morpholin-4-ylcarbonyl)-2-(2, 2, 2-trifluoroethoxy)phenyl]amino}[1,2,4]triazolo[1,5-a]pyridin-6-yl)benzamide, N-(4-fluorobenzyl)-4-(2-{[2-methoxy-4-(4-methylpiperazin-1-yl)phenyl]amino}[1,2,4]triazolo[1,5-a]pyridin-6-yl)benzamide, 4-(2-{[4-(4-tert-butylpiperazin-1-yl)-2-methoxyphenyl]amino}[1,2,4]triazolo[1,5-a] pyridin-6-yl)-N-(4-fluorobenzyl)benzamide, N-(4-fluorobenzyl)-4-(2-{[2-fluoro-4-(2-oxa-6-azaspiro[3.3] hept-6-ylcarbonyl)phenyl]amino}[1,2,4]triazolo[1,5-a]pyridin-6-yl)benzamide, N-(4-fluorobenzyl)-4-(2-{[2-fluoro-4-(morpholin-4-ylcarbonyl)phenyl]amino}[1,2,4]triazolo[1,5-a]pyridin-6-yl)benzamide, 4-(2-{[2-(2, 2-difluoroethoxy)-4-(morpholin-4-ylcarbonyl)phenyl]amino}[1,2,4]triazolo[1,5-a]pyridin-6-yl)-N-(4-fluorobenzyl)benzamide, N-(4-fluorobenzyl)-4-(2-{[4-(morpholin-4-ylcarbonyl)-2-(trifluoromethyl)phenyl]amino}[1,2,4]triazolo[1,5-a]pyridin-6-yl)benzamide, N-(4-fluorobenzyl)-4-[2-({2-methoxy-4-[(4-methylpiperazin-1-yl)methyl]phenyl}amino)[1,2,4]triazolo[1,5-a] pyridin-6-yl] benzamide, N-(4-fluorobenzyl)-4-(2-{[2-methoxy-4-(morpholin-4-ylmethyl) phenyl] amino}[1, 2,4]triazolo[1, 5-a] pyridin-6-yl)benzamide, N-(4-fluorobenzyl)-4-[2-({2-methoxy-4-[(1-methylpiperidin-4-yl)oxy]phenyl}amino)[1,2,4]triazolo[1,5-a]pyridin-6-yl]benzamide, N-(4-fluorobenzyl)-4-[2-({4-[(1-methylpiperidin-4-yl)oxy]-2-(methylsulfanyl)phenyl}amino) [1, 2, 4] triazolo[1,5-a] pyridin-6-yl] benzamide, N-(4-fluorobenzyl)-4-(2-{[2-methyl-4-(2-oxa-6-azaspiro[3.3] hept-6-ylcarbonyl)phenyl]amino}[1,2,4]triazolo[1,5-a]pyridin-6-yl)benzamide, N-(4-fluorobenzyl)-4-(2-{[2-methyl-4-(morpholin-4-ylcarbonyl)phenyl]amino}[1,2,4]triazolo[1,5-a]pyridin-6-yl)benzamide, N-(4-fluorobenzyl)-4-(2-{[4-(2-oxa-6-azaspiro[3.3]hept-6-ylcarbonyl)-2-(trifluoromethoxy)phenyl]amino}[1,2,4]triazolo[1,5-a] pyridin-6-yl)benzamide, N-(4-fluorobenzyl)-4-(2-{[4-(morpholin-4-ylcarbonyl)-2-(trifluoromethoxy)phenyl]amino}[1,2,4]triazolo[1,5-a] pyridin-6-yl)benzamide, N-(4-fluorobenzyl)-4-(2-{[2-methoxy-5-(morpholin-4-ylcarbonyl)phenyl]amino}[1,2,4]triazolo[1,5-a]pyridin-6-yl)benzamide, N-(4-fluorobenzyl)-4-(2-{[2-methyl-6-(morpholin-4-yl)pyridin-3-yl]amino}l[1,2,4]triazolo[1,5-a]pyridin-6-yl)benzamide, N-(4-fluorobenzyl)-4-(2-{[2-methyl-6-(pyrrolidin-1-yl)pyridin-3-yl]amino}l[1,2,4]triazolo[1,5-a]pyridin-6-yl)benzamide, 4-[2-({4-[(3-fluoroazetidin-1-yl)carbonyl]-2-methoxyphenyl}amino)[1,2,4]triazolo[1,5-a]pyridin-6-yl]-N-(4-fluorobenzyl)benzamide, N-(4-chlorobenzyl)-4-(2-{[2-methoxy-4-(morpholin-4-ylcarbonyl)phenyl]amino}[1,2,4]triazolo[1,5-a]pyridin-6-yl)benzamide, 4-(2-{[2-methoxy-4-(morpholin-4-ylcarbonyl)phenyl]amino}[1,2,4]triazolo[1,5-a]pyridin-6-yl)-N-(4-methylbenzyl)benzamide, 2-fluoro-N-(4-fluorobenzyl)-4-(2-{[2-methoxy-4-(morpholin-4-ylcarbonyl)phenyl]amino}[1,2,4]triazolo[1,5-a]pyridin-6-yl)benzamide, 2-fluoro-N-(4-fluorobenzyl)-4-(2-{[2-methoxy-4-(morpholin-4-ylmethyl)phenyl]amino}[1, 2,4]triazolo[1,5-a] pyridin-6-yl)benzamide, N-(4-fluorobenzyl)-4-(2-{[2-methoxy-4-(morpholin-4-ylcarbonyl)phenyl]amino}[1,2,4]triazolo[1, 5-a]pyridin-6-yl)-2-methylbenzamide, N-(4-fluorobenzyl)-4-(2-{[2-methoxy-4-(2-oxo-1,3-oxazolidin-3-yl)phenyl]amino}[1, 2,4]triazolo[1,5-a]pyridin-6-yl)-2-methylbenzamide, 2-chloro-N-(4-fluorobenzyl)-4-(2-{[2-methoxy-4-(morpholin-4-ylcarbonyl)phenyl]amino}[1,2,4]triazolo[1,5-a]pyridin-6-yl)benzamide, N-(4-fluorobenzyl)-2-methoxy-4-(2-{[2-methoxy-4-(morpholin-4-ylcarbonyl)phenyl]amino}[1,2,4]triazolo[1,5-a]pyridin-6-yl)benzamide, N-[2-fluoro-4-(2-{[2-methoxy-4-(morpholin-4-ylcarbonyl)phenyl]amino}[1, 5-a]pyridin-6-yl)phenyl]-2-(4-fluorophenyl)acetamide, 2-(4-fluorophenyl)-N-[5-(2-{[2-methoxy-4-(morpholin-4-ylcarbonyl)phenyl]amino}[1,2,4]triazolo[1, 5-a]pyridin-6-yl)pyridin-2-yl]acetamide, N-[5-(2-{[2-ethoxy-4-(morpholin-4-ylcarbonyl)phenyl]amino}[1,2,4]triazolo[1,5-a]pyridin-6-yl)pyridin-2-yl]-2-(4-fluorophenyl)acetamide, N-(2,4-difluorobenzyl)-4-(2-{[2-methoxy-4-(2-oxo-1,3-oxazolidin-3-yl)phenyl]amino}[1, 2,4]triazolo[1,5-a]pyridin-6-yl)-2-methylbenzamide, N-(4-fluorobenzyl)-5-(2-{[2-methoxy-4-(2-oxa-6-azaspiro[3.3]hept-6-ylcarbonyl)phenyl]amino}[1,2,4]triazolo[1, 5-a]pyridin-6-yl)pyridine-2-carboxamide, or a stereoisomer, a tautomer, an N-oxide, a hydrate, a solvate, or a salt thereof, or a mixture of same.

8. A method of preparing a compound of general formula (I) according to claim 1, in which method an intermediate compound of general formula (5):

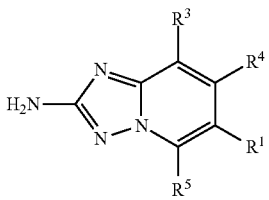

(5)

in which $R^1$, $R^3$, $R^4$, and $R^5$ are as defined for the compound of general formula (I) in claim 1, is allowed to react with a compound of general formula (5a):

$R^2$—Y  (5a)

in which $R^2$ is as defined for the compound of general formula (I) in claim 1 and Y represents a leaving group, thus providing a compound of general formula (I):

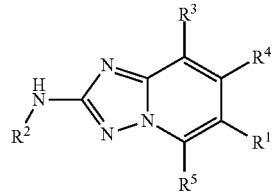

(I)

in which $R^1$, $R^2$, $R^3$, $R^4$, and $R^5$ are as defined for the compound of general formula (I) in claim 1.

9. A pharmaceutical composition comprising a compound of general formula (I) according to claim 1, or a stereoisomer, a tautomer, an N-oxide, a hydrate, a solvate, or a pharmaceutically acceptable salt thereof, or a mixture of same, and a pharmaceutically acceptable diluent or carrier.

10. A pharmaceutical combination comprising:

one or more compounds of general formula (I) according to claim 1, or a stereoisomer, a tautomer, an N-oxide, a hydrate, a solvate, or a pharmaceutically acceptable salt thereof, or a mixture of same;

and one or more agents selected from: a taxane; an epothilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2-deoxyadenosine; Thioguanine; an anti-androgen; Bortezomib; a platinum derivative; Chlorambucil; Methotrexate; and Rituximab.

11. A method for the treatment of breast cancer, non-small cell lung cancer, prostate cancer, cervical cancer, or melanoma, comprising administering to a patient in need thereof an effective amount of a compound of general formula (I) according to claim 1, or a stereoisomer, a tautomer, an N-oxide, a hydrate, a solvate, or a pharmaceutically acceptable salt thereof, or a mixture of same.

12. The pharmaceutical combination according to claim 10, in which the taxane is selected from Docetaxel and Paclitaxel.

13. The pharmaceutical combination according to claim 10, in which the epothilone is selected from Ixabepilone, Patupilone, and Sagopilone.

14. The pharmaceutical combination according to claim 10, in which the anti-androgen is selected from Flutamide, Cyproterone acetate, and Bicalutamide.

15. The pharmaceutical combination according to claim 10, in which the a platinum derivative is selected from Cisplatin and Carboplatin.

* * * * *